(12) United States Patent
Yang et al.

(10) Patent No.: US 9,879,036 B2
(45) Date of Patent: Jan. 30, 2018

(54) MITOCHONDRIAL ALDEHYDE DEHYDROGENASE-2 BINDING COMPOUNDS AND METHODS OF USE THEREOF

(71) Applicant: Aviv Therapeutics, Inc., Menlo Park, CA (US)

(72) Inventors: Wenjin Yang, Redwood City, CA (US); Yie-Teh Yu, Redwood City, CA (US); Chun Jiang, Redwood City, CA (US)

(73) Assignee: Aviv Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 15/120,476

(22) PCT Filed: Feb. 19, 2015

(86) PCT No.: PCT/US2015/016703
§ 371 (c)(1),
(2) Date: Aug. 19, 2016

(87) PCT Pub. No.: WO2015/127137
PCT Pub. Date: Aug. 27, 2015

(65) Prior Publication Data
US 2017/0057982 A1    Mar. 2, 2017

Related U.S. Application Data

(60) Provisional application No. 61/941,909, filed on Feb. 19, 2014.

(51) Int. Cl.
| | |
|---|---|
| C07F 9/58 | (2006.01) |
| C07D 213/81 | (2006.01) |
| C07D 213/82 | (2006.01) |
| C07D 213/89 | (2006.01) |
| C07D 231/12 | (2006.01) |
| C07D 333/24 | (2006.01) |
| C07D 233/64 | (2006.01) |
| C07D 401/04 | (2006.01) |
| C07D 405/12 | (2006.01) |
| C07D 409/04 | (2006.01) |
| C07D 413/04 | (2006.01) |
| C07D 261/08 | (2006.01) |
| C07C 235/60 | (2006.01) |
| C07D 277/30 | (2006.01) |
| C07D 213/56 | (2006.01) |
| C07D 307/54 | (2006.01) |
| C07C 237/32 | (2006.01) |

(52) U.S. Cl.
CPC ............ *C07F 9/585* (2013.01); *C07C 235/60* (2013.01); *C07C 237/32* (2013.01); *C07D 213/56* (2013.01); *C07D 213/81* (2013.01); *C07D 213/82* (2013.01); *C07D 213/89* (2013.01); *C07D 231/12* (2013.01); *C07D 233/64* (2013.01); *C07D 261/08* (2013.01); *C07D 277/30* (2013.01); *C07D 307/54* (2013.01); *C07D 333/24* (2013.01); *C07D 401/04* (2013.01); *C07D 405/12* (2013.01); *C07D 409/04* (2013.01); *C07D 413/04* (2013.01); *C07C 2601/02* (2017.05)

(58) Field of Classification Search
CPC ........................................... C07F 9/585
USPC .......................................... 546/298
See application file for complete search history.

(56) References Cited

FOREIGN PATENT DOCUMENTS

| | | |
|---|---|---|
| CN | 102600182 A | 7/2012 |
| CN | 102614198 A | 8/2012 |
| CN | 103880700 A | 6/2014 |
| WO | 2004046130 A1 | 6/2004 |
| WO | 2006/065946 A1 | 6/2006 |
| WO | 2008112164 A2 | 9/2008 |
| WO | 2010062308 A1 | 6/2010 |
| WO | 2014160185 A2 | 10/2014 |

OTHER PUBLICATIONS

Marcel Holzer et al: "Structural modifications of salicylates: inhibitors of human CD81-receptor HCV-E2 interaction," Arch IV Der Pharmazie, vol. 341, No. 8, 2008, pp. 478-484.
Guang-Xiang Zhong et al: "Synthesis and biological evaluation of amide derivatives of diflunisal as potential anti-tumor agents," Bioorganic & Medicinal Chemistry Letters, vol. 19, No. 15, 2009, pp. 4399-4402.
Dengyou Zhang et al: "Discovery of novel 2-aminopyridine-3-carboxamides as c-Met kinase inhibitors," Bioorganic & Medicinal Chemistry, vol. 20, No. 17, 2012, pp. 5169-5180.
S. Vadivelan et al: "Fragment and knowledge-based design of selective GSK-3beta inhibitors using virtual screening models," European Journal of Medicinal Chemistry, vol. 44, No. 6, 2009, pp. 2361-2371.
Che-Hong Chen et al: "Targeting aldehyde dehydrogenase 2: new therapeutic opportunities," Physiological Reviews, vol. 94, No. 1, Jan. 1, 2014, pp. 1-34.

*Primary Examiner* — Taofiq A Solola
(74) *Attorney, Agent, or Firm* — VLP Law Group LLP; Kent H. Chong

(57) ABSTRACT

The present invention provides compounds that bind to mitochondrial aldehyde dehydrogenase-2 (ALDH2), methods of using said compounds to treat patients with Fanconi Anemia, and methods of preparing said compounds.

18 Claims, 10 Drawing Sheets

MITOCHONDRIAL ALDEHYDE DEHYDROGENASE-2 BINDING COMPOUNDS AND METHODS OF USE THEREOF

RELATED APPLICATIONS

This is a U.S. national stage of application No. PCT/US2015/016703, filed on Feb. 19, 2015, the content of which is incorporated here by reference.

This application claims priority to, and the benefit of, U.S. provisional application No. 61/941,909, filed Feb. 19, 2014, the entire content of which is incorporated herein by reference in its entirety.

FIELD OF THE DISCLOSURE

This disclosure relates to compounds that modulate the activity of mitochondrial aldehyde dehydrogenase-2 (ALDH2), and methods of preparing and/or using such compounds.

BACKGROUND OF THE DISCLOSURE

Mitochondrial aldehyde dehydrogenase-2 (ALDH2) is an enzyme that catalyzes the conversion of conversion of xenogenic and biogenic aldehydic compounds to corresponding acids, such as acetaldehyde to acetic acid. ALDH2 is critical for alcohol metabolism in humans because it further breaks down the product of ethanol oxidation from alcohol dehydrogenase activity. The 56 kDa enzyme is encoded in the nuclear genome and is transported into mitochondria. ALDH2 exists in solution as a tetrameric protein composed of four identical subunits, each consisting of approximately 517 amino acid residues. The tetramer can be regarded as a dimer of dimers. The interface between monomers that form a dimer is different and more extensive than the interface between the two dimers that form the tetramer. Each subunit is composed of three domains: the catalytic domain, the coenzyme or $NAD^+$-binding domain, and the oligomerization domain.

Fanconi anemia (FA) is an autosomal recessive disorder characterized by congenital abnormalities, bone marrow failure, and a predisposition to malignancies, including myelodysplastic syndrome and acute myelogenous leukemia. See Auerbach, et al., In: The Metabolic and Molecular Basis of Inherited Diseases. 8th Ed. Scriver, et al., editors. New York: McGraw-Hill; 2001. pp. 753-768. Most patients experience bone marrow failure at a median age of five years. Progressive pancytopenia and congenital malformations, including short stature, radial aplasia, urinary tract abnormalities, hyperpigmentation, and developmental delay are common symptoms. Fanconi Anemia is associated with a predisposition to cancer, particularly acute myeloid leukemia and an increased risk of developing solid tumors.

Testing for Fanconi anemia is indicated in young patients with aplastic anemia, arm and/or thumb, cardiac, central nervous system, genitourinary, kidney, and/or skeletal system anomalies, hyper-pigmentation, small size, and/or bleeding disorders.

Several FA complementation groups (FA-A through FA-O) have been reported (see, e.g., Joenje, et al., Am J Hum Genet. (2000), 67:759-762), with FA-A (Online Mendelian Inheritance in Man, OMIM no. 227650) constituting approximately two-thirds of the patients. The FANCA, FANCB, FANCC, FANCD2, FANCE, FANCF, FANCG, FANCI, FANCJ (BRIP1), FANCL, FANCM, FANCN (PALB2) and FANCO (RAD51C) genes have been cloned and known to be the causative mutations of Fanconi Anemia. See, e.g., Lo Ten Foe, et al. Nat Genet. (1996), 14:320-323; Fanconi Anemia/Breast Cancer Consortium. Nat Genet. (1996), 14:324-328; Strathdee, et al. Nat Genet. (1992), 1:196-198; de Winter, et al. Am J Hum Genet. (2000), 67:1306-1308; de Winter, et al. Nat Genet. (2000), 24:15-16; and de Winter, et al. Nat Genet. (1998), 20:281-283. However, the specific function of these genes remains unclear.

The FA gene products play an important role in protecting the integrity of the human genome; mutations in any of the FA genes always lead to genomic instability due to failure to repair DNA damage. Over the last decade, the role for Fanconi Anemia gene products in DNA repair has been established. However, the source and chemical agents that cause excessive genomic instability leading to the phenotype of developmental abnormality, BMF, and predisposition malignancy in FA patients had been elusive. Environmental pollutants, carcinogens, and biogenic reactive chemical species that are capable of attacking DNA and causing genome instability under physiological conditions were the prime suspects of the molecular triggers of FA. Reactive aldehydes are known toxic molecules that can damage DNA by forming DNA-protein or DNA-DNA crosslinking. See Brooks, P. J. and Zakhari, S. *Acetaldehyde and the genome: Beyond nuclear DNA adducts and carcinogenesis*, Environ. Mol. Mutagen., 2014, 55: 77-91. It has been proposed that bone marrow failure in FA patients could result from endogenous aldehyde induced toxicity, which then leads to the depletion of hematopoietic stem cells (HSCs), as was observed in $Aldh2^{-/-}Fancd2^{-/-}$ mice. See Langevin F, et al. *Fancd2 counteracts the toxic effects of naturally produced aldehydes in mice*, Nature (2011), 475(7354):53-58; Garaycoechea J I, et al. Genotoxic consequences of endogenous aldehydes on mouse haematopoietic stem cell function. Nature (2012), 489 (7417):571-575. The ALDH2 genotype of a group of Japanese FA patients has recently been deciphered. See Hira A, et al. *Variant ALDH2 is associated with accelerated progression of bone marrow failure in Japanese Fanconi anemia patients*, Blood (2013), 122(18):3206-3209. In one study involving Japanese patient population, dramatic acceleration of bone marrow failure and increased frequency of malformation in some tissues was observed with ALDH2 deficiency (these patients carried double mutations in ALDH2 gene, i.e., homozygous mutant allele represented as ALDH*2/*2, thus, entirely devoid of ALDH2 activity). See Hira (2013). Most strikingly, those patients entirely deficient for ALDH2 developed bone marrow failure within the first 7 months of life, suggesting that reactive aldehydes play an important role in Fanconi Anemia prognosis. See id.

The current disclosure provides compounds that are agonists of ALDH2, useful for treating and/or preventing diseases or disorders in which ALDH2 plays a role. For example, the compounds of the invention may be useful to treat Peripheral Artery Disease (PAD), Acute Inflammatory Pain, liver injury and damage such as liver fibrosis, alcohol-related disorders such as intolerance, addiction, intoxication, abuse, etc. Further, the compounds of the invention may be useful to treat Fanconi Anemia. The current disclosure also provides methods for treating and/or preventing cancer, for example, esophageal cancer and cancer in patients with Fanconi Anemia or those carrying a FANC* causative mutation for Fanconi Anemia, as well as prevention and/or protection against injuries and damages caused by ionized radiation or chemotherapy.

SUMMARY OF THE DISCLOSURE

The present invention provides compounds that modulate mitochondrial aldehyde dehydrogenase-2 (ALDH2) activity, and methods of preparing and/or using said compounds. In one aspect, the present disclosure features a compound of formula I:

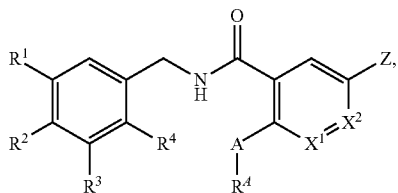
(I)

or a pharmaceutically acceptable salt, solvate, ester, or prodrug thereof,
wherein:
A is O, S, NH, or N—$R^C$;
$R^A$ is H, $C_1$-$C_6$ alkyl optionally substituted with one or more $R^B$, or $C_3$-$C_8$ cycloalkyl;
$R^B$ is $R^C$ or a 3-14 membered carbocycle optionally substituted with $R^C$;
$R^C$ is D or $C_1$-$C_6$ alkyl;
$X^1$ and $X^2$ are independently N or CH;
$R^1$, $R^2$, $R^3$, and $R^4$ are independently chosen from —H, —F, —Cl, —$CH_3$, —$CF_3$, —$C(CH_3)_3$, —$OCH_3$, and —$OCD_3$;
alternatively, $R^1$ and $R^2$ together form a 5-membered, partially saturated heterocycle containing two oxygen atoms;
Z is a substituted ring structure chosen from

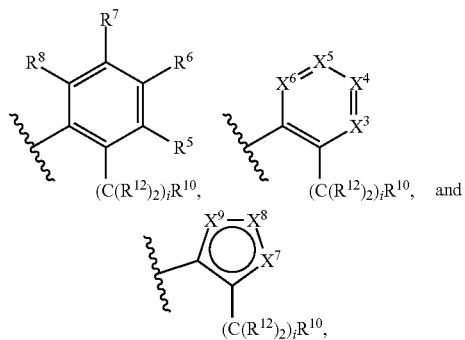

wherein i is
0, 1, 2, or 3;
$R^5$, $R^6$, $R^7$, and $R^8$ are independently chosen from H, F, and $N(CH_3)_2$;
$X^3$, $X^4$, $X^5$, and $X^6$ are independently chosen from N, NO, and CH;
$X^7$, $X^8$, and $X^9$ are independently chosen from S, O, N, $NR^9$, and $CR^9$;
$R^9$ is H or $CH_3$;
$R^{10}$ is $R^{11}$, —CH=$CHR^{11}$,

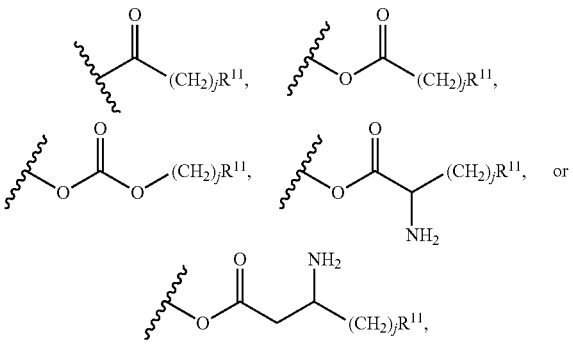

wherein j is 0, 1, 2, or 3;
$R^{11}$ is —$C(CH_3)_2NH_2$, —$CH(CH_3)_2$, —$CH(CH_3)OH$, —$NH_2$, —$NHR^C$, —$NR^C_2$, —$OCH_3$, —$C(O)CH_3$, —$OPO_3H_2$, —COOH, —CH=NOH, —$CH_3$, —SH, —OH, or —H; and
each $R^{12}$ is independently H or D.

In another subset, the compounds of formula (I) includes those in which at least two of $X^3$, $X^4$, $X^5$, and $X^6$ are CH. In some embodiments, the formula (I) compounds include those having both $X^1$ and $X^2$ as CH. In other embodiments, the formula (I) compounds include those having one of $X^1$ or $X^2$ as CH. The formula (I) compounds of the present disclosure include compounds in which one or two among $X^3$, $X^4$, $X^5$, and $X^6$ is N or NO.

The present disclosure provides compounds of formula (I) in which $R^A$ is $C_1$ alkyl substituted with $R^B$, where $R^B$ is an unsubstituted cyclopropyl. The compounds of formula (I) according to the current disclosure includes those in which A is O, $R^A$ is $C_1$ alkyl substituted with $R^B$, and $R^B$ is unsubstituted cyclopropyl. In some embodiments, the compounds of the present disclosure include those in which A is NH, $R^A$ is $C_1$ alkyl substituted with $R^B$, and $R^B$ is unsubstituted cyclopropyl. In some embodiments, the compound has a formula where A is O. In some embodiments, the compound has a formula where "i" is 1, $R^{10}$ is $R^{11}$, and $R^{11}$ is —OH. In one embodiment, $R^A$ is a $C_1$-$C_6$ straight saturated hydrocarbon chain or a $C_3$-$C_6$ branched saturated hydrocarbon chain. In another embodiment, $R^A$ is $C_3$-$C_8$ cycloalkyl. In yet another embodiment, one or both of $R^1$ and $R^3$ are F, $R^2$ is $OCD_3$, and $R^4$ is H.

The present disclosure provides a subset of compounds of formula (I) in which the substituted ring structure Z is chosen from furanyl, furazanyl, imidazolidinyl, imidazolinyl, imidazolyl, morpholinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, piperazinyl, piperidinyl, piperidinone, 4-piperidinone, pyridinyl, pyridyl, pyrimidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thiophenyl, triazinyl, 1,2,3-triazolyl, 1,2,4-triazolyl, 1,2,5-triazolyl, and 1,3,4-triazolyl.

The present disclosure provides ester, phosphoryloxymethyl (POM) and phosphoryloxymethyl oxymethyl (POMOM) derivatives of a compound of formula (I) or a pharmaceutically acceptable salt or solvate thereof.

One subset of the compounds of formula (I) includes compounds AC1-AC166 listed in Table 1.

TABLE 1
| Compound ID | Structure |
|---|---|
| AC1 | 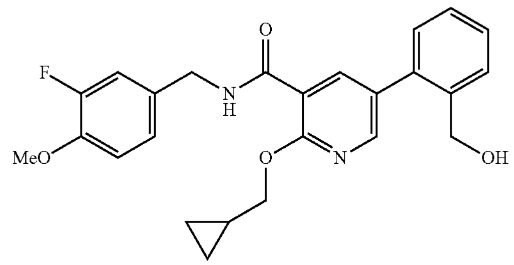 |
| AC2 | 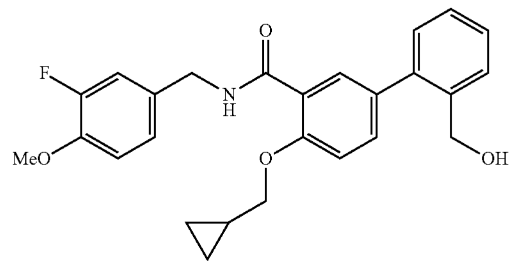 |
| AC3 | 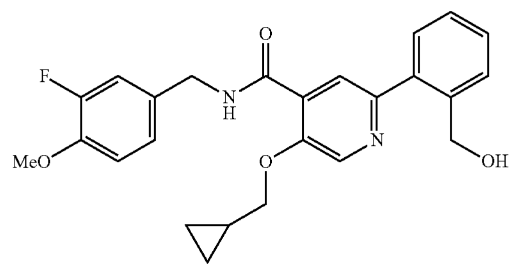 |
| AC4 | 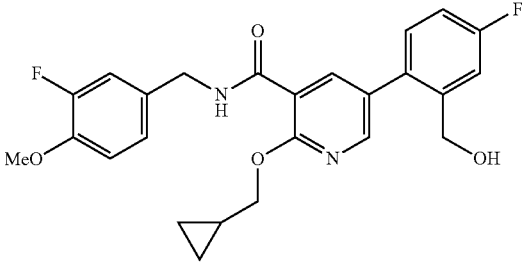 |
| AC5 | 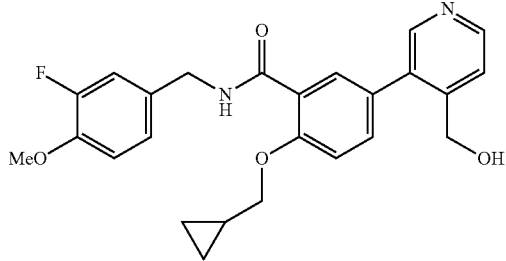 [SMILES: COc1ccc(CNC(=O)c2cc(-c3cnccc3CO)ccc2OCC2CC2)cc1F] |

TABLE 1-continued

| Compound ID | Structure |
|---|---|
| AC6 | 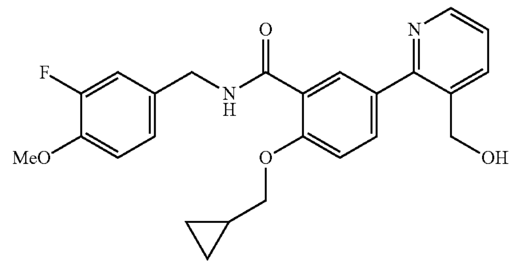 [SMILES: COc1ccc(CNC(=O)c2cc(-c3ncccc3CO)ccc2OCC2CC2)cc1F] |
| AC7 | 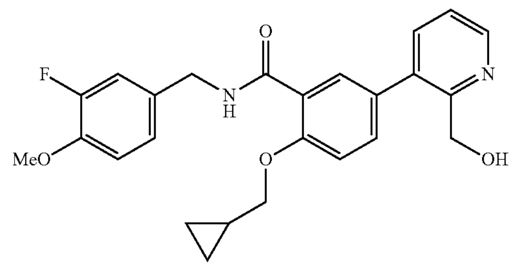 |
| AC8 | 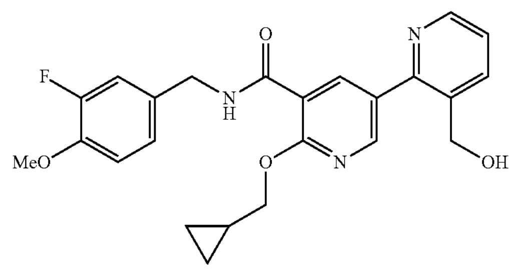 |
| AC9 | 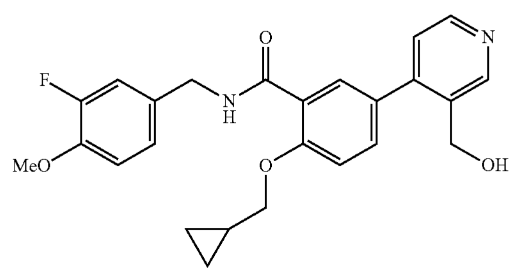 |
| AC10 | 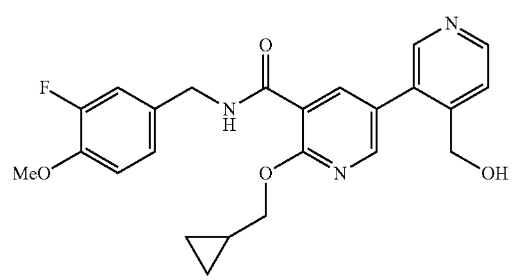 [SMILES: COc1ccc(CNC(=O)c2cc(-c3cnccc3CO)cnc2OCC2CC2)cc1F] |

TABLE 1-continued
| Compound ID | Structure |
|---|---|
| AC11 | 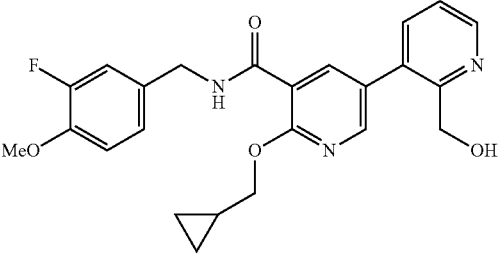 [SMILES: COc1ccc(CNC(=O)c2cc(-c3cccnc3CO)cnc2OCC2CC2)cc1F] |
| AC12 | 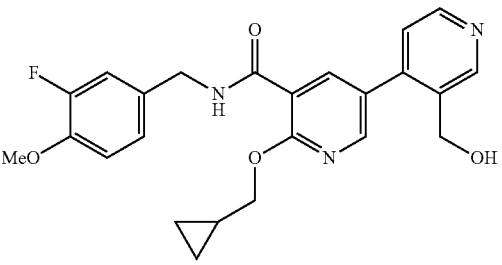 |
| AC13 | 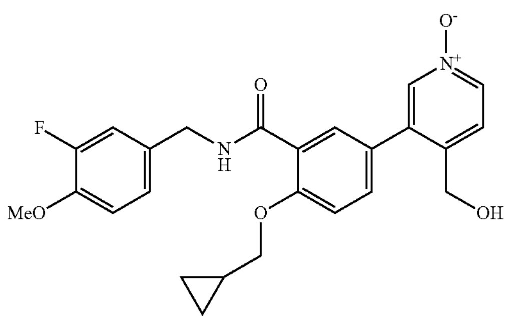 |
| AC14 | 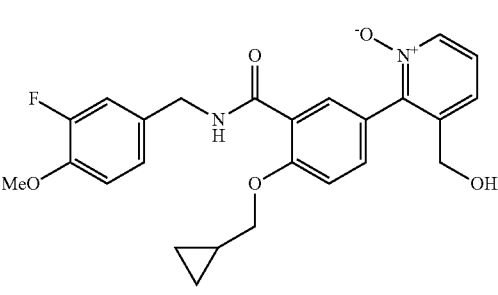 |
| AC15 | 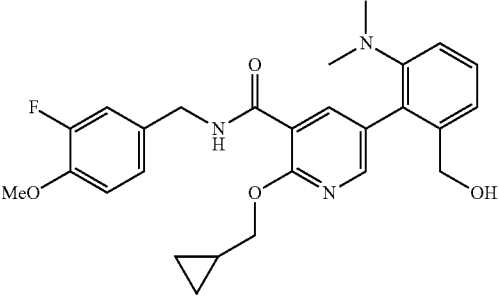 [SMILES: COc1ccc(CNC(=O)c2cc(-c3c(CO)cccc3N(C)C)cnc2OCC2CC2)cc1F] |

TABLE 1-continued
| Compound ID | Structure |
|---|---|
| AC16 | 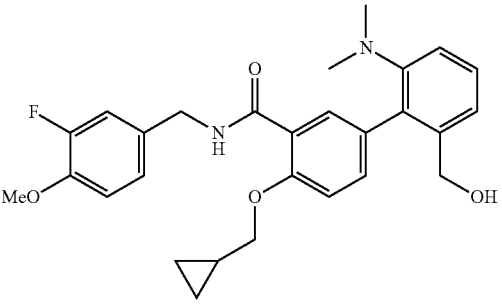 [SMILES: COc1ccc(CNC(=O)c2cc(-c3c(CO)cccc3N(C)C)ccc2OCC2CC2)cc1F] |
| AC17 | 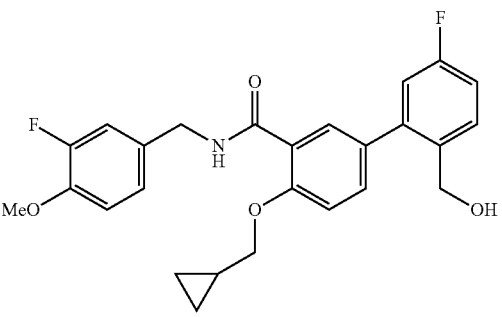 [SMILES: COc1ccc(CNC(=O)c2cc(-c3cc(F)ccc3CO)ccc2OCC2CC2)cc1F] |
| AC18 | 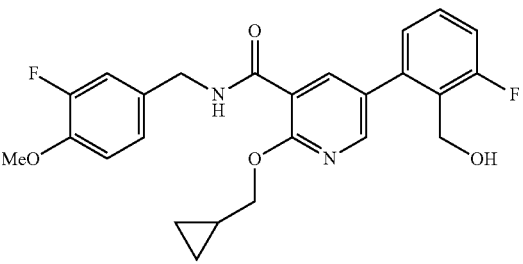 [SMILES: COc1ccc(CNC(=O)c2cc(-c3cccc(F)c3CO)cnc2OCC2CC2)cc1F] |
| AC19 | 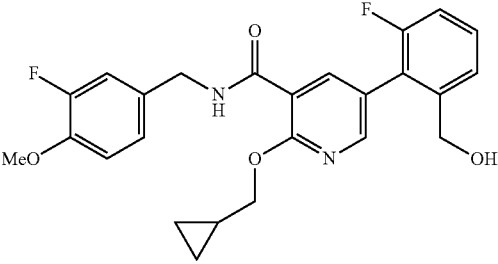 [SMILES: COc1ccc(CNC(=O)c2cc(-c3c(F)cccc3CO)cnc2OCC2CC2)cc1F] |
| AC20 | 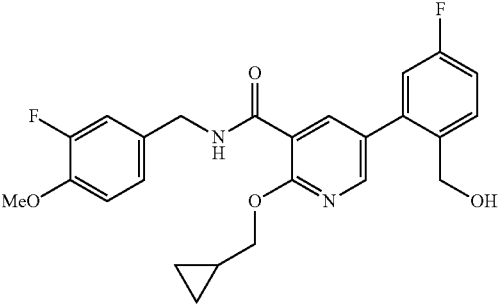 [SMILES: COc1ccc(CNC(=O)c2cc(-c3cc(F)ccc3CO)cnc2OCC2CC2)cc1F] |

TABLE 1-continued

| Compound ID | Structure |
|---|---|
| AC21 | 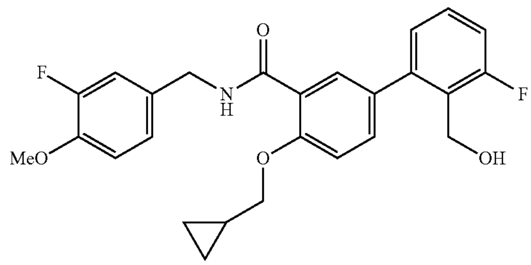 [SMILES: COc1ccc(CNC(=O)c2cc(-c3cccc(F)c3CO)ccc2OCC2CC2)cc1F] |
| AC22 | 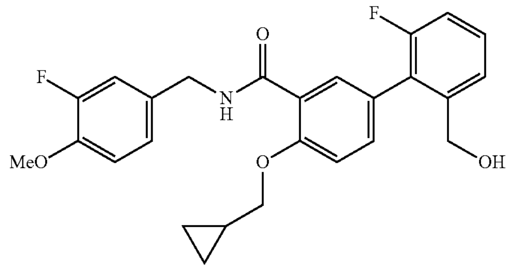 |
| AC23 | 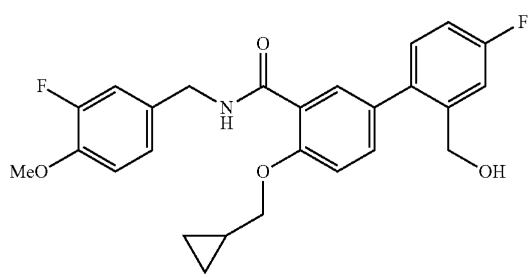 [SMILES: COc1ccc(CNC(=O)c2cc(-c3ccc(F)cc3CO)ccc2OCC2CC2)cc1F] |
| AC24 | 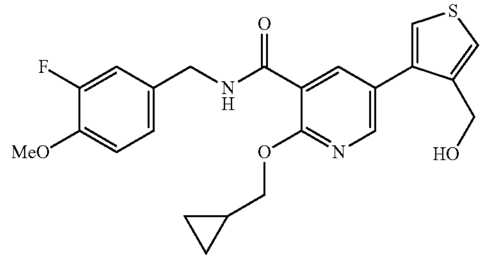 [SMILES: COc1ccc(CNC(=O)c2cc(-c3cscc3CO)cnc2OCC2CC2)cc1F] |
| AC25 | 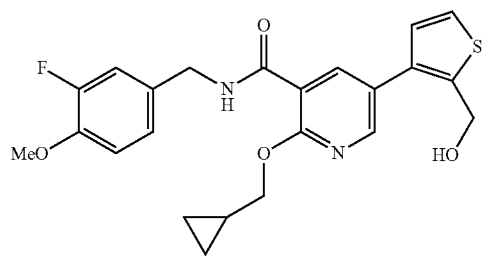 [SMILES: COc1ccc(CNC(=O)c2cc(-c3ccsc3CO)cnc2OCC2CC2)cc1F] |

TABLE 1-continued

| Compound ID | Structure |
|---|---|
| AC26 | *(structure: N-(3-fluoro-4-methoxybenzyl)-2-(cyclopropylmethoxy)-5-[3-(hydroxymethyl)thiophen-2-yl]nicotinamide)* |
| AC27 | *(structure: N-(3-fluoro-4-methoxybenzyl)-2-(cyclopropylmethoxy)-5-[2-(hydroxymethyl)thiophen-3-yl]benzamide)* |
| AC28 | *(structure: N-(3-fluoro-4-methoxybenzyl)-2-(cyclopropylmethoxy)-5-[3-(hydroxymethyl)thiophen-2-yl]benzamide)* |
| AC29 | *(structure: N-(3-fluoro-4-methoxybenzyl)-2-(cyclopropylmethoxy)-5-[4-(hydroxymethyl)thiophen-3-yl]benzamide)* |
| AC30 | *(structure: N-(3-fluoro-4-methoxybenzyl)-2-(cyclopropylmethoxy)-5-[3-(hydroxymethyl)-1H-pyrazol-4-yl]benzamide, with (Z) and (E) labels indicated)* |

TABLE 1-continued
| Compound ID | Structure |
|---|---|
| AC31 | 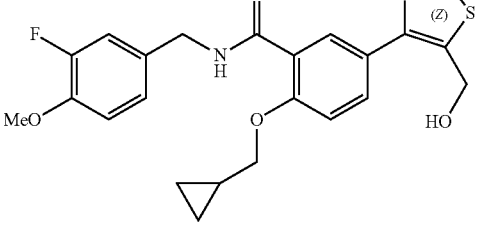 |
| AC32 | 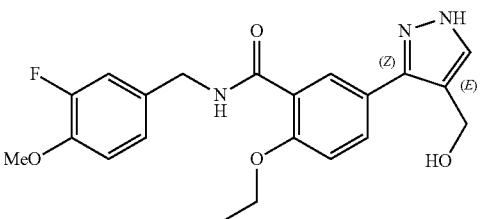 |
| AC33 | 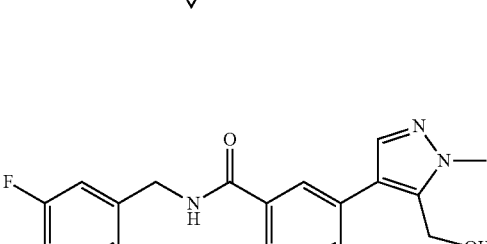 |
| AC34 | 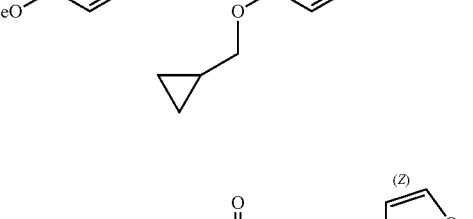 |
| AC35 | 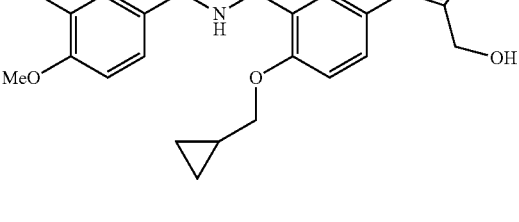 |

TABLE 1-continued

| Compound ID | Structure |
|---|---|
| AC36 | 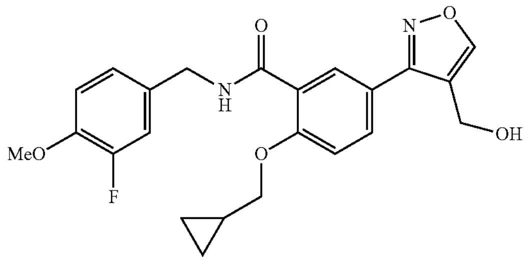 [SMILES: COc1ccc(CNC(=O)c2cc(-c3nocc3CO)ccc2OCC2CC2)cc1F] |
| AC37 | 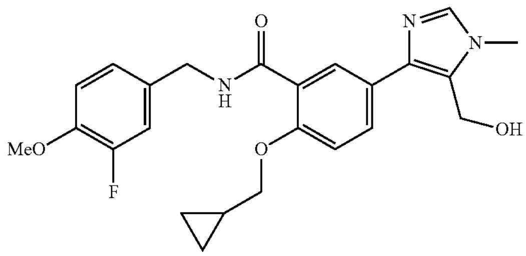 [SMILES: COc1ccc(CNC(=O)c2cc(-c3ncn(C)c3CO)ccc2OCC2CC2)cc1F] |
| AC38 | 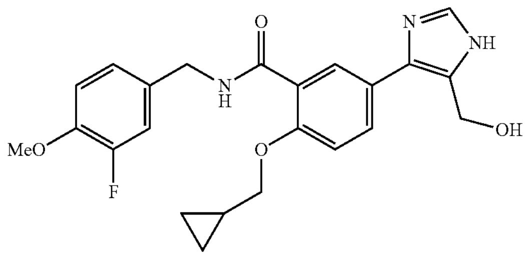 [SMILES: COc1ccc(CNC(=O)c2cc(-c3nc[nH]c3CO)ccc2OCC2CC2)cc1F] |
| AC39 | 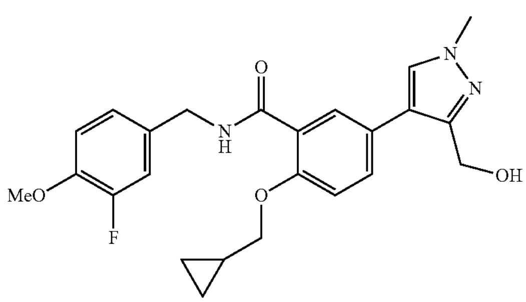 [SMILES: COc1ccc(CNC(=O)c2cc(-c3cn(C)nc3CO)ccc2OCC2CC2)cc1F] |
| AC40 | 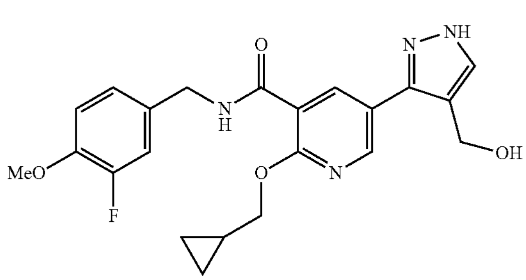 [SMILES: COc1ccc(CNC(=O)c2cc(-c3n[nH]cc3CO)cnc2OCC2CC2)cc1F] |

TABLE 1-continued
| Compound ID | Structure |
|---|---|
| AC41 | 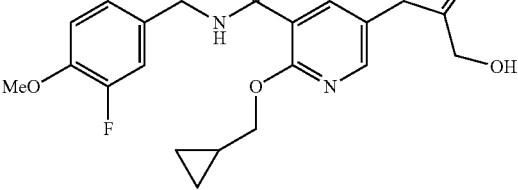 |
| AC42 | 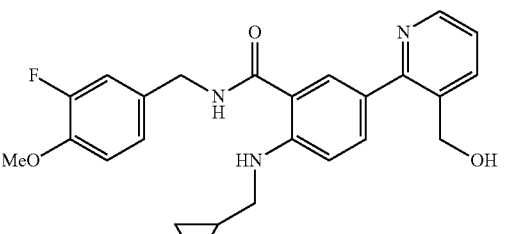 |
| AC43 | 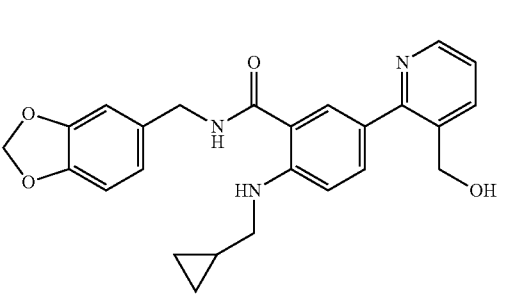 [SMILES: O=C(NCc1ccc2c(c1)OCO2)c1cc(-c2ncccc2CO)ccc1NCC1CC1] |
| AC44 | 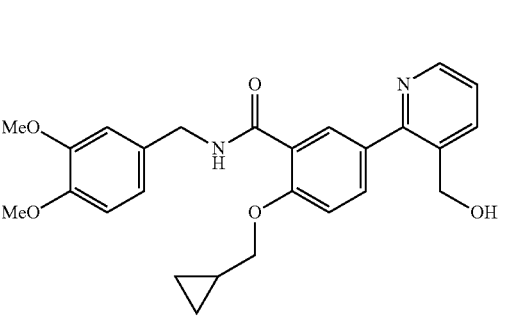 [SMILES: COc1ccc(CNC(=O)c2cc(-c3ncccc3CO)ccc2OCC2CC2)cc1OC] |
| AC45 | 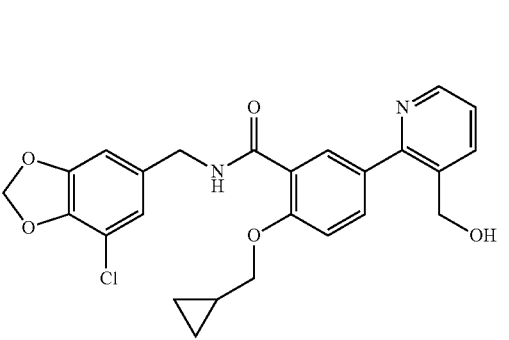 [SMILES: O=C(NCc1cc(Cl)c2c(c1)OCO2)c1cc(-c2ncccc2CO)ccc1OCC1CC1] |

TABLE 1-continued
| Compound ID | Structure |
|---|---|
| AC46 | 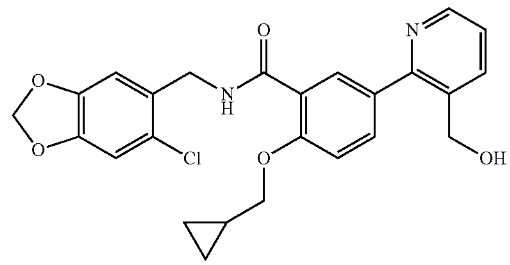 [SMILES: O=C(NCc1cc2c(cc1Cl)OCO2)c1cc(-c2ncccc2CO)ccc1OCC1CC1] |
| AC47 | 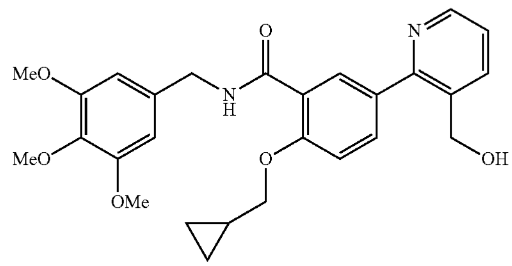 [SMILES: COc1cc(CNC(=O)c2cc(-c3ncccc3CO)ccc2OCC2CC2)cc(OC)c1OC] |
| AC48 | 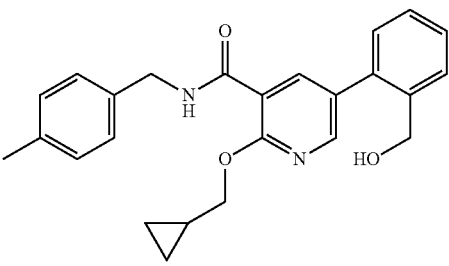 [SMILES: Cc1ccc(CNC(=O)c2cc(-c3ccccc3CO)cnc2OCC2CC2)cc1] |
| AC49 | 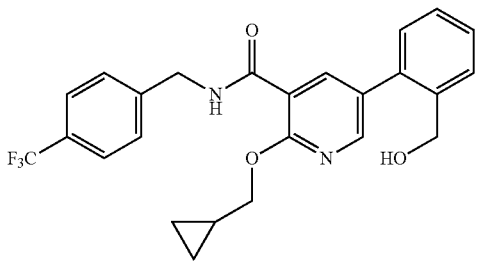 [SMILES: O=C(NCc1ccc(C(F)(F)F)cc1)c1cc(-c2ccccc2CO)cnc1OCC1CC1] |
| AC50 | 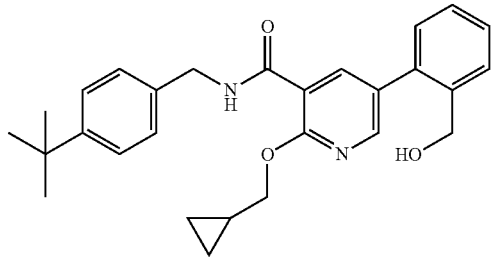 [SMILES: CC(C)(C)c1ccc(CNC(=O)c2cc(-c3ccccc3CO)cnc2OCC2CC2)cc1] |

TABLE 1-continued
| Compound ID | Structure |
|---|---|
| AC51 | 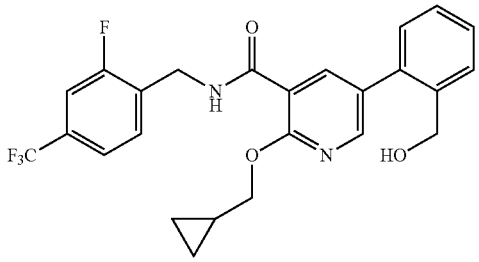 [SMILES: O=C(NCc1ccc(C(F)(F)F)cc1F)c1cc(-c2ccccc2CO)cnc1OCC1CC1] |
| AC52 | 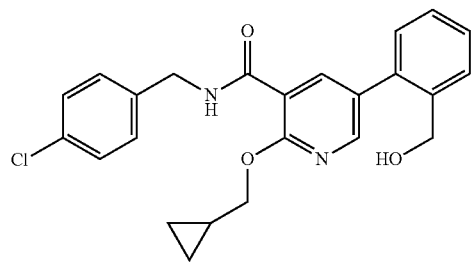 [SMILES: O=C(NCc1ccc(Cl)cc1)c1cc(-c2ccccc2CO)cnc1OCC1CC1] |
| AC53 | 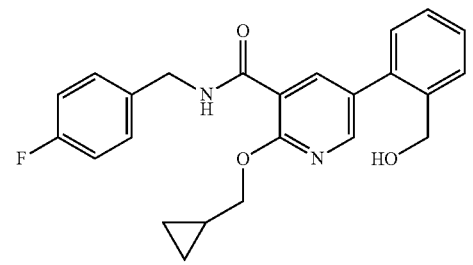 [SMILES: O=C(NCc1ccc(F)cc1)c1cc(-c2ccccc2CO)cnc1OCC1CC1] |
| AC54 | 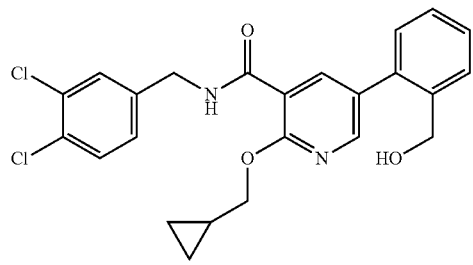 [SMILES: O=C(NCc1ccc(Cl)c(Cl)c1)c1cc(-c2ccccc2CO)cnc1OCC1CC1] |
| AC55 | 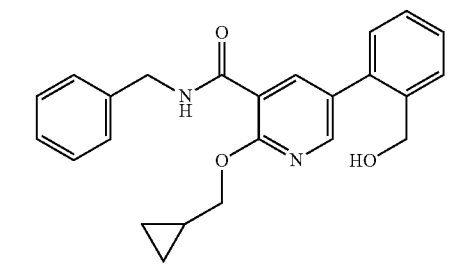 [SMILES: O=C(NCc1ccccc1)c1cc(-c2ccccc2CO)cnc1OCC1CC1] |

TABLE 1-continued

| Compound ID | Structure |
|---|---|
| AC56 | 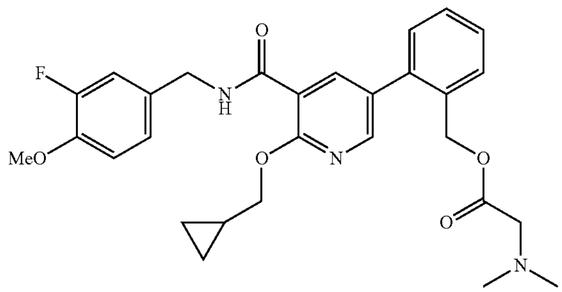 [SMILES: COc1ccc(CNC(=O)c2cc(-c3ccccc3COC(=O)CN(C)C)cnc2OCC2CC2)cc1F] |
| AC57 | 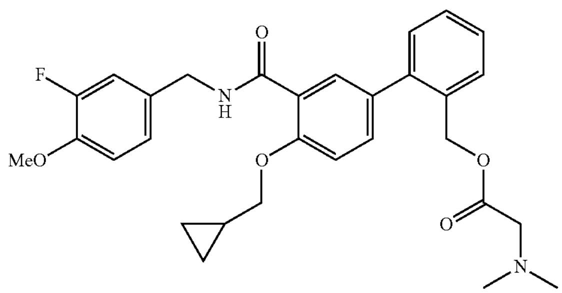 [SMILES: COc1ccc(CNC(=O)c2cc(-c3ccccc3COC(=O)CN(C)C)ccc2OCC2CC2)cc1F] |
| AC58 | 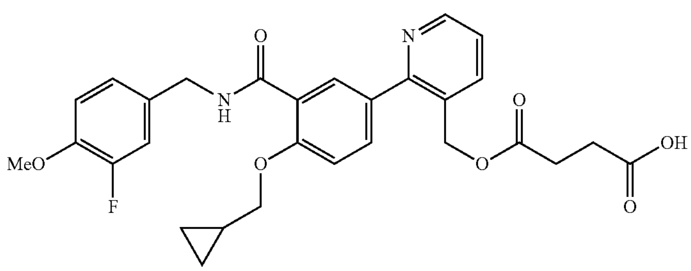 [SMILES: COc1ccc(CNC(=O)c2cc(-c3ncccc3COC(=O)CCC(=O)O)ccc2OCC2CC2)cc1F] |
| AC59 | 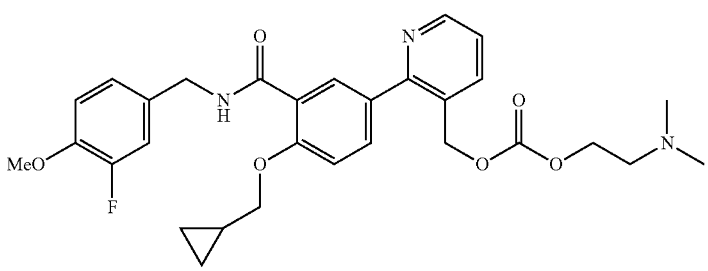 [SMILES: COc1ccc(CNC(=O)c2cc(-c3ncccc3COC(=O)OCCN(C)C)ccc2OCC2CC2)cc1F] |
| AC60 | 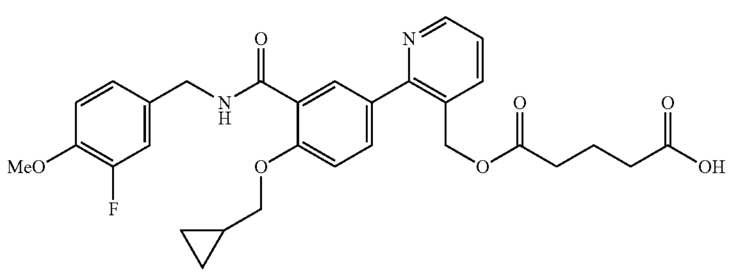 [SMILES: COc1ccc(CNC(=O)c2cc(-c3ncccc3COC(=O)CCCC(=O)O)ccc2OCC2CC2)cc1F] |

TABLE 1-continued

| Compound ID | Structure |
| --- | --- |
| AC61 | 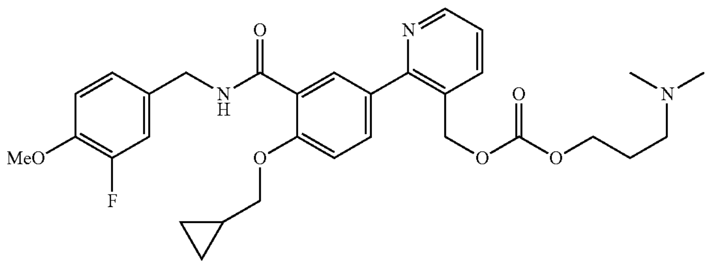 [SMILES: COc1ccc(CNC(=O)c2cc(-c3ncccc3COC(=O)OCCCN(C)C)ccc2OCC2CC2)cc1F] |
| AC62 | 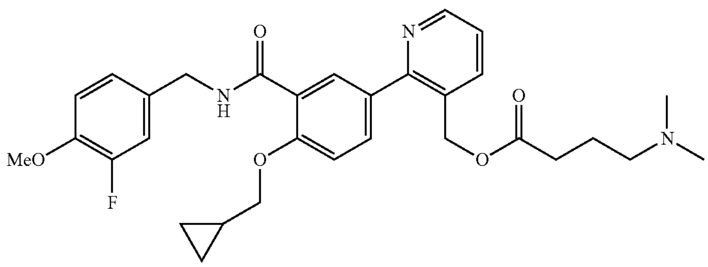 [SMILES: COc1ccc(CNC(=O)c2cc(-c3ncccc3COC(=O)CCCN(C)C)ccc2OCC2CC2)cc1F] |
| AC63 | 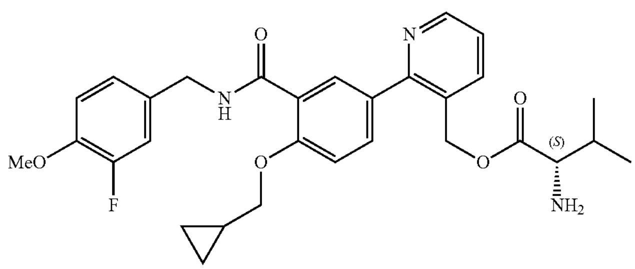 |
| AC64 | 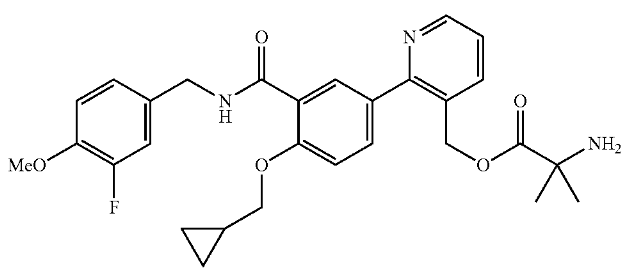 [SMILES: COc1ccc(CNC(=O)c2cc(-c3ncccc3COC(=O)C(C)(C)N)ccc2OCC2CC2)cc1F] |
| AC65 | 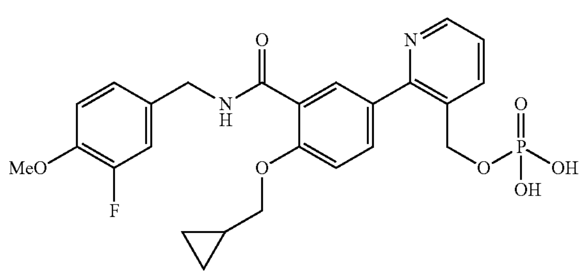 [SMILES: COc1ccc(CNC(=O)c2cc(-c3ncccc3COP(=O)(O)O)ccc2OCC2CC2)cc1F] |

TABLE 1-continued

| Compound ID | Structure |
|---|---|
| AC66 | 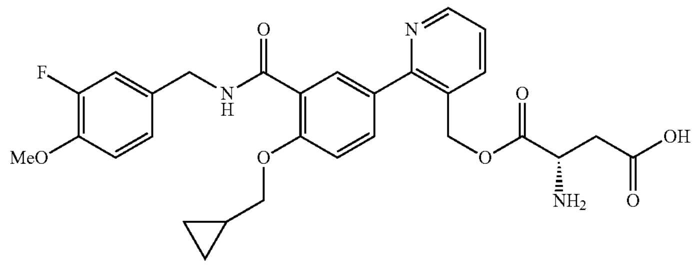 [SMILES: COc1ccc(CNC(=O)c2cc(-c3ncccc3COC(=O)[C@@H](N)CC(=O)O)ccc2OCC2CC2)cc1F] |
| AC67 | 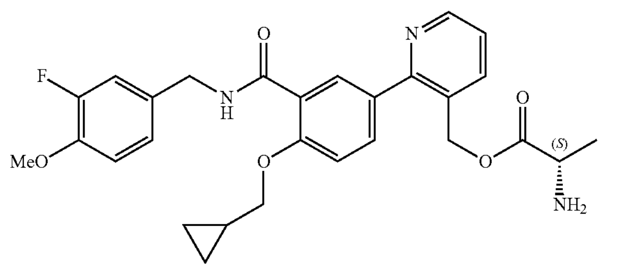 |
| AC68 | 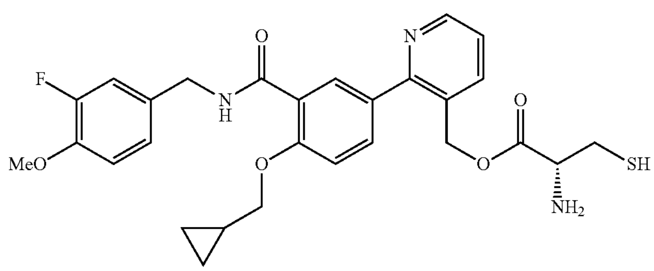 [SMILES: COc1ccc(CNC(=O)c2cc(-c3ncccc3COC(=O)[C@@H](N)CS)ccc2OCC2CC2)cc1F] |
| AC69 | 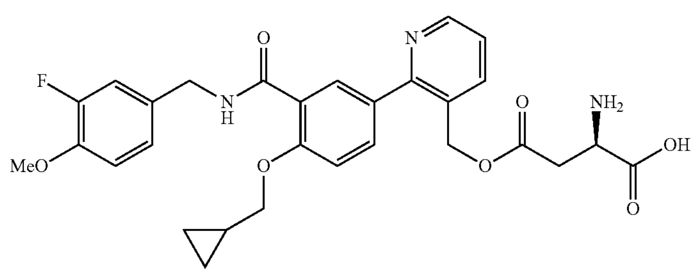 [SMILES: COc1ccc(CNC(=O)c2cc(-c3ncccc3COC(=O)C[C@@H](N)C(=O)O)ccc2OCC2CC2)cc1F] |
| AC70 | 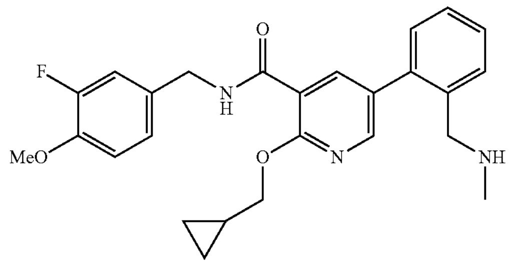 |

TABLE 1-continued

| Compound ID | Structure |
|---|---|
| AC71 | 2-(cyclopropylmethoxy)-N-(3-fluoro-4-methoxybenzyl)-5-(2-((ethylamino)methyl)phenyl)nicotinamide |
| AC72 | 2-(cyclopropylmethoxy)-N-(3-fluoro-4-methoxybenzyl)-5-(2-hydroxyphenyl)nicotinamide |
| AC73 | N-(3-fluoro-4-methoxybenzyl)-5-(2-(hydroxymethyl)phenyl)-2-isobutoxynicotinamide |
| AC74 | 2-(cyclopropylmethoxy)-N-(3-fluoro-4-methoxybenzyl)-5-(2-methoxyphenyl)nicotinamide |
| AC75 | 2-(cyclopropylmethoxy)-N-(3-fluoro-4-methoxybenzyl)-5-(2-carboxyphenyl)nicotinamide |

TABLE 1-continued

| Compound ID | Structure |
|---|---|
| AC76 | 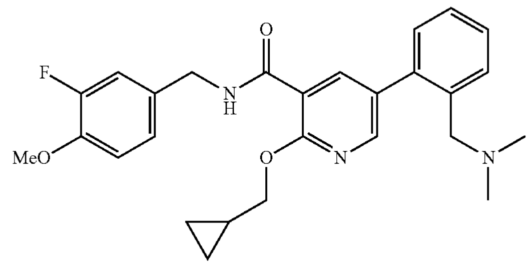 [SMILES: COc1ccc(CNC(=O)c2cc(-c3ccccc3CN(C)C)cnc2OCC2CC2)cc1F] |
| AC77 | 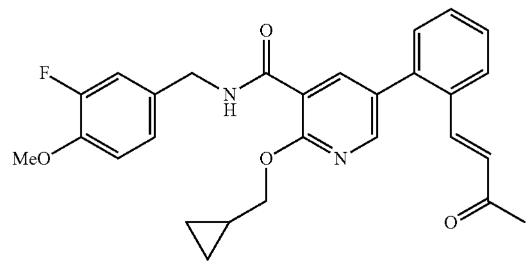 [SMILES: COc1ccc(CNC(=O)c2cc(-c3ccccc3/C=C/C(C)=O)cnc2OCC2CC2)cc1F] |
| AC78 | 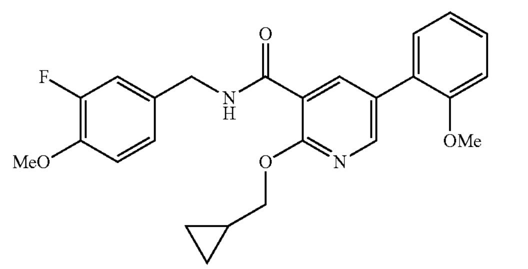 [SMILES: COc1ccc(CNC(=O)c2cc(-c3ccccc3OC)cnc2OCC2CC2)cc1F] |
| AC79 | 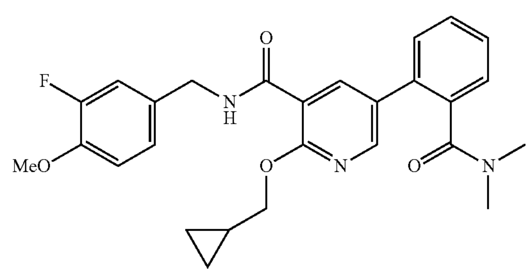 [SMILES: COc1ccc(CNC(=O)c2cc(-c3ccccc3C(=O)N(C)C)cnc2OCC2CC2)cc1F] |
| AC80 | 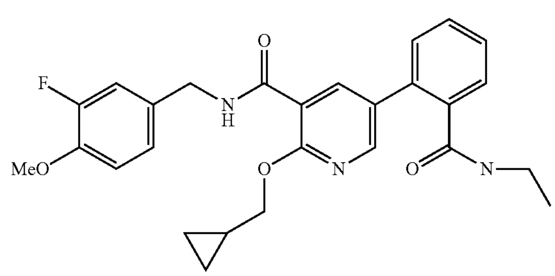 [SMILES: CCNC(=O)c1ccccc1-c1cnc(OCC2CC2)c(C(=O)NCc2ccc(OC)c(F)c2)c1] |

TABLE 1-continued
| Compound ID | Structure |
|---|---|
| AC81 | 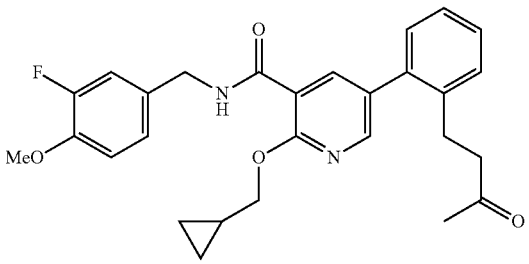 [SMILES: COc1ccc(CNC(=O)c2cc(-c3ccccc3CCC(C)=O)cnc2OCC2CC2)cc1F] |
| AC82 | 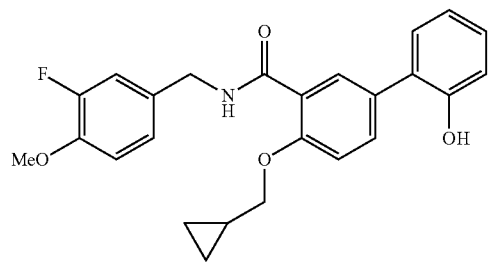 [SMILES: COc1ccc(CNC(=O)c2cc(-c3ccccc3O)ccc2OCC2CC2)cc1F] |
| AC83 | 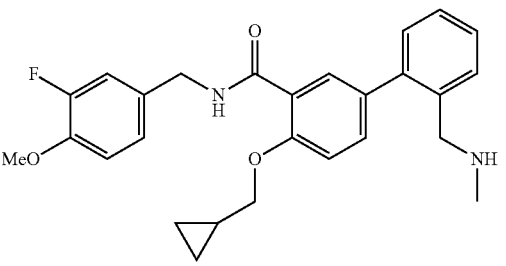 |
| AC84 | 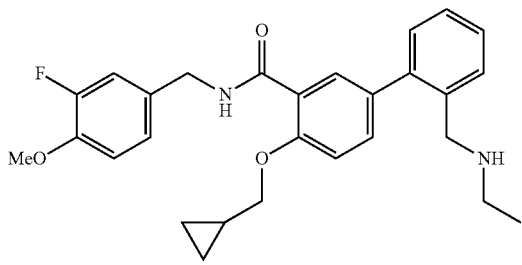 [SMILES: CCNCc1ccccc1-c1ccc(OCC2CC2)c(C(=O)NCc2ccc(OC)c(F)c2)c1] |
| AC85 | 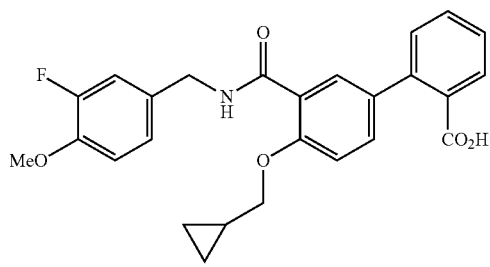 [SMILES: COc1ccc(CNC(=O)c2cc(-c3ccccc3C(=O)O)ccc2OCC2CC2)cc1F] |

TABLE 1-continued
| Compound ID | Structure |
|---|---|
| AC86 | 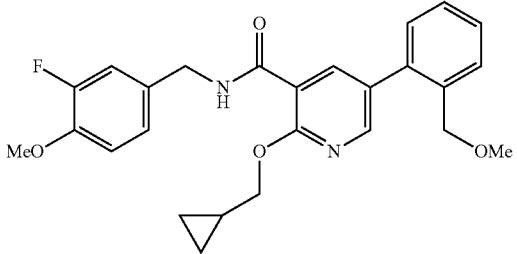 [SMILES: COCc1ccccc1-c1cnc(OCC2CC2)c(C(=O)NCc2ccc(OC)c(F)c2)c1] |
| AC87 | 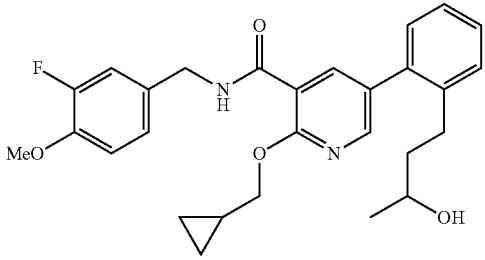 [SMILES: COc1ccc(CNC(=O)c2cc(-c3ccccc3CCC(C)O)cnc2OCC2CC2)cc1F] |
| AC88 | 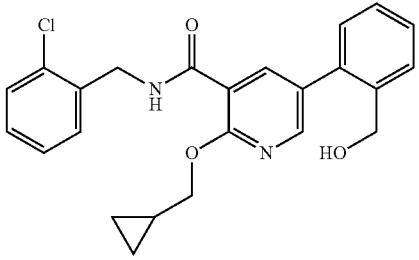 [SMILES: O=C(NCc1ccccc1Cl)c1cc(-c2ccccc2CO)cnc1OCC1CC1] |
| AC89 | 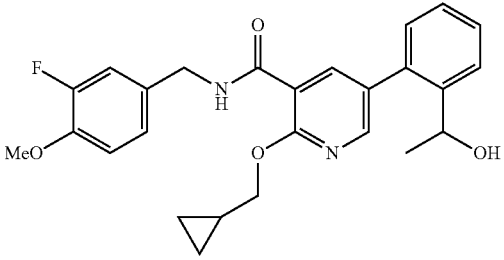 [SMILES: COc1ccc(CNC(=O)c2cc(-c3ccccc3C(C)O)cnc2OCC2CC2)cc1F] |
| AC90 | 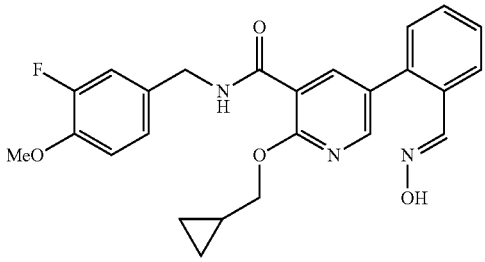 [SMILES: COc1ccc(CNC(=O)c2cc(-c3ccccc3/C=N/O)cnc2OCC2CC2)cc1F] |

TABLE 1-continued
| Compound ID | Structure |
|---|---|
| AC91 | 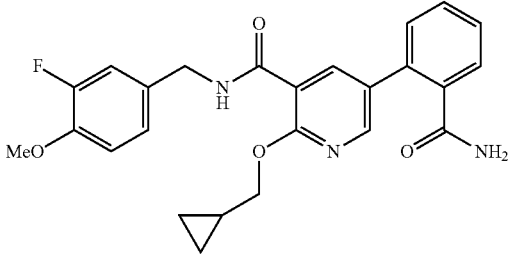 [SMILES: COc1ccc(CNC(=O)c2cc(-c3ccccc3C(N)=O)cnc2OCC2CC2)cc1F] |
| AC92 | 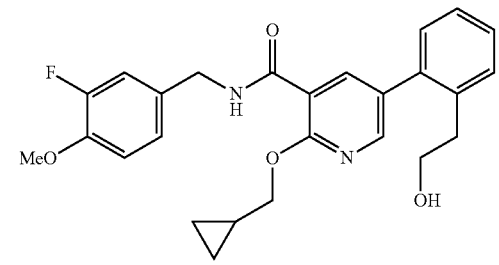 [SMILES: COc1ccc(CNC(=O)c2cc(-c3ccccc3CCO)cnc2OCC2CC2)cc1F] |
| AC93 | 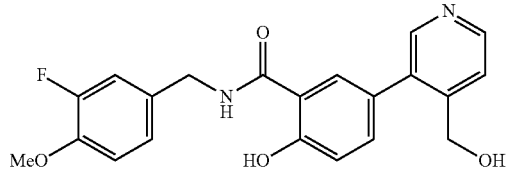 [SMILES: COc1ccc(CNC(=O)c2cc(-c3cnccc3CO)ccc2O)cc1F] |
| AC94 | 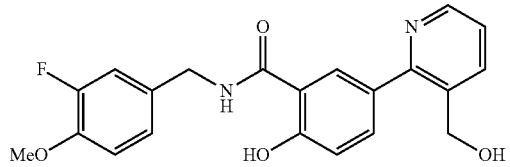 [SMILES: COc1ccc(CNC(=O)c2cc(-c3ncccc3CO)ccc2O)cc1F] |
| AC95 | 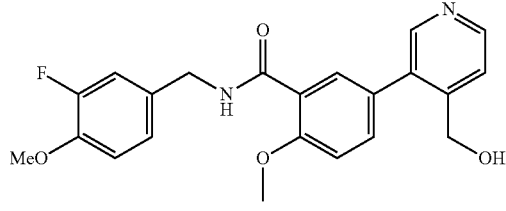 [SMILES: COc1ccc(CNC(=O)c2cc(-c3cnccc3CO)ccc2OC)cc1F] |
| AC96 | 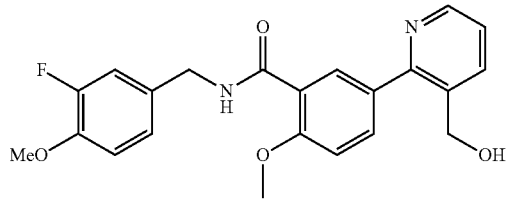 [SMILES: COc1ccc(CNC(=O)c2cc(-c3ncccc3CO)ccc2OC)cc1F] |
| AC97 | 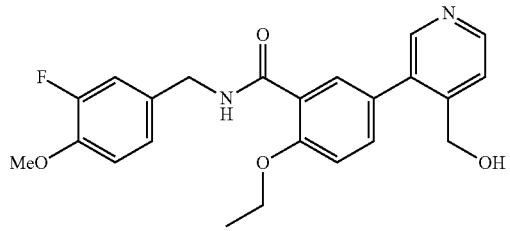 [SMILES: CCOc1ccc(-c2cnccc2CO)cc1C(=O)NCc1ccc(OC)c(F)c1] |

TABLE 1-continued
| Compound ID | Structure |
|---|---|
| AC98 | 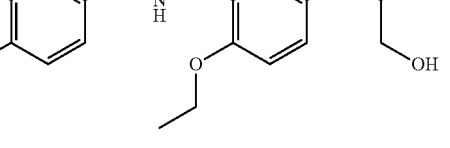 |
| AC99 | 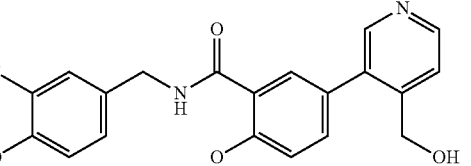 |
| A100 | 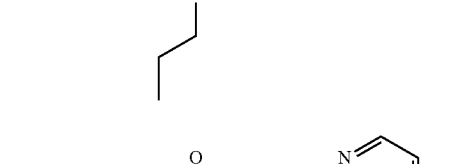 |
| AC101 | 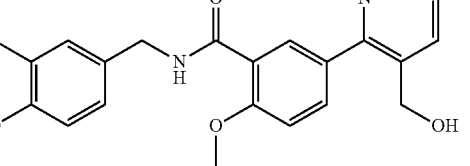 |
| AC102 | 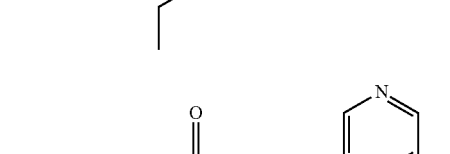 |
| AC103 | 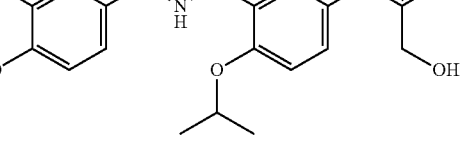 |

TABLE 1-continued
| Compound ID | Structure |
|---|---|
| AC104 | 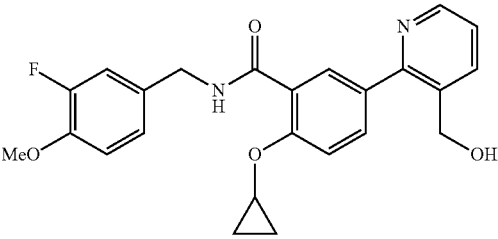 [SMILES: COc1ccc(CNC(=O)c2cc(-c3ncccc3CO)ccc2OC2CC2)cc1F] |
| AC105 | 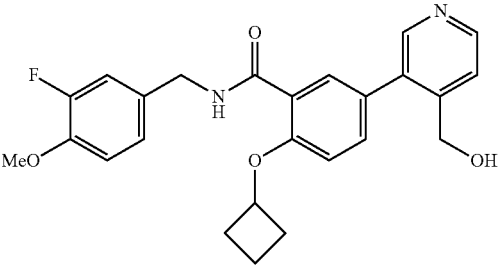 [SMILES: COc1ccc(CNC(=O)c2cc(-c3cnccc3CO)ccc2OC2CCC2)cc1F] |
| AC106 | 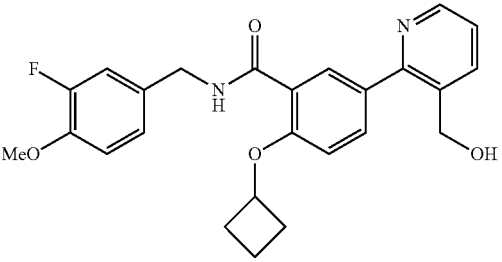 [SMILES: COc1ccc(CNC(=O)c2cc(-c3ncccc3CO)ccc2OC2CCC2)cc1F] |
| AC107 | 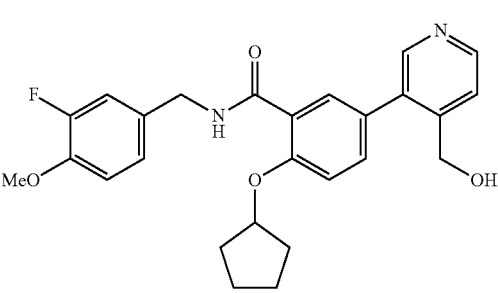 [SMILES: COc1ccc(CNC(=O)c2cc(-c3cnccc3CO)ccc2OC2CCCC2)cc1F] |
| AC108 | 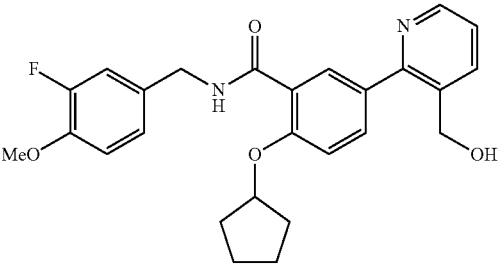 [SMILES: COc1ccc(CNC(=O)c2cc(-c3ncccc3CO)ccc2OC2CCCC2)cc1F] |

TABLE 1-continued

| Compound ID | Structure |
|---|---|
| AC109 | 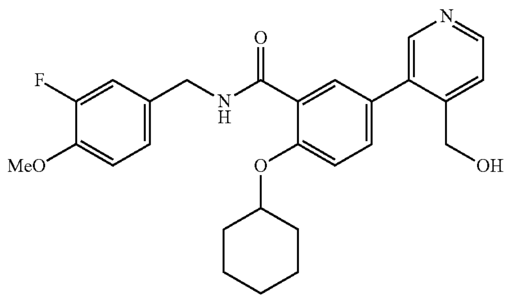 [SMILES: COc1ccc(CNC(=O)c2cc(-c3cnccc3CO)ccc2OC2CCCCC2)cc1F] |
| AC110 | 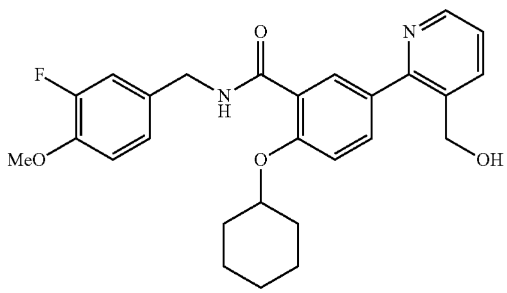 [SMILES: COc1ccc(CNC(=O)c2cc(-c3ncccc3CO)ccc2OC2CCCCC2)cc1F] |
| AC111 | 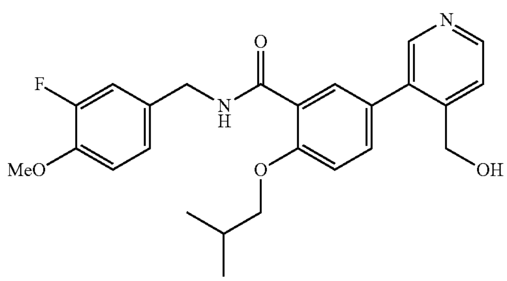 [SMILES: COc1ccc(CNC(=O)c2cc(-c3cnccc3CO)ccc2OCC(C)C)cc1F] |
| AC112 | 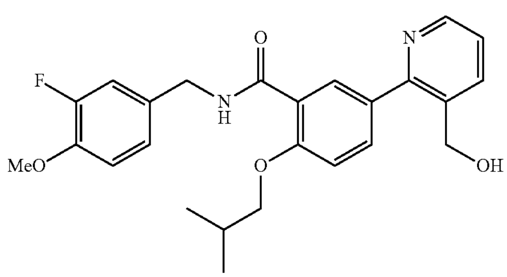 [SMILES: COc1ccc(CNC(=O)c2cc(-c3ncccc3CO)ccc2OCC(C)C)cc1F] |
| AC113 | 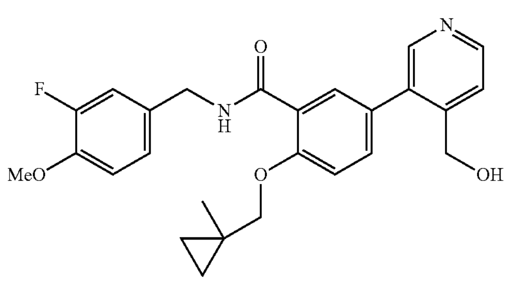 [SMILES: COc1ccc(CNC(=O)c2cc(-c3cnccc3CO)ccc2OCC2(C)CC2)cc1F] |

TABLE 1-continued

| Compound ID | Structure |
| --- | --- |
| AC114 | 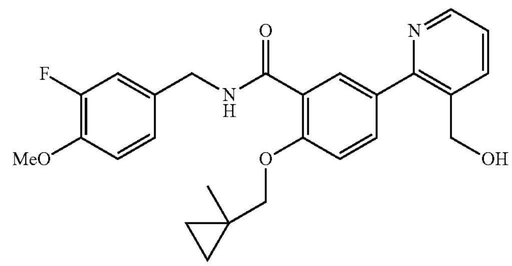 [SMILES: COc1ccc(CNC(=O)c2cc(-c3ncccc3CO)ccc2OCC2(C)CC2)cc1F] |
| AC115 | 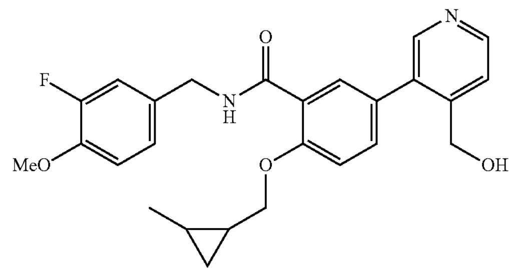 [SMILES: COc1ccc(CNC(=O)c2cc(-c3cnccc3CO)ccc2OCC2CC2C)cc1F] |
| AC116 | 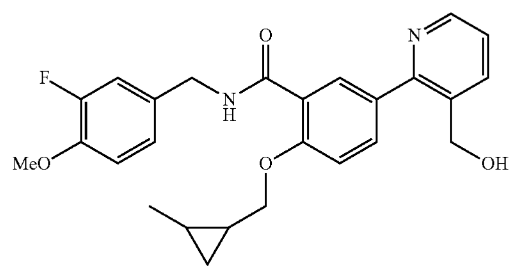 [SMILES: COc1ccc(CNC(=O)c2cc(-c3ncccc3CO)ccc2OCC2CC2C)cc1F] |
| AC117 | 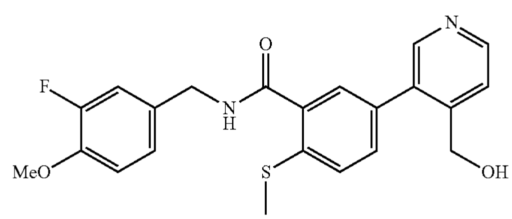 |
| AC118 | 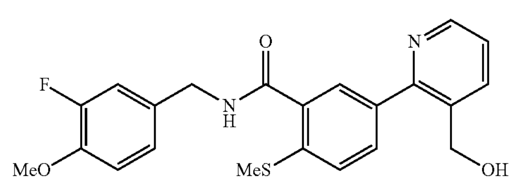 [SMILES: COc1ccc(CNC(=O)c2cc(-c3ncccc3CO)ccc2SC)cc1F] |
| AC119 | 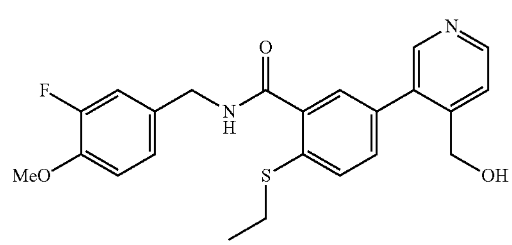 [SMILES: CCSc1ccc(-c2cnccc2CO)cc1C(=O)NCc1ccc(OC)c(F)c1] |

TABLE 1-continued
| Compound ID | Structure |
|---|---|
| AC120 | 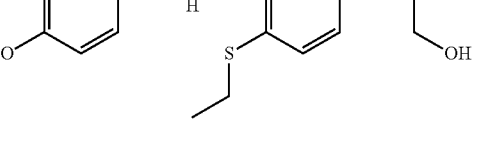 |
| AC121 | 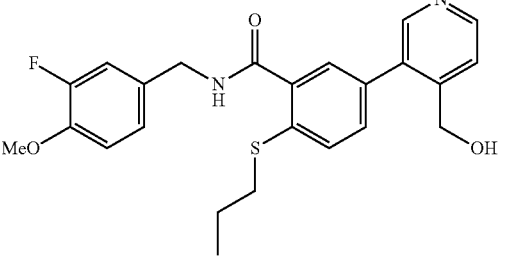 |
| AC122 | 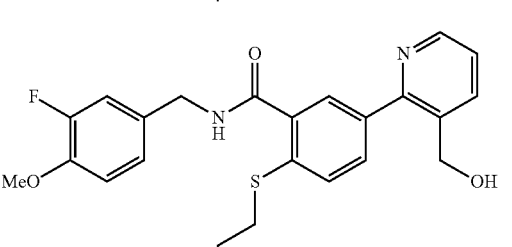 |
| AC123 | 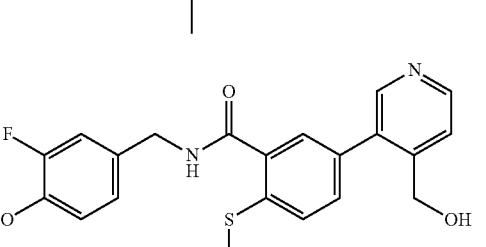 |
| AC124 | 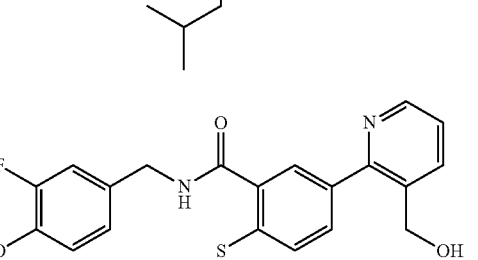 |
| AC125 | 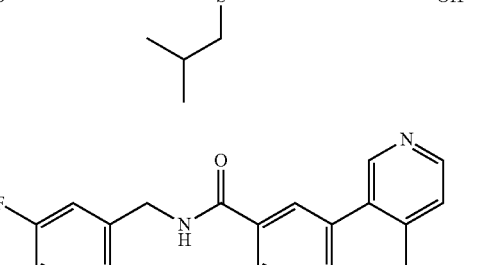 |

TABLE 1-continued

| Compound ID | Structure |
|---|---|
| AC126 | 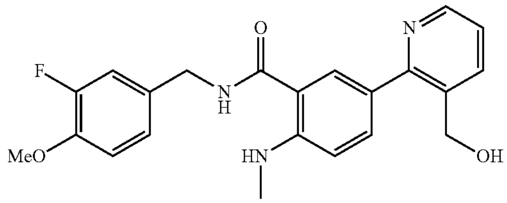 [SMILES: CNc1ccc(-c2ncccc2CO)cc1C(=O)NCc1ccc(OC)c(F)c1] |
| AC127 | 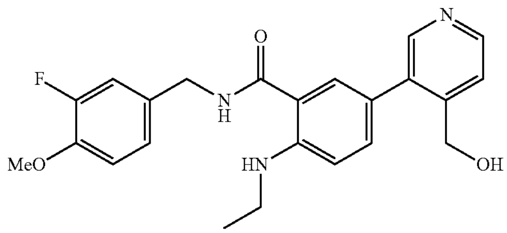 [SMILES: CCNc1ccc(-c2cnccc2CO)cc1C(=O)NCc1ccc(OC)c(F)c1] |
| AC128 | 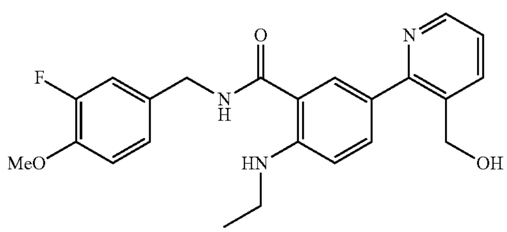 [SMILES: CCNc1ccc(-c2ncccc2CO)cc1C(=O)NCc1ccc(OC)c(F)c1] |
| AC129 | 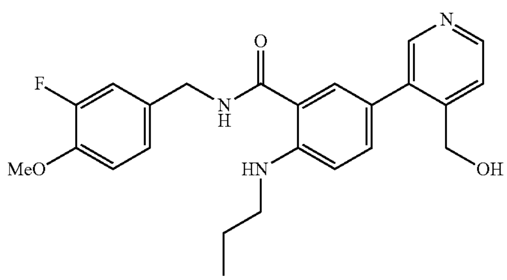 [SMILES: CCCNc1ccc(-c2cnccc2CO)cc1C(=O)NCc1ccc(OC)c(F)c1] |
| AC130 | 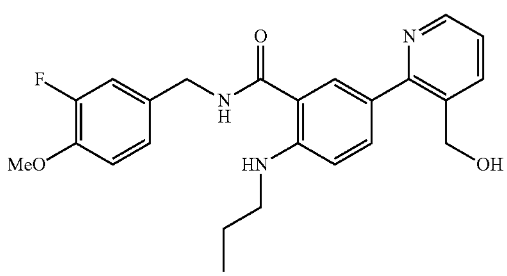 [SMILES: CCCNc1ccc(-c2ncccc2CO)cc1C(=O)NCc1ccc(OC)c(F)c1] |
| AC131 | 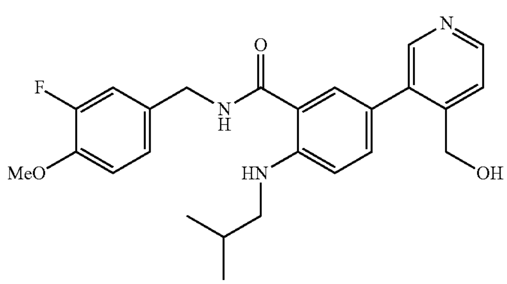 [SMILES: COc1ccc(CNC(=O)c2cc(-c3cnccc3CO)ccc2NCC(C)C)cc1F] |

TABLE 1-continued

| Compound ID | Structure |
|---|---|
| AC132 | 3-fluoro-4-methoxybenzyl 2-(isobutylamino)-5-(3-(hydroxymethyl)pyridin-2-yl)benzamide |
| AC133 | 4-methoxybenzyl 2-isobutoxy-5-(3-(hydroxymethyl)pyridin-2-yl)benzamide |
| AC134 | 4-methoxybenzyl 2-(cyclopropylmethoxy)-5-(3-(hydroxymethyl)pyridin-2-yl)benzamide |
| AC135 | 4-methoxybenzyl 2-(cyclopropylmethoxy)-5-(4-(hydroxymethyl)pyridin-3-yl)benzamide |
| AC136 | 4-methoxybenzyl 2-isobutoxy-5-(4-(hydroxymethyl)pyridin-3-yl)benzamide |

TABLE 1-continued
| Compound ID | Structure |
|---|---|
| AC137 | 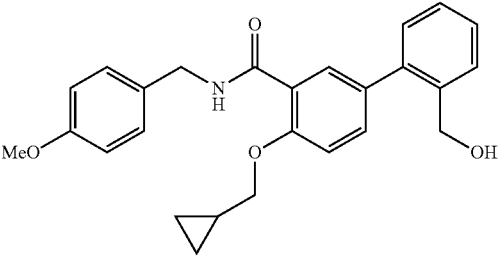 [SMILES: COc1ccc(CNC(=O)c2cc(-c3ccccc3CO)ccc2OCC2CC2)cc1] |
| AC138 | 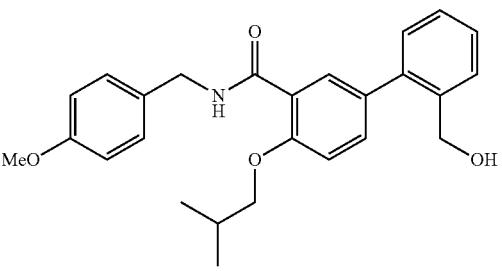 [SMILES: COc1ccc(CNC(=O)c2cc(-c3ccccc3CO)ccc2OCC(C)C)cc1] |
| AC139 | 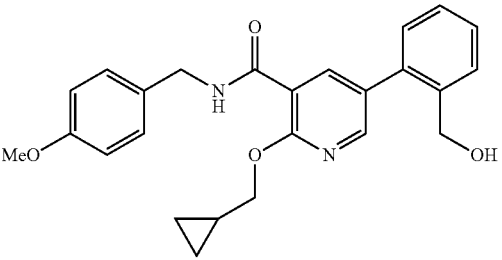 [SMILES: COc1ccc(CNC(=O)c2cc(-c3ccccc3CO)cnc2OCC2CC2)cc1] |
| AC140 | 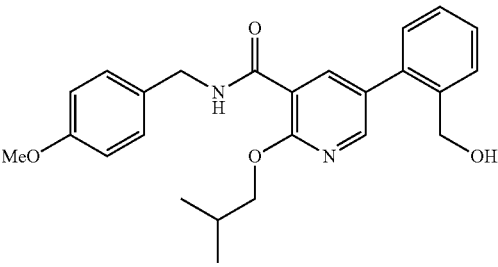 [SMILES: COc1ccc(CNC(=O)c2cc(-c3ccccc3CO)cnc2OCC(C)C)cc1] |
| AC141 | 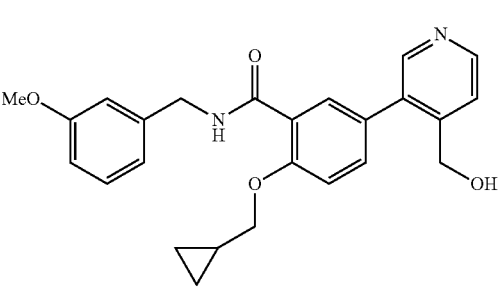 [SMILES: COc1cccc(CNC(=O)c2cc(-c3cnccc3CO)ccc2OCC2CC2)c1] |

TABLE 1-continued
| Compound ID | Structure |
|---|---|
| AC142 | 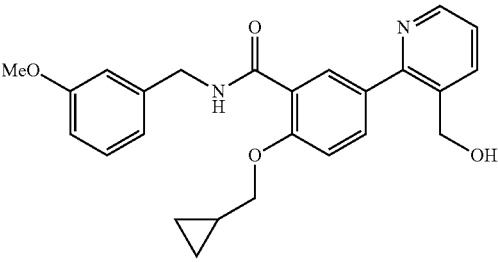 [SMILES: COc1cccc(CNC(=O)c2cc(-c3ncccc3CO)ccc2OCC2CC2)c1] |
| AC143 | 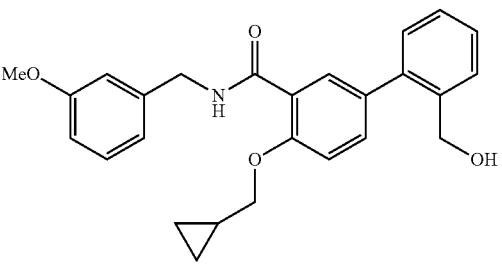 [SMILES: COc1cccc(CNC(=O)c2cc(-c3ccccc3CO)ccc2OCC2CC2)c1] |
| AC144 | 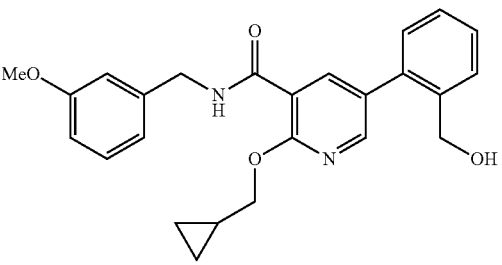 [SMILES: COc1cccc(CNC(=O)c2cc(-c3ccccc3CO)cnc2OCC2CC2)c1] |
| AC145 | 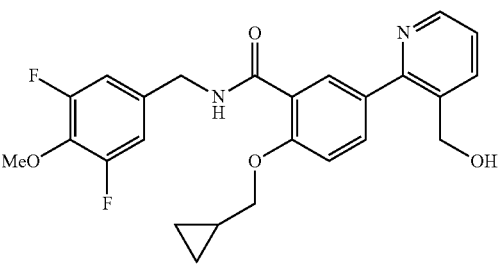 [SMILES: COc1c(F)cc(CNC(=O)c2cc(-c3ncccc3CO)ccc2OCC2CC2)cc1F] |
| AC146 | 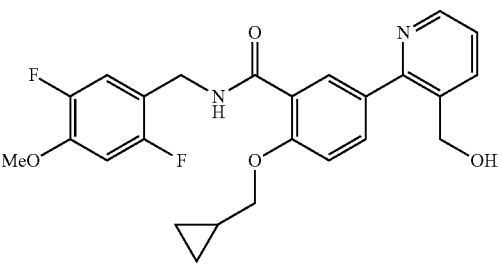 [SMILES: COc1cc(F)c(CNC(=O)c2cc(-c3ncccc3CO)ccc2OCC2CC2)cc1F] |

TABLE 1-continued
| Compound ID | Structure |
|---|---|
| AC147 | 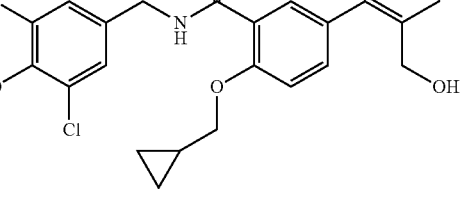 |
| AC148 | 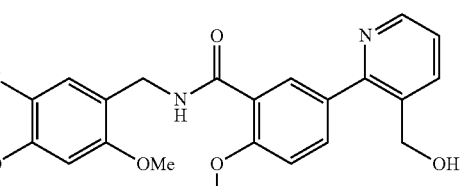 |
| AC149 | 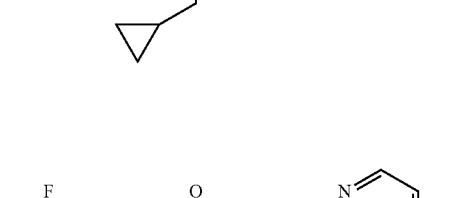 |
| AC150 | 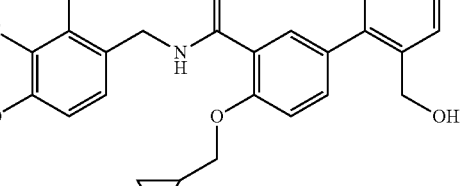 |
| AC151 | 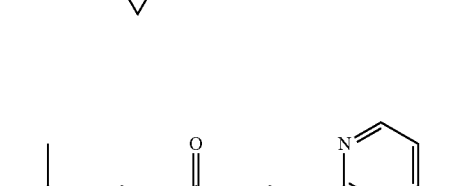 |

TABLE 1-continued

| Compound ID | Structure |
|---|---|
| AC152 | 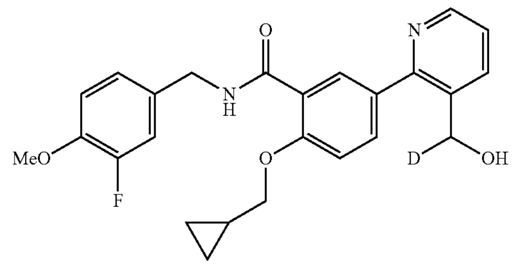 [SMILES: [2H]C(O)c1cccnc1-c1ccc(OCC2CC2)c(C(=O)NCc2ccc(OC)c(F)c2)c1] |
| AC153 | 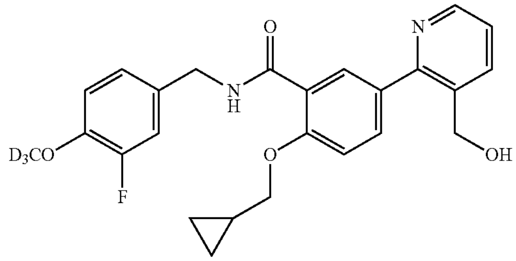 |
| AC154 | 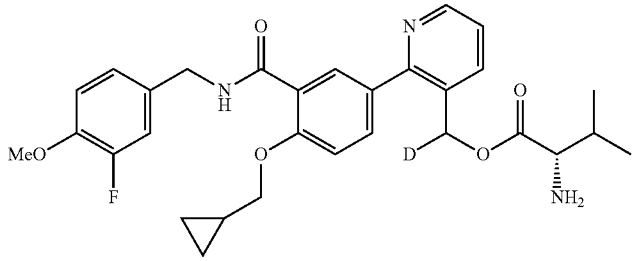 [SMILES: [2H]C(OC(=O)[C@@H](N)C(C)C)c1cccnc1-c1ccc(OCC2CC2)c(C(=O)NCc2ccc(OC)c(F)c2)c1] |
| AC155 | 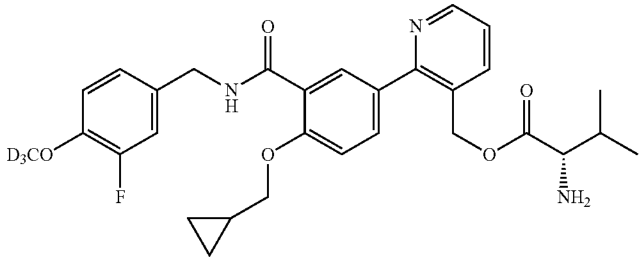 |
| AC156 | 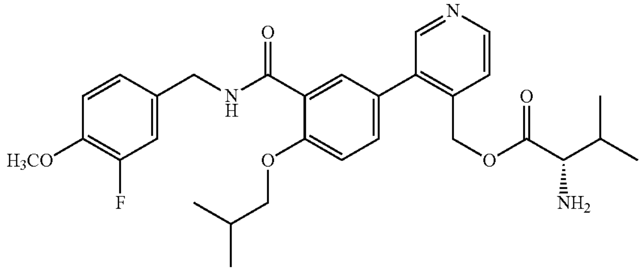 [SMILES: COc1ccc(CNC(=O)c2cc(-c3cnccc3COC(=O)[C@@H](N)C(C)C)ccc2OCC(C)C)cc1F] |

TABLE 1-continued

| Compound ID | Structure |
| --- | --- |
| AC157 | 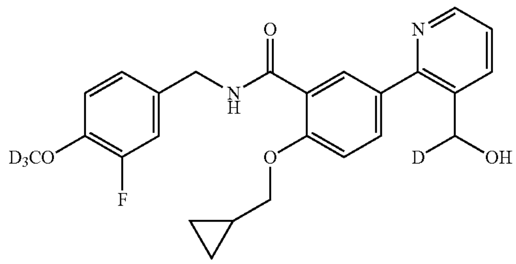 |
| AC158 | 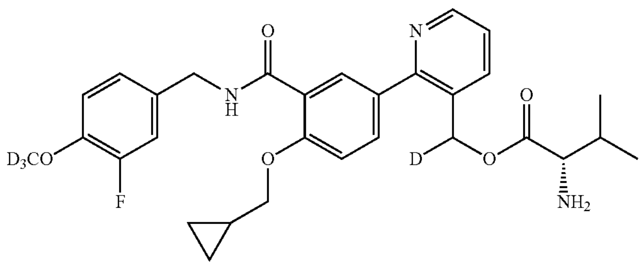 |
| AC159 | 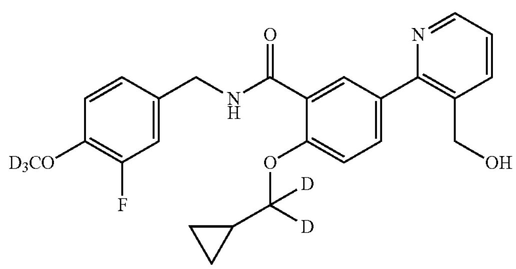 |
| AC160 | 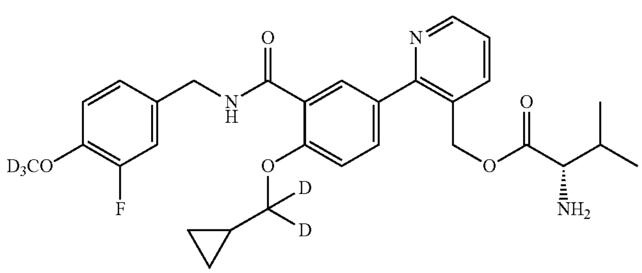 |
| AC161 | 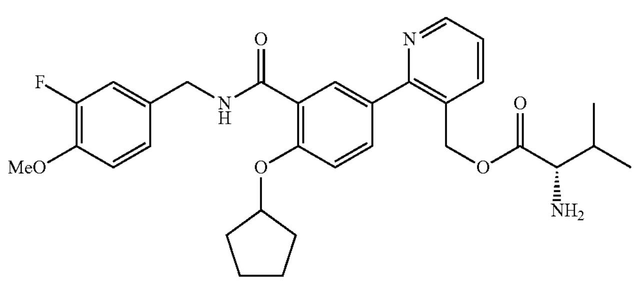 [SMILES: COc1ccc(CNC(=O)c2cc(-c3ncccc3COC(=O)[C@@H](N)C(C)C)ccc2OC2CCCC2)cc1F] |

TABLE 1-continued

| Compound ID | Structure |
|---|---|
| AC162 | 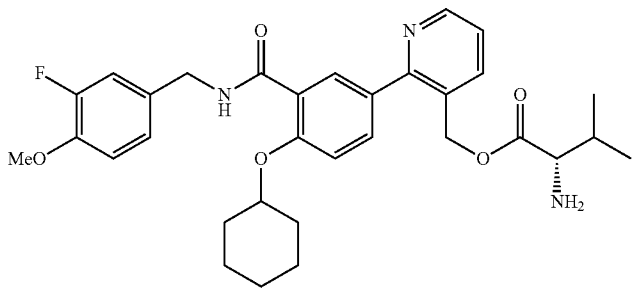 [SMILES: COc1ccc(CNC(=O)c2cc(-c3ncccc3COC(=O)[C@@H](N)C(C)C)ccc2OC2CCCCC2)cc1F] |
| AC163 | 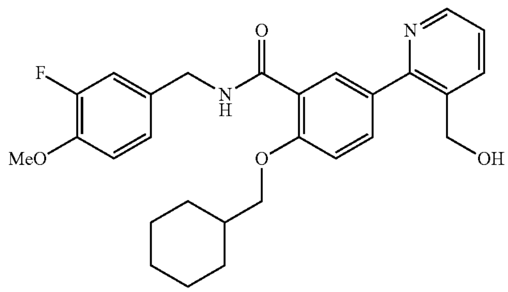 [SMILES: COc1ccc(CNC(=O)c2cc(-c3ncccc3CO)ccc2OCC2CCCCC2)cc1F] |
| AC164 | 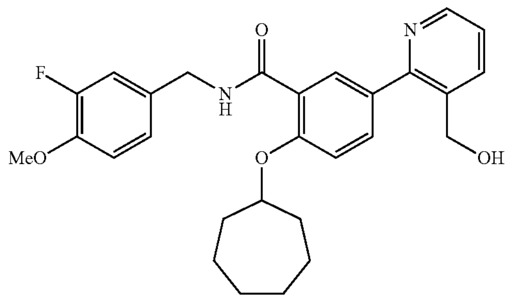 [SMILES: COc1ccc(CNC(=O)c2cc(-c3ncccc3CO)ccc2OC2CCCCCC2)cc1F] |
| AC165 | 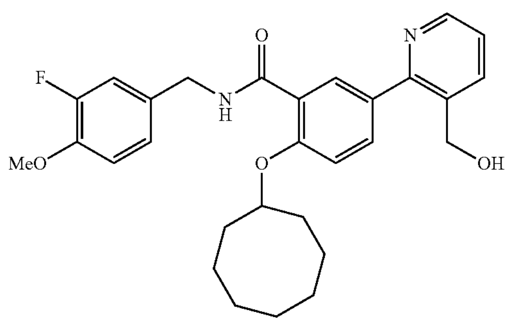 [SMILES: COc1ccc(CNC(=O)c2cc(-c3ncccc3CO)ccc2OC2CCCCCCC2)cc1F] |
| AC166 | 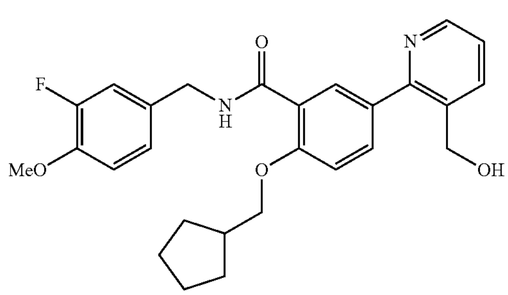 [SMILES: COc1ccc(CNC(=O)c2cc(-c3ncccc3CO)ccc2OCC2CCCC2)cc1F] |

The present disclosure also provides pharmaceutical compositions comprising one or more pharmaceutically acceptable carriers and one or more compounds chosen from those of any formula or compound disclosed herein.

Another aspect of this invention is a method of treating and/or preventing cancer. The method of the present disclosure reduces the incidence and/or progression of cancer. In one embodiment, the present disclosure provides a method of reducing the incidence and/or progression of oral cancer, lung cancer, head cancer, neck cancer, leukemia, lymphoma, and/or multiple myeloma in a subject in need thereof. The method includes administering to a subject in need thereof a therapeutically effective amount of one or more compounds chosen from those of any formula or compound disclosed herein or a pharmaceutically acceptable salt, solvate, ester, or prodrug thereof.

Unless otherwise stated, any description of a method of treatment and/or prevention includes uses of the compounds to provide such treatment and/or prevention as described in the specification, as well as uses of the compounds to prepare a medicament to treat and/or prevent such condition. The treatment includes humans or non-human animals including rodents and other animals in disease models.

In still another aspect, the present disclosure relates to a method of treating and/or preventing progression and/or recurrence of cancer in a subject in need thereof, the method includes administering: a) a compound of formula (I) or a pharmaceutically acceptable salt, solvate, ester, or prodrug thereof; and b) a cancer chemotherapeutic agent or ionizing radiation. The method includes that the compound and the cancer chemotherapeutic agent, or compound and the ionizing radiation, are administered in combined effective amounts to treat and/or prevent progression and/or recurrence of the cancer. The chemotherapeutic agent for administration with a compound of formula (I) is chosen from an alkylating agent, a nitrosourea, an antimetabolite, an antitumor antibiotic, a plant (vinca) alkaloid, and a steroid hormone.

The alkylating agent for administration with the compound of formula (I), or a pharmaceutically acceptable salt, solvate, ester, or prodrug thereof is chosen from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

In one embodiment, the method of treatment and/or prevention of progression and/or recurrence of cancer of the present disclosure involves administering the ionizing radiation via external beam radiation therapy or brachytherapy. In some embodiments, the administration of the compound or pharmaceutical composition reduces the amount of the chemotherapeutic agent or the ionizing radiation required to treat or prevent the cancer.

In one embodiment, the chemotherapeutic agent is selected from an alkylating agent, a nitrosourea, an antimetabolite, an antitumor antibiotic, a plant (vinca) alkaloid, and a steroid hormone. In one embodiment, the alkylating agent is selected from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

In one embodiment, the present invention relates to a method of reducing incidence, progression, and/or recurrence of a cancer in a subject at risk of developing oral cancer or lung cancer, the method includes administering to the subject in need thereof an effective amount of a compound of the invention, or a pharmaceutically acceptable salt, solvate, ester, or prodrug thereof. In one embodiment, the compound is administered by a route selected from intramuscular, intravenous, subcutaneous, oral, and topical.

In one embodiment, the present invention relates to a method of reducing incidence, progression, and/or recurrence of head and neck cancer in a subject in need thereof, the method includes administering to the subject an effective amount of a compound of the invention, or a pharmaceutically acceptable salt, solvate, ester, or prodrug thereof. In one embodiment, the subject is a habitual user of betel quid. In one embodiment, the compound for treating and/or preventing progression and/or recurrence of cancer is formulated as a toothpaste, a tooth gel, a tooth powder, a mouth rinse, a chewing gum, or a lozenge.

Another aspect of this invention is a method of treating and/or preventing Fanconi Anemia. The method of the present disclosure reduces the incidence and/or progression of Fanconi Anemia. The compound treats and/or prevents one or more symptoms of Fanconi Anemia such as progressive pancytopenia, short stature, radial aplasia, urinary tract abnormalities, hyperpigmentation, and congenital developmental delay. In one embodiment, the present disclosure provides a method of reducing the incidence and/or progression of Fanconi Anemia in a subject in need thereof. The method includes administering to a subject in need thereof a therapeutically effective amount of one or more compounds, or a pharmaceutically acceptable salt, solvate, ester, or prodrug thereof, chosen from those of any formula or compound disclosed herein. The present disclosure also provides methods of manufacture of a medicament for use in treating and/or preventing Fanconi Anemia. The medicament thus manufactured is used for treating and/or preventing symptoms of Fanconi Anemia such as pancytopenia, short stature, radial aplasia, urinary tract abnormalities, hyperpigmentation, and congenital developmental delay.

The compound of formula (I), or a pharmaceutically acceptable salt, solvate, ester, or prodrug thereof, reduces risk of cancer in the subject in need of treating and/or preventing Fanconi Anemia; the cancer in chosen from acute myeloid leukemia, squamous-cell cancers of the oral cavity, esophagus, the gastrointestinal tract, the anus, and vulva, head and neck squamous cell carcinoma (HNSCC), and breast cancer.

In one embodiment, the present invention relates to a method of treating and/or preventing radiation-induced damage to epithelial cells in a subject in need thereof, the method comprising administering to the subject a compound of the invention, or a pharmaceutically acceptable salt, solvae, ester, or prodrug thereof. In one embodiment, the radiation-induced damage results in radiation dermatitis. In one embodiment, the compound is administered before the subject is exposed to ionizing radiation. In one embodiment, the compound is administered after the subject is exposed to ionizing radiation. In one embodiment, the compound is administered both before and after the subject is exposed to ionizing radiation. In one embodiment, the radiation-induced damage results in mucositis. In one embodiment, the compound is administered to a mucosal surface in the subject.

In one embodiment, the ionizing radiation is administered via external beam radiation therapy or brachytherapy. In one embodiment, the administration of the compound reduces the amount of the chemotherapeutic agent or the ionizing radiation required to treat or prevent the cancer.

In one embodiment, the present invention relates to a method of sequestering aldehyde in a subject in need thereof exposed to alcohol or aldehyde, comprising administering to the subject an effective amount of a compound of formula (I), or a pharmaceutically acceptable salt, solvate, ester, or prodrug thereof.

In one embodiment, the present invention relates to a method of reducing a level of an aldehyde present at a toxic level in a subject in need thereof to below the toxic level, the method comprising administering to the subject an effective amount of a compound of the invention, or a pharmaceutically acceptable salt, solvate, ester, or prodrug thereof, wherein the aldehyde is a biogenic aldehyde or a xenogenic aldehyde. In one embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (4 HNE). In one embodiment, the xenogenic aldehyde is an environmental aldehyde that is ingested or inhaled.

In one embodiment, the present invention relates a method of treating and/or preventing alcohol intolerance, alcohol addiction, an alcohol abuse disorder, alcohol intoxication, alcohol dependence, alcohol poisoning, or symptoms of alcohol consumption, the method comprising administering to a subject in need thereof an effective amount of a compound of the invention, or a pharmaceutically acceptable salt, solvate, ester, or prodrug thereof. In one embodiment, the alcohol poisoning is methanol poisoning. In one embodiment, the alcohol poisoning is acute alcohol poisoning. In one embodiment, the alcohol intoxication is acute alcohol intoxication. In one embodiment, the symptom of alcohol consumption is a hangover symptom. In another embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In one embodiment, the method of treating and/or preventing alcohol intolerance, alcohol addiction, an alcohol abuse disorder, alcohol intoxication, alcohol dependence, alcohol poisoning, or symptoms of alcohol consumption further comprising administering an opioid receptor antagonist. In one embodiment, the opioid receptor antagonist is naltrexone.

In another aspect, the present invention relates to a method of treating and/or preventing peripheral artery disease in a subject in need thereof. The method comprises administering to the subject a therapeutically effective amount of a compound of Formula (I), or a pharmaceutically acceptable salt, solvate, ester, or prodrug thereof.

Another aspect of the present invention relates to a method of treating and/or preventing liver injury and/or damage to a subject in need thereof. The method comprises administering to the subject a therapeutically effective amount of a compound of Formula (I), or a pharmaceutically acceptable salt, solvate, ester, or prodrug thereof.

In another aspect, the present invention relates to a method of treating and/or preventing Acute Inflammatory Pain in a subject in need thereof. The method comprises administering to the subject in need thereof a therapeutically effective amount of a compound of Formula (I), or a pharmaceutically acceptable salt, solvate, ester, or prodrug thereof.

Another aspect of the present invention relates to a compound for use in a method for reducing the incidence or progression of oral cancer, esophageal cancer and/or lung cancer in a subject in need thereof, wherein the compound is selected from a compound of formula (I), or a pharmaceutically acceptable salt, solvate, ester, or prodrug, thereof.

In another aspect, the present invention relates to a compound for use in a method for reducing the incidence or progression of head and/or neck cancer in a subject in need thereof, wherein the compound is selected from a compound of formula (I), or a pharmaceutically acceptable salt, solvate, ester, or prodrug thereof. In one embodiment, the subject is a habitual user of betel quid.

Another aspect of the present invention relates to a compound for use in a combinational therapy for treating and/or preventing cancer in a subject in need thereof, wherein the compound is a compound of formula (I), or a pharmaceutically acceptable salt, solvate, ester, or prodrug thereof, used in combination with a cancer chemotherapeutic agent or ionizing radiation, wherein the compound and the cancer chemotherapeutic agent, or compound and the ionizing radiation, are administered in combined effective amounts to treat or prevent the cancer. In one embodiment, the chemotherapeutic agent is chosen from an alkylating agent, a nitrosourea, an antimetabolite, an antitumor antibiotic, a plant (vinca) alkaloid, and a steroid hormone. In another embodiment, the alkylating agent is chosen from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide. In another embodiment, the ionizing radiation is administered via external beam radiation therapy or brachytherapy. In yet another embodiment, the administration of the compound reduces the amount of the chemotherapeutic agent or the ionizing radiation required to treat or prevent the cancer.

In another aspect, the present invention relates to a compound for use in a method for treating and/or preventing Fanconi Anemia in a subject in need thereof, wherein the compound is selected from a compound of formula (I), or a pharmaceutically acceptable salt, solvate, ester, or prodrug thereof. In one embodiment, the compound treats and/or prevents one or more symptoms of Fanconi Anemia chosen from progressive pancytopenia, short stature, radial aplasia, urinary tract abnormalities, hyperpigmentation, and congenital developmental delay. In another embodiment, the compound reduces risk of cancer in the subject in need of treating and/or preventing Fanconi Anemia, wherein the cancer in chosen from acute myeloid leukemia, squamous-cell cancers of the oral cavity, esophagus, the gastrointestinal tract, the anus, and vulva, head and neck squamous cell carcinoma (HNSCC), and breast cancer.

Another aspect of the present invention relates to a compound for use in a method for sequestering aldehyde in a subject exposed to alcohol or aldehyde, wherein the compound is selected from a compound of formula (I), or a pharmaceutically acceptable salt, solvate, ester, or prodrug thereof.

In another aspect, the present invention relates to a compound for use in a method for reducing a level of an aldehyde present at a toxic level in a subject to below the toxic level, wherein the compound is selected from a compound of formula (I), or a pharmaceutically acceptable salt, solvate, ester, or prodrug thereof. In one embodiment, the aldehyde is a biogenic aldehyde or a xenogenic aldehyde. In another embodiment, the biogenic aldehyde is acetaldehyde, malondialdehyde (MDA), 3,4-dihydroxypheylacetaldehyde (DOPAL), 3,4-dihydroxyphenylglycolaldehye (DOPE-GAL), hexanal, acrolein, glyoxal, crotonaldehyde, trans-2-nonenal, 4-oxo-2-nonenal, or 4-hydroxy-2-nonenal (4 HNE). In yet another embodiment, the xenogenic aldehyde is an environmental aldehyde that is ingested or inhaled.

Another aspect of the present invention relates to a compound for use in a method for treating and/or preventing alcohol intolerance, alcohol addiction, an alcohol abuse disorder, alcohol intoxication, alcohol dependence, alcohol poisoning, or symptoms of alcohol consumption, wherein the compound is selected from a compound of formula (I), or a pharmaceutically acceptable salt, solvate, ester, or prodrug thereof. In one embodiment, the alcohol poisoning is methanol poisoning. In another embodiment, the alcohol poisoning is acute alcohol poisoning. In yet another embodiment, the alcohol intoxication is acute alcohol intoxication. In another embodiment, the symptom of alcohol consumption is a hangover symptom. In yet another embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In another aspect, the present invention relates to a compound for use in a combination therapy for treating and/or preventing alcohol intolerance, alcohol addiction, an alcohol abuse disorder, alcohol intoxication, alcohol dependence, alcohol poisoning, or symptoms of alcohol consumption, wherein the compound is a compound of formula (I), or a pharmaceutically acceptable salt, solvate, ester, or prodrug thereof, used in combination with an opioid receptor antagonist. In one embodiment, the opioid receptor antagonist is naltrexone.

Another aspect of the present invention relates to a compound for use in a method for treating and/or preventing peripheral artery disease in a subject in need thereof, wherein the compound is selected from a compound of formula (I), or a pharmaceutically acceptable salt, solvate, ester, or prodrug thereof.

In another aspect, the present invention relates to a compound for use in a method for treating and/or preventing liver injury and/or damage in a subject in need thereof, wherein the compound is selected from a compound of formula (I), or a pharmaceutically acceptable salt, solvate, ester, or prodrug thereof. In one embodiment, the liver injury and/or damage is liver fibrosis.

Another aspect of the present invention relates to a compound for use in a method for treating and/or preventing Acute Inflammatory Pain in a subject in need thereof, wherein the compound is selected from a compound of formula (I), or a pharmaceutically acceptable salt, solvate, ester, or prodrug thereof.

In another aspect, the present invention relates to a compound for use in the manufacture of a medicament for reducing the incidence or progression of oral cancer, esophageal cancer and/or lung cancer in a subject in need thereof, wherein the compound is selected from a compound of formula (I), or a pharmaceutically acceptable salt, solvate, ester, or prodrug, thereof.

Another aspect of the present invention relates to a compound for use in the manufacture of a medicament for reducing the incidence or progression of head and/or neck cancer in a subject in need thereof, wherein the compound is selected from a compound of formula (I), or a pharmaceutically acceptable salt, solvate, ester, or prodrug thereof. In one embodiment, the subject is a habitual user of betel quid.

In another aspect, the present invention relates to a combination for use in the manufacture of a medicament for treating and/or preventing cancer in a subject in need thereof, wherein the combination comprises: a) a compound of formula (I), or a pharmaceutically acceptable salt, solvate, ester, or prodrug thereof; and b) a cancer chemotherapeutic agent or ionizing radiation, wherein the compound and the cancer chemotherapeutic agent, or the compound and the ionizing radiation, are administered in combined effective amounts to treat or prevent the cancer. In one embodiment, the chemotherapeutic agent is chosen from an alkylating agent, a nitrosourea, an antimetabolite, an antitumor antibiotic, a plant (vinca) alkaloid, and a steroid hormone. In another embodiment, the alkylating agent is chosen from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide. In yet another embodiment, the ionizing radiation is administered via external beam radiation therapy or brachytherapy. In another embodiment, the administration of the compound reduces the amount of the chemotherapeutic agent or the ionizing radiation required to treat or prevent the cancer.

Another aspect of the present invention relates to a compound for use in the manufacture of a medicament for treating and/or preventing Fanconi Anemia in a subject in need thereof, wherein the compound is selected from a compound of formula (I), or a pharmaceutically acceptable salt, solvate, ester, or prodrug thereof. In one embodiment, the compound treats and/or prevents one or more symptoms of Fanconi Anemia chosen from progressive pancytopenia, short stature, radial aplasia, urinary tract abnormalities, hyperpigmentation, and congenital developmental delay. In another embodiment, the compound reduces risk of cancer in the subject in need of treating and/or preventing Fanconi Anemia, wherein the cancer in chosen from acute myeloid leukemia, squamous-cell cancers of the oral cavity, esophagus, the gastrointestinal tract, the anus, and vulva, head and neck squamous cell carcinoma (HNSCC), and breast cancer.

In another aspect, the present invention relates to a compound for use in the manufacture of a medicament for sequestering aldehyde in a subject exposed to alcohol or aldehyde, wherein the compound is selected from a compound of formula (I), or a pharmaceutically acceptable salt, solvate, ester, or prodrug thereof.

Another aspect of the present invention relates to a compound for use in the manufacture of a medicament for reducing a level of an aldehyde present at a toxic level in a subject to below the toxic level, wherein the compound is selected from a compound of formula (I), or a pharmaceutically acceptable salt, solvate, ester, or prodrug thereof. In one embodiment, the aldehyde is a biogenic aldehyde or a xenogenic aldehyde. In another embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (4 HNE). In yet another embodiment, the xenogenic aldehyde is an environmental aldehyde that is ingested or inhaled.

In another aspect, the present invention relates to a compound for use in the manufacture of a medicament for treating and/or preventing alcohol intolerance, alcohol addiction, an alcohol abuse disorder, alcohol intoxication, alcohol dependence, alcohol poisoning, or symptoms of alcohol consumption, wherein the compound is selected from a compound of formula (I), or a pharmaceutically acceptable salt, solvate, ester, or prodrug thereof. In one embodiment, the alcohol poisoning is methanol poisoning. In another embodiment, the alcohol poisoning is acute alcohol poisoning. In yet another embodiment, the alcohol intoxication is acute alcohol intoxication. In another embodiment, the symptom of alcohol consumption is a hangover symptom. In another embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

Another aspect of the present invention relates to a combination for use in the manufacture of a medicament for treating and/or preventing alcohol intolerance, alcohol addiction, an alcohol abuse disorder, alcohol intoxication, alcohol dependence, alcohol poisoning, or symptoms of alcohol consumption, wherein the combination comprises a compound of formula (I), or a pharmaceutically acceptable salt, solvate, ester, or prodrug thereof, and an opioid receptor antagonist. In one embodiment, the opioid receptor antagonist is naltrexone.

In another aspect, the present invention relates to a compound for use in the manufacture of a medicament for treating and/or preventing peripheral artery disease in a subject in need thereof, wherein the compound is selected from a compound of formula (I), or a pharmaceutically acceptable salt, solvate, ester, or prodrug thereof.

Another aspect of the present invention relates to a compound for use in the manufacture of a medicament for treating and/or preventing liver injury and/or damage in a subject in need thereof, wherein the compound is selected from a compound of formula (I), or a pharmaceutically acceptable salt, solvate, ester, or prodrug thereof. In one embodiment, the liver injury and/or damage is liver fibrosis.

In another aspect, the present invention relates to a compound for use in the manufacture of a medicament for treating and/or preventing Acute Inflammatory Pain in a subject in need thereof, wherein the compound is selected from a compound of formula (I), or a pharmaceutically acceptable salt, solvate, ester, or prodrug thereof.

In one embodiment, the present invention relates to a method of synthesizing a compound of the invention, or a pharmaceutically acceptable salt or solvate thereof.

BRIEF DESCRIPTION OF THE DRAWINGS

In order to understand the invention and to demonstrate how it may be carried out in practice, embodiments now described, by way of non-limiting example only, with reference to the accompanying drawings in which:

FIG. 3B depicts line graphs showing AC32 and AC6 rescue of FANCA-deficiency cells from growth inhibition by 6 µM 4 HNE, 3(A) cell growth measured by fluorescence, 3(B) relative cell growth.

DETAILED DESCRIPTION OF THE DISCLOSURE

Figure 1A:
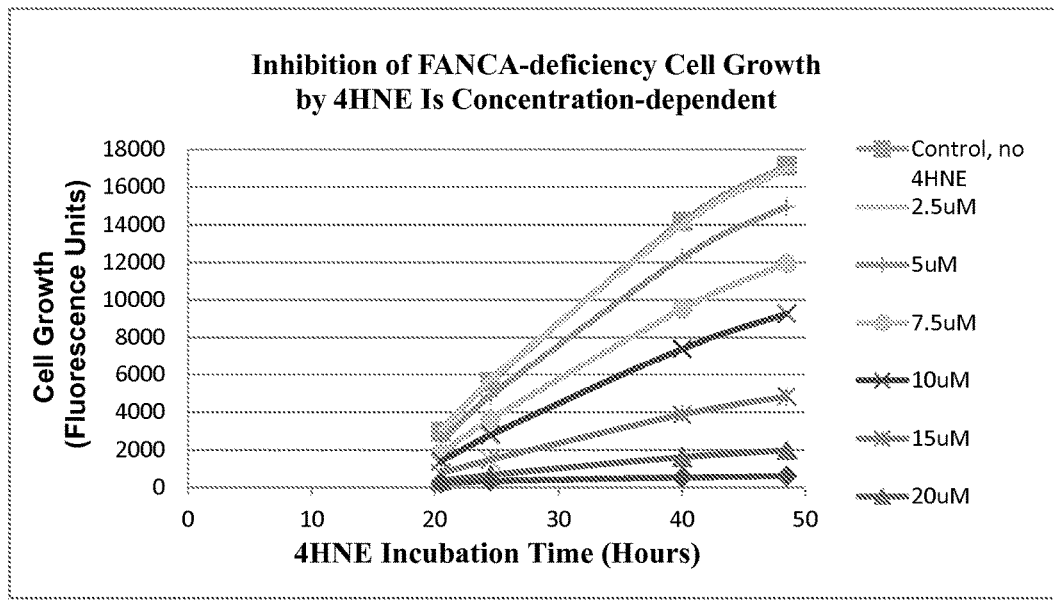
FIGS. 1(A)-(B) depict line graphs showing the inhibition of FANCA-deficient cell growth over time at concentrations of 4 HNE (trans-4-Hydroxynonenal (4 HNE) is a peroxidation product of $\omega$-6 polyunsaturated fatty acids) ranging from zero to 30 µM, 1(A) cell growth measured by fluorescence, 1(B), relative cell growth.

The details of one or more embodiments of the present disclosure have been set forth in the accompanying description below. Although any methods and materials similar or equivalent to those described herein can be used in the practice or testing of the present invention, the preferred methods and materials are now described. Other features, objects, and advantages of the disclosure will be apparent from the description and from the claims. In the specification and the appended claims, the singular forms include plural references unless the context clearly dictates otherwise. All publications cited in this specification are incorporated by reference in their entirety.

For convenience, certain terms used in the specification, examples and claims are collected here. Unless otherwise defined, all technical and scientific terms used herein have the same meaning as commonly understood by one of ordinary skill in the art to which this disclosure pertains.

The present invention provides compounds that modulate mitochondrial aldehyde dehydrogenase-2 (ALDH2), and methods of preparing and/or using said compounds.

Compounds

The present invention relates to a compound of formula (I):

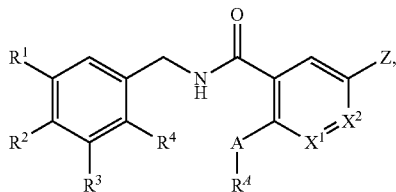
(I)

or a pharmaceutically acceptable salt, solvate, ester, or prodrug thereof,
wherein:
A is O, S, NH, or N—$R^C$;
$R^A$ is H, $C_1$-$C_6$ alkyl optionally substituted with one or more $R^B$, or $C_3$-$C_8$ cycloalkyl;
$R^B$ is $R^C$ or a 3-14 membered carbocycle optionally substituted with $R^C$;
$R^C$ is D or $C_1$-$C_6$ alkyl;
$X^1$ and $X^2$ are independently N or CH;
$R^1$, $R^2$, $R^3$, and $R^4$ are independently chosen from —H, —F, —CH$_3$, —CF$_3$, —C(CH$_3$)$_3$, —OCH$_3$, and —OCD$_3$;
alternatively, $R^1$ and $R^2$ together form a 5-membered, partially saturated heterocycle containing two oxygen atoms;
Z is a substituted ring structure chosen from

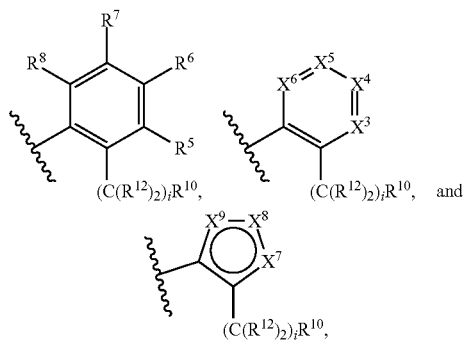

wherein i is 0, 1, 2, or 3;
$R^5$, $R^6$, $R^7$, and $R^8$ are independently chosen from H, F, and N(CH$_3$)$_2$;
$X^3$, $X^4$, $X^5$, and $X^6$ are independently chosen from N, NO, and CH;
$X^7$, $X^8$, and $X^9$ are independently chosen from S, O, N, NR$^9$, and CR$^9$;

$R^9$ is H or CH$_3$;
$R^{10}$ is $R^{11}$, —CH=CHR$^{11}$,

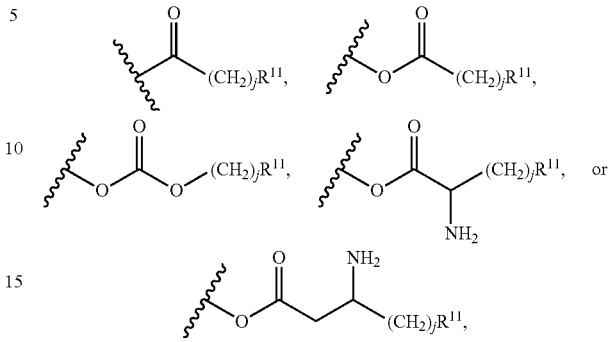

wherein j is 0, 1, 2, or 3;
$R^{11}$ is —C(CH$_3$)$_2$NH$_2$, —CH(CH$_3$)$_2$, —CH(CH$_3$)OH, —NH$_2$, —NHR$^C$, —NR$^C_2$, —OCH$_3$, —C(O)CH$_3$, —OPO$_3$H$_2$, —COOH, —CH=NOH, —CH$_3$, —SH, —OH, or —H; and
each $R^{12}$ is independently H or D.

In one embodiment, the compounds of formula I have the structure of formula (Ia):

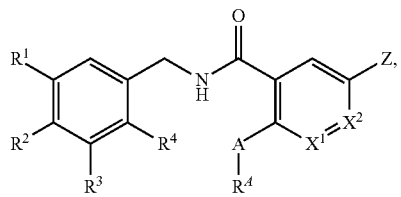
(Ia)

and pharmaceutically acceptable salts, solvates, esters, or prodrugs thereof,
wherein:
A is O, S, NH, or N—$R^C$;
$R^A$ is H, $C_1$-$C_6$ alkyl optionally substituted with $R^B$, or $C_3$-$C_6$ cycloalkyl;
$R^B$ is $R^C$ or a 3-14 membered carbocycle optionally substituted with $R^C$;
$R^C$ is $C_1$-$C_6$ alkyl;
$X^1$ and $X^2$ are independently N or CH;
$R^1$, $R^2$, $R^3$, and $R^4$ are independently chosen from —H, —F, —Cl, —CH$_3$, —CF$_3$, —C(CH$_3$)$_3$, and —OCH$_3$;
alternatively, $R^1$ and $R^2$ together form a 5-membered, partially saturated heterocycle containing two oxygen atoms;
Z is a substituted ring structure chosen from

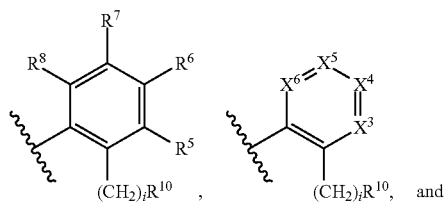

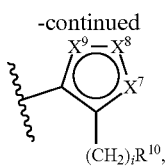

wherein i is 0, 1, 2, or 3;
R⁵, R⁶, R⁷, and R⁸ are independently chosen from H, F, and N(CH₃)₂;
X³, X⁴, X⁵, and X⁶ are independently chosen from N, NO, and CH;
X⁷, X⁸, and X⁹ are independently chosen from S, O, N, NR⁹, and CR⁹;
R⁹ is H or CH₃; and
R¹⁰ is R¹¹, —CH=CHR¹¹,

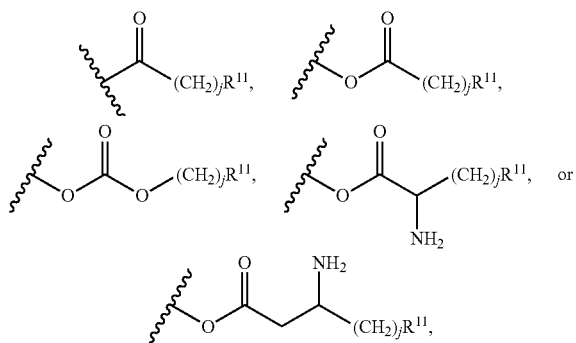

wherein j is 0, 1, 2, or 3; and
R¹¹ is —C(CH₃)₂NH₂, —CH(CH₃)₂, —CH(CH₃)OH, —NH₂, —NHR$^C$, —NR$^C$₂, —OCH₃, —C(O)CH₃, —OPO₃H₂, —COOH, —CH=NOH, —CH₃, —SH, —OH, or —H.

In another embodiment, the compounds of formula I have the structure of formula (Ib):

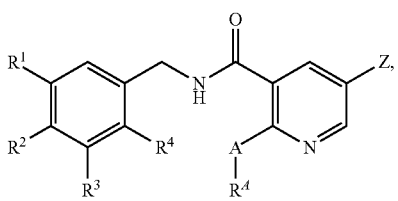

or a pharmaceutically acceptable salt, solvate, ester, or prodrug thereof,
wherein, R¹, R², R³, R⁴, R$^A$, A, and Z are as defined herein for Formula (I) or (Ia).

In another embodiment, the compounds of formula I have the structure of formula (Ic):

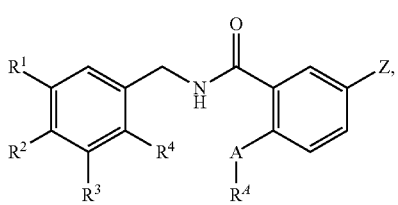

or a pharmaceutically acceptable salt, solvate, ester, or prodrug thereof, wherein, R¹, R², R³, R⁴, R$^A$, A, and Z are as defined herein for Formula (I) or (Ia).

In another embodiment, the compounds of formula I have the structure of formula (Id):

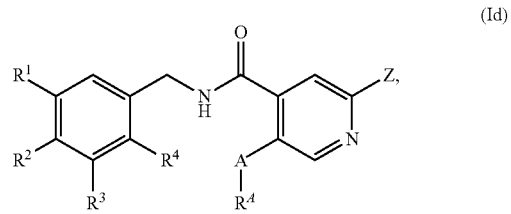

or a pharmaceutically acceptable salt, solvate, ester, or prodrug thereof,
wherein, R¹, R², R³, R⁴, R$^A$, A, and Z are as defined herein for Formula (I) or (Ia).

In some embodiments, the compounds of formula (I) include those in which A is O. In yet other embodiments, the compounds of formula (I) include those in which A is NH. The present disclosure also provides compounds of formula (I) in which A is S. In some embodiments, A is N—R$^C$, R$^C$ being C₁-C₆ alkyl.

In some embodiments, the compounds of formula (I) include those in which R$^C$ is methyl or ethyl. In some embodiments, the compounds of formula (I) include those in which R¹¹ is methyl or ethyl. In some embodiments, the compounds of formula (I) include those in which R¹¹ is methyl or ethyl and R$^C$ is methyl or ethyl. In additional embodiments, compounds of formula (I) include those in which R¹¹ is —N(CH₃)₂, —NHCH₂CH₃—NHCH₃.

One subset of the compounds of formula (I) includes those in which both X¹ and X² are CH. Another subset of the compounds of formula (I) includes those in which one of X¹ or X² is CH. In certain compounds, at least one of R¹, R², R³, and R⁴ is not H. For example, either X¹ or X² is not CH, and at least one of R¹, R², R³, and R⁴ is F or OCH₃. In one embodiment, either X¹ or X² is N, and one of R¹, R², R³, and R⁴ is F and at least one other R¹, R², R³, and R⁴ is OCH₃. In other embodiments, when X¹ or X² is N, and at least one of R¹, R², R³, and R⁴ is F and one other R¹, R², R³, and R⁴ is CF₃ or CH₃.

In some embodiments, the compounds of formula (I) include those in which in R$^A$ is C₃-C₈ cycloalkyl. In another embodiment, the compounds of formula (I) include those in which in one or both of R¹ and R³ are F, R² is OCD₃, and R⁴ is H. In one embodiment, either X¹ or X² is N, and one of R¹, R², R³, and R⁴ is F and at least one other R¹, R², R³, and R⁴ is OCH₃ or OCD₃. In other embodiments, when X¹ or X² is N, and at least one of R¹, R², R³, and R⁴ is F and one other R¹, R², R³, and R⁴ is CF₃ or CH₃.

In some embodiments, the compounds of formula (I) include those in which in R$^A$ is C₃-C₈ cycloalkyl. In another embodiment, the compounds of formula (I) include those in which in one or both of R¹ and R³ are F, R² is OCH₃ or OCD₃, and R⁴ is H.

In some embodiments, the compounds of formula (I) include those in which in R$^A$ is C₇-C₈ cycloalkyl.

In some embodiments, the compounds of formula (I) include those in which in R$^A$ is C₃-C₆ cycloalkyl. In another embodiment, the compounds of formula (I) include those in which in one or both of R¹ and R³ are F, R² is OCH₃, and R⁴ is H.

In some embodiments, the compounds of formula (I) include those in which $R^C$ is D, methyl, or ethyl. In some embodiments, the compounds of formula (I) include those in which $R^{11}$ is methyl or ethyl. In some embodiments, the compounds of formula (I) include those in which $R^{11}$ is methyl or ethyl and $R^C$ is D, methyl, or ethyl. In additional embodiments, compounds of formula (I) include those in which $R^{11}$ is —N(CH$_3$)$_2$, —NHCH$_2$CH$_3$—NHCH$_3$. In other embodiments, the compounds of formula (I) include those in which $R^{12}$ is H or D.

The present disclosure also provides a subset of compounds of formula (I) in which one or both of $R^1$ and $R^3$ is F, $R^2$ is OCH$_3$. Compounds of formula (I) include those in which one or both of $R^1$ and $R^3$ are OCH$_3$, CF$_3$, or H and $R^2$ or $R^4$ is F. Additional subsets of the compounds of formula (I) include those in which two, three or all of $R^1$, $R^2$, $R^3$, and $R^4$ are H. In one embodiment, one of $R^1$, $R^2$, $R^3$, and $R^4$ is F, and one other is OCH$_3$ or CF$_3$. In other embodiments, $R^2$ is OCH$_3$, $R^3$ is F, and $R^1$ and $R^4$ are both H. In additional embodiments, $R^2$ is OCH$_3$, le is F, and $R^3$ and $R^4$ are both H. In some embodiments, one or both of $R^1$ and $R^3$ are F, $R^2$ is OCH$_3$, and $R^4$ is H. In other embodiments at least one of $R^1$, $R^2$, $R^3$, and $R^4$ is not H. In some embodiments, one, two, three or all of $R^1$, $R^2$, $R^3$, and $R^4$ are not H. The disclosure also provides compounds of formula (I) in which each of $X^1$, $X^2$, $X^3$, $X^4$, $X^5$ is CH, $X^6$ is N, i is 1, $R^{10}$ is $R^{11}$, and $R^2$ is OCH$_3$, wherein $R^{11}$ is OH, and $R^1$, $R^3$, or $R^4$ is F, —OCH$_3$, —Cl, or $R^C$.

In another subset, the compounds of formula (I) includes those in which at least two of $X^3$, $X^4$, $X^5$, and $X^6$ are CH. In some embodiments, the formula (I) compounds include those having both $X^1$ and $X^2$ as CH. In other embodiments, the formula (I) compounds include those having one of $X^1$ or $X^2$ as CH. The formula (I) compounds of the present disclosure include compounds in which one or two among $X^3$, $X^4$, $X^5$, and $X^6$ is N or NO.

The present disclosure provides compounds of formula (I) in which $R^A$ is $C_1$ alkyl substituted with $R^B$, where $R^B$ is an unsubstituted cyclopropyl. The compounds of formula (I) according to the current disclosure includes those in which A is O, $R^A$ is $C_1$ alkyl substituted with $R^B$, and $R^B$ is unsubstituted cyclopropyl. In some embodiments, the compounds of the present disclosure include those in which A is NH, $R^A$ is $C_1$ alkyl substituted with $R^B$, and $R^B$ is unsubstituted cyclopropyl. In some embodiments, the compound has a formula where A is O. In some embodiments, the compound has a formula where "i" is 1, $R^{10}$ is $R^{11}$, and $R^{11}$ is —OH. In one embodiment, $R^A$ is a $C_1$-$C_6$ straight saturated hydrocarbon chain or a $C_3$-$C_6$ branched saturated hydrocarbon chain.

The present disclosure provides a subset of compounds of formula (I) in which the substituted ring structure Z is chosen from furanyl, furazanyl, imidazolidinyl, imidazolinyl, imidazolyl, morpholinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, isooxazolyl, pyrazolyl, piperazinyl, piperidinyl, piperidinone, 4-piperidinone, pyridinyl (or pyridyl), pyrimidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thiophenyl, triazinyl, 1,2,3-triazolyl, 1,2,4-triazolyl, 1,2,5-triazolyl, and 1,3,4-triazolyl.

In some embodiments of Formula (I), each of the substituents defined for any one of $X^1$, $X^2$, $R^1$, $R^2$, $R^3$, $R^4$, $R^A$, A, and Z can be combined with any of the substituents defined for the remainder of $X^1$, $X^2$, $R^1$, $R^2$, $R^3$, $R^4$, $R^A$, A, and Z.

In some embodiments of Formula (Ia), each of the substituents defined for any one of $X^1$, $X^2$, $R^1$, $R^2$, $R^3$, $R^4$, $R^A$, A, and Z can be combined with any of the substituents defined for the remainder of $X^1$, $X^2$, $R^1$, $R^2$, $R^3$, $R^4$, $R^A$, A, and Z.

In some embodiments of Formula (Ib), each of the substituents defined for any one of $R^1$, $R^2$, $R^3$, $R^4$, $R^A$, A, and Z can be combined with any of the substituents defined for the remainder of $R^1$, $R^2$, $R^3$, $R^4$, $R^A$, A, and Z.

In some embodiments of Formula (Ic), each of the substituents defined for any one of $R^1$, $R^2$, $R^3$, $R^4$, $R^A$, A, and Z can be combined with any of the substituents defined for the remainder of $R^1$, $R^2$, $R^3$, $R^4$, $R^A$, A, and Z.

In some embodiments of Formula (Ic), each of the substituents defined for any one of $R^1$, $R^2$, $R^3$, $R^4$, $R^A$, A, and Z can be combined with any of the substituents defined for the remainder of $R^1$, $R^2$, $R^3$, $R^4$, $R^A$, A, and Z.

The present disclosure provides ester, phosphoryloxymethyl (POM) and phosphoryloxymethyl oxymethyl (POMOM) derivatives of a compound of formula (I) or a pharmaceutically acceptable salt or solvate thereof.

In some embodiments of the Formulae above, $X^1$ is CH. In another embodiment, $X^1$ is CH and $X^2$ is CH. In yet another embodiment, $X^1$ is CH, $X^2$ is CH, and A is O. In another embodiment, $X^1$ is CH, $X^2$ is CH, A is O, and $R^1$ is —H, —F, —Cl, or —OCH$_3$. In yet another embodiment, $X^1$ is CH, $X^2$ is CH, A is O, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In another embodiment, $X^1$ is CH, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is CH, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is CH, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$ and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is CH, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isoxazolyl, and $R^A$ is H, $C_1$-$C_6$ alkyl optionally substituted with one or more $R^B$, or $C_3$-$C_8$ cycloalkyl. In another embodiment, $X^1$ is CH, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isoxazolyl, and $R^A$ is H, $C_1$-$C_6$ alkyl optionally substituted with one or more $R^B$, or $C_3$-$C_6$ cycloalkyl.

In some embodiments of the Formulae above, $X^1$ is N. In another embodiment, $X^1$ is N and $X^2$ is CH. In yet another embodiment, $X^1$ is N, $X^2$ is CH, and A is O. In another embodiment, $X^1$ is N, $X^2$ is CH, A is O, and $R^1$ is —H, —F, —Cl, or —OCH$_3$. In yet another embodiment, $X^1$ is N, $X^2$ is CH, A is O, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In another embodiment, $X^1$ is N, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is N, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is N, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is N, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isoxazolyl, and $R^A$ is H, $C_1$-$C_6$ alkyl optionally substituted with one or more $R^B$, or $C_3$-$C_8$ cycloalkyl. In another embodiment, $X^1$ is N, $X^2$ is CH, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isoxazolyl, and $R^A$ is H, $C_1$-$C_6$ alkyl optionally substituted with one or more $R^B$, or $C_3$-$C_6$ cycloalkyl.

In some embodiments of the Formulae above, $X^1$ is CH. In another embodiment, $X^1$ is CH and $X^2$ is N. In yet another embodiment, $X^1$ is CH, $X^2$ is N, and A is O. In another embodiment, $X^1$ is CH, $X^2$ is N, A is O, and $R^1$ is —H, —F, —Cl, or —OCH$_3$. In yet another embodiment, $X^1$ is CH, $X^2$ is N, A is O, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In another embodiment, $X^1$ is CH, $X^2$ is N, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is CH, $X^2$ is N, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is CH, $X^2$ is N, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is CH, $X^2$ is N, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, $C_1$-$C_6$ alkyl optionally substituted with one or more $R^B$, or $C_3$-$C_5$ cycloalkyl. In another embodiment, $X^1$ is CH, $X^2$ is N, A is O, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, $C_1$-$C_6$ alkyl optionally substituted with one or more $R^B$, or $C_3$-$C_6$ cycloalkyl.

In some embodiments of the Formulae above, $X^1$ is CH. In another embodiment, $X^1$ is CH and $X^2$ is CH. In yet another embodiment, $X^1$ is CH, $X^2$ is CH, and A is S. In another embodiment, $X^1$ is CH, $X^2$ is CH, A is S, and $R^1$ is —H, —F, —Cl, or —OCH$_3$. In another embodiment, $X^1$ is CH, $X^2$ is CH, A is S, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In yet another embodiment, $X^1$ is CH, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is CH, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is CH, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is CH, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, $C_1$-$C_6$ alkyl optionally substituted with one or more $R^B$, or $C_3$-$C_8$ cycloalkyl. In another embodiment, $X^1$ is CH, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, $C_1$-$C_6$ alkyl optionally substituted with one or more $R^B$, or $C_3$-$C_6$ cycloalkyl.

In some embodiments of the Formulae above, $X^1$ is N. In another embodiment, $X^1$ is N and $X^2$ is CH. In yet another embodiment, $X^1$ is N, $X^2$ is CH, and A is S. In another embodiment, $X^1$ is N, $X^2$ is CH, A is S, and $R^1$ is —H, —F, —Cl, or —OCH$_3$. In yet another embodiment, $X^1$ is N, $X^2$ is CH, A is S, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In another embodiment, $X^1$ is N, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is N, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is N, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is N, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, $C_1$-$C_6$ alkyl optionally substituted with one or more $R^B$, or $C_3$-$C_6$ cycloalkyl. In another embodiment, $X^1$ is N, $X^2$ is CH, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, $C_1$-$C_6$ alkyl optionally substituted with one or more $R^B$, or $C_3$-$C_6$ cycloalkyl.

In some embodiments of the Formulae above, $X^1$ is CH. In another embodiment, $X^1$ is CH and $X^2$ is N. In yet another embodiment, $X^1$ is CH, $X^2$ is N, and A is S. In another embodiment, $X^1$ is CH, $X^2$ is N, A is S, and $R^1$ is —H, —F, —Cl, or —OCH$_3$. In yet another embodiment, $X^1$ is CH, $X^2$ is N, A is S, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In another embodiment, $X^1$ is CH, $X^2$ is N, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is CH, $X^2$ is N, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is CH, $X^2$ is N, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is CH, $X^2$ is N, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, $C_1$-$C_6$ alkyl optionally substituted with one or more $R^B$, or $C_3$-$C_6$ cycloalkyl. In another embodiment, $X^1$ is CH, $X^2$ is N, A is S, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, $C_1$-$C_6$ alkyl optionally substituted with one or more $R^B$, or $C_3$-$C_6$ cycloalkyl.

In some embodiments of the Formulae above, $X^1$ is CH. In another embodiment, $X^1$ is CH and $X^2$ is CH. In yet another embodiment, $X^1$ is CH, $X^2$ is CH, and A is NH. In another embodiment, $X^1$ is CH, $X^2$ is CH, A is NH, and $R^1$ is —H, —F, —Cl, or —OCH$_3$. In yet another embodiment, $X^1$ is CH, $X^2$ is CH, A is NH, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In another embodiment, $X^1$ is CH, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is CH, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is CH, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is CH, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_8$ cycloalkyl. In another embodiment, $X^1$ is CH, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_6$ cycloalkyl.

In some embodiments of the Formulae above, $X^1$ is N. In another embodiment, $X^1$ is N and $X^2$ is CH. In yet another embodiment, $X^1$ is N, $X^2$ is CH, and A is NH. In another embodiment, $X^1$ is N, $X^2$ is CH, A is NH, and $R^1$ is —H, —F, —Cl, or —OCH$_3$. In yet another embodiment, $X^1$ is N, $X^2$ is CH, A is NH, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In another embodiment, $X^1$ is N, $X^2$ is CH, A is NH, le is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is N, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is N, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is N, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_8$ cycloalkyl. In another embodiment, $X^1$ is N, $X^2$ is CH, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_6$ cycloalkyl.

In some embodiments of the Formulae above, $X^1$ is CH. In another embodiment, $X^1$ is CH and $X^2$ is N. In yet another embodiment, $X^1$ is CH, $X^2$ is N, and A is NH. In yet another embodiment, $X^1$ is CH, $X^2$ is N, A is NH, and $R^1$ is —H, —F, —Cl, or —OCH$_3$. In yet another embodiment, $X^1$ is CH, $X^2$ is N, A is NH, $R^1$ is —H, —F, —Cl, or —OCH$_3$, and $R^2$ is —H, —F, —Cl, —CH$_3$, —CF$_3$, —C(CH$_3$)$_3$, —OCH$_3$, or —OCD$_3$. In another embodiment, $X^1$ is CH, $X^2$ is N, A is NH, le is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, and $R_3$ is —H, —F, —Cl, or —OCH$_3$. In yet another embodiment, $X^1$ is CH, $X^2$ is N, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, and $R^4$ is —H, —F, —Cl, —CH$_3$, or —OCH$_3$. In another embodiment, $X^1$ is CH, $X^2$ is N, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is CH, $X^2$ is N, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_8$ cycloalkyl. In another embodiment, $X^1$ is CH, $X^2$ is N, A is NH, $R^1$ is —H, —F, —Cl, or —OCH$_3$, $R^2$ is —H, —F, —Cl, —CH$_3$, —CF$_3$, —C(CH$_3$)$_3$, —OCH$_3$, or —OCD$_3$, $R_3$ is —H, —F, —Cl, or —OCH$_3$, $R^4$ is —H, —F, —Cl, —CH$_3$, or —OCH$_3$, Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_6$ cycloalkyl.

In another embodiment, $X^1$ is CH, $X^2$ is CH, A is O, NH or S, and $R^1$ and $R^2$ together form a 5-membered, partially saturated heterocycle containing two oxygen atoms. In yet another embodiment, $X^1$ is CH, $X^2$ is CH, A is O, NH or S, $R^1$ and $R^2$ together form a 5-membered, partially saturated heterocycle containing two oxygen atoms, and $R^3$ is —H, —F, —Cl, —CH$_3$, —CF$_3$, —C(CH$_3$)$_3$, and —OCH$_3$. In yet another embodiment, $X^1$ is CH, $X^2$ is CH, A is O, NH or S, $R^1$ and $R^2$ together form a 5-membered, partially saturated heterocycle containing two oxygen atoms, $R^3$ is —H, —F, —Cl, or —OCH$_3$, and $R^4$ is —H, —F, —Cl, —CH$_3$, or —OCH$_3$. In another embodiment, $X^1$ is CH, $X^2$ is CH, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is CH, $X^2$ is CH, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^4$ is H, C$_1$-C$_6$ alkyl optionally substituted with one or more $R^B$, or C$_3$-C$_8$ cycloalkyl. In another embodiment, $X^1$ is CH, $X^2$ is CH, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_6$ cycloalkyl.

In another embodiment, $X^1$ is N, $X^2$ is CH, A is O, NH or S, and $R^1$ and $R^2$ together form a 5-membered, partially saturated heterocycle containing two oxygen atoms. In yet another embodiment, $X^1$ is N, $X^2$ is CH, A is O, NH or S, $R^1$ and $R^2$ together form a 5-membered, partially saturated heterocycle containing two oxygen atoms, and $R^3$ is —H, —F, —Cl, —CH$_3$, —CF$_3$, —C(CH$_3$)$_3$, and —OCH$_3$. In yet another embodiment, $X^1$ is N, $X^2$ is CH, A is O, NH or S, $R^1$ and $R^2$ together form a 5-membered, partially saturated heterocycle containing two oxygen atoms, $R^3$ is —H, —F, —Cl, or —OCH$_3$, and $R^4$ is —H, —F, —Cl, —CH$_3$, or —OCH$_3$. In another embodiment, $X^1$ is N, $X^2$ is CH, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is N, $X^2$ is CH, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_8$ cycloalkyl. In another embodiment, $X^1$ is N, $X^2$ is CH, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_6$ cycloalkyl.

In another embodiment, $X^1$ is CH, $X^2$ is N, A is O, NH or S, and $R^1$ and $R^2$ together form a 5-membered, partially saturated heterocycle containing two oxygen atoms. In yet another embodiment, $X^1$ is CH, $X^2$ is N, A is O, NH or S, $R^1$ and $R^2$ together form a 5-membered, partially saturated heterocycle containing two oxygen atoms, and $R^3$ is —H, —F, —Cl, —CH$_3$, —CF$_3$, —C(CH$_3$)$_3$, and —OCH$_3$. In yet another embodiment, $X^1$ is CH, $X^2$ is N, A is O, NH or S, $R^1$ and $R^2$ together form a 5-membered, partially saturated heterocycle containing two oxygen atoms, $R^3$ is —H, —F, —Cl, or —OCH$_3$, and $R^4$ is —H, —F, —Cl, —CH$_3$, or —OCH$_3$. In another embodiment, $X^1$ is CH, $X^2$ is N, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ and Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl. In yet another embodiment, $X^1$ is CH, $X^2$ is N, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_8$ cycloalkyl. In another embodiment, $X^1$ is CH, $X^2$ is N, A is O, NH or S, $R^1$ and $R^2$ together form a 5-membered, partially saturated heterocycle containing two oxygen atoms, $R^3$ is —H, —F, —Cl, or —OCH$_3$, $R^4$ is —H, —F, —Cl, —CH$_3$, or —OCH$_3$ Z is optionally substituted phenyl, an optionally substituted pyridinyl, an optionally substituted pyridinyl oxide, an optionally substituted thiophenyl, an optionally substituted pyrazolyl, an optionally substituted thiazolyl, an optionally substituted imidazolyl, an optionally substituted imidazolyl furanyl, or an optionally substituted isooxazolyl, and $R^A$ is H, C$_1$-C$_6$ alkyl optionally substituted with one or more $R^B$, or C$_3$-C$_6$ cycloalkyl.

One subset of the compounds of formula (I) includes compounds AC1-AC166 listed in Table 1. The invention also relates to salts of such compounds. For example, acid addition salt, such as hydrochloride. For example, the salt is a di-hydrochloride salt.

In some embodiments, the compounds of the present invention are selective over the other ALDH family members. As used herein "selective," "selective ALDH2 activator," or "selective ALDH2 compound" refers to a compound, for example a compound of the invention, that effectively activates or ALDH2 to a greater extent than any other ALDH family member, (i.e., ALDH1A1, ALDH1A2, ALDH1A3, ALDH1B1, ALDH1L1, ALDH1L2, ALDH3A1, ALDH3A2, ALDH3B1, ALDH3B2, ALDH4A1, ALDH5A1, ALDH6A1, ALDH7A1, ALDH8A1, ALDH9A1, ALDH16A1, and/or ALDH18A).

A "selective ALDH2 activator," can be identified, for example, by comparing the ability of a compound to activate ALDH2 to its ability to activate the other members of the ALDH family. For example, a substance may be assayed for its ability to activate ALDH2 activity, as well as ALDH1A1, ALDH1A2, ALDH1A3, ALDH1B1, ALDH1L1, ALDH1L2, ALDH3A1, ALDH3A2, ALDH3B1, ALDH3B2, ALDH4A1, ALDH5A1, ALDH6A1, ALDH7A1, ALDH8A1, ALDH9A1, ALDH16A1, and/or ALDH18A.

In certain embodiments, the compounds of the invention exhibit at least 2-fold, 3-fold, 5-fold, 10-fold, 25-fold, 50-fold or 100-fold selectivity over the other ALDH family members. In various embodiments, the compounds of the invention exhibit up to 1000-fold selectivity over the other ALDH family members.

Pharmaceutical Composition

In one embodiment, the present invention relates to a pharmaceutical composition comprising a compound of formula (I), for example compounds AC1-AC166, or a pharmaceutically acceptable salt, solvate, ester, or prodrug thereof, and a pharmaceutical acceptable excipient. A compound of formula (I) can be formulated with one or more pharmaceutically acceptable excipients. A wide variety of pharmaceutically acceptable excipients is known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The present disclosure further provides a composition, which includes a compound of formula (I) or a pharmaceutically acceptable salt, solvate, ester, or prodrug thereof. Formula (I) compounds of the present disclosure include, but are not limited to compounds AC1-AC166 listed in Table 1.

A "pharmaceutical composition" of a compound of formula (I) is a formulation containing the disclosed compounds in a form suitable for administration to a subject. In one embodiment, the pharmaceutical composition of a compound of formula (I) is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or a pharmaceutically acceptable salt, solvate, ester, or prodrug thereof) in a unit dose of the composition is an effective amount and is varied according to the particular treatment involved. In pharmaceutical dosage forms, a subject active agent may be administered in the form of their pharmaceutically acceptable salts, or a subject active agent may be used alone or in appropriate association, as well as in combination, with other pharmaceutically active compounds. The following methods and excipients are merely exemplary and are in no way limiting.

A compound of formula (I) or a pharmaceutically acceptable salt, solvate, ester, or prodrug thereof, can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. A variety of routes are contemplated, including topical, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

For oral preparations, a compound of formula (I) or a pharmaceutically acceptable salt, solvate, ester, or prodrug thereof can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A compound of formula (I) or a pharmaceutically acceptable salt, solvate, ester, or prodrug thereof, can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A compound of formula (I) or a pharmaceutically acceptable salt, solvate, ester, or prodrug thereof can be utilized in aerosol formulation to be administered via inhalation. A compound of formula (I) or a pharmaceutically acceptable salt, solvate, ester, or prodrug thereof can be formulated into pressurized acceptable propellants such as dichlorodifluoromethane, propane, nitrogen and the like.

Furthermore, a compound of formula (I) or a pharmaceutically acceptable salt, solvate, ester, or prodrug thereof can be made into suppositories by mixing with a variety of bases such as emulsifying bases or water-soluble bases. A compound of formula (I) or a pharmaceutically acceptable salt, solvate, ester, or prodrug thereof can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject active agent. Similarly, unit dosage forms for injection or intravenous administration may comprise a subject active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject active agent calculated in an amount sufficient to produce the desired effect in association with a pharmaceutically acceptable diluent, carrier or vehicle. The specifications for a subject active agent depend on the particular compound employed and the effect to be achieved, and the pharmacodynamics associated with each compound in the host.

A compound of formula (I) or a pharmaceutically acceptable salt, solvate, ester, or prodrug thereof can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a compound of formula (I) or a pharmaceutically acceptable salt, solvate, ester, or prodrug thereof is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Depending on the subject and condition being treated and on the administration route, the compound of formula (I) or a pharmaceutically acceptable salt, solvate, ester, or prodrug thereof may be administered in dosages of, for example, 0.1 μg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

An exemplary dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

In some embodiments, multiple doses of a subject compound are administered. The frequency of administration of a compound of formula (I) or a pharmaceutically acceptable salt, solvate, ester, or prodrug thereof can vary depending on any of a variety of factors, e.g., severity of the symptoms, etc. For example, in some embodiments, a compound of formula (I) or a pharmaceutically acceptable salt, solvate, ester, or prodrug thereof is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in some embodiments, a compound of formula (I) or a pharmaceutically acceptable salt, solvate, ester, or prodrug thereof is administered continuously.

The duration of administration of a compound of formula (I) or a pharmaceutically acceptable salt, solvate, ester, or prodrug thereof, e.g., the period of time over which a compound of formula (I) or a pharmaceutically acceptable salt, solvate, ester, or prodrug thereof is administered, can vary, depending on any of a variety of factors, e.g., patient response, etc. For example, a compound of formula (I) or a pharmaceutically acceptable salt, solvate, ester, or prodrug thereof can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, a compound of formula (I) or a pharmaceutically acceptable salt, solvate, ester, or prodrug thereof is administered for the lifetime of the subject.

A subject ALDH2 activity modulator of formula (I) or a pharmaceutically acceptable salt, solvate, ester, or prodrug thereof is administered to a subject using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time from about 2 weeks to about one month, from about one month to about 3 months, from about 3 months to about 6 months, from about 6 months to about 1 year, or longer than one year).

Conventional and pharmaceutically acceptable routes of administration include intranasal, intramuscular, intratracheal, subcutaneous, intradermal, transdermal, sublingual, topical application, intravenous, rectal, nasal, oral, and other enteral and parenteral routes of administration. Routes of administration may be combined, if desired, or adjusted depending upon the agent and/or the desired effect. The compound can be administered in a single dose or in multiple doses.

An active agent of formula (I) or a pharmaceutically acceptable salt, solvate, ester, or prodrug thereof can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The compound or agent of formula (I) or a pharmaceutically acceptable salt, solvate, ester, or prodrug thereof can also be delivered to the subject by enteral administration. Enteral routes of administration include, but are not necessarily limited to, oral and rectal (e.g., using a suppository) delivery.

Methods of administration of the compound or agent of formula (I) or a pharmaceutically acceptable salt, solvate, ester, or prodrug thereof through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Pharmaceutical Salts and Excipients

The compounds of formula (I) are capable of forming salts. All of these forms are also contemplated within the scope of the claimed invention. The present disclosure provides pharmaceutically acceptable salts of a compound of formula (I), for example, pharmaceutically acceptable salts of compounds AC1-AC166. "Pharmaceutically acceptable salt" of a compound means a salt that is pharmaceutically acceptable and that possesses the desired pharmacological activity of the parent compound.

As used herein, "pharmaceutically acceptable salts" refer to derivatives of the compounds of formula (I), for example compounds AC1-AC166, wherein the parent compound is modified by making acid or base salts thereof. Examples of pharmaceutically acceptable salts of a compound of formula (I) include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, succinic, sulfamic, sulfanilic, sulfuric, tannic, tartaric, toluene sulfonic, and the commonly occurring amino acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the compounds of formula (I) can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

Esters and Prodrugs

The compounds of the present invention can also be prepared as esters, for example pharmaceutically acceptable esters. For example a carboxylic acid functional group in a compound can be converted to its corresponding ester, e.g., a methyl, ethyl, acetate, dialkylaminoacetates, formates, phosphates, sulfates, and benzoate derivatives. Also, an alcohol group in a compound can be converted to its corresponding ester, e.g., acetate, propionate, or other esters.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound.

Prodrugs include compounds of the present invention wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl)N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p. 1-92, Elesevier, New York-Oxford (1985).

General Methods of Treatment and Prevention

The present invention provides various treatment and prevention methods, generally involving administering to a subject an effective amount of a compound of the invention. Diseases and conditions associated with ALDH2 include cancer, Fanconi Anemia and related disorders, Peripheral Artery Disease, Acute Inflammatory Pain, liver injuries and/or damages, alcoholism, alcohol intolerance, alcohol addiction, an alcohol abuse disorder, alcohol intoxication, alcohol dependence, alcohol poisoning, symptoms of alcohol consumption, and narcotic addition.

Methods of Treating and/or Preventing Cancer

The present invention provides methods of treating and/or preventing cancer in a subject with a compound of formula (I) or a pharmaceutically acceptable salt, solvate, ester, or prodrug thereof. The methods generally involve administering to a subject an effective amount of a compound of formula (I) or a pharmaceutically acceptable salt, solvate, ester, or prodrug thereof in conjunction with a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

The present invention provides methods for reducing the damages and/or injuries due to cancer treatments including surgery, chemotherapy and/or ionizing radiation by increasing the level and/or activity of ALDH2. The methods generally involve administering to a subject having a solid tumor and/or a liquid tumor an effective amount of an agent that increases a level and/or activity of ALDH2.

In some embodiments, a compound of formula (I) or a pharmaceutically acceptable salt, solvate, ester, or prodrug thereof that increases a level and/or activity of ALDH2 is administered as adjuvant therapy to a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan®), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide, 17α-ethinylestradiol, diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore, compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL®, TAXOTERE® (a formulation of docetaxel), 10-desacetyl analogs of paclitaxel and 3N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., TAXOTERE® docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-.alpha.; (7) IFN-.gamma.; (8) colony-stimulating factors; (9) inhibitors of angiogenesis; and (10) antagonists of tumor necrosis factor.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large.

Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness.

Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin, some internal cancers can cause skin signs that can be seen. These changes include the skin looking darker (hyperpigmentation), yellow (jaundice), or red (erythema); itching; or excessive hair growth. Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer. Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat). Recent changes in a wart or mole could be indicative of cancer. Any wart, mole, or freckle that changes in color, size, or shape, or loses its definite borders indicates the potential development of cancer. For example, the skin lesion may be a melanoma. A persistent cough or hoarseness could be indicative of cancer. A cough that does not go away may be a sign of lung cancer. Hoarseness can be a sign of cancer of the larynx (voice box) or thyroid. While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen); computed tomography scanning, magnetic resonance imaging, and/or x-ray imaging of the tumor to estimate and/or monitor tumor size; measuring the amount of tumor-associated antigen in a biological sample, e.g., blood; and the like.

In one embodiment, the present invention relates to a method of reducing the likelihood that a subject will develop head and neck cancer, the method comprising administering to the subject an effective amount of a compound or composition of the invention. In one embodiment, the subject is a habitual use of betel quid. In one embodiment, the composition is toothpaste, a tooth gel, a tooth powder, a mouth rinse, a chewing gum, or a lozenge.

In one embodiment, the present invention relates to a method of treating and/or preventing cancer in a subject, the method comprising administering: a) a compound or pharmaceutical composition of the invention; and b) a cancer chemotherapeutic agent or ionizing radiation, wherein the compound or composition and the cancer chemotherapeutic agent, or compound or composition and the ionizing radiation, are administered in combined effective amounts to treat or prevent the cancer. In one embodiment, the chemotherapeutic agent is selected from an alkylating agent, a nitrosourea, an antimetabolite, an antitumor antibiotic, a plant (vinca) alkaloid, and a steroid hormone. In one embodiment, the ionizing radiation is administered via external beam radiation therapy or brachytherapy. In one embodiment, the administration of the compound or pharmaceutical composition reduces the amount of the chemotherapeutic agent or the ionizing radiation required to treat or prevent the cancer.

In one embodiment, the present invention relates to a method of reducing the likelihood that a subject will develop oral cancer or lung cancer, the method comprising administering to the subject an effective amount of a compound or pharmaceutical composition of the invention. In one embodiment, the compound or pharmaceutical composition is administered by a route selected from intramuscular, intravenous, subcutaneous, oral, and topical.

Another aspect of the present invention relates to a compound for use in a method for reducing the incidence or progression of oral cancer, esophageal cancer and/or lung cancer in a subject in need thereof, wherein the compound is selected from a compound of formula (I), or a pharmaceutically acceptable salt, solvate, ester, or prodrug, thereof, and a pharmaceutical composition of a compound of formula (I), or a pharmaceutically acceptable salt, solvate, ester, or prodrug, thereof.

In another aspect, the present invention relates to a compound for use in a method for reducing the incidence or progression of head and/or neck cancer in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the subject is a habitual user of betel quid.

Another aspect of the present invention relates to a compound for use in a combinational therapy for treating and/or preventing cancer in a subject in need thereof, wherein the compound is a compound of formula (I), or a pharmaceutically acceptable salt, solvate, ester, or prodrug thereof, or a pharmaceutical composition of a compound of formula (I), or a pharmaceutically acceptable salt, solvate, ester, or prodrug, thereof, used in combination with a cancer chemotherapeutic agent or ionizing radiation, wherein the compound or composition and the cancer chemotherapeutic agent, or compound or composition and the ionizing radiation, are administered in combined effective amounts to treat or prevent the cancer. In one embodiment, the chemotherapeutic agent is chosen from an alkylating agent, a nitrosourea, an antimetabolite, an antitumor antibiotic, a plant (vinca) alkaloid, and a steroid hormone. In another embodiment, the alkylating agent is chosen from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide. In another embodiment, the ionizing radiation is administered via external beam radiation therapy or brachytherapy. In yet another embodiment, the administration of the compound reduces the amount of the chemotherapeutic agent or the ionizing radiation required to treat or prevent the cancer.

In another aspect, the present invention relates to a compound for use in the manufacture of a medicament for reducing the incidence or progression of oral cancer, esophageal cancer and/or lung cancer in a subject in need thereof, wherein the compound is selected from a compound of formula (I), or a pharmaceutically acceptable salt, solvate, ester, or prodrug, thereof, and a pharmaceutical composition of a compound of formula (I), or a pharmaceutically acceptable salt, solvate, ester, or prodrug, thereof.

Another aspect of the present invention relates to a compound for use in the manufacture of a medicament for reducing the incidence or progression of head and/or neck cancer in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the subject is a habitual user of betel quid. In another aspect, the present invention relates to a combination for use in the manufacture of a medicament for treating and/or preventing cancer in a subject in need thereof, wherein the combination comprises: a) a compound of formula (I), or a pharmaceutically acceptable salt, solvate, ester, or prodrug thereof, or a pharmaceutical composition of a compound of formula (I), or a pharmaceutically acceptable salt, solvate, ester, or prodrug, thereof; and b) a cancer chemotherapeutic agent or ionizing radiation, wherein the compound or composition and the cancer chemotherapeutic agent, or the compound or composition and the ionizing radiation, are administered in combined effective amounts to treat or prevent the cancer. In one embodiment, the chemotherapeutic agent is chosen from an alkylating agent, a nitrosourea, an antimetabolite, an antitumor antibiotic, a plant (vinca) alkaloid, and a steroid hormone. In another embodiment, the alkylating agent is chosen from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide. In yet another embodiment, the ionizing radiation is administered via external beam radiation therapy or brachytherapy. In another embodiment, the administration of the compound reduces the amount of the chemotherapeutic agent or the ionizing radiation required to treat or prevent the cancer.

Methods of Treating and/or Preventing Fanconi Anemia

The present invention provides methods of treating and/or preventing Fanconi Anemia and related disorders in a subject with a compound or a composition of formula (I) or a pharmaceutically acceptable salt, solvate, ester, or prodrug thereof. The method of the current disclosure treats and/or prevents incidence and/or progression of cancer in a subject diagnosed with Fanconi Anemia and/or a subject predisposed to Fanconi Anemia based on the presence of the genetic causative mutations, for examples, FANC (A-O).

The methods of the present disclosure includes administering an effective amount of a compound or a composition of formula (I) or a pharmaceutically acceptable salt, solvate, ester, or prodrug thereof for treating and/or preventing Fanconi Anemia and/or related diseases or disorders, e.g., cancer. The dosage and method of administering the compound or composition of formula (I) or a pharmaceutically acceptable salt, solvate, ester, or prodrug thereof for treating and/or preventing Fanconi Anemia are specified in this disclosure and are incorporated by reference herein.

For example, a compound of formula (I) or a pharmaceutically acceptable salt, solvate, ester, or prodrug thereof can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

A compound of formula (I) or a pharmaceutically acceptable salt, solvate, ester, or prodrug thereof, for treating and/or preventing Fanconi Anemia and/or related disorders and/or diseases, can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. A variety of routes are contemplated, including topical, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The methods of the present disclosure also include administering to a subject an effective amount of a compound of formula (I) or a pharmaceutically acceptable salt, solvate, ester, or prodrug thereof in conjunction with a standard Fanconi Anemia treatment. Standard Fanconi Anemia treatments include blood and bone marrow stem cell transplantation, androgen therapy, synthetic growth factor therapy, gene therapy, and certain combinations thereof. The dosage and method of administering the compound or composition of formula (I) or a pharmaceutically acceptable salt, solvate, ester, or prodrug thereof for treating and/or preventing Fanconi Anemia, in combination with a standard therapy are specified in this disclosure and are incorporated by reference herein.

Fanconi anemia proteins are involved in DNA repair. Fanconi Anemia proteins are expression products of the Fanconi Anemia genes A, B, C, D1 (BRCA2), D2, E, F, G, I, J (BRIP1), L, M, N (PALB2) and P (SLX4). The present invention provides methods for treating and/or preventing Fanconi Anemia by increasing the level and/or activity of ALDH2. The methods generally involve administering to a subject afflicted with Fanconi Anemia an effective amount of a compound of formula (I) or a pharmaceutically acceptable salt, solvate, ester, or prodrug thereof, for increasing the level and/or activity of ALDH2. The dosage and method of administering the compound or composition of formula (I) or a pharmaceutically acceptable salt, solvate, ester, or prodrug thereof for treating and/or preventing Fanconi Anemia are specified in this disclosure and are incorporated by reference herein.

In some embodiments, a compound of formula (I) or a pharmaceutically acceptable salt, solvate, ester, or prodrug thereof, that increases the level and/or activity of ALDH2 is administered as adjuvant therapy to a blood and/or bone marrow stem cell transplantation subject. The dosage and method of administering the compound or composition of formula (I) or a pharmaceutically acceptable salt, solvate, ester, or prodrug thereof for treating and/or preventing Fanconi Anemia in combination with blood and/or bone marrow stem cell transplantation are based on the dosage specified in this disclosure and are incorporated by reference herein.

Blood and bone marrow stem cell transplantation involves extracting bone marrow from a healthy donor (allogeneic transplantation) or the patient (autologous transplantation), suppressing the patient's immune system, and subsequently administering to the patient the extracted bone marrow. Allogeneic transplantation involves a healthy donor and an afflicted patient, and requires that the donor have a tissue type that matches that of the patient. Autologous transplantation involves extracting hematopoietic stem cells from the patient, storing them at temperatures below freezing, destroying the patient's malignant cells and immune system, and finally, administering to the patient their extracted stem cells.

In some embodiments, a compound of formula (I) or a pharmaceutically acceptable salt, solvate, ester, or prodrug thereof, that increases the level and/or activity of ALDH2 is administered as adjuvant therapy to a subject receiving androgen therapy. The dosage and method of administering the compound or composition of formula (I) or a pharmaceutically acceptable salt, solvate, ester, or prodrug thereof for treating and/or preventing Fanconi Anemia in combination with androgen therapy are based on the dosage specified in this disclosure and are incorporated by reference herein.

Androgen therapy involves administering synthetically prepared or natural male hormones to patients of Fanconi Anemia to affect an increase in blood cell production. Androgen hormones are either prepared synthetically or obtained as natural extracts. Oxymetholone is a 17-α-alkylated androgen that is most commonly used in androgen therapy for Fanconi Anemia patients.

In some embodiments, a compound of formula (I) or a pharmaceutically acceptable salt, solvate, ester, or prodrug thereof that increases the level and/or activity of ALDH2 is administered as adjuvant therapy to a subject receiving synthetic growth factor therapy. The dosage and method of administering the compound or composition of formula (I) or a pharmaceutically acceptable salt, solvate, ester, or prodrug thereof for treating and/or preventing Fanconi Anemia in combination with growth factor therapy are based on the dosage specified in this disclosure and are incorporated by reference herein.

Synthetic growth factor therapy involves administering synthetically prepared hematopoietic growth factor proteins to patients of Fanconi Anemia to affect an increase in blood cell production.

In some embodiments, a compound of formula (I) or a pharmaceutically acceptable salt, solvate, ester, or prodrug thereof, that increases the level and/or activity of ALDH2 is administered as adjuvant therapy to a subject receiving gene therapy. The dosage and method of administering the compound or composition of formula (I) or a pharmaceutically acceptable salt, solvate, ester, or prodrug thereof for treating and/or preventing Fanconi Anemia in combination with gene therapy are based on the dosage specified in this disclosure and are incorporated by reference herein.

Gene therapy involves administering synthetically prepared DNA to patients of Fanconi Anemia in order to affect an increase in blood cell production. The synthetically prepared DNA, such as the retroviral vector containing the cDNA for FANC(A-O), encodes for healthy Fanconi Anemia proteins when properly introduced into a patient.

In some embodiments, a compound of formula (I) or a pharmaceutically acceptable salt, solvate, ester, or prodrug thereof that is administered to reduce the incidence of solid tumors and leukemia in patients of Fanconi Anemia.

In some embodiments, a compound of formula (I) or a pharmaceutically acceptable salt, solvate, ester, or prodrug thereof that is administered in conjunction with DNA crosslinking agents to treat or prevent both Fanconi Anemia and cancer.

In some embodiments, a compound of formula (I) or a pharmaceutically acceptable salt, solvate, ester, or prodrug thereof that is administered in conjunction with other pharmaceutically active small molecules to delay tumor onset in patients of Fanconi Anemia. The dosage and method of administering the compound or composition of formula (I) or a pharmaceutically acceptable salt, solvate, ester, or prodrug thereof for treating and/or preventing Fanconi Anemia in combination with small molecules are based on the dosage specified in this disclosure and are incorporated by reference herein.

In some embodiments, a compound of formula (I) or a pharmaceutically acceptable salt, solvate, ester, or prodrug thereof is administered to patients of Fanconi Anemia with low blood cell counts.

In some embodiments, a compound of formula (I) or a pharmaceutically acceptable salt, solvate, ester, or prodrug thereof is administered to patients of Fanconi Anemia with healthy blood cell counts.

In some embodiments, a compound of formula (I) or a pharmaceutically acceptable salt, solvate, ester, or prodrug thereof is administered to patients of Fanconi Anemia along with patient-specific induced pluripotent stem cells for gene therapy and cell therapy.

In some embodiments, a compound of formula (I) or a pharmaceutically acceptable salt, solvate, ester, or prodrug thereof that is administered to treat autosomal recessive disorder.

Growth factors are naturally-occurring proteins or steroids that promote cell growth or differentiation. Synthetic growth factors are growth factors that have been prepared or isolated in a laboratory for medical use. Examples of growth factor proteins include granulocyte-macrophage colony-stimulating factor, granulocyte colony-stimulating factor, and recombinant interleukin.

Subjects suitable for treatment with a subject agent and/or a subject method, where the agent increases a level and/or activity of ALDH2, include subjects who are afflicted with Fanconi Anemia.

In one embodiment, the present invention relates to a method of reducing the likelihood that a subject will develop Fanconi Anemia, the method comprising administering to the subject an effective amount of a compound or composition of the invention.

In one embodiment, the present invention relates to a method of reducing the likelihood that a subject afflicted by Fanconi Anemia will develop cancer, the method comprising administering to the subject an effective amount of a compound or composition of the invention. In one embodiment, the present invention relates to a method of treating and/or preventing Fanconi Anemia in a subject, the method comprising administering: a) a compound or pharmaceutical composition of the invention; and b) a hormone or growth factor.

In one embodiment, the compound or pharmaceutical composition is administered by a route selected from intramuscular, intravenous, subcutaneous, oral, and topical.

The present disclosure provides methods of rescuing cell proliferation of cells, e.g., lymphocytes, exposed to a DNA adduct, with a genetic mutation in any one of the genes linked to Fanconi Anemia, e.g., FANCA-FANCO, with a compound of formula (I) or a pharmaceutically acceptable salt, solvate, ester, or prodrug thereof. The methods disclosed provide a reduction of cell proliferation with a compound of formula (I) or a pharmaceutically acceptable salt, solvate, ester, or prodrug thereof, in a concentration-dependent manner.

The present disclosure provides a method of administering a compound of formula (I) or a pharmaceutically acceptable salt, solvate, ester, or prodrug thereof, for rescuing cell proliferation of DNA adduct exposed cells, e.g., lymphocytes.

trans-4-Hydroxynonenal (4 HNE) is produced from the metabolism of membrane lipids. See Huang et al. Environ. Mol. Mutagen, (2011), 51(6): 625-634. It is the major peroxidation product of ω-6 polyunsaturated fatty acids in vivo. See Huang (2011). Several routes for the formation of HNE from ω-6 polyunsaturated fatty acids have been described. See Huang (2011). 4 HNE exposures modulate gene expression, cell signaling, cell proliferation, and apoptosis. See Huang (2011). Human exposures are associated with oxidative stress, and 4 HNE has been implicated in the etiologies of Alzheimer's disease, Parkinson's disease, arteriosclerosis, and hepatic ischemia reperfusion injury. See Huang (2011). Chromosomal aberrations are observed upon exposures in a variety of mammalian cells, including human lymphocytes. See Huang (2011). 4 HNE is mutagenic in rodent and human cells. Mammalian genotoxicity depends upon glutathione, which is chemo-protective against the formation of 4 HNE-DNA adducts. See Huang (2011).

The present disclosure provides pretreating of FANCA-deficiency cells, e.g., lymphocytes, with a compound of formula (I) or a pharmaceutically acceptable salt, solvate, ester, or prodrug thereof, e.g. with AC32 or AC6, for about 2 hours before about 1-5 µM 4 HNE, e.g., 3.5 µM 4 HNE, challenge, which results in higher levels of cell growth than those of cells without any ALDH2 activator (4 HNE only). This protection of cell growth by ALDH2 activators is concentration-dependent. The embodiments also provide that AC6 having higher efficacy than AC32 at similar concentrations. The current disclosure provides complete rescue of cell proliferation inhibition by a DNA adduct, e.g., 4 HNE, by a compound of formula (I) or a pharmaceutically acceptable salt, solvate, ester, or prodrug thereof, in about 1 hour, in about 2 hours, in about 3 hours, in about 4 hours, in about 5 hours, in about 6 hours, in about 7 hours, in about 8 hours, in about 9 hours, in about 10 hours, in about 11 hours, in about 12 hours, in about 13 hours, in about 14 hours, in about 15 hours, in about 16 hours, in about 17 hours, in about 18 hours, in about 19 hours, in about 20 hours, in about 25 hours, in about 30 hours, in about 35 hours, in about 40 hours, in about 45 hours, in about 46 hours, in about 47 hours, in about 48 hours, in about 1-10 hours, in about 2-15 hours, in about 3-20 hours, in about 4-25 hours, in about 5-30 hours, or in about 10-50 hours after 4 HNE treatment.

The present disclosure provides concentration dependent rescue of cell proliferation of FANCA cells, e.g., FANCA lymphocytes, from growth inhibition by higher concentration of 4 HNE, by a compound of formula (I) or a pharmaceutically acceptable salt, solvate, ester, or prodrug thereof, e.g. AC6 and AC32. Pretreatment of FANCA-deficiency lymphocytes with 10 µM AC32 or AC6 for about 2 hours before about 6 µM 4 HNE challenge results in higher levels of cell growth than those of cells without any ALDH2 activator (4 HNE only) or with 2 µM ALDH2 activators. Only higher ALDH2 activities in FANCA cells resulting from treatment with either 10 µm AC6 or 10 µM AC32 were able to rescue the inhibition of FANCA cell growth by 6 µM 4 HNE.

Another aspect of this invention is a method of treating and/or preventing Fanconi Anemia. The method of the present disclosure reduces the incidence and/or progression of Fanconi Anemia. The compound or composition treats and/or prevents one or more symptoms of Fanconi Anemia such progressive pancytopenia, short stature, radial aplasia, urinary tract abnormalities, hyperpigmentation, and congenital developmental delay. In one embodiment, the present disclosure provides a method of reducing the incidence and/or progression of Fanconi Anemia in a subject in need thereof. The method includes administering to a subject in need thereof a therapeutically effective amount of one or more compounds chosen from those of any formula or compound disclosed herein or a pharmaceutical composition of one or more such formula or compound. The present disclosure also provides methods of manufacture of a medicament for use in treating and/or preventing Fanconi Anemia. The medicament thus manufactured is used for treating and/or preventing symptoms of Fanconi Anemia such as pancytopenia, short stature, radial aplasia, urinary tract abnormalities, hyperpigmentation, and congenital developmental delay.

The compound or composition of formula (I) or a pharmaceutically acceptable salt, solvate, ester, or prodrug thereof, reduces risk of cancer in the subject in need of treating and/or preventing Fanconi Anemia; the cancer in chosen from acute myeloid leukemia, squamous-cell cancers of the oral cavity, esophagus, the gastrointestinal tract, the anus, and vulva, head and neck squamous cell carcinoma (HNSCC), and breast cancer.

In another aspect, the present invention relates to a compound for use in a method for treating and/or preventing Fanconi Anemia in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the compound or composition treats and/or prevents one or more symptoms of Fanconi Anemia chosen from progressive pancytopenia, short stature, radial aplasia, urinary tract abnormalities, hyperpigmentation, and congenital developmental delay. In another embodiment, the compound or composition reduces risk of cancer in the subject in need of treating and/or preventing Fanconi Anemia, wherein the cancer in chosen from acute myeloid leukemia, squamous-cell cancers of the oral cavity, esophagus, the gastrointestinal tract, the anus, and vulva, head and neck squamous cell carcinoma (HNSCC), and breast cancer.

Another aspect of the present invention relates to a compound for use in the manufacture of a medicament for treating and/or preventing Fanconi Anemia in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the compound treats and/or prevents one or more symptoms of Fanconi Anemia chosen from progressive pancytopenia, short stature, radial aplasia, urinary tract abnormalities, hyperpigmentation, and congenital developmental delay. In another embodiment, the compound reduces risk of cancer in the subject in need of treating and/or preventing Fanconi Anemia, wherein the cancer in chosen from acute myeloid leukemia, squamous-cell cancers of the oral cavity, esophagus, the gastrointestinal tract, the anus, and vulva, head and neck squamous cell carcinoma (HNSCC), and breast cancer.

Methods of Treating and/or Preventing Peripheral Artery Disease

The present invention provides methods of treating and/or preventing Peripheral Artery Disease and related disorders in a subject with a compound or a composition of formula (I) or a pharmaceutically acceptable salt, solvate, ester, or prodrug thereof. The method of the current disclosure treats and/or prevents incidence and/or progression of Peripheral Artery Disease.

ALDH2 activation increases the removal of reactive aldehydes in the ischemic limb. ALDH2 activation also preserves mitochondrial structure and function, thereby enhancing skeletal muscle viability and function. Since reactive aldehydes such as 4-hydroxy-nonenal (4-HNE) and malondialdehyde (MDA) damage the mitochondria, accelerated removal of 4-HNE and other toxic aldehydes will reduce the burden of carbonyl stress and reactive oxygen species (RO), thus reducing tissue damage. The compounds of the present invention through ALDH2 activation enhance functional capacity in PAD.

The methods of the present disclosure includes administering an effective amount of a compound or a composition of formula (I) or a pharmaceutically acceptable salt, solvate, ester, or prodrug thereof for treating and/or preventing Peripheral Artery Disease. The dosage and method of administering the compound or composition of formula (I) or a pharmaceutically acceptable salt, solvate, ester, or prodrug thereof for treating and/or preventing Peripheral Artery Disease are specified in this disclosure and are incorporated by reference herein.

For example, a compound of formula (I) or a pharmaceutically acceptable salt, solvate, ester, or prodrug thereof can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

A compound of formula (I) or a pharmaceutically acceptable salt, solvate, ester, or prodrug thereof, for treating and/or preventing Peripheral Artery Disease can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. A variety of routes are contemplated, including topical, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The methods of the present disclosure also include administering to a subject an effective amount of a compound of formula (I) or a pharmaceutically acceptable salt, solvate, ester, or prodrug thereof in conjunction with a standard Peripheral Artery Disease treatment. Standard Peripheral Artery Disease treatments include, but are not limited to, anti-platelet agents, statins, ACE inhibitors, and beta-blockers. The dosage and method of administering the compound or composition of formula (I) or a pharmaceutically acceptable salt, solvate, ester, or prodrug thereof for treating and/or preventing Peripheral Artery Disease, in combination with a standard therapy are specified in this disclosure and are incorporated by reference herein.

The present invention provides methods for treating and/or preventing Peripheral Artery Disease by increasing the activity and/or the level of ALDH2. The methods generally involve administering to a subject afflicted with Peripheral Artery Disease an effective amount of a compound of formula (I) or a pharmaceutically acceptable salt, solvate, ester, or prodrug thereof, for reducing the level and/or activity of ALDH2. The dosage and method of administering the compound or composition of formula (I) or a pharmaceutically acceptable salt, solvate, ester, or prodrug thereof for treating and/or preventing Peripheral Artery Disease are specified in this disclosure and are incorporated by reference herein.

Subjects suitable for treatment with a subject agent and/or a subject method, where the agent increases a level and/or activity of ALDH2, include subjects who are afflicted with Peripheral Artery Disease.

In one embodiment, the present invention relates to a method of reducing the likelihood that a subject will develop peripheral artery disease, the method comprising administering to the subject an effective amount of a compound or composition of the invention.

In one embodiment, the compound or pharmaceutical composition is administered by a route selected from intramuscular, intravenous, subcutaneous, oral, and topical.

Another aspect of the present invention relates to a compound for use in a method for treating and/or preventing peripheral artery disease in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof.

In another aspect, the present invention relates to a compound for use in the manufacture of a medicament for treating and/or preventing peripheral artery disease in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof.

Methods of Treating and/or Preventing Liver Injuries and/or Damages

The present invention provides methods of treating and/or preventing liver injuries and/or damages such as liver Fibrosis in a subject with a compound or a composition of formula (I) or a pharmaceutically acceptable salt, solvate, ester, or prodrug thereof. The method of the current disclosure treats and/or prevents incidence and/or progression of Liver Fibrosis.

Acute liver injuries and/or damages occurs due to an acute toxic insult to the liver such as acute alcohol poisoning; and overdose of acetaminophen. Acetaminophen overdose causes hepatic injury after a potentially hepatotoxic quantity of acetaminophen is ingested. Acetaminophen overdose incidences are divided into two types; Acute Ingestion or Repeated Supratherapeutic Ingestion (RSI).

Liver injury and/or damage also occurs due to a chronic toxic insult to the liver such as hepatitis C virus (HCN) or hepatitis B virus (HBV) infection, autoimmune injury, and chronic exposure to toxins such as alcohol. Chronic toxic insult leads to repeated cycles of hepatocyte injury and repair accompanied by chronic inflammation. Over a variable period of time, abnormal extracellular matrix progressively accumulates as a consequence of the host's wound repair response. Left unchecked, this leads to increasing deposition of fibrous material until liver architecture becomes distorted and the liver's regenerative ability is compromised. The progressive accumulation of scar tissue within the liver finally results in the histopathologic picture of cirrhosis, defined as the formation of fibrous septae throughout the liver with the formation of micronodules.

As used herein, the term "hepatic fibrosis," used interchangeably herein with "liver fibrosis," refers to the growth of scar tissue in the liver due to any of a variety of chronic toxic insults, including, but not limited to, chronic alcohol abuse; chronic exposure to drugs, including, but not limited to acetaminophen, amiodarone, aspirin, azathioprine, isoniazid, methyldopa, methotrexate, mitrfurantoin, propylthiouracil, and sulfonamides; chronic exposure to certain chemical agents, including, but not limited to, carbon tetrachloride, dimethyl nitrosamine, vinyl chloride, polychlorinated biphenyl s, aflatoxins, and pesticides; infection with *Schistosoma mansoni*; diabetes; autoimmune disorders, including, but not limited to, primary sclerosing cholangitis, primary biliary cirrhosis, autoimmune hepatitis, lupoid hepatitis, and inflammatory bowel disease; hemochromatosis; alpha-1-antitrypsin deficiency; chronic cholestatic hepatitis; non-alcoholic steatohepatitis; chronic binary obstruction; Wilson's disease; and other conditions known to cause cirrhosis.

The methods of the present disclosure includes administering an effective amount of a compound or a composition of formula (I) or a pharmaceutically acceptable salt, solvate, ester, or prodrug thereof for treating and/or preventing liver injuries and/or damages. The dosage and method of administering the compound or composition of formula (I) or a pharmaceutically acceptable salt, solvate, ester, or prodrug thereof for treating and/or preventing liver injury and/or damage are specified in this disclosure and are incorporated by reference herein. In one embodiment, the liver injury and/or damage is liver fibrosis.

For example, a compound of formula (I) or a pharmaceutically acceptable salt, solvate, ester, or prodrug thereof can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

A compound of formula (I) or a pharmaceutically acceptable salt, solvate, ester, or prodrug thereof, for treating and/or preventing liver injury and/or damage, e.g., liver fibrosis can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. A variety of routes are contemplated, including topical, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The methods of the present disclosure also include administering to a subject an effective amount of a compound of formula (I) or a pharmaceutically acceptable salt, solvate, ester, or prodrug thereof in conjunction with a standard Liver Fibrosis treatment.

The present invention provides methods for treating and/or preventing liver fibrosis by increasing the activity and/or the level of ALDH2. The methods generally involve administering to a subject afflicted with Liver Fibrosis an effective amount of a compound of formula (I) or a pharmaceutically acceptable salt, solvate, ester, or prodrug thereof, for increasing the level and/or activity of ALDH2. The dosage and method of administering the compound or composition of formula (I) or a pharmaceutically acceptable salt, solvate, ester, or prodrug thereof for treating and/or preventing liver fibrosis are specified in this disclosure and are incorporated by reference herein.

Subjects suitable for treatment with a subject agent and/or a subject method, where the agent increases a level and/or activity of ALDH2, include subjects who are afflicted with liver fibrosis.

In one embodiment, the present invention relates to a method of reducing the likelihood that a subject will develop liver fibrosis, the method comprising administering to the subject an effective amount of a compound or composition of the invention.

In one embodiment, the compound or pharmaceutical composition is administered by a route selected from intramuscular, intravenous, subcutaneous, oral, and topical.

Liver fibrosis is a precursor to the complications associated with liver cirrhosis, such as portal hypertension, progressive liver insufficiency, and hepatocellular carcinoma. A reduction in liver fibrosis thus reduces the incidence of such complications. Accordingly, the present invention further provides methods of reducing the likelihood that an individual will develop complications associated with cirrhosis of the liver.

Infection by viruses and parasites can cause inflammation and hepatic fibrosis. Some examples are the Hepadnaviridae (Hepatitis A and B viruses); Hepatitis D virus, Hepatitis E virus, and unclassified viruses (e.g., the etiological agents of Spongiform encephalopathies, the agent of delta hepatitis (thought to be a defective satellite of hepatitis B virus), the agents of non-A, non-B hepatitis (class 1=enterally transmitted; class 2=parenterally transmitted (i.e., Hepatitis C); Norwalk and related viruses, and astroviruses). Exemplary parasites include, but are not limited to: *Entamoeba histolytica*; the malaria parasite *Plasmodium* species (*Plasmodium falciparum, P. malariae, P. ovale, P. vivax*), the nematode *Trichinella spiralis*, the trematods *Clonorchis sinensis, Schistosoma mansoni, S. haematobium*, and *S. japonicum* and any combination thereof.

In other embodiments, administration of a compound of formula (I), or a pharmaceutically acceptable salt, solvate, ester, or prodrug thereof, is performed in combination with an anti-viral medicament or agent. Exemplary antiviral agents useful for the methods described herein include, but are not limited to, immunoglobulins, amantadine, interferon, nucleoside analogues, and protease inhibitors. Specific examples of antiviral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

In another aspect, the present invention relates to a compound for use in a method for treating and/or preventing liver injury and/or damage in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the liver injury and/or damage is liver fibrosis.

Another aspect of the present invention relates to a compound for use in the manufacture of a medicament for treating and/or preventing liver injury and/or damage in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the liver injury and/or damage is liver fibrosis.

Methods of Treating and/or Preventing Acute Inflammatory Pain

The present invention provides methods of treating and/or preventing Acute Inflammatory Pain and related disorders in a subject with a compound or a composition of formula (I) or a pharmaceutically acceptable salt, solvate, ester, or prodrug thereof. The method of the current disclosure treats and/or prevents incidence and/or progression of Acute Inflammatory Pain.

The methods of the present disclosure includes administering an effective amount of a compound or a composition of formula (I) or a pharmaceutically acceptable salt, solvate, ester, or prodrug thereof for treating and/or preventing Acute Inflammatory Pain. The dosage and method of administering the compound or composition of formula (I) or a pharmaceutically acceptable salt, solvate, ester, or prodrug thereof for treating and/or preventing Acute Inflammatory Pain are specified in this disclosure and are incorporated by reference herein.

For example, a compound of formula (I) or a pharmaceutically acceptable salt, solvate, ester, or prodrug thereof can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

A compound of formula (I) or a pharmaceutically acceptable salt, solvate, ester, or prodrug thereof, for treating and/or preventing Acute Inflammatory Pain can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. A variety of routes are contemplated, including topical, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The methods of the present disclosure also include administering to a subject an effective amount of a compound of formula (I) or a pharmaceutically acceptable salt, solvate, ester, or prodrug thereof in conjunction with additional agents useful in the treatment of pain. For example the compounds of formula (I) or a pharmaceutically acceptable salt, solvate, ester, or prodrug thereof, can be administered with one or more antidepressants, analgesics, muscle relaxants, anorectics, stimulants, antiepileptic drugs, sedative/hypnotics, and combinations thereof. Specific examples of compounds that can be administered with the compound of formula (I) include, but are not limited to, milnacipran, gabapentin, pregabalin, pramipexole, 1-DOPA, amphetamine, tizanidine, clonidine, tramadol, morphine, tricyclic antidepressants, codeine, carbamazepine, sibutramine, amphetamine, valium, trazodone and combinations thereof (including salts and/or solvates thereof). The dosage and method of administering the compound or composition of formula (I) or a pharmaceutically acceptable salt, solvate, ester, or prodrug thereof for treating and/or preventing Acute Inflammatory Pain, in combination with additional agents useful in the treatment of pain are specified in this disclosure and are incorporated by reference herein.

The present invention provides methods for treating and/or preventing Acute Inflammatory Pain by increasing the activity and/or level of ALDH2. The methods generally involve administering to a subject afflicted with Acute Inflammatory Pain an effective amount of a compound of formula (I) or a pharmaceutically acceptable salt, solvate, ester, or prodrug thereof, for reducing the level and/or activity of ALDH2. The dosage and method of administering the compound or composition of formula (I) or a pharmaceutically acceptable salt, solvate, ester, or prodrug thereof for treating and/or preventing Acute Inflammatory Pain are specified in this disclosure and are incorporated by reference herein.

Subjects suitable for treatment with a subject agent and/or a subject method, where the agent increases a level and/or activity of ALDH2, include subjects who are afflicted with Acute Inflammatory Pain.

In one embodiment, the present invention relates to a method of reducing the likelihood that a subject will develop Acute Inflammatory Pain, the method comprising administering to the subject an effective amount of a compound or composition of the invention.

In one embodiment, the compound or pharmaceutical composition is administered by a route selected from intramuscular, intravenous, subcutaneous, oral, and topical.

Another aspect of the present invention relates to a compound for use in a method for treating and/or preventing Acute Inflammatory Pain in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof.

In another aspect, the present invention relates to a compound for use in the manufacture of a medicament for treating and/or preventing Acute Inflammatory Pain in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof.

Methods of Treating and/or Preventing Alcohol-related Diseases or Conditions

The present invention provide a method of treating and/or preventing alcohol intolerance, alcohol addiction, an alcohol abuse disorder, alcohol intoxication, alcohol dependence, alcohol poisoning, or symptoms of alcohol consumption, the method comprising administering to a subject an effective amount of a compound or pharmaceutical composition of formula (I) or a pharmaceutically acceptable salt, solvate, ester, or prodrug thereof. A compound of formula (I) or a pharmaceutically acceptable salt, solvate, ester, or prodrug thereof can be administered to a subject on a regular basis to treat or prevent alcohol addiction. For example, in some embodiments, a compound of formula (I) or a pharmaceutically acceptable salt, solvate, ester, or prodrug thereof is administered to a subject twice daily, daily, every other day, twice weekly, once per week, or twice per month. A compound of formula (I) or a pharmaceutically acceptable salt, solvate, ester, or prodrug thereof can be administered in the form of a transdermal "patch" to treat or prevent alcohol addiction.

"Treating alcohol addiction," as used herein, includes achieving one or more of the following: a reduction in the amount of alcohol consumed; a reduction in the frequency at which alcohol is consumed; a reduction in the craving for alcohol; and a reduction in one or more of the symptoms of excessive alcohol consumption. "Alcohol," as used herein in the context of alcohol addiction, refers to ethanol, e.g., beverages containing 2%, 3%, 4%, 5%, or more, by volume, ethanol, e.g., wine, beer, vodka, whiskey, and the like.

Subjects suitable for treatment with a compound of formula (I) or a pharmaceutically acceptable salt, solvate, ester, or prodrug thereof include subjects who have alcohol addiction, including subjects who are considered to be alcoholics (e.g., subject having a primary, chronic disease characterized by one or more of: impaired control over drinking alcohol, preoccupation with the drug alcohol, use of alcohol despite adverse consequences, and distortions in thinking following consumption of alcohol); subjects suffering from withdrawal symptoms following cessation of alcohol consumption; subjects experiencing alcohol dependence (e.g., alcohol abuse combined with tolerance, withdrawal, and an uncontrollable urge to drink alcohol); and the like.

Alcohol intoxication (also known as drunkenness or inebriation) refers to the physiological state of a subject induced by the consumption of alcohol, when it builds up in the bloodstream faster than it can be metabolized by the liver. Common effects are euphoria and lowered social inhibitions. Common symptoms of alcohol intoxication include slurred speech, euphoria, impaired balance, loss of muscle coordination (ataxia), flushed face, dehydration, vomiting, reddened eyes, reduced inhibitions, and erratic behavior. Sufficiently high levels of blood-borne alcohol will cause coma and death from the depressive effects of alcohol upon the central nervous system.

Compounds of formula (I) or a pharmaceutically acceptable salt, solvate, ester, or prodrug thereof can also treat or prevent alcohol poisoning, such as acute alcohol poisoning, which refers to a high concentration of alcohol in the blood, e.g., high enough to induce coma or respiratory depression. Acute alcohol poisoning is considered a medical emergency. Symptoms of acute alcohol poisoning include e.g., severe confusion, unpredictable behavior, stupor, sudden lapses into and out of unconsciousness or semi-consciousness (with later alcoholic amnesia), vomiting while unconscious or semi-conscious seizures, respiratory depression (fewer than eight breaths a minute), and pale, bluish, cold and clammy skin due to insufficient oxygen.

In one embodiment, treatment or prevention of alcohol intoxication or alcohol poisoning comprises of administering a compound of the invention to a subject in an emergency room. In another embodiment, compounds of formula (I) or a pharmaceutically acceptable salt, solvate, ester, or prodrug thereof can be used to treat or prevent symptoms of alcohol intoxication, alcohol poisoning, or alcohol consumption in subject. Some examples of symptoms of alcohol intoxication and alcohol poisoning are listed above. Symptoms as a result of alcohol consumption include e.g., hangover. Hangover (also known as veisalgia) is the experience of various unpleasant physiological effects following the consumption of alcohol. Characteristics of a hangover include e.g., headache, nausea, sensitivity to light and noise, lethargy, dysphoria, diarrhea and thirst, typically after the intoxicating effect of the alcohol begins to wear off. While a hangover can be experienced at any time, generally a hangover is experienced the morning after a night of heavy drinking. In addition to the physical symptoms, a hangover may also induce psychological symptoms including heightened feelings of depression and anxiety.

Hangover symptoms may persist for several days after alcohol was last consumed. Some aspects of a hangover are viewed as symptoms of acute ethanol withdrawal. An alcohol hangover is associated with a variety of symptoms that may include dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor functions (including tremor), trouble sleeping, severe hunger, halitosis, and lack of depth perception. Some subjects may also be repulsed by the thought, taste or smell of alcohol during a hangover. The symptoms vary significantly from subject to subject.

The present invention provides methods of providing maintenance for a subject with an ALDH2 deficiency gene to remove acetaldehyde in the subject, comprising administering to the subject an effective amount of a compound of formula (I) or a pharmaceutically acceptable salt, solvate, ester, or prodrug thereof, before, after, or contemporaneous with alcohol consumption.

In some embodiments, the subject has two "wild-type" ALDH2 alleles, e.g., the ALDH2 encoded by the two wild-type ALDH2 alleles have a glutamic acid at position 487. In other embodiments, the subject has one or two "ALDH2*2" alleles, e.g., the ALDH2 encoded by one or both ALDH2 alleles comprises a lysine as amino acid position 487. The E487K polymorphism is a semi-dominant polymorphism, and results in an ALDH2 tetramer that has significantly lower enzymatic activity than "wild-type" ALDH2. Thus, subjects who are heterozygous or homozygous for the ALDH2*2 allele have much lower in vivo ALDH2 activity levels than subjects who are homozygous for the "wild-type" ALDH2 allele. The subjects with such an ALDH2 deficiency gene, e.g., heterozygous or homozygous for the ALDH2*2 allele, are expected to benefit from treatment with a compound of the invention, because the level of ALDH2 activity in such subject is particularly low, and any increase of ALDH2 activity levels would be expected to provide a therapeutic effect.

Approximately 40% of the East Asian population carries the semi-dominant ALDH2*2 allele. Such subjects can be characterized by a response to ethanol consumption that includes one or more of facial flushing, nausea, and tachycardia. Subjects who are heterozygous or homozygous for the ALDH2*2 allele are suitable for treatment with a subject method involving administration of a compound of the invention.

The compounds of formula (I) or a pharmaceutically acceptable salts, solvates, ester, or prodrugs thereof, can be used to sequester aldehydes in a subject exposed to alcohol or aldehyde. The compounds of the invention can be used as aldehyde sequestering agents. The sequestering agent can be administered before, after, or contemporaneous with alcohol consumption and/aldehyde exposure. A compound of the invention can sequester the aldehyde in a subject by e.g., binding or reacting with the aldehyde to form a stable and non-toxic form, and thus preventing the aldehyde from causing damaging effects in the subject.

In some embodiments, the compound of formula (I) or pharmaceutically acceptable salts, solvates, ester, or prodrug thereof can be administered in combination with an opioid receptor antagonist to treat or prevent alcohol-related diseases and/or conditions. The opioid antagonist include e.g., naltrexone, which is a competitive antagonists that binds to the opioid receptors with higher affinity than agonists but do not activate the receptors. This effectively blocks the receptor, preventing the body from responding to opiates and endorphins. Naltrexone is also a partial inverse agonist, which can be used for the treatment or prevention of opioid addiction.

In one embodiment, the present invention relates to a method of treating and/or preventing alcohol intolerance, alcohol addiction, an alcohol abuse disorder, alcohol intoxication, alcohol dependence, alcohol poisoning, or symptoms of alcohol consumption, the method comprising administering to a subject an effective amount of a compound or pharmaceutical composition of formula (I) or a pharmaceutically acceptable salt, solvate, ester, or prodrug thereof. In one embodiment, the alcohol poisoning is methanol poisoning. In one embodiment, the alcohol poisoning is acute alcohol poisoning. In one embodiment, the alcohol intoxication is acute alcohol intoxication. In one embodiment, the symptom of alcohol consumption is a hangover symptom. In another embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In one embodiment, the method of treating and/or preventing alcohol intolerance, alcohol addiction, an alcohol abuse disorder, alcohol intoxication, alcohol dependence, alcohol poisoning, or symptoms of alcohol consumption further comprising administering an opioid receptor antagonist. In one embodiment, the opioid receptor antagonist is naltrexone.

In one embodiment, the present invention relates to a method of sequestering aldehyde in a subject exposed to alcohol or aldehyde, comprising administering to the subject an effective amount of a compound or pharmaceutical composition of formula (I) or a pharmaceutically acceptable salt, solvate, ester, or prodrug thereof.

In one embodiment, the present invention relates to a method of reducing a level of an aldehyde present at a toxic level in a subject to below the toxic level, the method comprising administering to the subject an effective amount of a compound or pharmaceutical composition of the invention, wherein the aldehyde is a biogenic aldehyde or a xenogenic aldehyde. In one embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (HNE). In one embodiment, the xenogenic aldehyde is an environmental aldehyde that is ingested or inhaled.

In one embodiment, the present invention relates to a method of sequestering aldehyde in a subject in need thereof exposed to alcohol or aldehyde, comprising administering to the subject an effective amount of a compound of formula (I), or a pharmaceutically acceptable salt, solvate, ester, or prodrug thereof.

In one embodiment, the present invention relates to a method of reducing a level of an aldehyde present at a toxic level in a subject in need thereof to below the toxic level, the method comprising administering to the subject an effective amount of a compound of the invention, or a pharmaceutically acceptable salt, solvate, ester, or prodrug thereof, wherein the aldehyde is a biogenic aldehyde or a xenogenic aldehyde. In one embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (4 HNE). In one embodiment, the xenogenic aldehyde is an environmental aldehyde that is ingested or inhaled.

In one embodiment, the present invention relates a method of treating and/or preventing alcohol intolerance, alcohol addiction, an alcohol abuse disorder, alcohol intoxication, alcohol dependence, alcohol poisoning, or symptoms of alcohol consumption, the method comprising administering to a subject in need thereof an effective amount of a compound of the invention, or a pharmaceutically acceptable salt, solvate, ester, or prodrug thereof. In one embodiment, the alcohol poisoning is methanol poisoning. In one embodiment, the alcohol poisoning is acute alcohol poisoning. In one embodiment, the alcohol intoxication is acute alcohol intoxication. In one embodiment, the symptom of alcohol consumption is a hangover symptom. In another embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In one embodiment, the method of treating and/or preventing alcohol intolerance, alcohol addiction, an alcohol abuse disorder, alcohol intoxication, alcohol dependence, alcohol poisoning, or symptoms of alcohol consumption further comprising administering an opioid receptor antagonist. In one embodiment, the opioid receptor antagonist is naltrexone.

Another aspect of the present invention relates to a compound for use in a method for sequestering aldehyde in a subject exposed to alcohol or aldehyde, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof.

In another aspect, the present invention relates to a compound for use in a method for reducing a level of an aldehyde present at a toxic level in a subject to below the toxic level, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the aldehyde is a biogenic aldehyde or a xenogenic aldehyde. In another embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (4 HNE). In yet another embodiment, the xenogenic aldehyde is an environmental aldehyde that is ingested or inhaled.

Another aspect of the present invention relates to a compound for use in a method for treating and/or preventing alcohol intolerance, alcohol addiction, an alcohol abuse disorder, alcohol intoxication, alcohol dependence, alcohol poisoning, or symptoms of alcohol consumption, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug thereof. In one embodiment, the alcohol poisoning is methanol poisoning. In another embodiment, the alcohol poisoning is acute alcohol poisoning. In yet another embodiment, the alcohol intoxication is acute alcohol intoxication. In another embodiment, the symptom of alcohol consumption is a hangover symptom. In yet another embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In another aspect, the present invention relates to a compound for use in a combination therapy for treating and/or preventing alcohol intolerance, alcohol addiction, an alcohol abuse disorder, alcohol intoxication, alcohol dependence, alcohol poisoning, or symptoms of alcohol consumption, wherein the compound is a compound of formula (I), or a pharmaceutically acceptable salt, solvate, ester, or prodrug thereof, or a pharmaceutical composition of a compound of formula (I), or a pharmaceutically acceptable salt, solvate, ester, or prodrug, thereof, used in combination with an opioid receptor antagonist. In one embodiment, the opioid receptor antagonist is naltrexone.

Methods of Detoxification

The present invention provides methods of reducing the levels of a toxic compound in a subject, the methods generally involving administering to a subject an effective amount of a compound of the invention. The present invention provides methods of treating and/or preventing a disorder associated with or resulting from a toxic level of a compound (e.g., a xenogenic aldehyde; a biogenic aldehyde; or a compound that, when ingested, absorbed, or inhaled, gives rise to an aldehyde substrate for ALDH2), the methods generally involving administering to subject an effective amount of a compound of the invention, where the level of the compound in the subject is reduced to a non-toxic level.

Toxic compounds whose levels can be reduced in a subject using a subject method include, but are not limited to, ethanol, methanol, ethylene glycol monomethyl ether, xenogenic aldehydes, biogenic aldehydes, and an aldehyde produced by in vivo metabolism of a compound that is ingested, absorbed, or inhaled. A compound of the invention is administered in an amount that is effective, when administered in one or more doses, to reduce a toxic level of a compound such as ethanol, methanol, ethylene glycol monomethyl ether, xenogenic aldehydes, biogenic aldehydes, or an aldehyde produced by in vivo metabolism of a compound that is ingested, absorbed, or inhaled. In some embodiments, the aldehyde is acetaldehyde.

The present invention provides methods of reducing aldehyde toxicity, the methods generally involving administering an effective amount of a compound of the invention. In some embodiments, an effective amount of a compound of the invention is an amount that is effective to reduce one or more symptoms of aldehyde toxicity. For example, in some embodiments, an effective amount of a compound of the invention is an amount that is effective to reduce one or more symptoms of excess ethanol consumption, where such symptoms include, e.g., headache, dehydration, fatigue, nausea, vomiting, diarrhea, weakness, anxiety, irritability, photophobia, phonophobia, etc.

In another aspect, the present invention relates to a compound for use in a method for reducing aldehyde toxicity in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof.

Another aspect of the present invention relates to a compound for use in the manufacture of a medicament for reducing aldehyde toxicity in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof.

Subjects suitable for treatment with a compound of the invention include subjects who have toxic levels of an aldehyde, e.g., via ingestion of a toxic compound, via inhalation of a toxic compound, via ingestion or inhalation of toxic levels of a compound, or via production of the aldehyde during normal metabolism. Such subjects include, but are not limited to, subjects who have ingested or inhaled ethanol, methanol, ethylene glycol monomethyl ether, or other xenogenic or biogenic aldehyde compounds. For example, such subjects include subjects who have ingested or inhaled pesticides, fungicides, or other such compounds; subjects who have consumed excessive levels of ethanol; and the like.

Methods of Treating and/or Preventing Conditions Involving Ischemic Stress

The present invention provides methods for treating and/or preventing conditions involving ischemic stress, including prophylactic methods, in an individual, the methods generally involving administering to an individual in need thereof an effective amount of a subject ALDH2 agonist. Conditions involving ischemic stress include ischemic conditions, ischemic events, conditions that can give rise to ischemia, and conditions that result from an ischemic event. Conditions involving ischemic stress that are amenable to treatment with a subject method include ischemia that result from any condition or event, including, but not limited to, myocardial infarct (e.g., acute myocardial infarction), cardiac surgery, brain trauma, cerebrovascular disease, stroke, spinal cord injury, subarachnoid hemorrhage, major surgery in which ischemia to variety of organs occur, organ transplantation, limb ischemia (e.g., resulting from Type 1 or Type 2 diabetes), and the like.

The methods of the present disclosure includes administering an effective amount of a compound or a composition of formula (I) or a pharmaceutically acceptable salt, solvate, ester, or prodrug thereof for treating and/or preventing conditions involving ischemic stress. The dosage and method of administering the compound or composition of formula (I) or a pharmaceutically acceptable salt, solvate, ester, or prodrug thereof for treating and/or preventing conditions involving ischemic stress are specified in this disclosure and are incorporated by reference herein. In one embodiment, the conditions involving ischemic stress are selected from ischemia resulting from cardiac surgery, ischemia resulting from stroke, ischemia resulting from brain trauma, ischemia resulting from prolonged surgery, and ischemia resulting from organ transplantation.

For example, a compound of formula (I) or a pharmaceutically acceptable salt, solvate, ester, or prodrug thereof can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

A compound of formula (I) or a pharmaceutically acceptable salt, solvate, ester, or prodrug thereof, for treating and/or preventing conditions involving ischemic stress can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. A variety of routes are contemplated, including topical, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The methods of the present disclosure also include administering to a subject an effective amount of a compound of formula (I) or a pharmaceutically acceptable salt, solvate, ester, or prodrug thereof in conjunction with additional agents useful in the treatment of conditions involving ischemic stress. The dosage and method of administering the compound or composition of formula (I) or a pharmaceutically acceptable salt, solvate, ester, or prodrug thereof, for treating and/or preventing conditions involving ischemic stress, in combination with additional agents useful in the treatment of conditions involving ischemic stress are specified in this disclosure and are incorporated by reference herein.

The present invention provides methods for treating and/or preventing conditions involving ischemic stress by increasing the activity and/or level of ALDH2. The methods generally involve administering to a subject afflicted with conditions involving ischemic stress an effective amount of a compound of formula (I) or a pharmaceutically acceptable salt, solvate, ester, or prodrug thereof, for increasing the level and/or activity of ALDH2. The dosage and method of administering the compound or composition of formula (I) or a pharmaceutically acceptable salt, solvate, ester, or prodrug thereof for treating and/or preventing conditions involving ischemic stress are specified in this disclosure and are incorporated by reference herein.

In one embodiment, the present invention relates to a method of reducing the likelihood that a subject will develop conditions involving ischemic stress, the method comprising administering to the subject an effective amount of a compound or composition of the invention.

In one embodiment, the compound or pharmaceutical composition is administered by a route selected from intramuscular, intravenous, subcutaneous, oral, and topical.

In another aspect, the present invention relates to a compound for use in a method for treating and/or preventing conditions involving ischemic stress in a subjectin need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the conditions involving ischemic stress are selected from ischemia resulting from cardiac surgery, ischemia resulting from stroke, ischemia resulting from brain trauma, ischemia resulting from prolonged surgery, and ischemia resulting from organ transplantation.

Another aspect of the present invention relates to a compound for use in the manufacture of a medicament for treating and/or preventing conditions involving ischemic stress in a subject in need thereof, wherein the compound is selected from a compound of formula (I), or a pharmaceutically acceptable salt, solvate, ester, or prodrug thereof, and a pharmaceutical composition of a compound of formula (I), or a pharmaceutically acceptable salt, solvate, ester, or prodrug, thereof. In one embodiment, the conditions involving ischemic stress are selected from ischemia resulting from cardiac surgery, ischemia resulting from stroke, ischemia resulting from brain trauma, ischemia resulting from prolonged surgery, and ischemia resulting from organ transplantation.

Subjects suitable for treatment with a subject agent and/or a subject method, where the agent increases a level and/or activity of ALDH2, include subjects who are afflicted with conditions involving ischemic stress.

Subjects suitable for treatment with a subject agent and/or a subject method, where the agent increases a level and/or activity of ALDH2, include subjects who are scheduled to undergo cardiac surgery or who have undergone cardiac surgery; subjects who have experienced a stroke;

subjects who have suffered brain trauma; subjects who have prolonged surgery; and subjects who will be subjected to organ transplantation.

Methods of Synthesis

In one embodiment, the present invention relates to a method of synthesizing a compound of the invention, or a pharmaceutically acceptable salt, solvate, ester or prodrug thereof.

General Procedure for the Preparation of Benzyl Amines:

The benzyl amines applied in this invention are either commercially available or are prepared as described in the scheme below from the following commercially available starting materials: 1) benzonitriles; 2) benzaldehydes; 3) benzyl chlorides; and 4) benzoic acids.

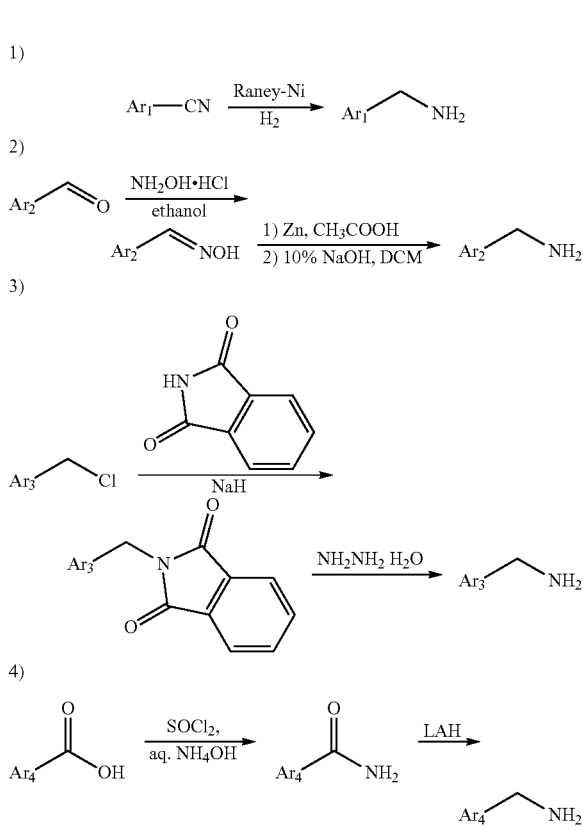

General Procedure for the Preparation of the Compounds of Formula (II):

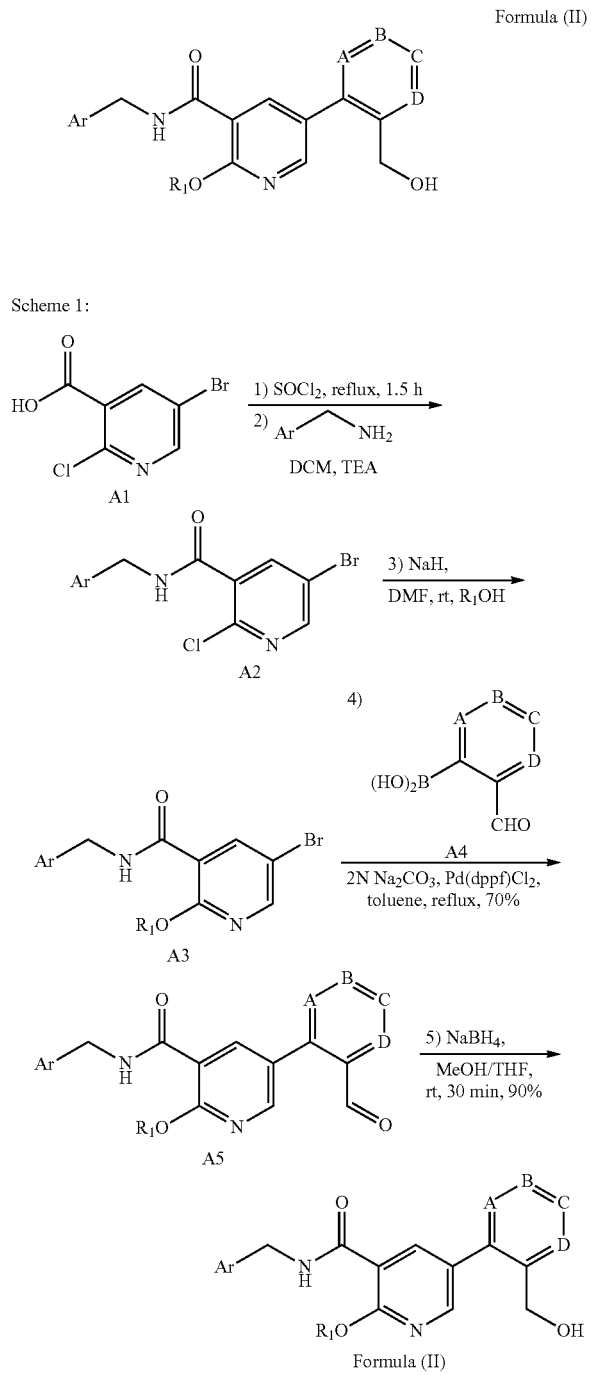

Scheme 1:

Preparation of Compound AC1 According to Scheme 1

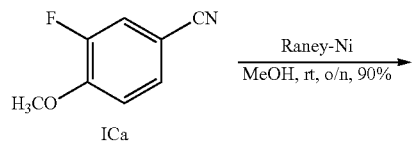

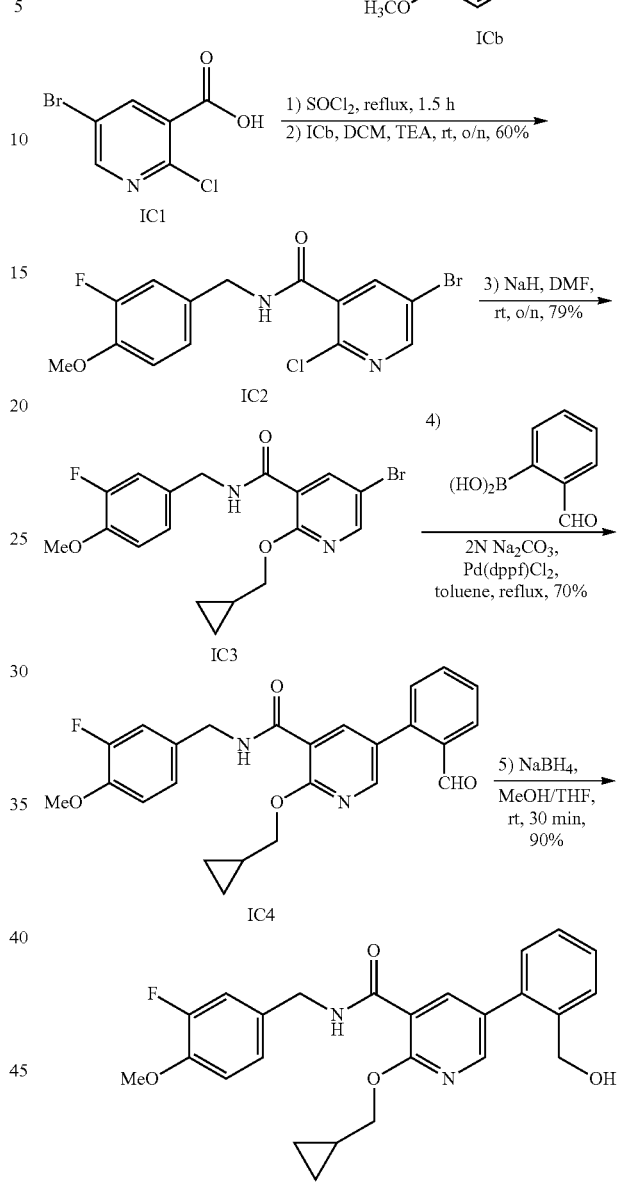

The present disclosure includes a procedure for the preparation of Intermediate Compound ICb. ICb is prepared by adding to a solution of commercially available ICa in an alcohol, e.g., methanol, a catalyst such as a fine grained solid composite, e.g., a nickel-aluminum alloy such as Raney-Nickel (Raney-Ni). The reaction is stirred at room temperature for several hours, e.g., overnight. The solid product of the reaction is removed by filtration, and washed with an alcohol, e.g., methanol. A clear solution is collected as the filtrate, which is then concentrated at reduced pressure to obtain a yellow oil of ICb.

The present disclosure provides a procedure for the preparation of Intermediate Compound (IC2). In this procedure, a solution of Intermediate Compound (IC1) in an organochlorine compound, e.g., thionyl chloride (SOCl$_2$), is refluxed for about 1-2 hours, and then concentrated to obtain a crude acetyl chloride intermediate. To a solution of ICb, a base, e.g., triethylamine, in an organic solvent, e.g., dichloromethane (DCM), the acetyl chloride intermediate obtained previously in dichloromethane is added. After stirring for several hours, e.g., overnight at room temperature (rt), the reaction is diluted with water. The aqueous portion is separated and an organic solvent, e.g., dichloromethane, is used for extraction. The combined organic layers are washed with a salt solute, e.g., brine, dried over a drying agent, e.g., sodium sulfate ($Na_2SO_4$), concentrated, and triturated to obtain IC2 as a white solid.

The present disclosure provides a procedure for the preparation of Intermediate Compound (IC3). At room temperature, an insoluble base, e.g., sodium hydride (NaH), is added to a solution of an alcohol, e.g., cyclopropanemethanol, in a polar aprotic organic solvent, e.g., dimethylformamide (DMF). After stirring about one hour, the reaction is cooled to about 0° C. before adding IC2 dissolved in a non-polar aprotic solvent, e.g., DMF. After stirring several hours, e.g., overnight, at room temperature, the reaction is quenched with water and extracted with a solvent/diluent, e.g., ethyl acetate (EA). The combined organic layer that is generated is washed with a salt solute e.g., brine, dried over a drying agent, e.g., sodium sulfate ($Na_2SO_4$), concentrated, and triturated to afford IC3 as a white solid.

The present disclosure provides a procedure for the preparation of Intermediate Compound 4 (IC4). To a solution of IC3 and a boronic acid, e.g., (2-formylphenyl)boronic acid, in a non-polar solvent, e.g., toluene, is added an aqueous base solution, e.g., sodium carbonate solution, and a palladium (II) catalyst, e.g., [1,1'-bis(diphenylphosphino)ferrocene]dichloropalladium(II) ($Pd(dppf)Cl_2$). The reaction is then heated for about 3 hours. The reaction is quenched with water. The aqueous portion is separated and extracted with a polar organic solvent, e.g., ethyl acetate. The combined organic layers are washed with a salt solute, e.g., brine, dried over a drying agent, e.g., sodium sulfate ($Na_2SO_4$), and concentrated to afford a crude product, which is purified by silica gel chromatography to obtain IC4 as a white solid.

The present disclosure provides a procedure for the preparation of AC1. To a solution of IC4 in a first organic solvent, e.g., tetrahydrofuran (THF), and a second organic solvent, e.g., methanol, a reducing agent, e.g., sodium borohydride ($NaBH_4$) is added. After stirring for about 30 minutes, the reaction is quenched with cold water and the pH of the reaction mixture is adjusted to a pH value of about 5 with and acid, e.g. hydrochloric acid. After stirring for about an additional 15 minutes, the reaction mixture is extracted with a polar organic solvent, e.g., ethyl acetate. The combined organic layers are washed with a salt solute, e.g., brine, dried over a drying agent, e.g., sodium sulfate ($Na_2SO_4$), and concentrated to afford AC1 as a white solid.

Scheme 2: Alternate scheme for synthesizing compounds of formula (II)

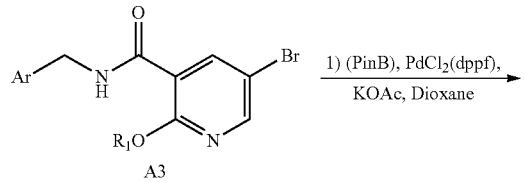
A3

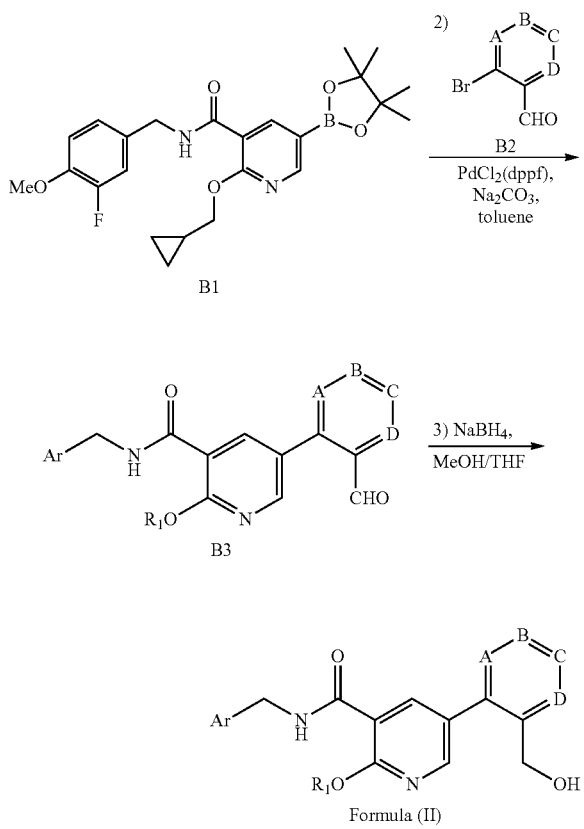

General Procedure for the Preparation of the Compounds of Formula (III):

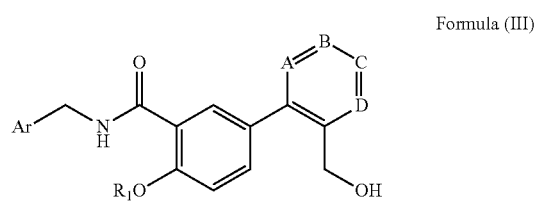

Scheme 3:

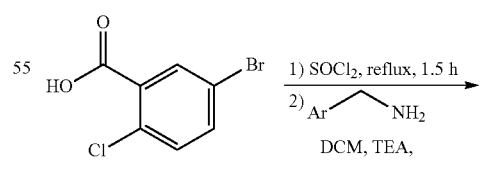

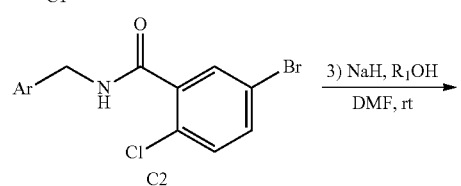

-continued

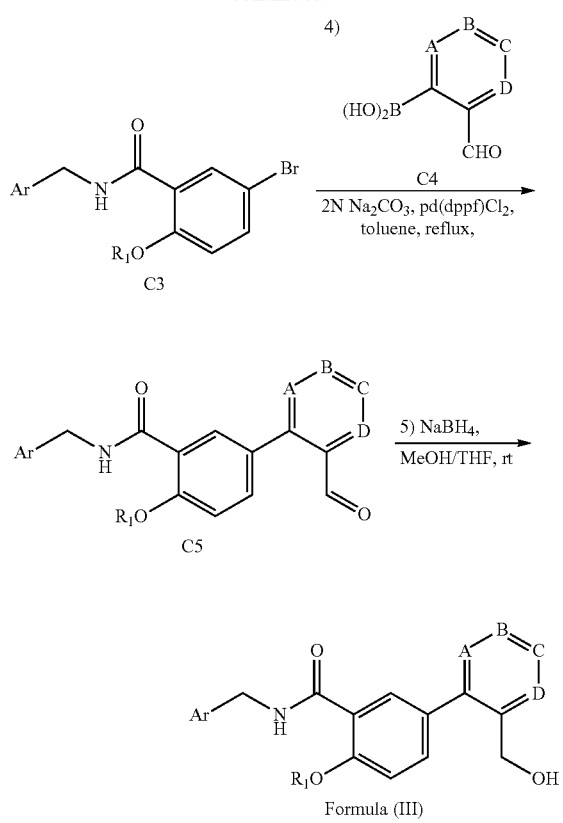

Formula (III)

Preparation of AC2 Via Scheme 3:

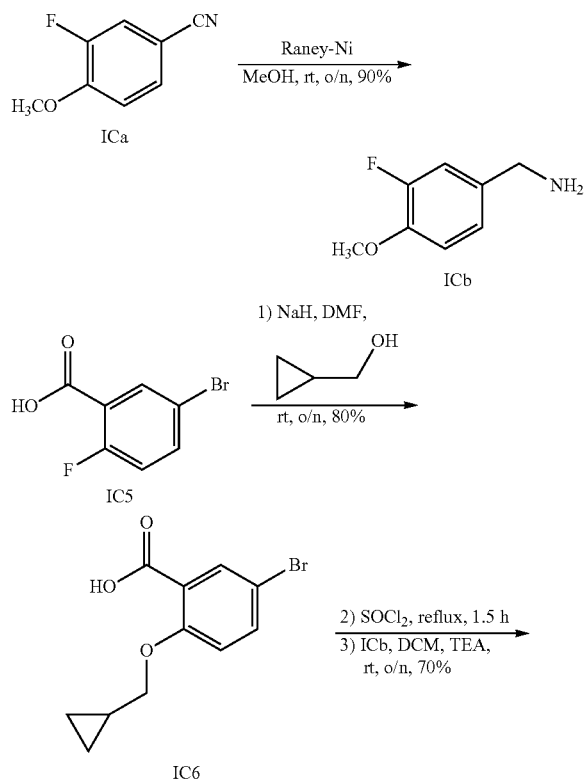

-continued

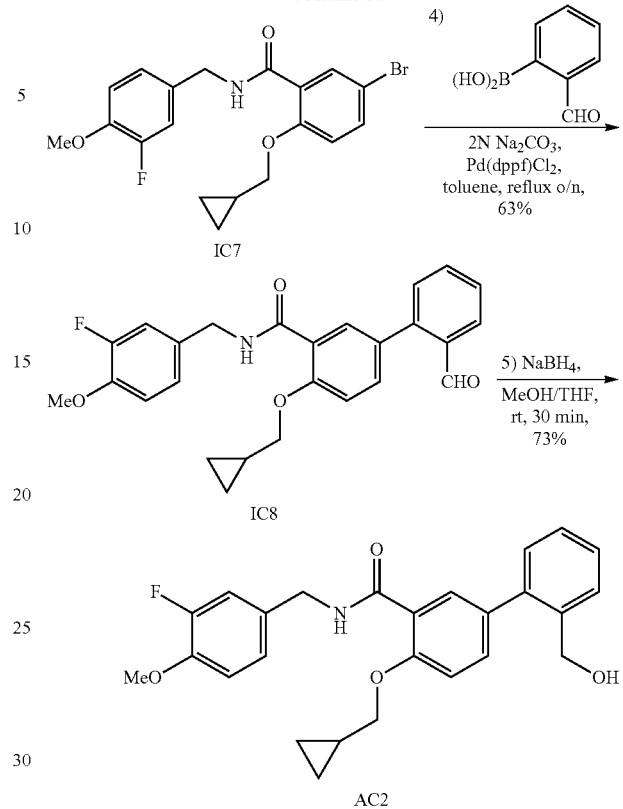

AC2

The present disclosure includes a procedure for the preparation of Intermediate Compound ICb. ICb is prepared by adding to a solution of commercially available ICa in an alcohol, e.g., methanol, a catalyst such as a fine grained solid composite, e.g., a nickel-aluminum alloy such as Raney-Nickel (Raney-Ni). The reaction is stirred at room temperature for several hours, e.g., overnight. The solid product of the reaction is removed by filtration, and washed with an alcohol, e.g., methanol. A clear solution is collected as the filtrate, which is then concentrated at reduced pressure to obtain a yellow oil of ICb.

The present disclosure includes a procedure for the preparation of Intermediate Compound IC6. To a solution of an alcohol, e.g., cyclopropanemethanol dissolved in a non-polar aprotic solvent, e.g., dimethylformamide, at about 0° C. is added an insoluble base, e.g., sodium hydride (NaH). The mixture is stirred for about 1 hour. Then a solution of ICa in an organic solvent, e.g., dimethylformnamide (DMF) is added. The reaction mixture is stirred at about 75° C. overnight. After cooling to room temperature, the reaction solution is acidified to a pH value of about 5 at about 0° C. with acid, e.g., hydrochloric acid, and diluted with water. The aqueous layer is separated and extracted with a polar organic solvent, e.g., ethyl acetate. The organic layer is washed with brine, dried over a drying agent, e.g., sodium sulfate, and concentrated, to obtain a crude material, which is purified by silica gel chromatography to give compound IC6.

The present disclosure includes a procedure for the preparation of Intermediate Compound IC7. A mixture of compound IC6 in an organochlorine compound, e.g., thionyl chloride (SOCl$_2$), is heated to reflux for about 1-2 hours, cooled to room temperature and concentrated. The resulting residue is dissolved in an organic solvent, e.g., dichloromethane and the solution is added dropwise to a mixture of (3-fluoro-4-methoxyphenyl)methanamine (ICb) and a base, e.g., triethylamine, dissolved in an organic solvent, e.g., dichloromethane, at about 0° C. The reaction mixture is stirred for several hours, e.g., overnight, at about room temperature. The next day, the reaction mixture is quenched with water and extracted with an organic solvent, e.g., dichloromethane. The organic layer is separated and washed with a salt solute, e.g., brine, dried over a drying agent, e.g., sodium sulfate, and concentrated. The crude material is purified by silica gel chromatography to afford compound IC7 as a solid.

The present disclosure includes a procedure for the preparation of Intermediate Compound IC8. To a solution of IC7 and a boronic acid, e.g., (2-formylphenyl)boronic acid, in a nonpolar solvent, e.g., toluene, is added a base, e.g, sodium carbonate, and a palladium (II) catalyst, e.g., [1,1'-bis(diphenylphosphino)ferrocene]dichloropalladium(II) (Pd(dppf)Cl$_2$). The reaction mixture is then heated to about 90° C., and stirred for several hours, e.g., overnight. The next day, the reaction mixture is quenched with water and extracted with a polar solvent, e.g., ethyl acetate. The combined organic layers are washed with a salt solute, e.g., brine, dried over a drying agent, e.g., sodium sulfate, and concentrated to afford the crude product, which is purified by silica gel chromatography with a PE:EA=5:1 mixture to obtain IC8 as a white solid.

The present disclosure includes a procedure for the preparation of Compound AC2. To a solution of IC8 in two organic solvents, e.g., tetrahydrofuran and methanol is added a reducing agent, e.g., sodium borohydride. After stirring for about 30 minutes, the reaction is quenched by cold water and the pH of the reaction mixture is adjusted to a pH value of about 5 with acid, e.g., hydrochloric acid. After stirring for about an additional 15 minutes, the reaction mixture is extracted with an organic solvent, e.g., ethyl acetate. The combined organic layers are washed with a salt solute, e.g., brine, dried over a drying agent, e.g., sodium sulfate, and concentrated to afford the crude product, which is purified by silica gel chromatography to obtain AC2.

Scheme 4: An alternate scheme for synthesis of the compounds of formula (III)

Preparation of AC6 according to scheme 4:

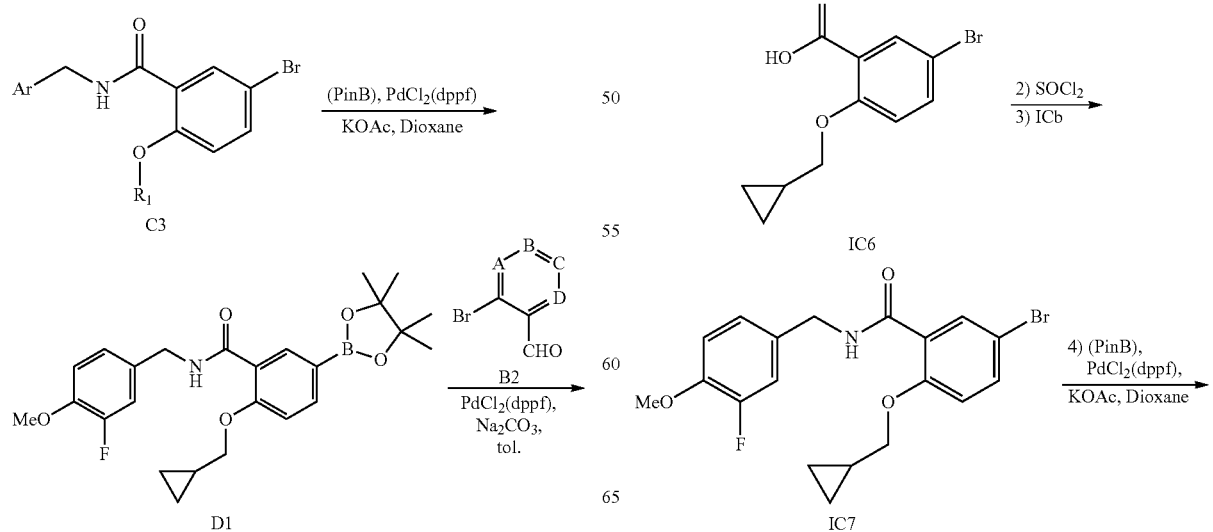

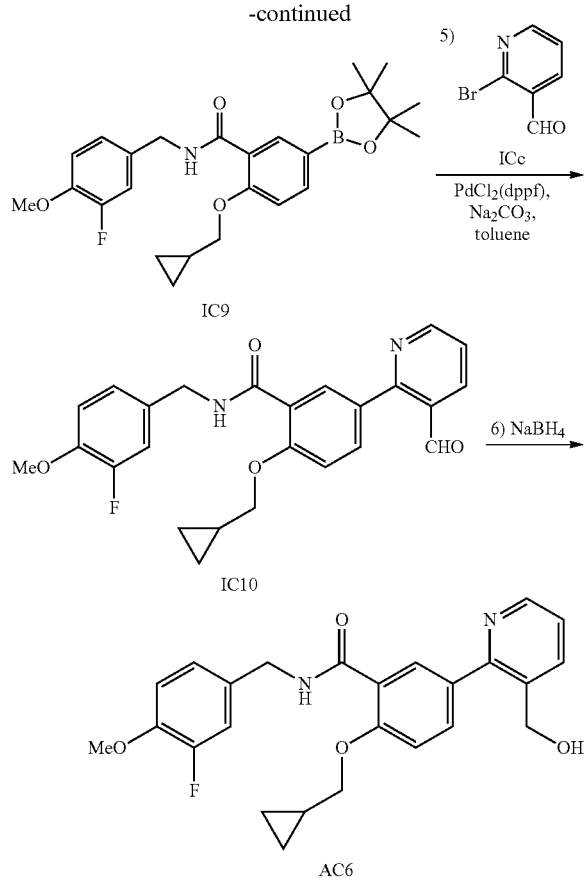

The present disclosure includes a procedure for the preparation of Intermediate Compound ICb. A mixture of ICa and a catalyst such as a fine grained solid composite, e.g., a nickel-aluminum alloy such as Raney-Nickel in an alcohol solvent e.g., methanol, is stirred for several hours, e.g., overnight, at about room temperature under a hydrogen atmosphere. The next day, the mixture is filtered and concentrated to obtain compound ICb, which is used for next step without further purification.

The present disclosure includes a procedure for the preparation of Intermediate Compound IC6. To a solution of an alcohol, e.g., cyclopropanemethanol, a non-polar organic solvent, e.g., dimethylformamide, at about 0° C. is added an insoluble base, e.g., sodium hydride. The mixture is stirred for about 1 hour. Then a solution of compound ICb in a non-polar solvent, e.g., dimethylformamide, is added. The mixture is stirred at about 75° C. overnight and monitored by TLC. After cooling to room temperature the next day, the reaction mixture is acidified to a pH value of about 5 at about 0° C. with an acid, e.g., hydrochloric acid, and diluted with water. The aqueous layer is separated and extracted with an organic solvent, e.g., ethyl acetate. The separated organic layer is washed with a salt solute, e.g., brine, dried over a drying agent, e.g., sodium sulfate, concentrated, and purified by crystallization from ethyl acetate to give compound IC6 as a light-yellow solid.

The present disclosure includes a procedure for the preparation of Intermediate Compound IC7. A mixture of IC6 in an organochlorine compound, e.g., thionyl chloride ($SOCl_2$), is heated to reflux for about 1.5 hours, cooled to room temperature and concentrated directly. The resulting residue is dissolved in an organic solvent, e.g., dichloromethane, and the solution is added dropwise into a mixture of compound IC6 and a base, e.g., triethylamine, dissolved in an organic solvent, e.g., dichloromethane, at about 0° C. The mixture is then stirred at about room temperature for several hours, e.g., overnight, and monitored by TLC. The next day, the reaction mixture is quenched with water and the separated aqueous layer is extracted with an organic solvent, e.g., dichloromethane. The combined organic layers are washed with a salt solute, e.g., brine, dried over a drying agent, e.g., sodium sulfate, and concentrated. The crude material is purified by silica gel column chromatography (PE: EA=2:1 mixture) to afford compound IC7 as a white solid.

The present disclosure includes a procedure for the preparation of Intermediate Compound IC10. To a solution of IC7 and a palladium ligand, e.g., bis (pinacolato)diboron, an organic solvent, e.g. dioxane, and a weak base, e.g., potassium acetate, is added a palladium (II) catalyst, e.g., [1,1'-bis(diphenylphosphino)ferrocene]dichloropalladium(II) (Pd(dppf)$Cl_2$). The resulting mixture is heated to about 95° C. After refluxing for about 3 hours, the reaction is diluted with water. The aqueous layer is extracted with a polar solvent, e.g., ethyl acetate. The combined organic layers are washed with a salt solute, e.g., brine, dried over a drying agent, e.g., sodium sulfate, and concentrated to afford compound IC9, which is used for next step without purification. The crude compound IC9 is re-dissolved in a non-polar solvent, e.g., toluene, and 3-bromo-4-formylpyridine, and a palladium (II) catalyst, e.g., [1, 1'-bis(diphenylphosphino)ferrocene]dichloropalladium(II) (Pd(dppf)$Cl_2$), a weak base, e.g., sodium carbonate ($Na_2CO_3$), are added. The mixture is heated to about 95° C. After refluxing for about 5 hours, the reaction is diluted with water. The aqueous layer is separated and extracted with a polar solvent, e.g., ethyl acetate, washed with a salt solute, e.g., brine, dried over a drying agent, e.g., sodium sulfate, and concentrated. The crude material is purified by silica gel column chromatography and subsequent recrystallization to afford IC10 as an off-white powder.

The present disclosure includes a procedure for the preparation of Compound AC6. To a solution of IC10 dissolved in an alcoholic solvent, e.g., methanol, and a second organic solvent, e.g., tetrahydrofuran, a reducing agent, e.g., sodium borohydride, is added. The mixture is stirred at room temperature for about 30 minutes. The reaction is diluted with ice-water, and the pH of the reaction mixture is adjusted to a pH value of about 6 with acid, e.g., hydrochloric acid. The aqueous layer is separated and extracted with an organic solvent, e.g., ethyl acetate. The organic layer is separated and washed with a salt solute, e.g., brine, and dried over a drying agent, e.g., sodium sulfate and concentrated. The crude material is recrystallized to obtain AC6 as a white solid.

Scheme 5: Preparation of AC14

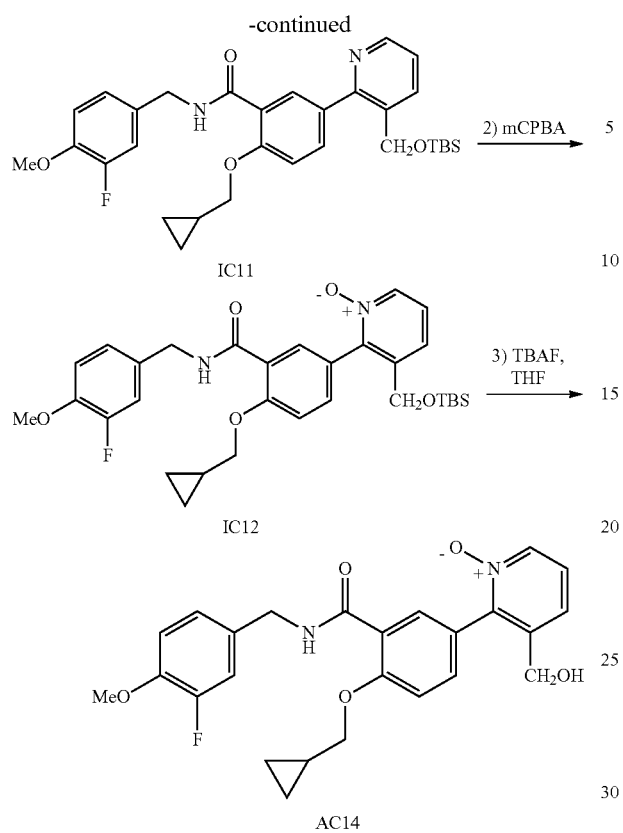

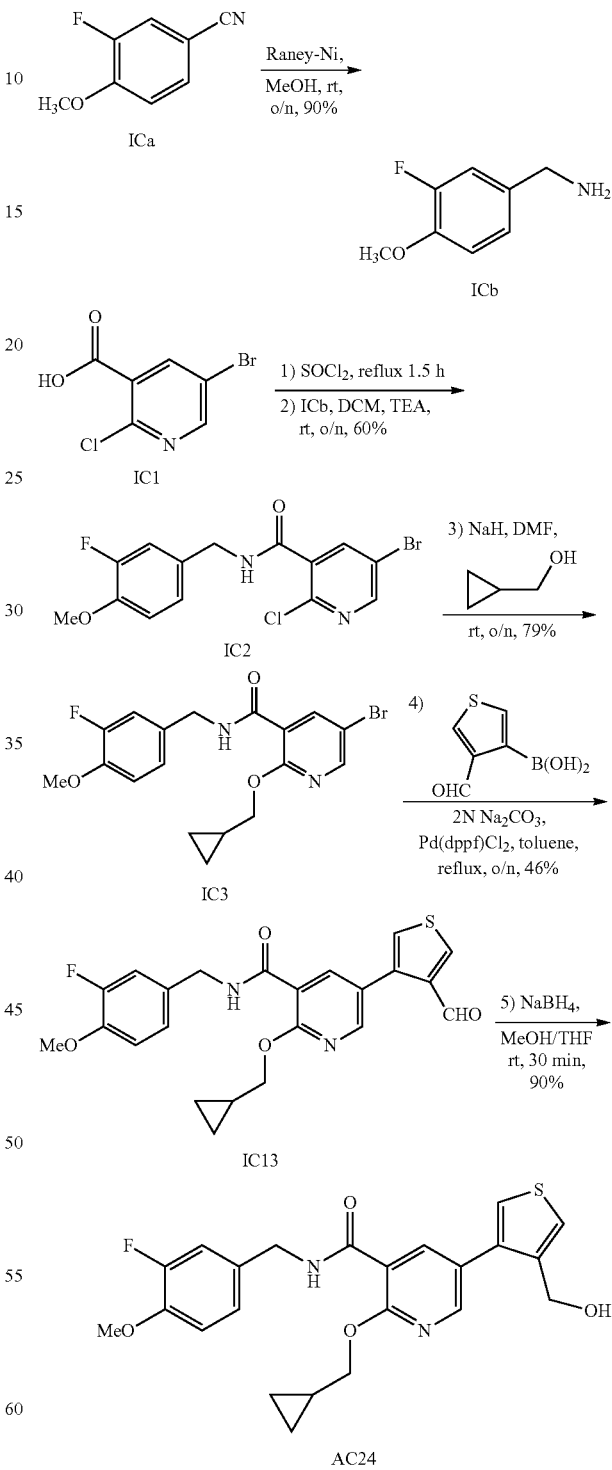

Scheme 6: Preparation of AC24

The present disclosure includes a procedure for the preparation of Intermediate Compound IC11. A mixture of AC6, a silyl chloride, e.g., tert-butyldimethylsilyl chloride (TB-SCl), a catalyst, e.g., dimethylamino pyridine (DMAP) and a weak base, e.g., imidazole in an organic solvent, e.g., dichloromethane is stirred at about 25° C. for about 2 hours. The reaction is monitored by TLC. The mixture is then quenched with water. The aqueous layer is separated and extracted with a polar organic solvent, e.g., dichloromethane. The combined organic layers are washed with a salt solute, e.g., brine, dried over a drying agent, e.g., sodium sulfate, concentrated, and purified by silica gel column chromatography to obtain compound IC11 as a white solid.

The present disclosure includes a procedure for the preparation of Intermediate Compound IC12. To a solution of IC11 dissolved in an organic solvent, e.g., dichloromethane, is added an oxidizing agent, e.g., 3-chloroperbenzoic acid (m-CPBA). The reaction mixture is stirred at about room temperature for about 3.5 hours, and then quenched with a sulfite, e.g., sodium sulfite ($Na_2SO_3$). The aqueous layer is separated and extracted with an organic solvent, e.g., dichloromethane. The combined organic layers are washed with a base, e.g., sodium carbonate, a salt solute, e.g., brine, dried over a drying agent, e.g., sodium sulfate and concentrated to obtain IC12, which is used without further purification.

The present disclosure includes a procedure for the preparation of Compound AC14. To a solution of IC12 in an organic solvent, e.g., tetrahydrofuran, a solution of tetrabutylammonium fluoride is added. The mixture is stirred at about room temperature for about 15 minutes. The reaction progress is monitored by TLC. The reaction mixture is diluted with water. The aqueous layer is extracted with an organic solvent, e.g., ethyl acetate. The combined organic layer is washed with a salt solute, e.g., brine, dried over a drying agent, e.g., sodium sulfate, concentrated, and purified by preparative thin layer chromatography to obtain AC14 as a white solid.

The present disclosure includes a procedure for the preparation of Intermediate Compound ICb. To a solution of compound ICa in an alcoholic solvent, e.g. methanol is added a catalyst such as a fine grained solid composite, e.g., a nickel-aluminum alloy such as Raney-Nickel. The reaction mixture is stirred at about room temperature for several hours, e.g., overnight. The next day, the solid is removed by filtration, and washed with a polar solvent, e.g., methanol. The clear filtrate solution is concentrated at reduced pressure to obtain compound ICb as a yellow oil.

The present disclosure includes a procedure for the preparation of Intermediate Compound IC2. A solution of IC1 in an organochlorine compound, e.g., thionyl chloride (SOCl$_2$), is refluxed for about 1.5 hours, and then concentrated to obtain the crude acetyl chloride intermediate. To a solution of compound ICb, a base, e.g., triethylamine, in an organic solvent, e.g., dichloromethane, is added the prior prepared acetyl chloride intermediate dissolved in an organic solvent, e.g., dichloromethane, at about 0° C. After stirring for several hours, e.g., overnight, at about room temperature, the reaction is diluted with water. The aqueous layer is separated and extracted with an organic solvent, e.g. dichloromethane. The combined organic layers are washed with a salt solute, e.g., brine, dried over a drying agent, e.g., sodium sulfate, concentrated, and triturated to obtain IC2 as a white solid.

The present disclosure includes a procedure for the preparation of Intermediate Compound IC3. To a solution of an alcohol, e.g., cyclopropanemethanol, in a non-polar aprotic solvent, e.g., dimethylformamide, is added an insoluble base, e.g., sodium hydride, at about room temperature. After stirring about 1 h, the reaction mixture is cooled to about 0° C., and compound IC2 dissolved in a non-polar aprotic solvent, e.g. dimethylformamide, is added. After stirring for several hours, e.g., overnight, at about room temperature, the reaction is quenched with water. The aqueous layer is separated and extracted with an organic solvent, e.g., ethyl acetate. The combined organic layers are washed with a salt solute, e.g., brine, dried over a drying agent, e.g., sodium sulfate, concentrated, and triturated to obtain IC3 as a white solid.

The present disclosure includes a procedure for the preparation of Intermediate Compound IC13. To a solution of IC3 and a boronic acid, e.g., (4-formylthiophen-3-yl)boronic acid, dissolved in a non-polar solvent, e.g., toluene, is added a base, e.g., sodium carbonate, and a palladium(II) catalyst, e.g., [1,1'-bis(diphenylphosphino)ferrocene]dichloropalladium(II) (Pd(dppf)Cl$_2$), The reaction mixture is then heated to about 90° C., and stirred for several hours, e.g., overnight. The next day, the reaction is quenched with water. The aqueous layer is extracted with a polar organic solvent, e.g., ethyl acetate. The combined organic layers are washed with a salt solute, e.g., brine, dried over a drying agent, e.g., sodium sulfate and concentrated to afford the crude product, which is purified by preparative thin layer chromatography to obtain IC13 as a white solid.

The present disclosure includes a procedure for the preparation of Compound AC24. To a solution of IC13 dissolved in a first organic solvent, e.g., tetrahydrofuran, and a second organic solvent, e.g., methanol, is added a reducing agent, e.g., sodium borohydride. After stirring for about 30 minutes, the reaction is quenched by cold water and the pH of the reaction mixture is adjusted to a pH value of 5 with acid, e.g., hydrochloric acid. After stirring for an additional 15 minutes, the aqueous layer is separated and extracted with a polar solvent, e.g., ethyl acetate. The combined organic layers are washed with a salt solute, e.g., brine, dried over a drying agent, e.g. sodium sulfate and concentrated to afford AC24 as a white solid.

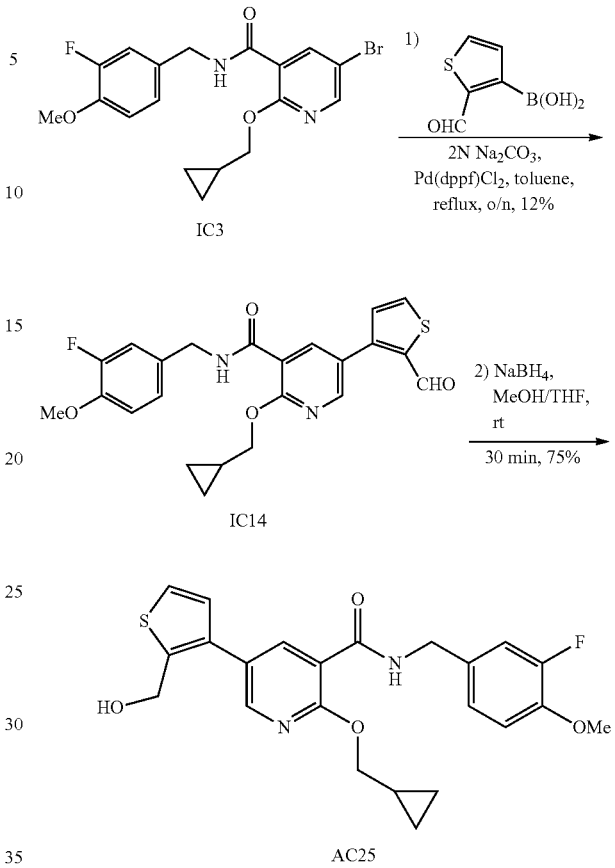

Scheme 7: Preparation of AC25

The present disclosure includes a procedure for the preparation of Intermediate Compound IC14. To a solution of compound IC3 and a boronic acid, e.g., (2-formylthiophen-3-yl)boronic acid in a non-polar solvent, e.g., toluene, is added a base, e.g., sodium carbonate, and a palladium(II) catalyst, e.g., [1,1'-bis(diphenylphosphino)ferrocene]dichloropalladium(II) (Pd(dppf). The reaction is then heated to about 90° C., and stirred for several hours, e.g., overnight. The next day, the reaction mixture is quenched with water. The aqueous layer is separated and extracted with an organic solvent, e.g., ethyl acetate. The combined organic layers are washed with a salt, solute, e.g., brine, dried over a drying agent, e.g., sodium sulfate and concentrated to afford the crude product, which is purified by preparative thin layer chromatography to obtain IC14 as a white solid.

The present disclosure includes a procedure for the preparation of Compound AC25. To a solution of compound IC14 dissolved in a first organic solvent, e.g., tetrahydrofuran and a second organic solvent, e.g., methanol, is added a reducing agent, e.g., sodium borohydride. After stirring for about 30 minutes, the reaction is quenched with cold water and then the pH of the reaction mixture is adjusted to a pH value of about 5 with acid, e.g. hydrochloric acid. After stirring for about an additional 15 minutes, the reaction mixture is partitioned and the aqueous layer is separated and extracted with a polar organic solvent, e.g., ethyl acetate. The combined organic layers are washed with a salt solute, e.g., brine, dried over a drying agent, e.g., sodium sulfate and concentrated to afford IC14 as a white solid.

Scheme 8: Preparation of AC26

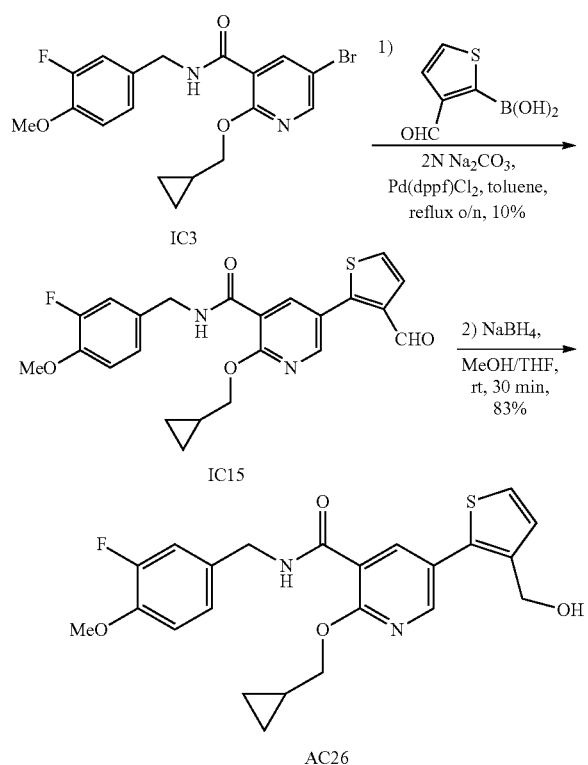

The present disclosure includes a procedure for the preparation of Intermediate Compound IC15. To a solution of compound IC3 and a boronic acid, e.g., (3-formylthiophen-2-yl)boronic acid, dissolved in a non-polar solvent, e.g., toluene is added a base, e.g., sodium carbonate, and a palladium(II) catalyst, e.g., [1,1'-bis(diphenylphosphino)ferrocene] dichloropalladium(II) (Pd(dppf)Cl$_2$. The reaction is then heated to about 90° C., and stirred for several hours, e.g., overnight. The next day, the reaction is quenched with water. The aqueous layer is separated and extracted with a polar solvent, e.g., ethyl acetate. The combined organic layers are washed with a salt, solute, e.g., brine, dried over a drying agent, e.g., sodium sulfate and concentrated to afford a crude product, which is purified by preparative thin layer chromatography to obtain IC15 as a white solid.

The present disclosure includes a procedure for the preparation of Compound IC15. AC26. To a solution of compound IC15 dissolved in a first organic solvent, e.g., tetrahydrofuran and a second organic solvent, e.g., methanol is added a reducing agent, e.g., sodium borohydride. After stirring for about 30 minutes, the reaction mixture is quenched with cold water and the pH of the reaction is adjusted to a pH value of about 5 with acid, e.g., hydrochloric acid. After stirring for about an additional 15 minutes, the reaction mixture is allowed to partition. The aqueous layer is extracted with an organic solvent, e.g., ethyl acetate. The combined organic layers are washed with a salt solute, e.g., brine, dried over a drying agent, e.g., sodium sulfate and concentrated to afford AC26 as a white solid.

Methods in Modulating Enzyme Activity

The compounds of the invention function as modulators of mitochondrial aldehyde dehydrogenase-2 (ALDH2) activity. Agonists of ALDH2 are useful for treating and/or preventing a variety of disorders, including alcohol-related diseases and disorders, cancer, and Fanconi Anemia. Agonists of ALDH2 are also useful for reducing the level in a subject of a compound such as ethanol, methanol, ethylene glycol monomethyl ether, polyvinyl chloride, xenogenic aldehydes, and biogenic aldehydes. Agonists of ALDH2 are also useful for reducing the level in a subject of a compound that, when ingested, absorbed, or inhaled, gives rise to an aldehyde substrate for ALDH2. Antagonists of ALDH2 are useful for treating and/or preventing disorders such as cancer, where the ALDH2 antagonist is used as an adjuvant to a standard cancer therapy. Antagonists of ALDH2 are also useful for treating and/or preventing alcoholism. Antagonists of ALDH2 are also useful for treating and/or preventing narcotic addiction. The present invention provides therapeutic methods involving administering a subject compound, or a subject pharmaceutical composition.

In some embodiments, subjects to be treated are humans. In some embodiments, a human to be treated according to a subject method is one that has two "wild-type" ALDH2 alleles, e.g., the ALDH2 encoded by the two wild-type ALDH2 alleles has a glutamic acid at position 487. In other embodiments, a human to be treated according to a subject method is one that has one or two "ALDH2*2" alleles, e.g., the ALDH2 encoded by one or both ALDH2 alleles comprises a lysine as amino acid position 487. US 2011/0105602 provides details of the amino acid sequence, which is incorporated by reference herein. The E487K polymorphism is a semidominant polymorphism, and results in an ALDH2 tetramer that has significantly lower enzymatic activity than "wild-type" ALDH2. Thus, subjects who are heterozygous or homozygous for the ALDH2*2 allele have much lower in vivo ALDH2 activity levels than subjects who are homozygous for the "wild-type" ALDH2 allele. Subjects who are heterozygous or homozygous for the ALDH2*2 allele are expected to benefit from treatment with a compound of the invention, because the level of ALDH2 activity in such subjects is particularly low, and any increase of ALDH2 activity levels would be expected to provide a therapeutic effect. Any increase in ALDH2 activity would be beneficial in treating conditions such as ischemic disorders, in increasing the responsiveness of such subjects to nitroglycerin, etc.

The use of ALDH2 variants, such as an E487K ALDH2 variant, in screening methods to identify ALDH2 activators (agonists) is also provided. Because the E487K ALDH2 variant has lower enzymatic activity than the "wild-type" ALDH2, the readout for agonist activity of a test compound is more sensitive. The wild-type is represented in this disclosure as ALDH*1/*1. The homozygous mutant allele is represented as ALDH*2/*2, and the heterozygous is represented as ALDH*1/*2.

In some embodiments, a compound that modulates ALDH2 activity modulates a dehydrogenase activity of ALDH2, e.g., the compound modulates dehydrogenase activity in oxidizing an aldehyde (e.g., a xenogenic aldehyde, a biogenic aldehyde, or an aldehyde produced from a compound that is ingested, inhaled, or absorbed) to the corresponding acid. In other embodiments, a compound that modulates ALDH2 activity modulates an esterase activity of ALDH2. In other embodiments, a compound that modulates ALDH2 activity modulates a reductase activity of ALDH2. For example, ALDH2 can convert nitroglycerin to nitric oxide (NO) via its reductase activity.

In some embodiments, a compound that modulates ALDH2 activity modulates a dehydrogenase activity of ALDH2, e.g., in oxidizing an aldehyde (e.g., a xenogenic aldehyde, a biogenic aldehyde, or an aldehyde produced from a compound that is ingested, inhaled, or absorbed) to the corresponding acid. A variety of compounds can give rise to aldehyde substrates for ALDH2. Non-limiting examples of compounds that can give rise to aldehyde substrates for ALDH2 include ethanol; a variety of insecticides; industrial toxins such as vinyl chlorides (e.g., polyvinyl chloride); and pyruvate. For example, a compound is ingested, absorbed (e.g., through the skin), or inhaled, by a mammal and is subsequently converted in the mammal into an aldehyde substrate for ALDH2.

Biogenic aldehydes include aldehydes that are produced by a mammal, e.g., are produced metabolically by a mammal. Non-limiting examples of biogenic aldehydes include .omega.-6 polyunsaturated fatty acids, such as malondialdehyde (MDA); hexanal; acrolein; glyoxal; crotonaldehyde; trans-2-nonenal; 4-oxo-2-nonenal; and 4-hydroxy-2-nonenal (HNE) (see e.g., Ellis, Pharmacology & Therapeutics (2007) 115:13, Picklo and Montine (2007) J. Alzheimer's Dis. 12:185); 3-aminopropanal (3-AP), a product of polyamine oxidase; and aldehyde products of tyrosine, serine and threonine (see Wood et al, Brain Res (2006)1095; 190).

Xenogenic aldehydes include aldehydes ingested, absorbed, or inhaled by a mammal from source outside the mammal. Xenogenic aldehydes include, e.g., formaldehyde and glutaraldehyde (e.g., McGregor et al., Crit. Rev Toxicol (2006) 36:821 and Pandey et al., Hum Exp. Toxicol. (2000) 19:360); chloroacetaldehyde (see e.g., Richardson et al., Mutat. Research (2007) 636:178); and reactive aldehydes present in cigarette smoke (see Smith et al., Inhal. Toxicol. (2006) 18:667).

Assays used to study the efficacy the compounds of the invention may be carried out using methods known in the art.

ALDH2 catalyzes the oxidative reaction of substrate acetaldehyde to acetic acid using $NAD^+$ as a cofactor. Enzymatic activity, or catalytic rate, of aldehyde dehydrogenase (ALDH2) are measured spectrophotometrically at UV wavelength $\lambda 340$ nm by the accumulation of reduced product NADH derived from $NAD^+$. Absorbance at $\lambda 340$ nm is quantitatively proportional to the amount of NADH being produced over time (6.22 O.D. unit=1 mmol of NADH, measured in a 1-cm width standard cuvette). This method is well-established in the literature [e.g. Rex et al., Alcohol Clin. Exp. Res. 9, 147 (1985)].

Full-length wild type human ALDH2 cDNA may be purchased from ATCC (No. MGC-1806. GenBank ID: BC002967). The 18-amino acid mitochondria transport signal sequence may be removed by PCR and cloned into the NheI/HindIII sites of a His-tag vector, pTrcHis, using standard molecular cloning techniques. The human ALDH2* cDNA construct containing the Asian E487K mutation can be obtained by site-directed mutagenesis to create the E487K substitution of the wild type ALDH2. Both human clones may be designed to express a recombinant protein with the His-tag at the N-terminus of the protein. For the co-expression experiments of human ALDH2 wild type and ALDH2*2 heterotetramers, a wild type ALDH2 gene and a ALDH2 E487K gene may be inserted separately into the two multiple cloning sites of pETDuet-1 vector. (Novagen, CA, USA). All the vectors may be transformed into BL21 E. coli host cells and subjected to 0.5 mM IPTG induction for protein expression at 30° C. Purifications of the recombinant proteins by affinity nickel columns (HisTrap, GE Healthy Science, USA) may be carried out using standard protocols according to manufacturer's instructions (Novagen, USA).

ALDH2 catalyzes the oxidative reaction of substrate acetaldehyde to acetic acid using $NAD^+$ as a cofactor. Enzymatic activity, or catalytic rate, of aldehyde dehydrogenase (ALDH2) can be measured spectrophotometrically at UV wavelength $\lambda 340$ nm by the accumulation of reduced product NADH derived from $NAD^+$. Absorbance at $\lambda 340$ nm is quantitatively proportional to the amount of NADH being produced over time (6.22 O.D. unit=1 mmol of NADH, measured in a 1-cm width standard cuvette). This method is well-established in the literature [e.g. Rex et al., Alcohol Clin. Exp. Res. 9, 147 (1985)].

Cloning, expression and purification of human ALDH2 wild type and ALDH2*2 recombinant mutant enzymes: Full-length wild type human ALDH2 cDNA was purchased from ATCC (No. MGC-1806. GenBank ID: BC002967). The 18-amino acid mitochondria transport signal sequence was removed by PCR and cloned into the NheI/HindIII sites of a His-tag vector, pTrcHis, using standard molecular cloning techniques. The human ALDH2* cDNA construct containing the Asian E487K mutation was obtained by site-directed mutagenesis to create the E487K substitution of the wild type ALDH2. Both human clones were designed to express a recombinant protein with the His-tag at the N-terminus of the protein. For the co-expression experiments of human ALDH2 wild type and ALDH2*2 heterotetramers, a wild type ALDH2 gene and a ALDH2 E487K gene were inserted separately into the two multiple cloning sites of pETDuet-1 vector. (Novagen, CA, USA). All the vectors were transformed into BL21 E. coli host cells and subjected to 0.5 mM IPTG induction for protein expression at 30° C. Purifications of the recombinant proteins by affinity nickel columns (HisTrap, GE Healthy Science, USA) were carried out using standard protocols according to manufacturer's instructions (Novagen, USA).

The present disclosure provides a formula (I) compound or a pharmaceutically acceptable salt, solvent ester, or prodrug thereof for modulating ALDH2 activity.

ALDH2 catalyzes the oxidative reaction of substrate acetaldehyde to acetic acid using $NAD^+$ as a cofactor. Enzymatic activity, or catalytic rate, of aldehyde dehydrogenase (ALDH2) can be measured spectrophotometrically at UV wavelength $\lambda 340$ nm by the accumulation of reduced product NADH derived from $NAD^+$. Because compounds of formula (I) are considered to be agonists or "activators" of ALDH2 the enzymatic activity measured will exceed 100% of the baseline enzymatic activity of the enzyme in its normal activation state. As the concentration of the compounds of formula (I) decreases from 20 micromolar to 0.16 micromolar in the presence of ALDH, a decrease in the activation of enzymatic activity is observed for the wild-type ALDH2*1/*1 and the heterozygous form ALDH2*1/*2. Table 2 shows the various activities for several representative compounds of formula (I). For example compounds exhibiting activities in the range of about 100-150% are designated as +, compounds with activities ranging from about 150-250% are designated as ++ and compounds with activities more than about 250% are designated with +++ for compounds AC1-29 (see Table 2).

TABLE 2

| AC # | ALDH2*1/*1 (Acetaldehyde) | | | | ALDH2*1/*2 (Acetaldehyde) | | | |
|---|---|---|---|---|---|---|---|---|
| | 20 µM | 10 µM | 5 µM | 2.5 µM | 20 µM | 10 µM | 5 µM | 2.5 µM |
| AC1 | 412 | 288 | 242 | 175 | 453 | 383 | 294 | 220 |
| AC2 | 443 | 328 | 275 | 215 | 471 | 408 | 338 | 256 |
| AC3 | 319 | 220 | 195 | 150 | 376 | 310 | 245 | 180 |

TABLE 2-continued

| AC # | ALDH2*1/*1 (Acetaldehyde) | | | | ALDH2*1/*2 (Acetaldehyde) | | | |
|---|---|---|---|---|---|---|---|---|
| | 20 μM | 10 μM | 5 μM | 2.5 μM | 20 μM | 10 μM | 5 μM | 2.5 μM |
| AC4  | 363 | 300 | 280 | 204 | 423 | 390 | 338 | 266 |
| AC5  | 487 | 352 | 330 | 266 | 504 | 428 | 382 | 318 |
| AC6  | 299 | 293 | 238 | 208 | 336 | 281 | 260 | 202 |
| AC7  | 331 | 266 | 181 | 133 | 434 | 291 | 244 | 176 |
| AC8  | 370 | 319 | 223 | 164 | 479 | 328 | 299 | 221 |
| AC9  | 376 | 354 | 276 | 218 | 402 | 317 | 287 | 224 |
| AC10 | 414 | 346 | 238 | 172 | 531 | 388 | 321 | 239 |
| AC11 | 211 | 169 | 135 | 123 | 248 | 185 | 158 | 125 |
| AC12 | 379 | 305 | 211 | 166 | 350 | 286 | 236 | 179 |
| AC13 | 237 | 215 | 168 | 164 | 296 | 247 | 195 | 146 |
| AC14 | 189 | 162 | 138 | 134 | 194 | 157 | 121 | 103 |
| AC15 | 169 | 143 | 106 | 124 | 203 | 160 | 129 | 105 |
| AC16 | 133 | 105 | 106 | 106 | 138 | 126 | 116 | 104 |
| AC17 | 318 | 340 | 262 | 229 | 195 | 176 | 173 | 156 |
| AC18 | 187 | 171 | 131 | 119 | 197 | 172 | 145 | 127 |
| AC19 | 236 | 214 | 143 | 132 | 230 | 191 | 163 | 133 |
| AC20 | 403 | 308 | 238 | 170 | 93  | 255 | 218 | 157 |
| AC21 | 370 | 272 | 209 | 161 | 250 | 247 | 198 | 110 |
| AC22 | 437 | 313 | 263 | 172 | 143 | 253 | 194 | 160 |
| AC23 | 375 | 291 | 262 | 210 | 196 | 263 | 252 | 187 |
| AC24 | 428 | 321 | 248 | 175 | 216 | 269 | 234 | 149 |
| AC25 | 382 | 422 | 341 | 273 | 260 | 343 | 321 | 267 |
| AC26 | 394 | 352 | 235 | 199 | 281 | 261 | 238 | 188 |
| AC27 | 364 | 379 | 315 | 293 | 410 | 419 | 420 | 323 |
| AC28 | 430 | 366 | 252 | 197 | 456 | 338 | 239 | 201 |
| AC29 | 445 | 422 | 334 | 283 | 423 | 392 | 349 | 260 |

Substrates of Mitochondrial ALDH2

Non-limiting examples of compounds that are substrates for mitochondrial ALDH2 include 3,4-dihydroxypheylacetaldehyde (DOPAL); formaldehyde; acetaldehyde; propionaldehyde; n-butyraldehyde; capronaldehyde; heptaldehyde; pentaldehyde; octylaldehyde; decylaldehyde; retinaldehyde; 3-hydroxybenzaldehyde; 2,5-dihydroxybenzaldehyde; phenylacetaldehyde; 3-phenylpropionaldehyde (see, e.g., Want et al. (2002) Drug Metabolism and Disposition 30:69); cinnamoyl and hydrocinnamoyl aldehydes and their derivative aldehydes (e.g. p-nitrocinnamaldehyde, p-(dimethylamino)cinnamaldehyde, hydrocinnamaldehyde, .alpha.-phenylpropionaldehyde); benzaldehyde and its derivative aldehydes (e.g. 2,4-dinitro-benzaldehyde, o-nitro-benzaldehyde, p-nitro-benzaldehyde, p-methyl-benzaldehyde, m-methyl-benzaldehyde, p-methoxy-benzaldehyde, p-(dimethylamino)-benzaldehyde, m-methoxy-benzaldehyde, m-hydroxy-benzaldehyde, 3,4-dimethoxy-benzaldehyde, o-methoxy-benzaldehyde); naphthaldehyde and its derivative aldehydes (e.g. 5-bromo-1-naphthaldehyde, 5-nitro-1-naphthaldehyde, 6-[O—$(CH_2)_5$—COOH]-2-naphthaldehyde, 6-(dimethylamino)-2-naphthaldehyde); coumarin-4-carboxaldehyde and its derivative aldehydes (e.g. 7-acetoxy-coumarin-4-carboxaldehyde, 7-(dimethylamino)-coumarin-4-carboxaldehyde, 7-methoxy-coumarin-4-carboxaldehyde, 6,7-dimethoxy-coumarin-4-carboxaldehyde); quinoline, quinolinonecarboxaldehyde, and their derivative aldehydes (e.g. quinoline-3-carboxaldehyde, 7-(dimethylamino)-2-quinolinone-4-carboxaldehyde, quinoline-4-carboxaldehyde, 6-methoxy-2-quinolinone-4-carboxaldehyde); phenanthrene-9-carboxaldehyde; indole-3-aldehyde, indole-3-acetaldehyde; 5-methoxyindole-3-carboxaldehyde; 3-pyridinecarboxaldehyde; fluorene-2-carboxaldehyde (see, e.g., Klyosov, (1996) Biochemstry 35:4457); 4-hydroxynonenal; malondialdehyde; 3,4-dihydroxyphenylacetaldehyde; and 5-hydroxylindole-3-acetaldehyde. See, also, e.g., Williams et al., (2005), Anal. Chem. 77:3383; Marchitti et al. (2007), Pharmacol. Rev. 59:125; and Hoffman and Maser (2007), Drug Metab. Rev. 39:87.

Agonists of ALDH2

The present invention provides ALDH2 agonists (also referred to as "activators"); and pharmaceutical compositions comprising ALDH2 agonists. Agonists of ALDH2 are useful for treating and/or preventing a variety of disorders, including, e.g., conditions involving ischemic stress, chronic free-radical associated diseases, acute free-radical associated diseases, insensitivity to nitroglycerin (e.g., in angina and heart failure), hypertension, diabetes, and osteoporosis. Agonists are also useful in the detoxification of alcohol abuse, methanol poisoning, ethylene glycol monomethyl ether poisoning, and poisoning due to other xenogenic or biogenic aldehyde compounds.

Whether a compound is an ALDH2 agonist can be readily ascertained. Assays for dehydrogenase activity of ALDH2 are known in the art, and any known assay can be used. Examples of dehydrogenase assays are found in various publications, including, e.g., Sheikh et al. ((1997) J. Biol. Chem. 272:18817-18822); Vallari and Pietruszko (1984) J. Biol. Chem. 259:4922; and Farres et al. ((1994) J. Biol. Chem. 269:13854-13860).

The present invention provides ALDH2 antagonists (also referred to as "ALDH2 inhibitors"), and pharmaceutical compositions comprising ALDH2 antagonists. In some embodiments, ALDH2 antagonists are useful for treating and/or preventing alcohol addiction. In other embodiments, ALDH2 antagonists increase the sensitivity of a cancerous cell to a cancer chemotherapeutic agent. Thus, in some embodiments, ALDH2 antagonists are useful as adjuvants to standard cancer therapies, in the treatment or prevention of cancer.

Whether a compound is an ALDH2 antagonist can be readily ascertained. Assays for ALDH2 are known in the art, and any known assay can be used. Examples of assays are found in various publications, including, e.g., Sheikh et al. ((1997) J. Biol. Chem. 272:18817-18822) and Farres et al. ((1994) J. Biol. Chem. 269:13854-13860). For example, ALDH2 is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and a substrate such as 14 μM propionaldehyde. Reduction of $NAD^+$ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043; and WO 2005/057213. In an exemplary assay, the reaction is carried out at 25° C. in 0.1 NaPPi buffer, pH 9.5, 2.4 mM $NAD^+$ and 10 mM acetaldehyde as the substrate. Enzymatic activity is measured by a reductive reaction of $NAD^+$ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213. Detection of fluorescent resorufin at 590 nm provides amplified and more sensitive signals for any change in ALDH2 enzymatic activity.

Assay for Dehydrogenase Activity

As an example of an assay for dehydrogenase activity, ALDH2 is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and an aldehyde substrate such as 14 μM propionaldehyde. Reduction of $NAD^+$ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043; and WO 2005/057213. In an exemplary assay, the reaction is carried out at 25° C. in 0.1 NaPPi buffer, pH 9.5, 2.4 mM $NAD^+$ and 10 mM acetaldehyde as the substrate. Enzymatic activity is measured by a reductive reaction of $NAD^+$ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213. Detection of fluorescent resorufin at 590 nm provides amplified and more sensitive signals for any change in ALDH2 enzymatic activity.

Whether a compound increases an esterase activity of ALDH2 can be determined using any known assay for esterase activity. For example, esterase activity of ALDH2 can be determined by monitoring the rate of p-nitrophenol formation at 400 nm in 25 mM N,N-Bis(2-hydroxyethyl)-2-amino ethanesulfonic acid (BES) (pH 7.5) with 800 μM p-nitrophenyl acetate as the substrate at room temperature in the absence or presence of added $NAD^+$. A pH-dependent molar extinction coefficient of 16 $mM^{-1}cm^{-1}$ at 400 nm for nitrophenol can be used. See, e.g., Larson et al. (2007) J. Biol. Chem. 282:12940). Esterase activity of ALDH2 can be determined by measuring the rate of p-nitrophenol formation at 400 nm in 50 mM Pipes (pH 7.4) with 1 mM p-nitrophenylacetate as the substrate. A molar extinction coefficient of $18.3 \times 10^3$ $M^{-1}cm^{-1}$ at 400 nm for p-nitrophenolate can be used for calculating its rate of formation. See, e.g., Ho et al. (2005) Biochemistry 44:8022).

Whether a compound increases a reductase activity of ALDH2 can be determined using any known assay for reductase activity. A reductase activity of ALDH2 can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence ALDH2. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 ml in ethanol for subsequent TLC separation and scintillation counting. See, e.g., Zhang and Stamler (2002) Proc. Natl. Acad. Sci. USA 99:8306.

Carrageenan Inflammatory Pain Model

Mice are acclimated to the colony room and maintained on a 12 hour/12 hour light/dark cycle. To induce plantar sensitivity to tactile stimuli, a single injection of carrageenan is administered to the plantar hindpaw of the mice and withdrawal from a mechanical stimulus is measured by applying Von Frey filaments of ascending bending force to the plantar surface of the hind paws.

A compound of formula (I) is dissolved and administered subcutaneous (sc) or orally (po) prior to carrageenan administration and after carrageenan injections. Data is analyzed by analysis of variance (ANOVA) followed by post-hoc comparisons with Fisher Tests when appropriate.

Carbon Tetrachloride Induced Fibrosis Model

Mice are acclimated to the colony room and maintained on a 12 hour/12 hour light/dark cycle. After the acclimation period, mice are administered $CCl_4$ for a total period of 8 weeks to establish liver fibrosis. From day 0, all animals except the animals in the sham control group are injected intraperitoneally (i.p.) with $CCl_4$ in olive oil twice per week for a total period of 8 weeks. At the end of week 3, $CCl_4$ treated mice are randomly grouped into 4 groups according to ALT and AST values and body weight second. Starting from week 4, animals are treated with vehicle or testing compounds correspondingly. Each dosing was administered from prior to $CCl_4$ administration.

Blood samples are collected to prepare serum samples for blood chemistry analysis (e.g., ALT and AST serum levels, TGF-beta levels). Whole liver tissue is collected and dissected into pieces for histopathology and immunohistochemistry (IHC) analysis. The left lobe and middle lobe is separately shock frozen in liquid nitrogen and stored at −80° C. for further analysis.

Limb Ischemia Model for Peripheral Arterial Disease (PAD).

Mice are anesthetized and hair is entirely removed from the surgical area. A longitudinal incision is inguinal crease along the femoral vessels and the connective tissue sheet between the femoral artery and vein is carefully dissected. An opening between the femoral artery and vein is made and the femoral artery is occluded using triple surgical knots. The incision is then closed.

The animals under permanent femoral artery occlusion are treated with compounds of formula (I) and the effects of the compounds on functional capacity is assessed in mice using treadmill exercise in a metabolic chamber.

$V_{O2}$ max and respiratory exchange ratios are measured as well as anaerobic threshold by serum lactate assays. Cristae regularity, intraorganelle condensation, mitochondrial membrane irregularity, and associated vacuolization/lysosomes) is also accessed. Biomarkers of mitochondrial damage including mitochondrial protein adducts with reactive aldehydes (i.e., 4-HNE) and mitochondrial structure is measured by transmission electron microscopy (TEM).

Mitochondrial function is also accessed by measuring mitochondrial membrane potential and activities of the respiratory chain complexes, as well as employing a Clark electrode to measure skeletal muscle $O_2$ consumption. In addition, the effect of pharmacologic or genetic modulation of ALDH2 activity on muscle structure by LM and TEM is accessed, the fragmentation of actin filaments within the myofibril with fluorescent phalloidin and apoptosis with TUNEL/Caspase-3 staining; and contractile function of gastrocnemius muscle in vitro using electrical stimulation and a force microtransducer is quantified.

Definitions

The term "compounds of the invention" refers to a compound according to formula (I), formula (Ia), formula (Ib), formula (Ic), and formula (Id).

With respect to the chemical compounds useful in the present invention, the following terms can be applicable: As used herein, "alkyl" is intended to include both branched and straight chain saturated aliphatic hydrocarbon groups having the specified number of carbon atoms. For example, $C_1$-$C_6$ alkyl is intended to include $C_1$, $C_2$, $C_3$, $C_4$, $C_5$, and $C_6$ alkyl groups. Examples of alkyl include, but are not limited to, methyl, ethyl, n propyl, i propyl, n butyl, s butyl, t butyl, n pentyl, s pentyl, and n-hexyl. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in another embodiment, cycloalkyls have five or six carbons in the ring structure.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

"Substituted alkyls" refers to alkyl moieties having substituents replacing one or more hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and in one embodiment, cycloalkenyl groups have five or six carbons in the ring structure. The term "$C_1$-$C_6$" includes alkenyl groups containing two to six carbon atoms. The term "$C_3$-$C_6$" includes alkenyl groups containing three to six carbon atoms.

"Substituted alkenyl" refers to alkenyl moieties having substituents replacing one or more hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When any variable (e.g., $R^C$) occurs more than one time in any constituent or formula for a compound, its definition at each occurrence is independent of its definition at every other occurrence. Thus, for example, if a group is shown to be substituted with 0-2 $R^C$ moieties, then the group may optionally be substituted with up to two $R^C$ moieties and at each occurrence is selected independently from the definition of $R^C$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N—O or N+—O—). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C1-6 alkyl, C1-6 alkenyl, C1-6 alkynyl, C3-14 carbocycle, or 3-14-membered heterocycle) derivatives.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and S(O)p, where p=1 or 2). When a nitrogen atom is included in the ring it is either N or NH, depending on whether or not it is attached to a double bond in the ring (i.e., a hydrogen is present if needed to maintain the trivalency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In one embodiment, when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidinone, piperidinonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H pyrrolyl, pyrrolyl, quinazolinyl, quinolinyl, 4 H quinolizinyl, quinoxalinyl, quinuclidinyl, tetrahydrofuranyl, tetrahydroisoquinolinyl, tetrahydroquinolinyl, tetrazolyl, 6 H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "hydroxy" or "hydroxyl" includes groups with an —OH or —O—. Additionally, the compounds of the present invention, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H2O, such combination being able to form one or more hydrate.

"Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form. Some compounds of the present invention can exist in tautomeric forms, which are also intended to be encompassed within the scope of the present invention.

The compounds and salts of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "mitochondrial aldehyde dehydrogenase-2" or "ALDH2" refers to an enzyme that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent reaction. For example, ALDH2 oxidizes aldehydes derived from the breakdown of compounds, e.g., toxic compounds that are ingested, that are absorbed, that are inhaled, or that are produced during normal metabolism.

"Treating", includes any effect, e.g., lessening, reducing, modulating, or eliminating, that results in the improvement of the condition, disease, disorder, etc. "Treating" or "treatment" of a disease state includes: (1) inhibiting the disease state, i.e., arresting the development of the disease state or its clinical symptoms; (2) relieving the disease state, i.e., causing temporary or permanent regression of the disease state or its clinical symptoms; or (3) reducing or lessening the symptoms of the disease state. As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

"Preventing" includes any effect in, e.g., causing the clinical symptoms of the disease state not to develop in a subject that may be exposed to or predisposed to the disease state, but does not yet experience or display symptoms of the disease state. A compound of the present invention, or a pharmaceutically acceptable salt, metabolite, polymorph or solvate thereof, can also be used to prevent a disease, condition or disorder, or used to identify suitable candidates for such purposes. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, ester, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, ester, prodrug, metabolite, polymorph or solvate thereof. The biological or medical response can be the treatment of cancer. The biological or medical response can be treatment or prevention of a cell proliferative disorder. The biological response or effect can also include a change in cell proliferation or growth that occurs in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

The term "ALDH2" encompasses ALDH2 from various species. Amino acid sequences of ALDH2 from various species are publicly available. For example, a human ALDH2 amino acid sequence is found under GenBank Accession Nos. AAH02967 and NP_000681; a mouse ALDH2 amino acid sequence is found under GenBank Accession No. NP_033786; and a rat ALDH2 amino acid sequence is found under GenBank Accession No. NP_115792. The term "ALDH2" as used herein also encompasses fragments, fusion proteins, and variants (e.g., variants having one or more amino acid substitutions, addition, deletions, and/or insertions) that retain ALDH2 enzymatic activity. Specific enzymatically active ALDH2 variants, fragments, fusion proteins, and the like can be verified by adapting the methods described herein. An example of an ALDH2 variant is an ALDH2 polypeptide that comprises a Glu-to-Lys substitution at amino acid position 487 of human ALDH2 or at a position corresponding to amino acid 487 of human ALDH2. This mutation is referred to as the "E487K mutation"; the "E487K variant"; or as the "Glu504Lys polymorphism". See, e.g., Larson et al. (2005) J. Biol. Chem. 280:30550; and Li et al. (2006) J. Clin. Invest. 116:506. An ALDH2 variant retains at least about 1% of the enzymatic activity of a corresponding wild-type ALDH2 enzyme.

For the purposes of promoting an understanding of the embodiments described herein, reference made to preferred embodiments and specific language are used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. All percentages and ratios used herein, unless otherwise indicated, are by weight.

The following examples are illustrative, but not limiting, of the methods and compositions of the present invention. Other suitable modifications and adaptations of the variety of conditions and parameters normally encountered in synthesis and use of the compounds of the present disclosure and that are obvious to those skilled in the art are within the spirit and scope of the present disclosure.

"Alda-1" refers to N-(1,3-Benzodioxol-5-ylmethyl)-2,6-dichlorobenzamide having the following structure:

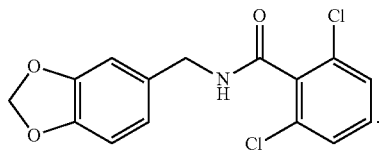

Alda-1

EXAMPLES

Example 1

General Procedure for the Preparation of Benzyl Amines

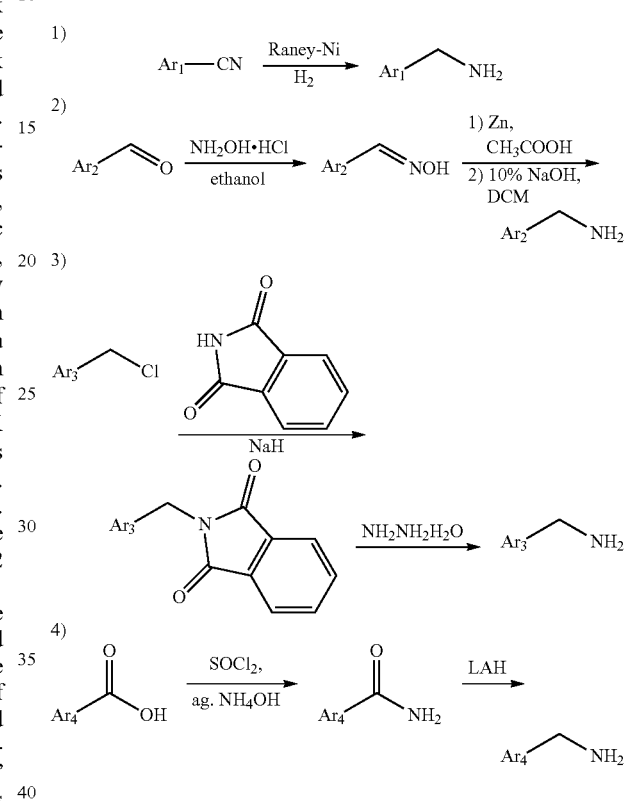

The benzyl amines used in this invention are either commercially available or are prepared as described in the above scheme. The reactions are based on commercially available starting materials such as 1) benzonitriles; 2) benzaldehydes; 3) benzyl chlorides; and 4) benzoic acids.

Example 2

General Procedures for the Preparation of Compounds of Formula (II)

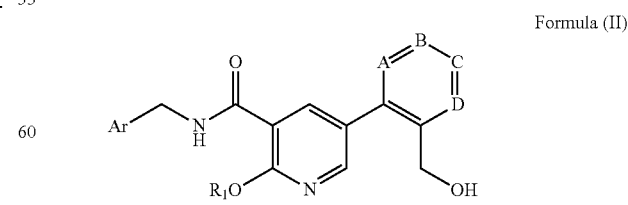

Formula (II)

Compounds of formula (II) can be prepared using two different reaction sequences, which are shown below in scheme 1 and 2.

Scheme 1

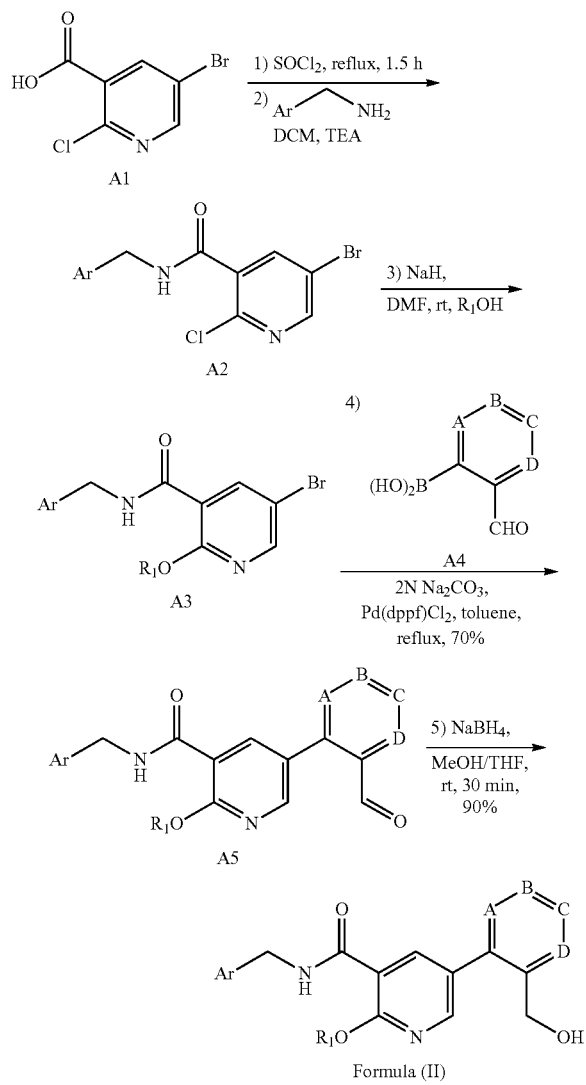

Example 2.1

Preparation of Compound AC1 According to Scheme 1

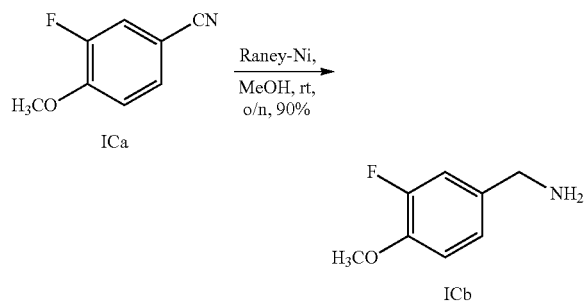

-continued

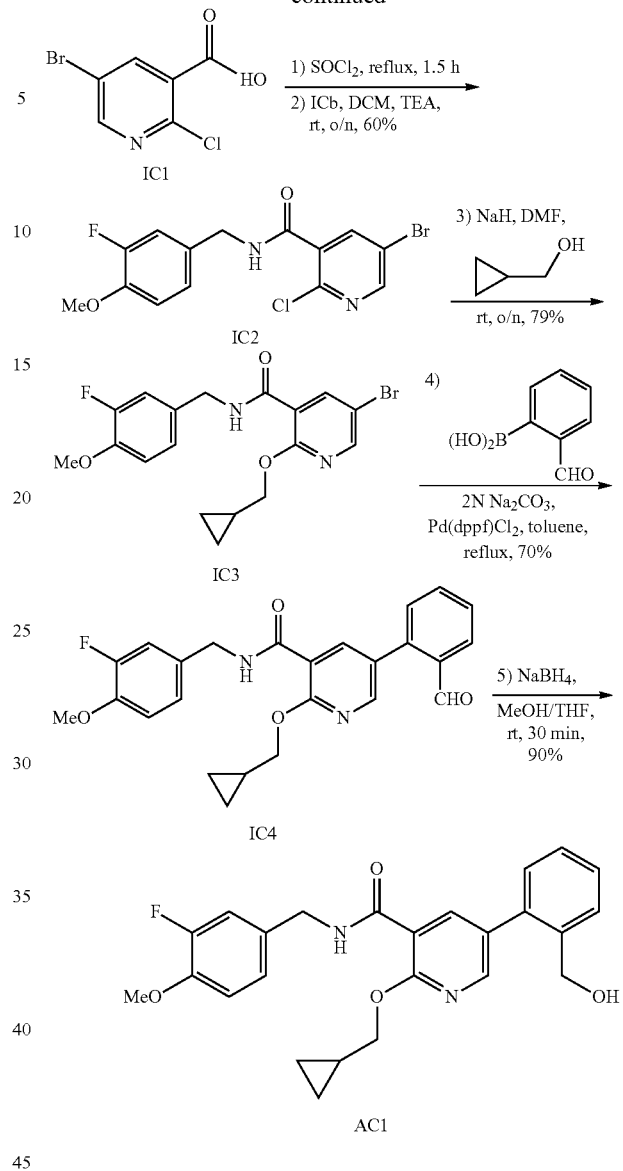

Example 2.1.1

Preparation of
(3-fluoro-4-methoxyphenyl)methanamine (ICb)

To a solution of 3-fluoro-4-methoxybenzonitrile ICa (68.0 g, 450 mmol, 1 eq) in methanol (2 L) was added Raney-Nickel (Raney, Ni; 70.0 g). After completion of addition, the reaction mixture stirred at room temperature overnight. A solid formed, which was removed by filtration, and washed with methanol. The clear filtrate was concentrated at reduced pressure to obtain (3-fluoro-4-methoxyphenyl)methanamine (62.8 g, 90%) as a yellow oil.

Example 2.1.2

Preparation of 5-bromo-2-chloro-N-(3-fluoro-4-methoxybenzyl)nicotinamide (IC2)

A solution of IC1 (40 g, 0.169 mol, 1 eq) in thionyl chloride (SOCl$_2$; 400 mL) was refluxed for 1.5 H, and then concentrated to obtain the crude acetyl chloride intermediate, which was dissolved in dichloromethane (DCM; 100 mL) and subsequently added to a cooled (0° C.) solution of ICb (28.8 g, 0.186 mol, 1.1 eq) and triethylamine (TEA; 51.35 g, 0.508 mmol, 3 eq) dissolved in dichloromethane (600 mL). After stirring at room temperature overnight, water was added to the reaction mixture and the layers of the resulting mixture were allowed to partition. The aqueous layer was separated and extracted with dichloromethane. The combined organic layers were washed with brine, dried over sodium sulfate ($Na_2SO_4$), concentrated, and triturated with PE:EA=10:1 to obtain 5-bromo-2-chloro-N-(3-fluoro-4-methoxybenzyl)niotinamide (40.8 g, 60%) as a white solid.

Example 2.1.3

Preparation of 5-bromo-2-(cyclopropylmethoxy)-N-(3-fluoro-4-methoxybenzyl)nicotinamide (IC3)

To a solution of cyclopropanemethanol (9.45 g, 0.131 mol, 1.2 eq) in dimethylformamide (DMF; 500 mL) was added sodium hydride (NaH; 6.55 g, 0.164 mol, 1.5 eq) at room temperature. After stirring for 1h, the reaction mixture was cooled to 0° C., and IC2 (40.8 g, 0.109 mol, 1 eq) dissolved in dimethylformamide (100 mL) was added. After stirring at room temperature overnight, the reaction mixture was quenched with water. The aqueous portion was separated and extracted with ethyl acetate. The combined organic layers were washed with brine, dried over sodium sulfate, concentrated, and triturated with PE:EA=10:1 to obtain 5-bromo-2-(cyclopropylmethoxy)-N-(3-fluoro-4-methoxybenzyl)nicotinamide (35 g, 79%) as a white solid.

Example 2.1.4

Preparation of 2-(cyclopropylmethoxy)-N-(3-fluoro-4-methoxybenzyl)-5-(2-formylphenyl)nicotinamide (IC4)

To a solution of IC3 (4.0 g, 9.78 mmol, 1 eq) and (2-formylphenyl)boronic acid (1.76 g, 11.7 mmol, 1.1 eq) in toluene was added 2N(aq.) sodium carbonate ($Na_2CO_3$; 8 mL, 1.64 eq) and [1,1'-bis(diphenylphosphino)ferrocene]dichloropalladium(II) (Pd(dppf)$Cl_2$; 400 mg, 0.490 mmol, 0.05 eq). After completion of addition the reaction mixture was heated to 90° C., and stirred for 3 h before being quenched with water. The aqueous layer was extracted with ethyl acetate and the combined organic layers were washed with brine, dried over sodium sulfate, and concentrated to afford the crude product, which was purified by silica gel chromatography (PE:EA=5:1) to obtain compound 2-(cyclopropylmethoxy)-N-(3-fluoro-4-methoxybenzyl)-5-(2-formylphenyl)nicotinamide (3.0 g, 6.91 mmol, 70%) as a white solid.

Example 2.1.5

Preparation of 2-(cyclopropylmethoxy)-N-(3-fluoro-4-methoxybenzyl)-5-(2-(hydroxymethyl)phenyl)nicotinamide (AC1)

To a solution of compound IC4 (1.1 g, 2.53 mmol, 1 eq) in tetrahydrofuran and methanol (20 mL: 20 mL) was added sodium borohydride ($NaBH_4$; 0.48 g, 12.6 mmol, 5 eq).

After stirring for 30 min, the reaction was quenched with cold water and the pH of the reaction mixture was adjusted to a pH value of 5 with 1N (aq.) hydrochloric acid. After stirring for an additional 15 min, the reaction mixture was then extracted with ethyl acetate. The combined organic layers were washed with brine, dried over sodium sulfate and concentrated to afford 2-(cyclopropylmethoxy)-N-(3-fluoro-4-methoxybenzyl)-5-(2-(hydroxymethyl)phenyl)nicotinamide (1.0 g, 90%) as a white solid.

Scheme 2: Alternate scheme for synthesizing compounds of formula (II)

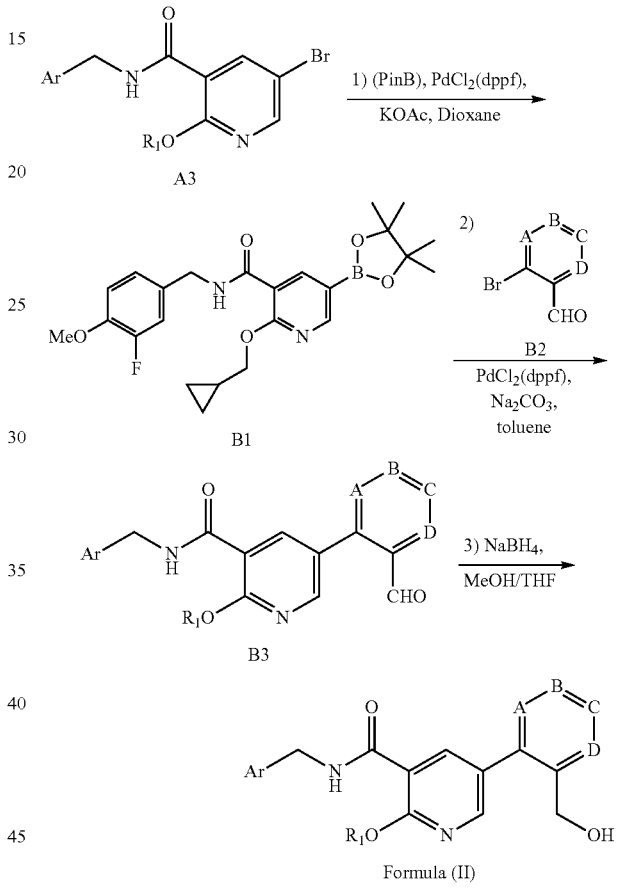

Example 3

General Procedure for the Preparation of Compounds of Formula (III)

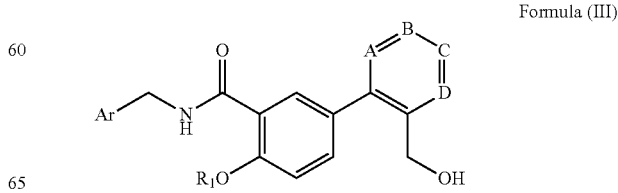

Formula (III)

161
Scheme 3
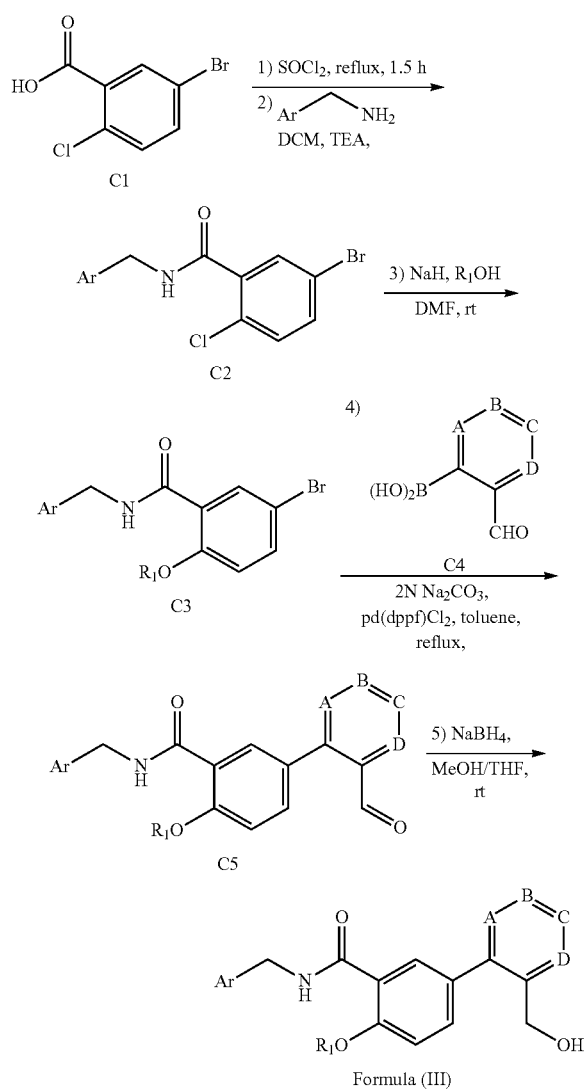
Example 3.1
Preparation of Compound AC2 According to Scheme 3
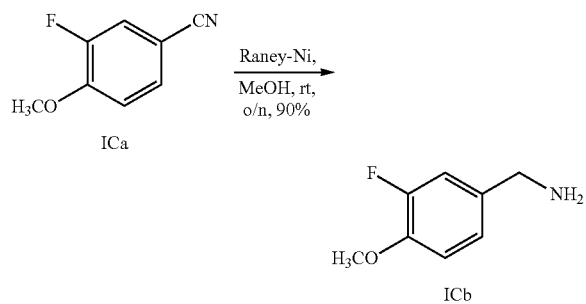
162
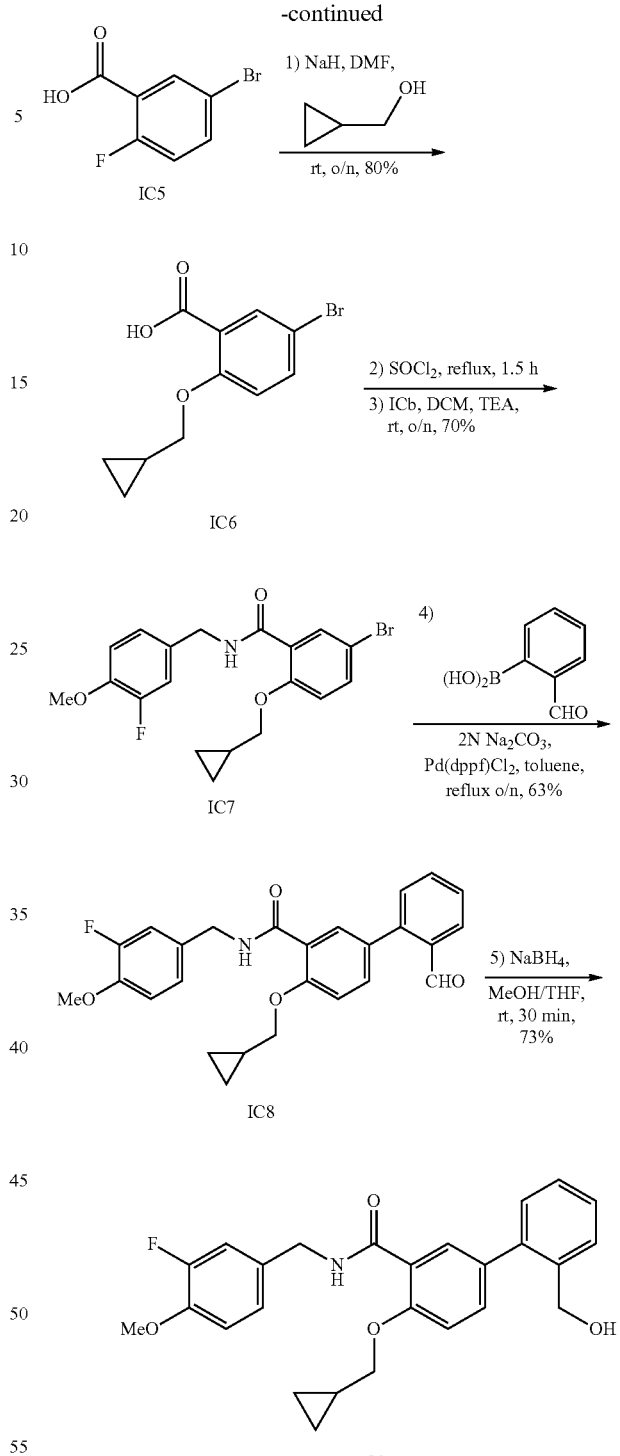
Example 3.1.1
Preparation of (3-fluoro-4-methoxyphenyl)methanamine (ICb)
To a solution of 3-fluoro-4-methoxybenzonitrile ICa (68.0 g, 450 mmol, 1 eq) in methanol (2 L) was added Raney-Nickel (Raney, Ni; 70.0 g). After completion of addition, the reaction mixture stirred at room temperature overnight. A solid formed, which was removed by filtration, and washed with methanol. The clear filtrate was concentrated at reduced pressure to obtain (3-fluoro-4-methoxyphenyl)methanamine (62.8 g, 90%) as a yellow oil.

Example 3.1.2

Preparation of 5-bromo-2-(cyclopropylmethoxy)benzoic acid (IC6)

To a solution of cyclopropanemethanol (7.9 g, 0.011 mol) in dimethylformamide at 0° C. was added sodium hydride (4.87 g, 0.2 mol, 60% in mineral oil). The mixture was stirred for 1h before adding a solution of IC5 (20.0 g, 0.092 mol) dissolved in dimethylformamide. After completion of addition, the reaction mixture was stirred at 75° C. overnight. The next day, the reaction mixture was cooled to 0° C., acidified to a pH=5, and diluted with water. The aqueous portion was separated and extracted with ethyl acetate. The combined organic layers were washed with brine, dried over sodium sulfate, and concentrated to afford a crude material. The crude material was purified using silica gel chromatography (PE:EA=1:1, $R_f$=0.2) to yield 5-bromo-2-(cyclopropylmethoxy)benzoic acid (20.0 g, 80%).

Example 3.1.3

Preparation of 5-bromo-2-(cyclopropylmethoxy)-N-(3-fluoro-4-methoxybenzyl)benzamide (IC7)

A solution of compound IC6 (20.0 g, 0.07 mol) in thionyl chloride was heated to reflux for 1.5 H, cooled to room temperature and concentrated to afford a crude residue, which was dissolved in dichloromethane (20 mL) and added dropwise to a solution of (3-fluoro-4-methoxyphenyl)methanamine (ICb) (11.5 g, 0.07 mol) and triethylamine (22.4 g, 0.22 mol) dissolved in dichloromethane (70 mL) at 0° C. The reaction mixture was stirred at room temperature overnight and monitored by thin layer chromatography (TLC). The next day, the reaction mixture was quenched with water. The aqueous portion was extracted with dichloromethane. All combined organic layers were washed with brine, dried over sodium sulfate, and concentrated to afford a crude material. The crude material was purified by silica gel chromatography (PE:EA=2:1, $R_f$=0.6) to afford 5-bromo-2-(cyclopropylmethoxy)-N-(3-fluoro-4-methoxybenzyl)benzamide (21.0 g, 70%) as a solid.

Example 3.1.4

Preparation of 4-(cyclopropylmethoxy)-N-(3-fluoro-4-methoxybenzyl)-2'-formyl-[1,1'-biphenyl]-3-carboxamide (IC8)

To a solution of compound IC7 (3.0 g, 7.35 mmol, 1 eq) and (2-formylphenyl)boronic acid (1.21 g, 8.08 mmol, 1.1 eq) in toluene was added 2N(aq.) sodium carbonate (9.6 mL, 2.61 eq) and [1,1'-bis(diphenylphosphino)ferrocene]dichloropalladium(II) (300 mg, 0.36 mmol, 0.05 eq). The reaction was then heated to 90° C., and stirred overnight. The next day, the reaction was quenched with water. The aqueous layer was separated and extracted with ethyl acetate. All combined organic layers were washed with brine, dried over sodium sulfate and concentrated to afford a crude product, which was purified by silica gel chromatography (PE:EA=5:1) to obtain 4-(cyclopropylmethoxy)-N-(3-fluoro-4-methoxybenzyl)-2'-formyl-[1,1'-biphenyl]-3-carboxamide (2.0 g, 4.62 mmol, 63%) as a white solid.

Example 3.1.5

Preparation of 4-(cyclopropylmethoxy)-N-(3-fluoro-4-methoxybenzyl)-2'-(hydroxymethyl)-[1,1-biphenyl]-3-carboxamide (AC2)

To a solution of compound IC8 (550 mg, 1.27 mmol, 1 eq) in tetrahydrofuran and methanol (10 mL: 10 mL) was added sodium borohydride (240 mg, 6.34 mmol, 5 eq). After stirring for 30 min, the reaction was quenched with cold water and the pH of the resulting mixture was adjusted to pH=5 with 1N(aq.) hydrochloric acid. After stirring for an additional 15 min, the reaction mixture was extracted with ethyl acetate. The combined organic layers were washed with brine, dried over sodium sulfate and concentrated to afford a crude product, which was purified by silica gel chromatography to obtain 4-(cyclopropylmethoxy)-N-(3-fluoro-4-methoxybenzyl)-2'-(hydroxymethyl)-[1,1'-biphenyl]-3-carboxamide (400 mg, 73%) as a white solid.

Scheme 4: Alternate scheme for synthesizing compounds of formula (III)

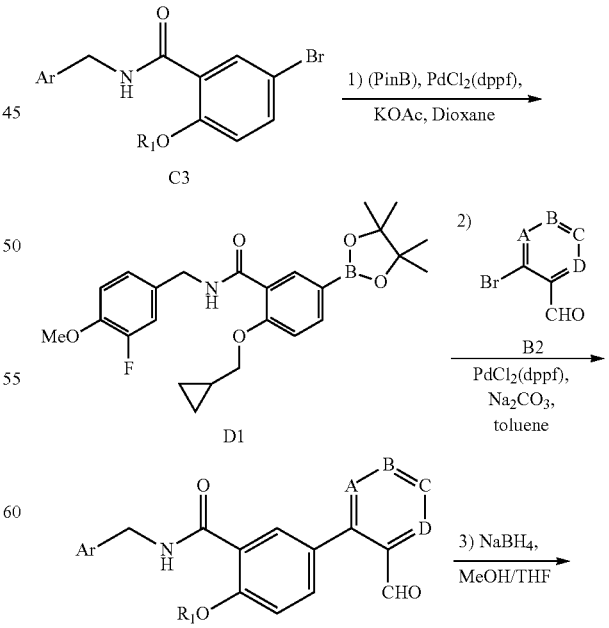

-continued

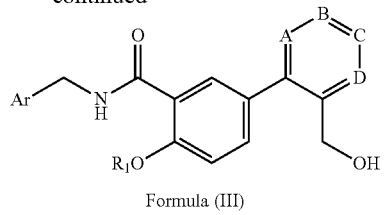

Formula (III)

Example 3.2

Preparation of Compound AC6 According to Scheme 4

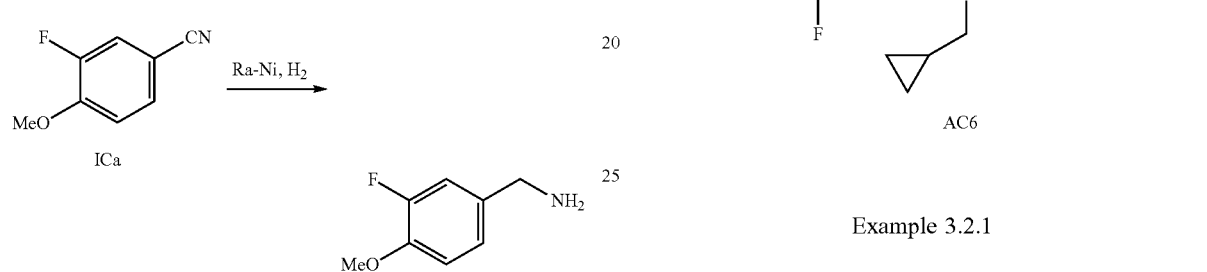

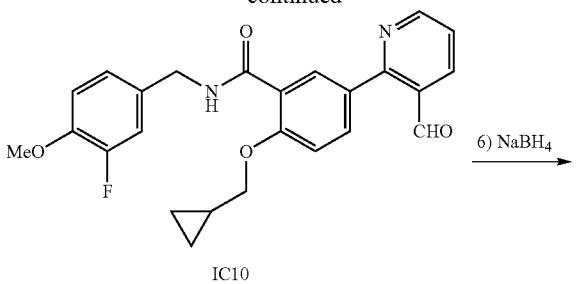

Example 3.2.1

Preparation of (3-fluoro-4-methoxyphenyl)methanamine (ICb)

A mixture of compound ICa (50.0 g, 0.33 mol) and Raney nickel (55.0 g, 50% in water) in methanol (400 mL) was stirred overnight at room temperature under hydrogen atmosphere. The reaction progress was monitored using thin layer chromatography (TLC). Upon completion of the reaction, the mixture was filtered and the collected filtrate was concentrated to obtain (3-fluoro-4-methoxyphenyl)methanamine (47.0 g, 91.6%), which was used without further purification.

Example 3.2.2

Preparation of 5-bromo-2-(cyclopropylmethoxy)benzoic acid (IC6)

To a solution of cyclopropanemethanol (13.1 g, 0.181 mol) in dimethylformamide (200 mL) at 0° C. was added sodium hydride (7.98 g, 0.20 mol, 60% in mineral oil). The mixture was stirred for 1 h before the addition of a solution of IC5 (36.0 g, 0.165 mol) dissolved in dimethylformamide (60 mL). The resulting reaction mixture was stirred at 75° C. overnight and monitored by thin layer chromatography (TLC). The next day, the reaction mixture was cooled to 0° C. and acidified to a pH=5 with 1N(aq.) hydrochloric acid and subsequently diluted with water. The aqueous portion was separated and extracted with ethyl acetate. All combined organic layers were washed with brine, dried over sodium sulfate, and concentrated to obtain a crude material. The crude material was purified by crystallization from ethyl acetate to give 5-bromo-2-(cyclopropylmethoxy)benzoic acid (40.0 g, 90%) as a light yellow solid.

Example 3.2.3

Preparation of 5-bromo-2-(cyclopropylmethoxy)-N-(3-fluoro-4-methoxybenzyl)benzamide (IC7)

A mixture of compound IC6 (40.0 g, 0.150 mol) in thionyl chloride (80 mL) was heated to reflux for 1.5 H, cooled to room temperature and concentrated. The residue obtained was dissolved in dichloromethane (60 mL) and the solution was added dropwise into a cooled (0° C.) solution of compound ICb (23.3 g, 0.15 mol) and triethylamine (22.8 g, 0.225 mol) dissolved in dichloromethane (80 mL). The resulting reaction mixture was stirred at room temperature overnight. The next day, the reaction was quenched with water. The aqueous layer was separated and extracted with dichloromethane. The combined organic layers were washed with brine, dried over sodium sulfate and concentrated to obtain a crude material. The crude material was purified using silica gel column chromatography (PE: EA=2:1, $R_f$=0.6) to afford 5-bromo-2-(cyclopropylmethoxy)-N-(3-fluoro-4-methoxybenzyl)benzamide (40.0 g, 65%) as a white solid.

Example 3.2.4

Preparation of 2-(cyclopropylmethoxy)-N-(3-fluoro-4-methoxybenzyl)-5-(3-formylpyridine-2-yl)benzamide (IC10)

To a solution of compound IC7 (35 g, 0.086 mol, 1 eq) and bis (pinacolato)diboron (PinB; 26.2 g, 0.103 mol) in dioxane (500 mL), potassium acetate (KOAc; 25.3 g, 0.258 mol) was added followed by [1,1'-bis(diphenylphosphino)ferrocene]dichloropalladium(II) (Pd(dppf)Cl$_2$; 7.0 g, 0.0086 mol). The reaction mixture was heated to 95° C. After refluxing for 3 h, the reaction was diluted with water. The aqueous portion was separated and extracted with ethyl acetate. All combined organic layers were washed with brine, dried over sodium sulfate and concentrated to afford 2-(cyclopropylmethoxy)-N-(3-fluoro-4-methoxybenzyl)-5-(4,4,5,5-tetramethyl-1,3,2-dioxaborolan-2-yl)benzamide (IC9), which is used for the next step without purification. The crude compound IC9 was re-dissolved in toluene (500 mL) and 3-bromo-4-formylpyridine (ICc) (19.1 g, 0.101 mol), Pd(dppf)Cl$_2$ (3.5 g, 0.0043 mol), 2N(aq.) and sodium carbonate (86 ml, 0.172 mol) were added. The resulting mixture was heated to 95° C. After refluxing for 5H, the reaction was diluted with water. The aqueous portion was separated and extracted with ethyl acetate, washed with brine, dried over sodium sulfate and concentrated to obtain a crude material, which was purified by silica gel chromatography and subsequent recrystallization to afford 2-(cyclopropylmethoxy)-N-(3-fluoro-4-methoxybenzyl)-5-(3-formylpyridine-2-yl)benzamide (24 g, 65%) as an off-white powder.

Example 3.2.5

Preparation of 2-(cyclopropylmethoxy)-N-(3-fluoro-4-methoxybenzyl)-5-(hydroxymethyl)pyridin-2-yl)benzamide (AC6)

To a mixture of compound IC10 (24 g, 0.055 mol, 1 eq) in methanol (300 mL) and tetrahydrofuran (300 mL) sodium borohydride (10.46 g, 0.276 mol, 5 eq) was added. After the addition, the reaction was stirred at room temperature for 0.5 H. The reaction mixture was then diluted with ice-water and the pH of the mixture was adjusted to a pH value of 6 with 2N(aq.) hydrochloric acid. The resulting aqueous layer was separated and extracted with ethyl acetate. The combined organic layers were washed with brine, dried over sodium sulfate and concentrated to afford a crude material, which was recrystallized from PE and EA (v/v=2:1) to obtain 2-(cyclopropylmethoxy)-N-(3-fluoro-4-methoxybenzyl)-5-(hydroxymethyl)pyridin-2-yl)benzamide (22 g, 91%) as a white solid.

Example 4

Preparation of 2-(4-(cyclopropylmethoxy)-3-((3-fluoro-4-methoxybenzyl)carbamoyl)phenyl)-3-(hydroxymethyl)pyridine 1-oxide (AC14)

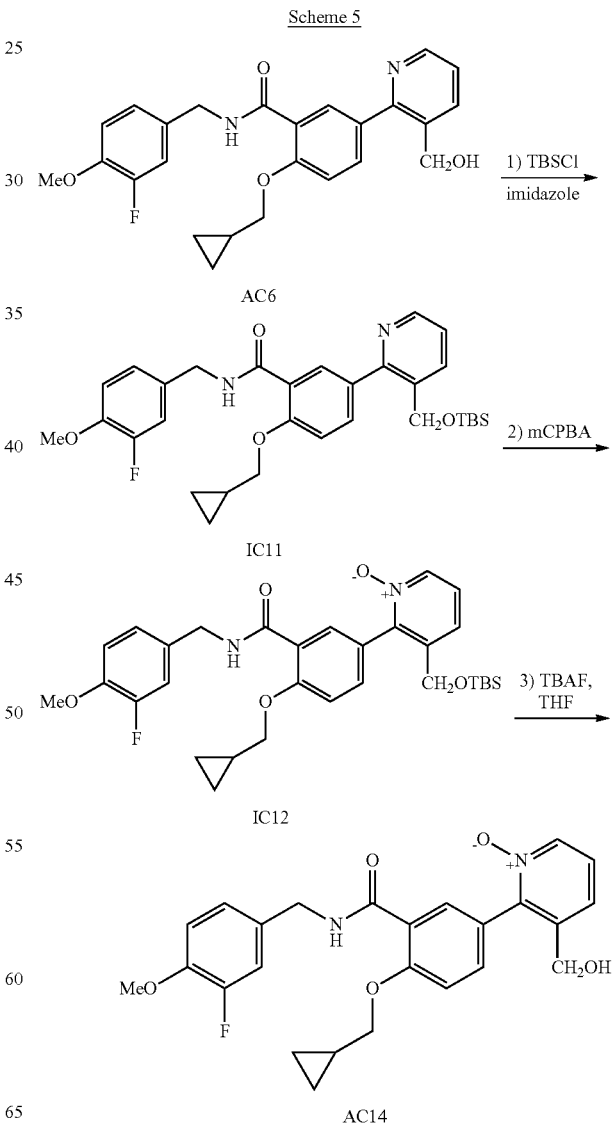

Scheme 5

Example 4.1.0

Preparation of 5-(3-(((tert-butyldimethylsilyl)oxy)methyl)pyridine-2-yl)-2-(cyclopropylmethoxy)-N-(3-fluoro-4-methoxybenzyl)benzamide (IC11)

A mixture of compound AC6 (2.8 g, 6.53 mmol), tert-butyldimethylsilyl chloride (TBSCl; 1.47 g, 9.79 mmol), dimethylamino pyridine (DMAP; 0.08 g, 0.65 mmol) and imidazole (1.33 g, 19.6 mmol) in dichloromethane (50 mL) was stirred at 25° C. for 2 h. The mixture was quenched with water. The aqueous layer was separated and extracted with dichloromethane. The combined organic layers were washed with brine, dried over sodium sulfate and concentrated to afford a crude material. The crude material was purified by silica gel chromatography (PE: EA=4:1, R=0.5) to obtain 5-(3-(((tert-butyldimethylsilyl)oxy)methyl)pyridine-2-yl)-2-(cyclopropylmethoxy)-N-(3-fluoro-4-methoxybenzyl)benzamide (3.2 g, 90%) as a white solid.

Example 4.1.1

Preparation of 3-(((tert-butyldimethylsilyl)oxy)methyl)-2-(4-(cyclopropylmethoxy)-3-((3-fluoro-4-methoxybenzyl)carbamoyl)phenyl)pyridine 1-oxide (IC12)

To a solution of compound IC11 (3.2 g, 5.8 mmol) in dichloromethane (50 mL) was added 3-chloroperbenzoic acid (m-CPBA; 4.05 g, 23.0 mmol). The reaction mixture was stirred at room temperature for 3.5 H before being quenched with sodium sulfite ($Na_2SO_3$; aq.). The aqueous layer was extracted with dichloromethane. The combined organic layers were washed with sodium carbonate ($Na_2CO_3$;aq.) and brine, dried over sodium sulfate and concentrated to afford 3-(((tert-butyldimethylsilyl)oxy)methyl)-2-(4-(cyclopropylmethoxy)-3-((3-fluoro-4-methoxybenzyl)carbamoyl)phenyl)pyridine 1-oxide (3.2 g, crude), which was used without further purification.

Example 4.1.2

Preparation of 2-(4-(cyclopropylmethoxy)-3-((3-fluoro-4-methoxybenzyl)carbamoyl)phenyl)-3-(hydroxymethyl)pyridine 1-oxide (AC14)

To a solution of compound IC12 (3.0 g, 5.47 mmol) dissolved in tetrahydrofuran (15 mL) a tetrabutylammonium fluoride (TBAF; 10 mL. 10.0 mmol, 1M in tetrahydrofuran) solution was added. The resulting reaction mixture was stirred at room temperature for 15 min. The reaction progress was monitored by TLC. Once the reaction was complete, the reaction mixture was diluted with water. The aqueous portion was separated and extracted with ethyl acetate. The combined organic layers were washed with brine, dried over sodium sulfate and concentrated to afford a crude material. The crude material was purified by preparative thin layer chromatography (dichloromethane:methanol (15:1), $R_f$=0.35) to yield 2-(4-(cyclopropylmethoxy)-3-((3-fluoro-4-methoxybenzyl)carbamoyl)phenyl)-3-(hydroxymethyl)pyridine 1-oxide (750 mg, 30%) as a white solid.

Example 5

Preparation of 2-(cyclopropylmethoxy)-N-(3-fluoro-4-methoxybenzyl)-5-(4-hydroxymethyl)thiophen-3-yl)nicotinamide (AC24)

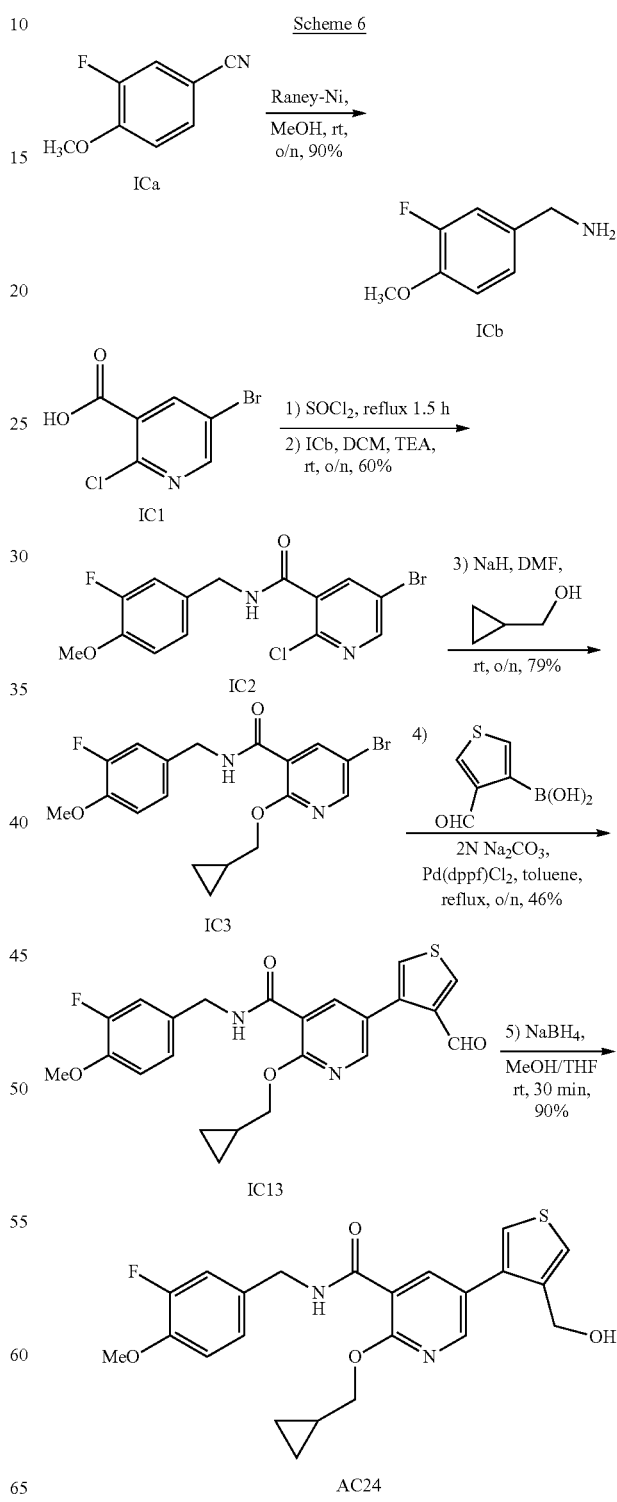

Scheme 6

Example 5.1.0

Preparation of (3-fluoro-4-methoxyphenyl)methanamine (ICb)

To a solution of compound ICa (68.0 g, 450 mmol, 1 eq) in methanol (2 L) was added Raney Nickel (70.0 g). The reaction mixture was stirred at room temperature overnight. A solid formed, which was removed by filtration and washed with methanol. The collected filtrate was a clear solution, which was concentrated at reduced pressure to yield (3-fluoro-4-methoxyphenyl)methanamine (62.8 g, 90%) as a yellow oil.

Example 5.1.1

Preparation of 5-bromo-2-chloro-N-(3-fluoro-4-methoxybenzyl)nicotinamide (IC2)

A solution of compound IC1 (40 g, 0.169 mol, 1 eq) in thionyl chloride (400 mL) was refluxed for 1.5 H, and then concentrated to obtain the crude acetyl chloride intermediate, which was dissolved in dichloromethane (100 mL) and added to a cooled (0° C.) solution of compound ICb (28.8 g, 0.186 mol, 1.1 eq), triethylamine (51.35 g, 0.508 mmol, 3 eq) in dichloromethane (600 mL). After stirring at room temperature overnight, the reaction mixture was diluted with water. The aqueous layer was separated and extracted with dichloromethane. The combined organic layers were washed with brine, dried over sodium sulfate, concentrated, and triturated with PE:EA=10:1 to afford 5-bromo-2-chloro-N-(3-fluoro-4-methoxybenzyl)nicotinamide (40.8 g, 60%) as a white solid.

Example 5.1.2

Preparation of 5-bromo-2-(cyclopropylmethoxy)-N-(3-fluoro-4-methoxybenzyl)nicotinamide (IC3)

To a solution of cyclopropanemethanol (9.45 g, 0.131 mol, 1.2 eq) in dimethylformamide (500 mL) was added sodium hydride (6.55 g, 0.164 mol, 1.5 eq) at room temperature. After stirring for 1 h, the reaction was cooled to 0° C., and compound IC2 (40.8 g, 0.109 mol, 1 eq) in dimethylformamide (100 mL) was added. After stirring at room temperature overnight, the reaction was quenched with water. The aqueous layer separated and extracted with ethyl acetate. The combined organic layers were washed with brine, dried over sodium sulfate, concentrated, and triturated with PE:EA=10:1 to afford 5-bromo-2-(cyclopropylmethoxy)-N-(3-fluoro-4-methoxybenzyl)nicotinamide (35 g, 79%) as a white solid.

Example 5.1.3

Preparation of 2-(cyclopropylmethoxy)-N-(3-fluoro-4-methoxybenzyl)-5-(4-formylthiophen-3-yl)nicotinamide (IC13)

To a solution of compound IC3 (200 mg, 0.489 mmol, 1 eq) and (4-formylthiophen-3-yl)boronic acid (84 mg, 0.538 mmol, 1.1 eq) in toluene was added 2N(aq.) sodium carbonate (0.5 mL, 2 eq) and [1,1'-bis(diphenylphosphino)ferrocene]dichloropalladium(II) (Pd(dppf)Cl₂; 20 mg, 0.0244 mmol, 0.05 eq). The reaction mixture was then heated to 90° C., and stirred overnight. The next day, the reaction was quenched with water. The aqueous layer was separated and extracted with ethyl acetate. The combined organic layers were washed with brine, dried over sodium sulfate and concentrated to afford a crude product, which was purified by preparative thin layer chromatography (PE:EA=1:1) to yield 2-(cyclopropylmethoxy)-N-(3-fluoro-4-methoxybenzyl)-5-(4-formylthiophen-3-yl)nicotinamide (100 mg, 46%) as a white solid.

Example 5.1.4

Preparation of 2-(cyclopropylmethoxy)-N-(3-fluoro-4-methoxybenzyl)-5-(4-hydroxymethyl)thiophen-3-yl)nicotinamide (AC24)

To a solution of compound IC13 (100 mg, 0.227 mmol, 1 eq) in tetrahydrofuran (5 mL) and methanol (5 mL) was added sodium borohydride (43 mg, 1.136 mmol, 5 eq). After stirring for 30 min, the reaction was quenched with cold water and the pH of the reaction mixture was adjusted to a pH=5 with 1N(aq.) hydrochloric acid. After stirring for an additional 15 min, the reaction mixture was partitioned. The aqueous layer was removed and extracted with ethyl acetate. The combined organic layers were washed with brine, dried over sodium sulfate and concentrated to afford 2-(cyclopropylmethoxy)-N-(3-fluoro-4-methoxybenzyl)-5-(4-hydroxymethyl)thiophen-3-yl)nicotinamide (90 mg, 90%) as a white solid.

Example 5.2.0

Preparation of 2-(cyclopropylmethoxy)-N-(3-fluoro-4-methoxybenzyl)-5-(2-(hydroxymethyl)thiophen-3-yl)nicotinamide (AC25)

-continued

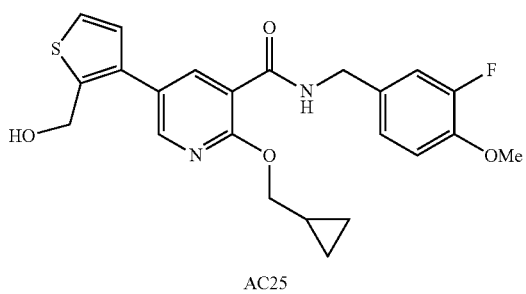

AC25

Example 5.2.1

Preparation of 2-(cyclopropylmethoxy)-N-(3-fluoro-4-methoxybenzyl)-5-(2-formylthiophen-3-yl)nicotinamide (IC14)

To a solution of compound IC3 (200 mg, 0.489 mmol, 1 eq) and (2-formylthiophen-3-yl)boronic acid (84 mg, 0.538 mmol, 1.1 eq) in toluene was added 2N(aq.) sodium carbonate (0.5 mL, 2N, 2 eq) and [1,1'-bis(diphenylphosphino)ferrocene]dichloropalladium(II) (Pd(dppf)Cl$_2$; 20 mg, 0.0244 mmol, 0.05 eq). The reaction was then heated to 90° C., and stirred overnight. The next day, the reaction mixture was quenched with water. The aqueous layer was separated and extracted with ethyl acetate. The combined organic layers were washed with brine, dried over sodium sulfate and concentrated to afford the crude product, which was purified by preparative thin layer chromatography (PE:EA=1:1) to obtain 2-(cyclopropylmethoxy)-N-(3-fluoro-4-methoxybenzyl)-5-(2-formylthiophen-3-yl)nicotinamide (27 mg, 12%) as a white solid.

Example 5.2.2

Preparation of 2-(cyclopropylmethoxy)-N-(3-fluoro-4-methoxybenzyl)-5-(2-(hydroxymethyl)thiophen-3-yl)nicotinamide (AC25)

To a solution of compound IC14 (20 mg, 0.045 mmol, 1 eq) in tetrahydrofuran (1 mL) and methanol (1 mL) was added sodium borohydride (9 mg, 0.227 mmol, 5 eq.). After stirring for 30 min, the reaction was quenched with cold water and then the pH of the reaction mixture was adjusted to a pH=5 with 1N(aq.) hydrochloric acid. After stirring for an additional 15 min, the reaction mixture was partitioned and the aqueous layer was separated and extracted with ethyl acetate. The combined organic layers were washed with brine, dried over sodium sulfate and concentrated to afford 2-(cyclopropylmethoxy)-N-(3-fluoro-4-methoxybenzyl)-5-(2-(hydroxymethyl)thiophen-3-yl)nicotinamide (15 mg, 75%) as a white solid.

Example 6

Preparation of 2-(cyclopropylmethoxy)-N-(3-fluoro-4-methoxybenzyl)-5-(3-(hydroxymethyl)thiophen-2-yl)nicotinamide (AC26)

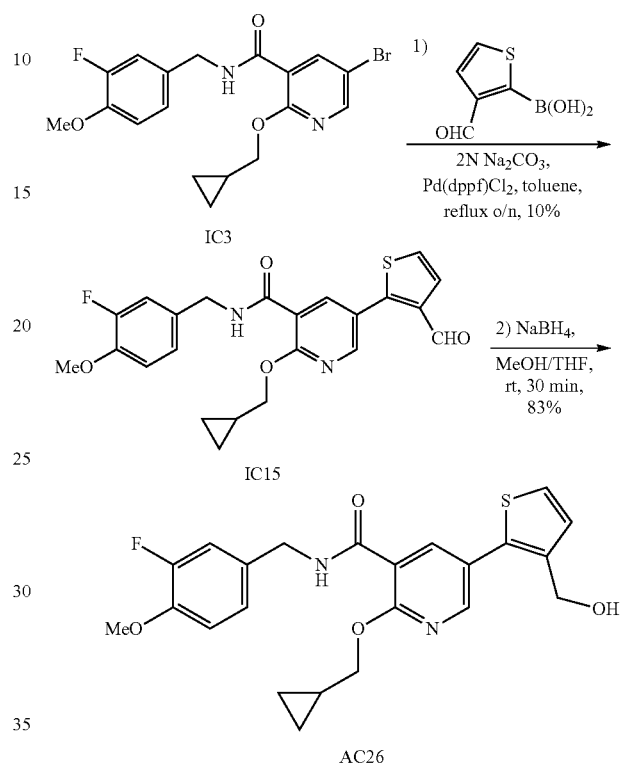

Example 6.1.0

Preparation of 2-(cyclopropylmethoxy)-N-(3-fluoro-4-methoxybenzyl)-5-(3-formylthiophen-2-yl)nicotinamide (IC15)

To a solution of compound IC3 (200 mg, 0.489 mmol, 1 eq) and (3-formylthiophen-2-yl)boronic acid (84 mg, 0.538 mmol, 1.1 eq) in toluene was added sodium carbonate (0.5 mL, 2N, 2 eq) and [1,1'-bis(diphenylphosphino)ferrocene]dichloropalladium(II) (Pd(dppf)Cl$_2$; 20 mg, 0.0244 mmol, 0.05 eq). The reaction was then heated to 90° C., and stirred overnight. The next day, the reaction was quenched with water. The aqueous layer was separated and extracted with ethyl acetate. The combined organic layers were washed with brine, dried over sodium sulfate and concentrated to afford a crude product, which was purified by preparative thin layer chromatography (PE:EA=1:1) to obtain 2-(cyclopropylmethoxy)-N-(3-fluoro-4-methoxybenzyl)-5-(3-formylthiophen-2-yl)nicotinamide (23 mg, 10%) as a white solid.

Example 6.1.1

Preparation of 2-(cyclopropylmethoxy)-N-(3-fluoro-4-methoxybenzyl)-5-(3-(hydroxymethyl)thiophen-2-yl)nicotinamide (AC26)

To a solution of compound IC15 (18 mg, 0.041 mmol, 1 eq) in tetrahydrofuran (1 mL) and methanol (1 mL) was added sodium borohydride (9 mg, 0.227 mmol, 5 eq). After stirring for 30 min, the reaction was quenched with cold water and the pH of the reaction was adjusted to a pH=5 with 1N(aq.) HCl. After stirring for an additional 15 min, the reaction mixture was allowed to partition. The aqueous layer was extracted with ethyl acetate. The combined organic layers were washed with brine, dried over sodium sulfate and concentrated to afford 2-(cyclopropylmethoxy)-N-(3-fluoro-4-methoxybenzyl)-5-(3-(hydroxymethyl)thiophen-2-yl)nicotinamide (AC26) (15 mg, 83%) as a white solid.

TABLE 3

Analytical Data of Compounds

| ID | Structure | MW | Analytical Data | ALDH2 Activity with 20 µM of the compound* |
|---|---|---|---|---|
| AC1 | 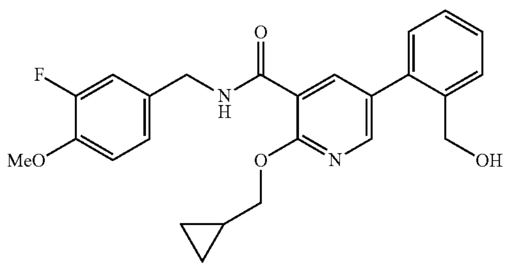 | 436.48 | $^1$H NMR (400 MHz, CDCl$_3$): δ 8.57 (d, J = 2.4 Hz, 1 H), 8.54-8.52 (m, 1 H), 8.27 (d, J = 2.4 Hz, 1 H), 7.58 (d, J = 7.6 Hz, 1 H), 7.43-7.36 (m, 2 H), 7.25 (s, 1 H), 7.16-7.09 (m, 2 H), 6.94 (t, J = 8.0 Hz, 1 H), 4.61 (s, 2 H), 4.59 (s, 2 H), 4.31 (d, J = 7.6 Hz, 2 H), 3.89 (s, 3 H), 1.25-1.22 (m, 2 H), 0.58-0.53 (m, 2 H), 0.33-0.30 (m, 2 H); m/z (ESI+) (M + H)$^+$ = 437.40; HPLC tR = 6.75 min | +++ |
| AC2 | 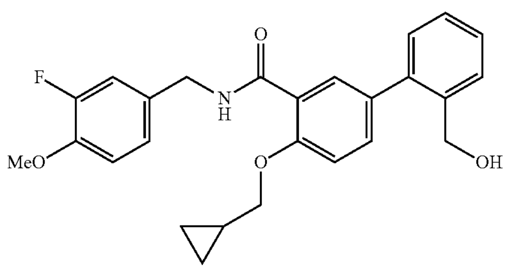 | 435.49 | $^1$H NMR (400 MHz, CDCl$_3$): δ 8.57-8.55 (m, 1 H), 8.25 (d, J = 2.8 Hz, 1 H), 7.53 (d, J = 6.8 Hz, 1 H), 7.45 (dd, J1 = 8.4 Hz, J2 = 2.4 Hz, 1 H), 7.38-7.33 (m, 2 H), 7.27 (d, J = 8.4 Hz, 1 H) 7.16-7.09 (m, 2 H), 6.95-6.90 (m, 2 H), 4.61 (s, 2 H), 4.60 (s, 2 H), 3.94 (d, J = 7.2 Hz, 2 H), 3.88 (s, 3 H), 1.25-1.20 (m, 2 H), 0.55-0.52 (m, 2 H), 0.31-0.29 (m, 2 H); m/z (ESI+) (M + H)$^+$ = 436.25; HPLC tR = 7.68 min | +++ |
| AC3 | 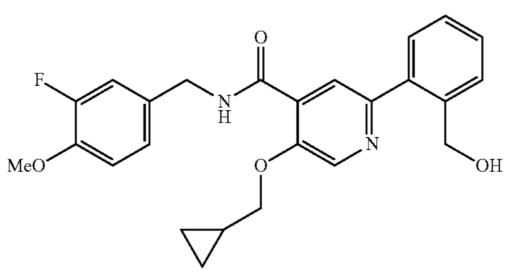 | 436.48 | $^1$H NMR (400 MHz, d$^6$-DMSO): δ 8.83-8.80 (m, 1 H), 8.55 (s, 1 H), 7.71 (s, 1 H), 7.56 (d, J = 7.2 Hz, 1 H), 7.44-7.32 (m, 3 H), 7.24-7.08 (m, 3 H), 4.49 (s, 2 H), 4.44 (d, J = 5.6 Hz, 2 H), 4.10 (d, J = 7.2 Hz, 2 H), 3.81 (s, 3 H), 1.27-1.21 (m, 1 H), 0.55-0.50 (m, 2 H), 0.35-0.31 (m, 2 H); m/z (ESI+) (M + H)$^+$ = 437.25; HPLC tR = 7.11 min | ++ |
| AC4 | 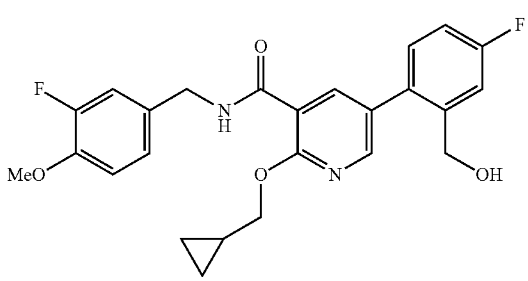 [SMILES: COc1ccc(CNC(=O)c2cc(-c3ccc(F)cc3CO)cnc2OCC2CC2)cc1F] | 454.47 | $^1$H NMR (400 MHz, CDCl$_3$): δ 8.51 (d, J = 2.4 Hz, 1 H), 8.51 (br s, 1 H), 8.20 (d, J = 2.8 Hz, 1 H), 7.33 (dd, J1 = 9.6 Hz, J2 = 2.4 Hz, 1 H), 7.22 (dd, J1 = 8.4 Hz, J2 = 6.0 Hz, 1 H), 7.15-7.03 (m, 3 H), 6.94 (t, J = 8.4 Hz, 1 H), 4.60 (d, J = 5.2 Hz, 2 H), 4.58 (d, J = 7.6 Hz, 2 H), 4.30 (d, J = 7.2 Hz, 2 H), 3.88 (s, 3 H), 1.25-1.21 (m, 1 H), 0.56-0.53 (m, 2 H), 0.33-0.30 (m, 2 H); m/z (ESI+) (M + H)$^+$ = 455.35; HPLC tR = 6.15 min | +++ |

TABLE 3-continued

Analytical Data of Compounds

| ID | Structure | MW | Analytical Data | ALDH2 Activity with 20 μM of the compound* |
|---|---|---|---|---|
| AC5 | 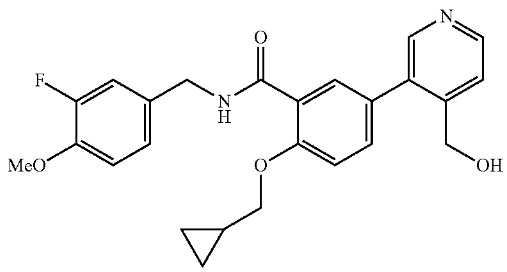 [SMILES: COc1ccc(CNC(=O)c2cc(-c3cnccc3CO)ccc2OCC2CC2)cc1F] | 436.48 | ¹H NMR (400 MHz, CDCl₃): δ 8.58-8.52 (m, 2 H), 8.37 (s, 1 H), 8.13 (d, J = 2.4 Hz, 1 H), 7.58 (d, J = 5.2 Hz, 1 H), 7.34 (dd, J1 = 8.4 Hz, J2 = 2.4 Hz, 1 H), 7.14-7.08 (m, 2 H), 6.96 (d, J = 8.8 Hz, 1 H), 6.92 (t, J = 8.4 Hz, 1 H), 4.64 (s, 2 H), 4.58 (d, J = 5.6 Hz, 2 H), 3.94 (d, J = 7.2 Hz, 2 H), 3.87 (s, 3 H), 1.27-1.22 (m, 1 H), 0.56-0.53 (m, 2 H), 0.31-0.29 (m, 2 H); m/z (ESI+) (M + H)⁺ = 437.40; HPLC tR = 6.04 min | +++ |
| AC6 | 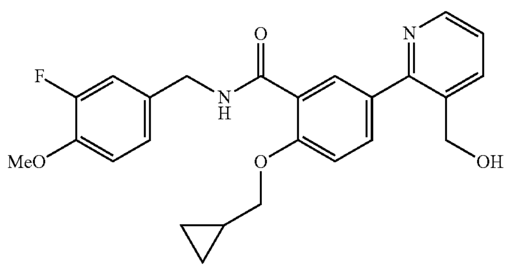 | 436.48 | ¹H NMR (400 MHz, DMSO-d⁶): δ 8.69 (t, J = 5.6 Hz, 1 H), 8.56 (d, J = 4.8 Hz, 1 H), 8.01-7.99 (m, 2 H), 7.71 (dd, J = 8.4, 2.0 Hz, 1 H), 7.43 (dd, J = 7.6, 4.8 Hz, 1 H), 7.23-7.13 (m, 4 H), 6.53 (s, 1 H), 4.50 (s, 2 H), 4.46 (d, J = 5.6 Hz, 2 H), 4.02 (d, J = 6.8 Hz, 2 H), 3.82 (s, 3 H), 1.29-1.25 (m, 1 H), 0.51 (d, J = 8.0 Hz, 2 H), 0.35 (d, J = 4.8 Hz, 2 H); m/z (ESI+) (M + H)⁺ = 437.25; HPLC tR = 5.96 min | +++ |
| AC7 | 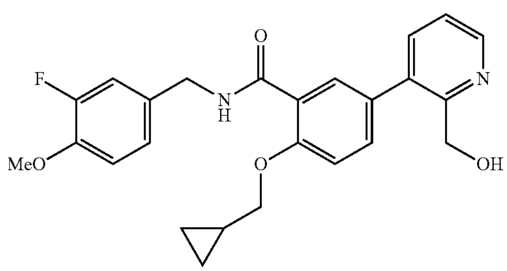 | 436.48 | ¹H NMR (400 MHz, CDCl₃): δ 8.58-8.53 (m, 2 H), 8.20 (d, J = 2.0 Hz, 1 H), 7.60 (d, J = 7.6 Hz, 1 H), 7.35 (dd, J1 = 8.4 Hz, J2 = 2.4 Hz, 1 H), 7.32 (t, J = 6.4 Hz, 1 H), 7.14 (dd, J1 = 13.6 Hz, J2 = 1.6 Hz, 1 H), 7.11 (d, J = 8.8 hz, 1 H), 6.98-6.91 (m, 2 H), 4.65 (s, 2 H), 4.60 (d, J = 5.2 Hz, 2 H), 3.95 (d, J = 7.2 Hz, 2 H), 3.88 (s, 3 H), 1.17-1.14 (m, 1 H), 0.51-0.49 (m, 2 H), 0.27-0.26 (m, 2 H); m/z (ESI+) (M + Na)⁺ = 437.45; HPLC tR = 6.28 min | +++ |
| AC8 | 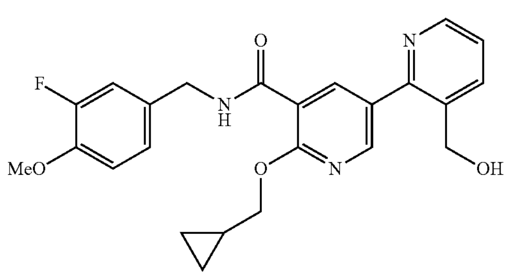 | 437.46 | ¹H NMR (400 MHz, CDCl₃): δ 8.77 (d, J = 2.4 Hz, 1 H), 8.63 (dd, J = 4.8, 1.6 Hz, 1 H), 8.52 (s, 1 H), 8.49 (t, J = 7.6 Hz, 1 H), 7.94 (d, J = 6.8 Hz, 1 H), 7.33 (dd, J = 7.6, 4.8 Hz, 1 H), 7.16 (d, J = 12.4 Hz, 1 H), 7.13 (d, J = 12.0 Hz, 1 H), 6.94 (t, J = 8.4 Hz, 1 H), 4.72 (d, J = 4.8 Hz, 2 H), 4.60 (d, J = 5.6 Hz, 2 H), 4.33 (d, J = 7.6 Hz, 2 H), 3.89 (s, 3 H), 1.28-1.22 (m, 1 H), 0.55 (d, J = 6.8 Hz, 2 H), 0.31 (q, J = 4.2 Hz, 2 H); m/z (ESI+) (M + H)⁺ = 438.25; HPLC tR = 6.14 min | +++ |

TABLE 3-continued

Analytical Data of Compounds

| ID | Structure | MW | Analytical Data | ALDH2 Activity with 20 μM of the compound* |
|---|---|---|---|---|
| AC9 | 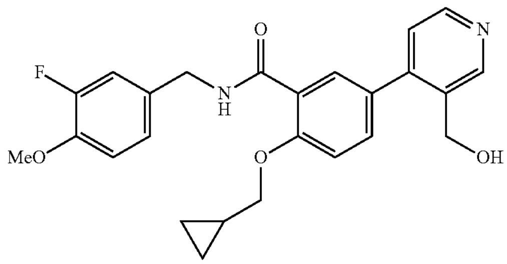 | 436.48 | $^1$H NMR (400 MHz, CDCl$_3$): δ 9.12 (s, 1 H), 8.63 (s, 1 H), 8.57 (s, 1 H), 8.31 (s, 1 H), 7.74 (s, 1 H), 7.14-7.07 (m, 4 H), 7.94 (t, J = 8.0 Hz, 1 H), 4.83 (s, 2 H), 4.61 (s, 2 H), 4.00 (d, J = 7.2 Hz, 2 H), 3.88 (s, 3 H), 1.25-1.19 (m, 1 H), 0.57 (d, J = 7.2 Hz, 2 H), 0.33 (d, J = 4.4 Hz, 2 H); m/z (ESI+) (M + H)$^+$ = 437.30; HPLC tR = 6.20 min | +++ |
| AC10 | 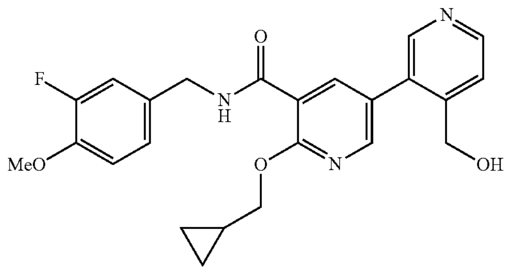 [SMILES: COc1ccc(CNC(=O)c2cc(-c3cnccc3CO)cnc2OCC2CC2)cc1F] | 437.46 | $^1$H NMR (400 MHz, CDCl$_3$): δ 8.58-8.52 (m, 2 H), 8.45 (d, J = 2.4 Hz, 1 H), 8.38 (s, 1 H), 8.18 (d, J = 2.0 Hz, 1 H), 7.60 (d, J = 4.4 Hz, 1 H), 7.12 (d, J = 11.6 Hz, 1 H), 7.09 (d, J = 9.2 Hz, 1 H), 6.93 (t, J = 8.4 Hz, 1 H), 4.63 (s, 2 H), 4.58 (d, J = 9.2 Hz, 2 H), 4.30 (d, J = 7.6 Hz, 2 H), 3.88 (s, 3 H), 1.89 (s, 1 H), 1.24-1.21 (m, 2 H), 0.50 (d, J = 8.0 Hz, 2 H), 0.31 (d, J = 5.6 Hz, 2 H); m/z (ESI+) (M + H)$^+$ = 438.40; HPLC tR = 6.17 min | +++ |
| AC11 | 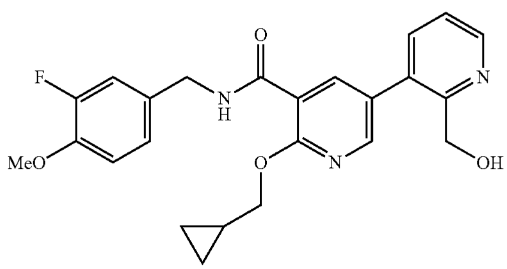 | 437.46 | $^1$H NMR (400 MHz, CDCl$_3$): δ 8.62 (d, J = 3.6 Hz, 1 H), 8.51 (d, J = 2.4 Hz, 1 H), 8.18 (d, J = 2.4 Hz, 1 H), 7.60 (d, J = 6.8 Hz, 1 H), 7.35 (dd, J = 7.6, 5.2 Hz, 1 H), 7.13 (t, J = 12.0 Hz, 2 H), 6.94 (t, J = 6.6 Hz, 1 H), 4.66 (s, 2 H), 4.61 (d, J = 5.6 Hz, 2 H), 4.55 (s, 1 H), 4.32 (d, J = 8.0 Hz, 2 H), 3.89 (s, 3 H), 1.57 (s, 1 H), 1.28-1.21 (m, 2 H), 0.57 (d, J = 7.6 Hz, 2 H), 0.32 (d, J = 4.8 Hz, 2 H); m/z (ESI+) (M + H)$^+$ = 438.45; HPLC tR = 6.31 min | ++ |
| AC12 | 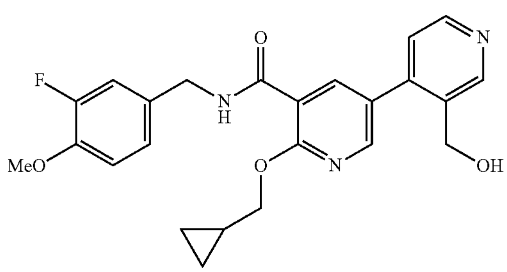 | 437.46 | $^1$H NMR (400 MHz, CDCl$_3$): δ 8.77 (s, 1 H), 8.64 (d, J = 2.0 Hz, 1 H), 8.57 (d, J = 5.2 Hz, 1 H), 8.50 (s, 1 H), 8.36 (d, J = 2.8 Hz, 1 H), 7.26 (s, 1 H), 7.21 (d, J = 4.2 Hz, 1 H), 7.13 (d, J = 12.4 Hz, 1 H), 7.10 (d, J = 11.2 Hz, 1 H), 6.94 (t, J = 8.4 Hz, 1 H), 4.67 (s, 2 H), 4.61 (d, J = 5.2 Hz, 2 H), 4.32 (d, J = 7.6 Hz, 2 H), 3.89 (s, 3 H), 1.25-1.21 (m, 2 H), 0.56 (d, J = 7.6 Hz, 2 H), 0.32 (d, J = 4.8 Hz, 2 H); m/z (ESI+) (M + H)$^+$ = 438.40; HPLC tR = 6.23 min | +++ |

TABLE 3-continued

Analytical Data of Compounds

| ID | Structure | MW | Analytical Data | ALDH2 Activity with 20 μM of the compound* |
|---|---|---|---|---|
| AC13 | 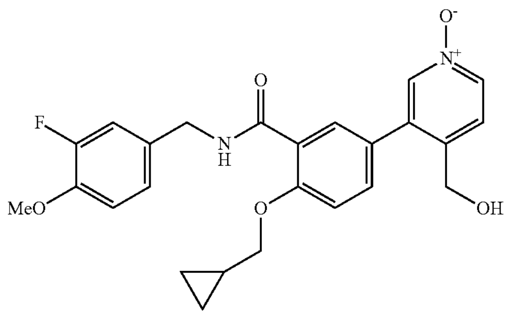 [SMILES: COc1ccc(CNC(=O)c2cc(-c3c[n+]([O-])ccc3CO)ccc2OCC2CC2)cc1F] | 452.47 | ¹H NMR (400 MHz, CDCl₃): δ 8.53 (s, 1 H), 8.16 (s, 1 H), 8.14 (d, J = 6.8 Hz, 1 H), 8.07 (s, 1 H), 7.56 (d, J = 6.4 Hz, 1 H), 7.37 (dd, J = 8.4, 2.4 Hz, 1 H), 7.15-7.09 (m, 2 H), 7.00 (d, J = 8.4 Hz, 1 H), 6.93 (t, J = 8.4 Hz, 1 H), 4.60 (s, 1 H), 4.59 (s, 3 H), 3.96 (d, J = 7.2 Hz, 2 H), 3.88 (s, 3 H), 1.25-1.19 (m, 1 H), 0.55 (d, J = 7.2 Hz, 2 H), 0.30 (d, J = 5.2 Hz, 2 H); m/z (ESI+) (M + H)+ = 453.45; HPLC tR = 6.61 min | ++ |
| AC14 | 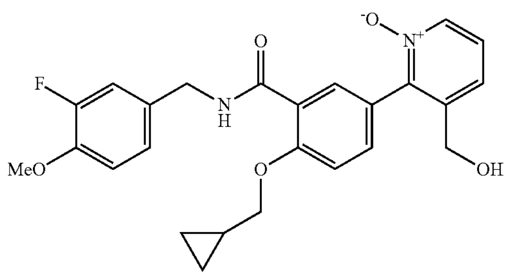 | 452.47 | ¹H NMR (400 MHz, CDCl₃): δ 8.53 (s, 1 H), 8.16 (s, 1 H), 8.01 (s, 1 H), 7.58 (d, J = 8.0 Hz, 1 H), 7.45 (dd, J = 4.8, 2.8, 1 H), 7.24 (d, J = 11.2 Hz, 1 H), 7.11 (d, J = 13.2 Hz, 1 H), 7.06 (d, J = 8.4 Hz, 1 H), 6.99 (d, J = 8.4 Hz, 1 H), 6.91 (t, J = 8.4 Hz, 1 H), 4.55 (s, 2 H), 4.31 (s, 2 H), 3.93 (d, J = 6.8 Hz, 2 H), 3.86 (s, 3 H), 1.18-1.15 (m, 1 H), 0.51 (d, J = 7.2 Hz, 2 H), 0.27 (d, J = 4.4 Hz, 2 H); m/z (ESI+) (M + H)⁺ = 453.50; HPLC tR = 6.56 min | ++ |
| AC15 | 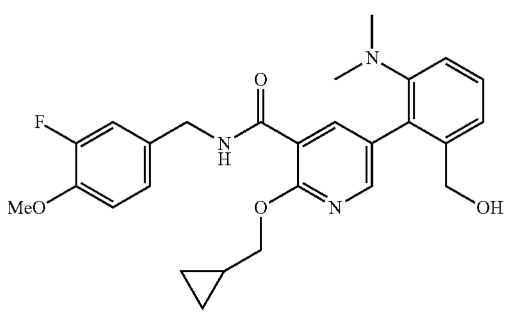 | 479.54 | ¹H NMR (400 MHz, CDCl₃): δ 8.56 (s, 1 H), 8.53 (d, J = 2.4 Hz, 1 H), 8.20 (d, J = 2.0 Hz, 1 H), 7.36 (t, J = 8.0 Hz, 1 H), 7.25 (d, J = 8.0 Hz, 1 H), 7.18-7.09 (m, 3 H), 6.94 (t, J = 8.8 Hz, 1 H), 4.61 (s, 2 H), 4.40 (s, 2 H), 4.30 (d, J = 7.2 Hz, 2 H), 3.89 (s, 3 H), 2.45 (s, 6 H), 1.27-1.23 (m, 1 H), 0.55 (d, J = 7.2 Hz, 2 H), 0.32 (d, J = 5.6 Hz, 2 H); m/z (ESI+) (M + H)⁺ = 480.50; HPLC tR = 6.20 min | ++ |
| AC16 | 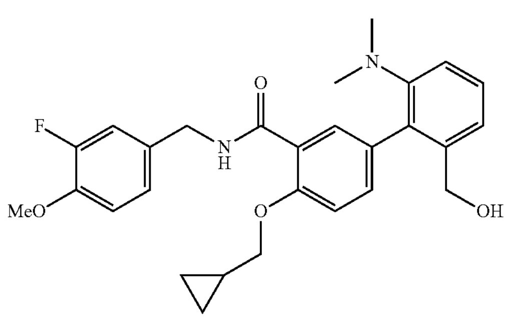 [SMILES: COc1ccc(CNC(=O)c2cc(-c3c(CO)cccc3N(C)C)ccc2OCC2CC2)cc1F] | 478.56 | ¹H NMR (400 MHz, CDCl₃): δ 8.67 (s, 1 H), 8.01 (s, 1 H), 7.73 (s, 1 H), 7.59 (s, 1 H), 7.51 (d, J = 3.6 Hz, 1 H), 7.46 (d, J = 6.8 Hz, 2 H), 7.29 (d, J = 6.8 Hz, 1 H), 7.14-7.08 (m, 2 H), 7.01 (d, J = 8.0 Hz, 1 H), 6.93 (t, J = 8.4 Hz, 1 H), 4.63-4.49 (m, 2 H), 4.30 (s, 2 H), 3.98 (d, J = 7.6 Hz, 1 H), 3.88 (s, 3 H), 3.15 (s, 6 H), 1.27-1.23 (m, 1 H), 0.54-0.45 (m, 2 H), 0.30 (d, J = 4.4 Hz, 2 H); m/z (ESI+) (M + H)⁺ = 479.40; HPLC tR = 6.24 min | + |

TABLE 3-continued

Analytical Data of Compounds

| ID | Structure | MW | Analytical Data | ALDH2 Activity with 20 μM of the compound* |
|---|---|---|---|---|
| AC17 | 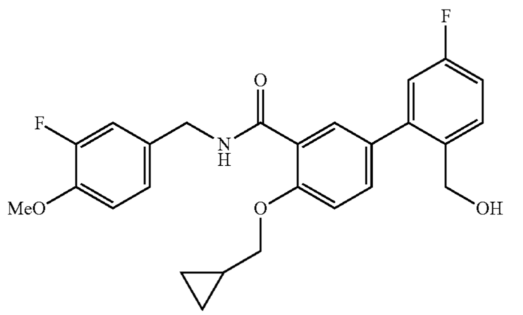 [SMILES: COc1ccc(CNC(=O)c2cc(-c3cc(F)ccc3CO)ccc2OCC2CC2)cc1F] | 453.48 | ¹H NMR (400 MHz, CDCl₃): δ 8.55 (s, 1 H), 8.25 (d, J = 2.8 Hz, 1 H), 7.52-7.45 (m, 2 H), 7.17-7.00 (m, 3 H), 6.99-6.91 (m, 3 H), 4.61 (d, J = 4.8 Hz, 2 H), 4.67 (s, 2 H), 3.95 (d, J = 7.2 Hz, 2 H), 3.89 (s, 3 H), 1.25-1.19 (m, 1 H), 0.55 (d, J = 7.2 Hz, 2 H), 0.30 (d, J = 5.6 Hz, 2 H); m/z (ESI+) (M + H)⁺ = 454.40; HPLC tR = 7.83 min | +++ |
| AC18 | 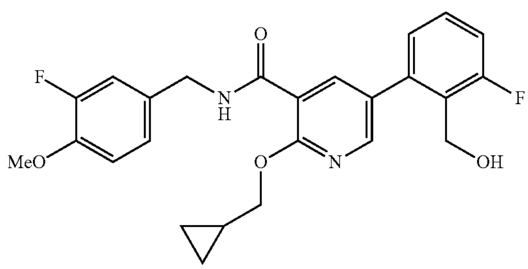 [SMILES: COc1ccc(CNC(=O)c2cc(-c3cccc(F)c3CO)cnc2OCC2CC2)cc1F] | 454.47 | ¹H NMR (400 MHz, CDCl₃): δ 8.63 (d, J = 2.0 Hz, 1 H), 8.51 (t, J = 4.8 Hz, 1 H), 8.36 (d, J = 2.8 Hz, 1 H), 7.35 (dd, J = 13.6, 8.0 Hz, 1 H), 7.16-7.10 (m, 4 H), 6.94 (t, J = 8.4 Hz, 1 H), 4.60 (d, J = 5.2 Hz, 4 H), 4.30 (d, J = 7.6 Hz, 2 H), 3.89 (s, 3 H), 1.27-1.20 (m, 1 H), 0.55 (d, J = 7.2 Hz, 2 H), 0.31 (d, J = 5.6 Hz, 2 H); m/z (ESI+) (M + H)⁺ = 455.35; HPLC tR = 7.89 min | ++ |
| AC19 | 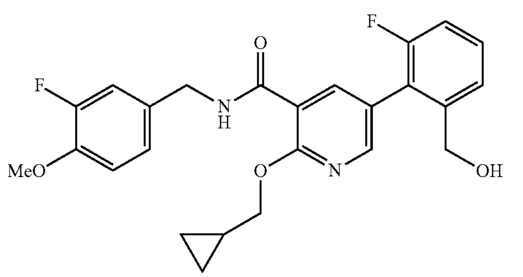 [SMILES: COc1ccc(CNC(=O)c2cc(-c3c(F)cccc3CO)cnc2OCC2CC2)cc1F] | 454.47 | ¹H NMR (400 MHz, CDCl₃): δ 8.5 (s, 1 H), 8.21 (s, 1 H), 7.38 (s, 2 H), 7.15-7.09 (m, 3 H), 6.94 (t, J = 8.4 Hz, 1 H), 4.61 (s, 2 H), 4.53 (s, 2 H), 4.31 (d, J = 7.6 Hz, 2 H), 3.89 (s, 3 H), 1.25-1.21 (m, 1 H), 0.55 (d, J = 8.0 Hz, 2 H), 0.31 (d, J = 4.8 Hz, 2 H); m/z (ESI+) (M + H)+ = 455.35; HPLC tR = 7.65 min | +++ |
| AC20 | 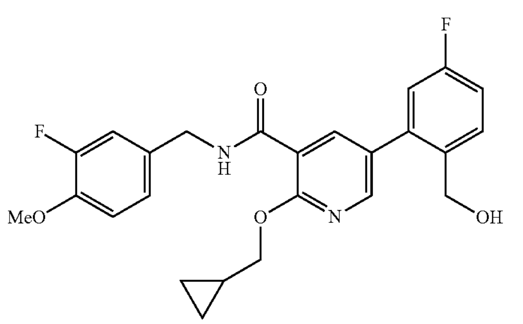 [SMILES: COc1ccc(CNC(=O)c2cc(-c3cc(F)ccc3CO)cnc2OCC2CC2)cc1F] | 454.47 | ¹H NMR (400 MHz, CDCl₃): δ 8.55 (d, J = 2.8 Hz, 1 H), 8.51 (t, J = 4.8 Hz, 1 H), 8.25 (d, J = 2.8 Hz, 1 H), 7.53 (dd, J = 8.4, 6.0 Hz, 1 H), 7.15-7.05 (m, 3 H), 6.97-6.91 (m, 2 H), 4.58 (d, J = 5.2 Hz, 2 H), 4.53 (s, 2 H), 4.29 (d, J = 7.6 Hz, 2 H), 3.88 (s, 3 H), 1.25-1.20 (m, 1 H), 0.55 (d, J = 7.2 Hz, 2 H), 0.30 (d, J = 5.2 Hz, 2 H); m/z (ESI+) (M + H)⁺ = 455.30; HPLC tR = 7.90 min | +++ |

TABLE 3-continued

Analytical Data of Compounds

| ID | Structure | MW | Analytical Data | ALDH2 Activity with 20 μM of the compound* |
|---|---|---|---|---|
| AC21 | 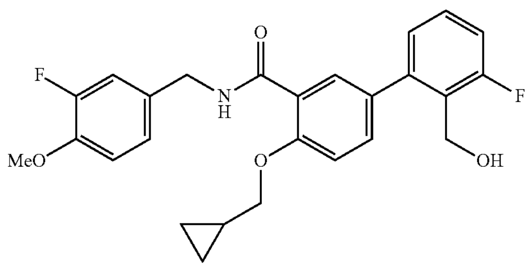 [SMILES: COc1ccc(CNC(=O)c2cc(-c3cccc(F)c3CO)ccc2OCC2CC2)cc1F] | 453.48 | $^1$H NMR (400 MHz, CDCl$_3$): δ 8.56 (s, 1 H), 8.30 (s, 1 H), 7.56 (d, J = 8.8 Hz, 1 H), 7.31 (dd, J = 8.0, 5.6 Hz, 1 H), 7.16-7.06 (m, 4 H), 6.98-6.91 (m, 2 H), 4.61 (d, J = 4.8 Hz, 2 H), 3.94 (d, J = 7.6 Hz, 2 H), 3.88 (s, 3 H), 1.25-1.18 (m, 1 H), 0.54 (d, J = 7.6 Hz, 2 H), 0.31 (d, J = 4.8 Hz, 2 H); m/z (ESI+) (M + H)$^+$ = 454.35; HPLC tR = 7.69 min | +++ |
| AC22 | 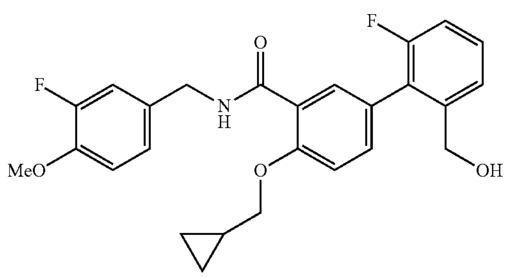 | 453.48 | $^1$H NMR (400 MHz, CDCl$_3$): δ 8.64 (s, 1 H), 8.19 (s, 1 H), 7.41-7.34 (m, 3 H), 7.16-6.99 (m, 3 H), 6.98 (d, J = 8.4 Hz, 1 H), 6.93 (t, J = 8.4 Hz, 1 H), 4.60 (d, J = 5.2 Hz, 2 H), 4.51 (s, 2 H), 3.95 (d, J = 7.6 Hz, 2 H), 3.90 (s, 3 H), 1.29-1.16 (m, 1 H), 0.53 (d, J = 7.6 Hz, 2 H), 0.30 (d, J = 4.4 Hz, 2 H); m/z (ESI+) (M + H)$^+$ = 454.45; HPLC tR = 7.69 min | +++ |
| AC23 | 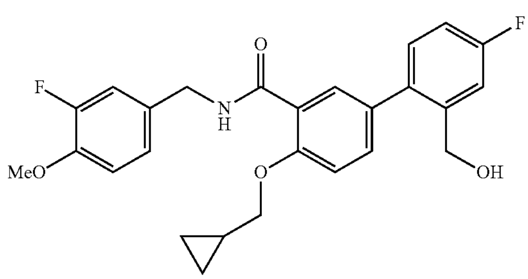 [SMILES: COc1ccc(CNC(=O)c2cc(-c3ccc(F)cc3CO)ccc2OCC2CC2)cc1F] | 453.48 | $^1$H NMR (400 MHz, CDCl$_3$): δ 8.58 (s, 1 H), 8.18 (d, J = 2.0 Hz, 1 H), 7.39 (d, J = 2.0 Hz, 1 H), 7.37-7.26 (m, 1 H), 7.20 (dd, J = 8.4, 6.0 Hz, 1 H), 7.15-7.09 (m, 2 H), 7.02 (t, J = 3.2 Hz, 1 H), 6.93 (t, J = 8.4 Hz, 2 H), 4.60 (t, J = 5.6 Hz, 4 H), 3.94 (d, J = 7.2 Hz, 2 H), 3.88 (s, 3 H), 1.25-1.20 (m, 1 H), 0.54 (d, J = 7.6 Hz, 2 H), 0.30 (d, J = 4.4 Hz, 2 H); m/z (ESI+) (M + H)$^+$ = 454.25; HPLC tR = 7.84 min | +++ |
| AC24 | 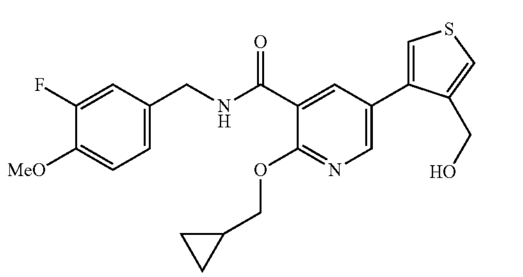 [SMILES: COc1ccc(CNC(=O)c2cc(-c3cscc3CO)cnc2OCC2CC2)cc1F] | 442.50 | $^1$H NMR (400 MHz, CDCl$_3$): δ 8.61 (d, J = 2.8 Hz, 1 H), 8.46 (s, 1 H), 8.33 (d, J = 2.4 Hz, 1 H), 7.38 (d, J = 3.6 Hz, 1 H), 7.26 (d, J = 3.6 Hz, 1 H), 7.11-7.05 (m, 2 H), 6.89 (t, J = 8.0 Hz, 1 H), 4.62 (s, 2 H), 4.56 (d, J = 5.2 Hz, 2 H), 4.25 (d, J = 7.2 Hz, 2 H), 3.84 (s, 3 H), 1.23-1.16 (m, 1 H), 0.51 (d, J = 6.0 Hz, 2 H), 0.25 (d, J = 5.2 Hz, 2 H); m/z (ESI+) (M + H)$^+$ = 443.25; HPLC tR = 7.72 min | +++ |

TABLE 3-continued

Analytical Data of Compounds

| ID | Structure | MW | Analytical Data | ALDH2 Activity with 20 μM of the compound* |
|---|---|---|---|---|
| AC25 | 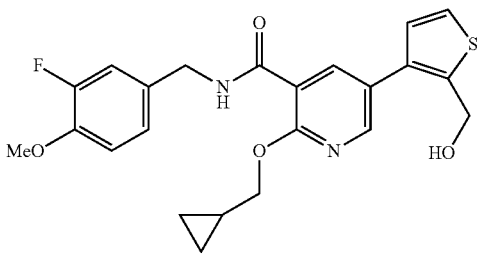 | 442.50 | $^1$H NMR (400 MHz, CDCl$_3$): δ 8.63 (d, J = 1.6 Hz, 1 H), 8.53 (s, 1 H), 8.36 (d, J = 2.0 Hz, 1 H), 7.34 (d, J = 4.8 Hz, 1 H), 7.16-7.10 (m, 3 H), 6.95 (t, J = 8.0 Hz, 1 H), 4.83 (s, 2 H), 4.62 (d, J = 5.2 Hz, 2 H), 4.30 (d, J = 7.2 Hz, 2 H), 3.90 (s, 3 H), 1.28-1.21 (m, 1 H), 0.56 (d, J = 7.2 Hz, 2 H), 0.32 (d, J = 5.2 Hz, 2 H); m/z (ESI+) (M + H)$^+$ = 443.30; HPLC tR = 7.60 min | +++ |
| AC26 | 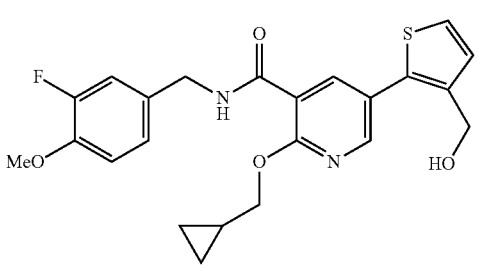 | 442.50 | $^1$H NMR (400 MHz, CDCl$_3$): δ 8.65 (d, J = 2.4 Hz, 1 H), 8.50 (s, 1 H), 8.38 (d, J = 2.4 Hz, 1 H), 7.31 (d, J = 5.2 Hz, 1 H), 7.21 (d, J = 5.2 Hz, 1 H), 7.16-7.10 (m, 2 H), 6.94 (t, J = 8.0 Hz, 1 H), 4.65 (s, 2 H), 4.60 (d, J = 5.2 Hz, 2 H), 4.30 (d, J = 7.6 Hz, 2 H), 3.89 (s, 3 H), 1.26-1.20 (m, 1 H), 0.56 (d, J = 7.2 Hz, 2 H), 0.31 (d, J = 5.2 Hz, 2 H); m/z (ESI+) (M + H)$^+$ = 443.20; HPLC tR = 7.83 min | +++ |
| AC27 | 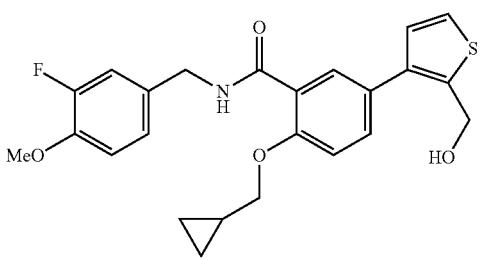 | 441.52 | $^1$H NMR (400 MHz, CDCl$_3$): δ 8.53 (s, 1 H), 8.29 (s, 1 H), 7.49 (d, J = 8.4 Hz, 1 H), 7.24 (d, J = 5.2 Hz, 1 H), 7.10-7.04 (m, 3 H), 6.91-6.85 (m, 2 H), 4.77 (s, 2 H), 4.56 (s, 2 H), 3.88 (d, J = 7.2 Hz, 2 H), 3.83 (s, 3 H), 1.21-1.12 (m, 1 H), 0.49 (d, J = 4.0 Hz, 2 H), 0.24 (d, J = 4.8 Hz, 2 H); m/z (ESI+) (M + H)$^+$ = 442.20; HPLC tR = 8.12 min | +++ |
| AC28 | 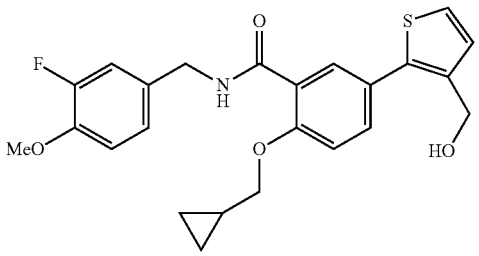 | 441.52 | $^1$H NMR (400 MHz, CDCl$_3$): δ 8.52 (s, 1 H), 8.36 (d, J = 2.8 Hz, 1 H), 7.57 (dd, J = 8.8, 2.8 Hz, 1 H), 7.26 (d, J = 3.2 Hz, 1 H), 7.18-7.09 (m, 3 H), 6.96-6.93 (m, 2 H), 4.67 (s, 2 H), 4.61 (d, J = 5.6 Hz, 2 H), 3.94 (d, J = 7.6 Hz, 2 H), 3.89 (s, 3 H), 1.29-1.25 (m, 1 H), 0.54 (d, J = 8.0 Hz, 2 H), 0.30 (d, J = 5.2 Hz, 2 H); m/z (ESI+) (M + H)$^+$ = 442.30; HPLC tR = 7.59 min | +++ |

TABLE 3-continued

Analytical Data of Compounds

| ID | Structure | MW | Analytical Data | ALDH2 Activity with 20 μM of the compound* |
|---|---|---|---|---|
| AC29 | 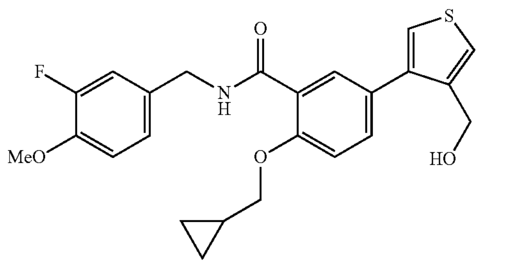 | 441.52 | ¹H NMR (400 MHz, CDCl₃): δ 8.35 (s, 1 H), 8.34 (s, 1 H), 7.57 (d, J = 8.8 Hz, 1 H), 7.39 (d, J = 2.8 Hz, 1 H), 7.26 (d, J = 4.4 Hz, 1 H), 7.16-7.10 (m, 2 H), 6.94 (d, J = 8.4 Hz, 2 H), 4.67 (s, 2 H), 4.61 (d, J = 5.6 Hz, 2 H), 3.94 (d, J = 6.8 Hz, 2 H), 3.89 (s, 3 H), 1.28-1.26 (m, 1 H), 0.54 (d, J = 8.0 Hz, 2 H), 0.30 (d, J = 4.8 Hz, 2 H); m/z (ESI+) (M + H)⁺ = 442.25; HPLC tR = 7.55 min | +++ |
| AC30 | 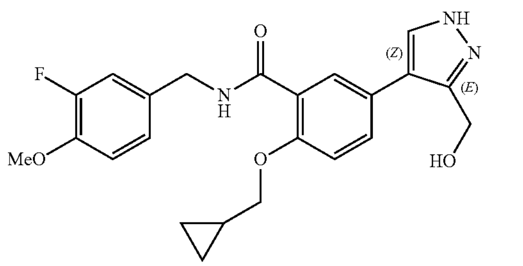 [SMILES: COc1ccc(CNC(=O)c2cc(-c3c[nH]nc3CO)ccc2OCC2CC2)cc1F] | 425.45 | ¹H NMR (400 MHz, CDCl₃): δ 8.60 (br. s, 1 H), 8.22 (br. s, 1 H), 7.50-7.45 (m, 1 H), 7.14-7.00 (m, 2 H), 6.94-6.92 (m, 2 H), 4.91-4.87 (m, 2 H), 4.60 (s, 2 H), 3.92 (s, 2 H), 3.84 (s, 3 H), 1.25-1.20 (m, 1 H), 0.52-0.48 (m, 2 H), 0.30-0.28 (m, 2 H); m/z (ESI+) (M + H)⁺ = 426.20; HPLC tR = 6.33 min | +++ |
| AC31 | 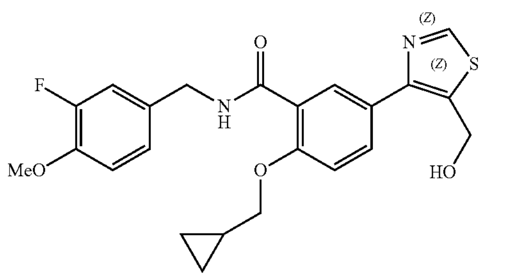 [SMILES: COc1ccc(CNC(=O)c2cc(-c3ncsc3CO)ccc2OCC2CC2)cc1F] | 442.50 | ¹H NMR (400 MHz, CDCl₃): δ 8.77 (br. s, 1 H), 8.54 (br. s, 1 H), 8.45 (s, 1 H), 7.88 (d, J = 6.4 Hz, 1 H), 7.24-7.09 (m, 2 H), 7.01-6.90 (m, 2 H), 5.04-5.02 (m, 2 H), 6.62-4.60 (m, 2 H), 3.97-3.93 (m, 2 H), 3.86 (s, 3 H), 1.25-1.20 (m, 1 H), 0.52-0.48 (m, 2 H), 0.30-0.28 (m, 2 H); m/z (ESI+) (M + H)⁺ = 443.20; HPLC tR = 6.67 min | +++ |
| AC32 | 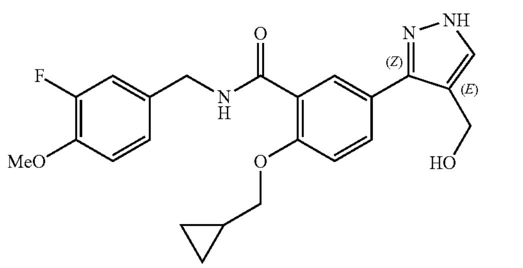 [SMILES: COc1ccc(CNC(=O)c2cc(-c3n[nH]cc3CO)ccc2OCC2CC2)cc1F] | 425.45 | ¹H NMR (400 MHz, CDCl₃): δ 8.56-8.51 (m, 2 H), 7.79-7.75 (m, 2 H), 7.12-7.06 (m, 2 H), 6.97-6.89 (m, 2 H), 4.68 (s, 2 H), 4.56 (s, 2 H), 3.92-3.82 (m, 5 H), 1.25-1.20 (m, 1 H), 0.54-0.48 (m, 2 H), 0.28-0.23 (m, 2 H); m/z (ESI+) (M + H)⁺ = 426; HPLC tR = 6.60 min | +++ |
| AC33 | 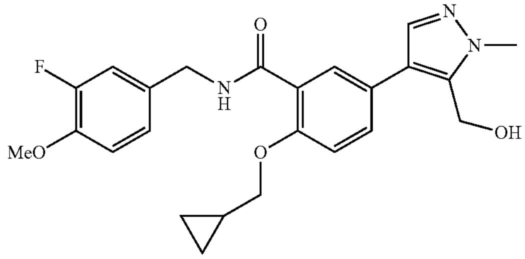 [SMILES: COc1ccc(CNC(=O)c2cc(-c3cnn(C)c3CO)ccc2OCC2CC2)cc1F] | 439.48 | ¹H NMR (400 MHz, CDCl₃): δ 8.60(s, 1 H), 8.23 (s, 1 H), 7.54 (s, 1 H), 7.45-7.43 (m, 1 H), 7.15-7.08 (m, 2 H), 6.94-6.92 (m, 2 H), 4.73 (s, 2 H), 4.59 (s, 2 H), 3.99 (s, 3 H), 3.98-3.80 (m, 5 H), 1.22-1.20 (m, 1 H), 0.53-0.51 (m, 2 H), 0.32-0.30 (m, 2 H); m/z (ESI+) (M + H)⁺ = 440.30; HPLC tR = 6.92 min | +++ |

TABLE 3-continued

Analytical Data of Compounds

| ID | Structure | MW | Analytical Data | ALDH2 Activity with 20 μM of the compound* |
|---|---|---|---|---|
| AC34 | 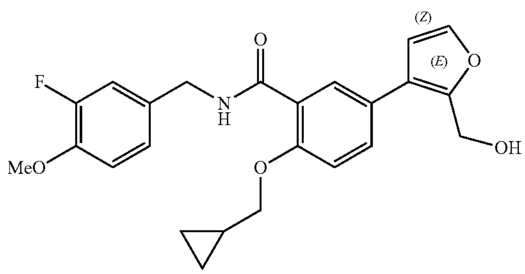 [SMILES: COc1ccc(CNC(=O)c2cc(-c3ccoc3CO)ccc2OCC2CC2)cc1F] | 425.45 | $^1$H NMR (400 MHz, CDCl$_3$): δ 8.55 (s, 1 H), 8.32 (s, 1 H), 7.55 (dd, J1 = 8.4 Hz, J2 = 2.4 Hz, 1 H), 7.16-7.08 (m, 2 H), 6.94-6.90 (m, 2 H), 6.58 (d, J = 2.0 Hz, 1 H), 4.70 (s, 2 H), 4.60 (d, J = 5.6 Hz, 2 H), 3.92 (d, J = 7.2 Hz, 2 H), 3.88 (s, 3 H), 1.25-1.20 (m, 1 H), 0.55-0.53 (m, 2 H), 0.29-0.27 (m, 2 H); m/z (ESI+) (M + H)$^+$ = 426.25; HPLC tR = 7.28 min | |
| AC35 | 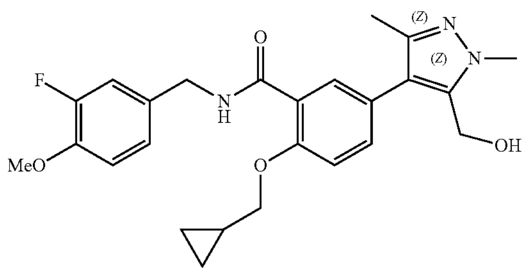 [SMILES: COc1ccc(CNC(=O)c2cc(-c3c(C)nn(C)c3CO)ccc2OCC2CC2)cc1F] | 453.51 | $^1$H NMR (400 MHz, CDCl$_3$): δ 8.64 (br. s, 1 H), 8.11 (s, 1 H), 7.36-7.25 (m, 3 H), 7.14-7.07 (m, 1 H), 6.97-6.92 (m, 2 H), 4.60-4.58 (m, 4 H), 4.00-3.80 (m, 8 H), 2.29-2.26 (m, 3 H), 1.22-1.20 (m, 1 H), 0.53-0.51 (m, 2 H), 0.32-0.30 (m, 2 H); m/z (ESI+) (M + H)$^+$ = 454.40; HPLC tR = 6.69 min | |
| AC36 | 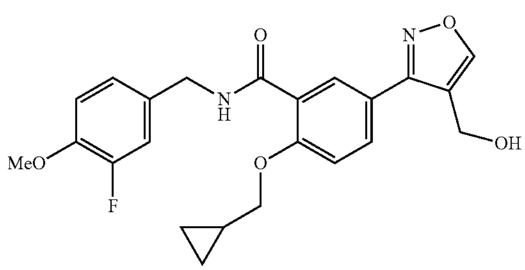 [SMILES: COc1ccc(CNC(=O)c2cc(-c3nocc3CO)ccc2OCC2CC2)cc1F] | 426.44 | $^1$H NMR (400 MHz, CDCl$_3$): δ 8.64 (s, 1 H), 8.50-8.45 (m, 2 H), 7.95 (d, J = 8.4 Hz, 1 H), 7.15-7.07 (m, 2 H), 6.96 (d, J = 8.8 Hz, 1 H), 6.92 (t, J = 8.8 Hz, 1 H), 4.75 (d, J = 7.2 Hz, 2 H), 4.60 (d, J = 5.6 Hz, 2 H), 3.96 (d, J = 7.2 Hz, 2 H), 3.88 (s, 3 H), 1.22-1.20 (m, 1 H), 0.53-0.51 (m, 2 H), 0.32-0.30 (m, 2 H); m/z (ESI+) (M + H)$^+$ = 427.30; HPLC tR = 7.14 min | |
| AC37 | 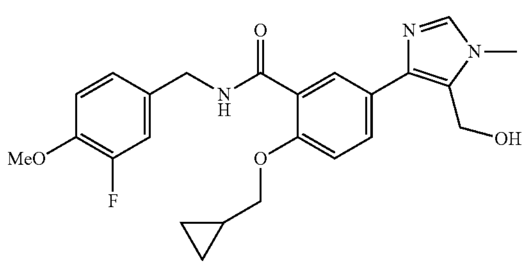 [SMILES: COc1ccc(CNC(=O)c2cc(-c3ncn(C)c3CO)ccc2OCC2CC2)cc1F] | 439.48 | $^1$H NMR (400 MHz, CDCl$_3$): δ 8.59 (s, 2 H), 8.32 (s, 1 H), 7.80 (d, J = 8.0 Hz, 1 H), 7.13-7.05 (m, 2 H), 6.95-6.93 (m, 2 H), 8.64 (s, 1 H), 8.50-8.45 (m, 2 H), 5.45-5.33 (m, 2 H), 4.77 (s, 2 H), 4.57 (d, J = 5.2 Hz, 2 H), 3.96-3.85 (m, 6 H), 0.53-0.51 (m, 2 H), 0.32-0.30 (m, 2 H); m/z (ESI+) (M + H)$^+$ = 440.35; HPLC tR = 6.31 min | |
| AC38 | 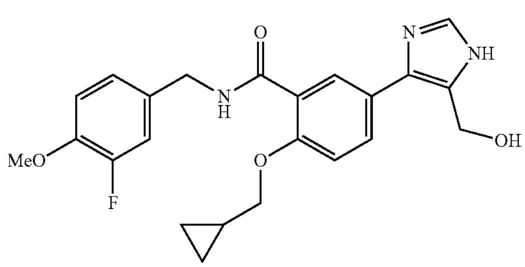 [SMILES: COc1ccc(CNC(=O)c2cc(-c3nc[nH]c3CO)ccc2OCC2CC2)cc1F] | 425.45 | $^1$H NMR (400 MHz, CDCl$_3$): δ 8.62 (s, 2 H), 8.50 (s, 1 H), 8.14 (s, 1 H), 7.68 (d, J = 8.0 Hz, 1 H), 7.07-7.00 (m, 3 H), 6.90-6.85 (m, 2 H), 4.63 (s, 2 H), 4.51 (d, J = 7.6 Hz, 2 H), 3.92-3.86 (m, 2 H), 3.75 (s, 3 H), 1.28-1.24 (m, 1 H), 0.49-0.46 (m, 2 H), 0.25-0.23 (m, 2 H); m/z (ESI+) (M + H)$^+$ = 426.30; HPLC tR = 6.00 min | ++ |

TABLE 3-continued

Analytical Data of Compounds

| ID | Structure | MW | Analytical Data | ALDH2 Activity with 20 μM of the compound* |
|---|---|---|---|---|
| AC39 | 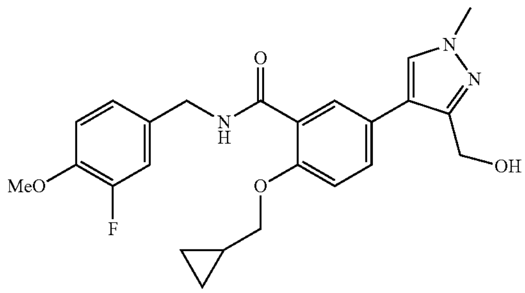 [SMILES: COc1ccc(CNC(=O)c2cc(-c3cn(C)nc3CO)ccc2OCC2CC2)cc1F] | 439.48 | $^1$H NMR (400 MHz, CDCl$_3$): δ 8.57 (s, 1 H), 8.29 (s, 1 H), 7.61 (d, J = 8.0 Hz, 1 H), 7.54 (s, 1 H), 7.16-7.09 (m, 2 H), 6.94-6.92 (m, 2 H), 4.75 (s, 2 H), 4.61 (d, J = 4.8 Hz, 2 H), 3.92-3.88 (m, 9 H), 1.28-1.24 (m, 1 H), 0.49-0.46 (m, 2 H), 0.25-0.23 (m, 2 H); m/z (ESI+) (M + H)$^+$ = 440.20; HPLC tR = 7.22 min | ++ |
| AC40 | 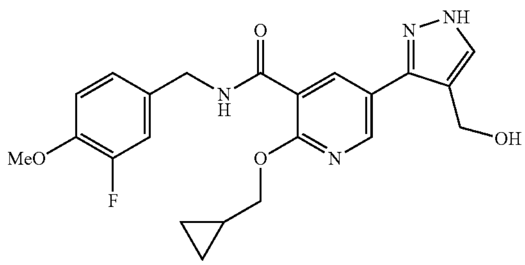 [SMILES: COc1ccc(CNC(=O)c2cc(-c3n[nH]cc3CO)cnc2OCC2CC2)cc1F] | 426.44 | $^1$H NMR (400 MHz, CDCl$_3$): δ 7.73-7.71 (m, 1 H), 7.38-7.36 (m, 1 H), 7.20-7.15 (m, 2 H), 7.09-7.07 (m, 1 H), 6.91-6.89 (m, 1 H), 4.56 (s, 2 H), 4.35-4.30 (m, 2 H), 3.90-3.80 (m, 5 H), 1.25-1.20 (m, 1 H), 0.54-0.48 (m, 2 H), 0.28-0.23 (m, 2 H); m/z (ESI+) (M + H)$^+$ = 427.05; HPLC tR = 6.72 min | + |
| AC41 | 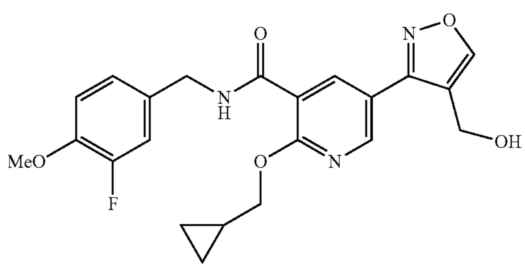 | 427.43 | $^1$H NMR (400 MHz, CDCl$_3$): δ 8.94 (s, 1 H), 8.73 (s, 1 H), 8.50-8.45 (m, 2 H), 7.15-7.07 (m, 2 H), 6.94 (t, J = 8.0 Hz, 1 H), 4.71 (s, 2 H), 4.58 (d, J = 4.8 Hz, 2 H), 4.31 (d, J = 7.2 Hz, 2 H), 3.88 (s, 3 H), 1.22-1.20 (m, 1 H), 0.56-0.54 (m, 2 H), 0.32-0.30 (m, 2 H); m/z (ESI+) (M + H)$^+$ = 428.91; HPLC tR = 7.86 min | + |
| AC42 | 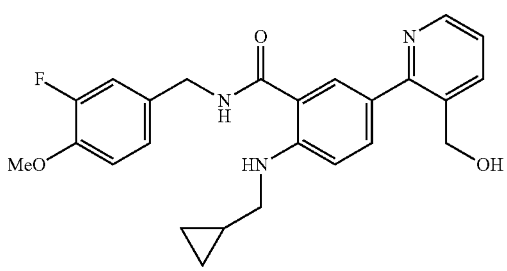 | 435.49 | $^1$H NMR (400 MHz, CDCl$_3$): δ 8.41 (s, 1 H), 7.87 (s, 1 H), 8.80-8.70 (m, 2 H), 7.50-7.46 (m, 1 H), 7.16-7.14 (m, 1 H), 7.05-6.97 (m, 2 H), 6.84 (d, J = 6.8 Hz, 1 H), 6.66 (d, J = 7.2 Hz, 1 H), 4.59 (s, 2 H), 4.45 (d, J = 4.0 Hz, 2 H), 3.82 (s, 3 H), 3.05 (s, 2 H), 1.22-1.20 (m, 1 H), 0.56-0.54 (m, 2 H), 0.32-0.30 (m, 2 H); m/z (ESI+) (M + H)$^+$ = 436.65; HPLC tR = 6.26 min | ++ |
| AC43 | 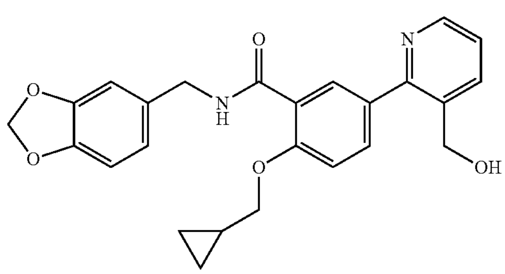 [SMILES: O=C(NCc1ccc2c(c1)OCO2)c1cc(-c2ncccc2CO)ccc1OCC1CC1] | 432.47 | $^1$H NMR (400 MHz, CDCl$_3$): δ 8.53-8.52 (m, 2 H), 8.35 (s, 1 H), 7.92 (d, J = 7.2 Hz, 1 H), 7.89-7.66 (m, 1 H), 7.26-7.23 (m, 1 H), 7.98-6.75 (m, 4 H), 5.93 (s, 2 H), 4.70 (s, 2 H), 4.55 (d, J = 4.8 Hz, 2 H), 3.92 (d, J = 7.2 Hz, 2 H), 1.22-1.20 (m, 1 H), 0.56-0.54 (m, 2 H), 0.32-0.30 (m, 2 H); m/z (ESI+) (M + H)$^+$ = 433.55; HPLC tR = 6.29 min | ++ |

TABLE 3-continued

Analytical Data of Compounds

| ID | Structure | MW | Analytical Data | ALDH2 Activity with 20 μM of the compound* |
|---|---|---|---|---|
| AC44 | 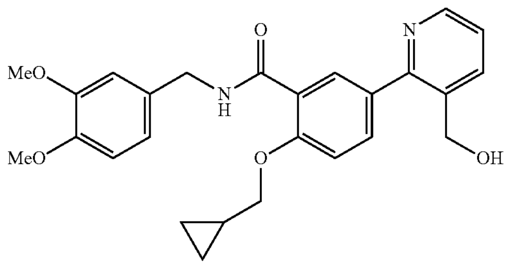 [SMILES: COc1ccc(CNC(=O)c2cc(-c3ncccc3CO)ccc2OCC2CC2)cc1OC] | 448.51 | $^1$H NMR (400 MHz, CDCl$_3$): δ 8.62-8.45 (m, 3 H), 7.93 (d, J = 4.4 Hz, 1 H), 7.71 (d, J = 4.0 Hz, 1 H), 7.02-6.83 (m, 4 H), 4.77 (s, 2 H), 4.61 (d, J = 4.0 Hz, 2 H), 3.94-3.88 (m, 8 H), 1.22-1.20 (m, 1 H), 0.56-0.54 (m, 2 H), 0.32-0.30 (m, 2 H); m/z (ESI+) (M + H)$^+$ = 449.15; HPLC tR = 5.94 min | ++ |
| AC45 | 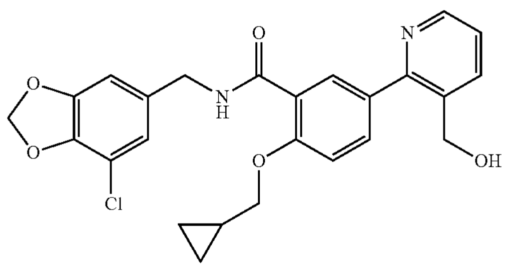 [SMILES: O=C(NCc1cc(Cl)c2c(c1)OCO2)c1cc(-c2ncccc2CO)ccc1OCC1CC1] | 466.91 | $^1$H NMR (400 MHz, CDCl$_3$): δ 8.66-8.59 (m, 2 H), 8.40 (s, 1 H), 7.94 (d, J = 7.2 Hz, 1 H), 7.71 (d, J = 4.8 Hz, 1 H), 7.26-7.25 (m, 1 H), 7.03-6.99 (m, 2 H), 6.85 (s, 1 H), 5.96 (s, 2 H), 4.75 (s, 2 H), 4.65 (d, J = 4.4 Hz, 2 H), 3.97 (d, J = 6.0 Hz, 2 H), 1.22-1.20 (m, 1 H), 0.56-0.54 (m, 2 H), 0.32-0.30 (m, 2 H); m/z (ESI+) (M + H)$^+$ = 467.60; HPLC tR = 6.32 min | + |
| AC46 | 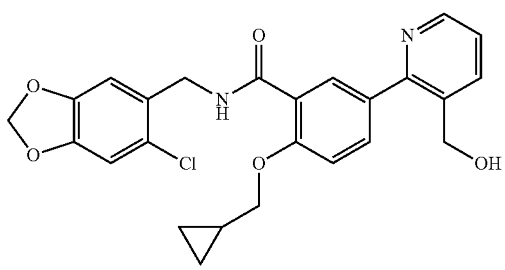 [SMILES: O=C(NCc1cc2c(cc1Cl)OCO2)c1cc(-c2ncccc2CO)ccc1OCC1CC1] | 466.91 | $^1$H NMR (400 MHz, CDCl$_3$): δ8.66-8.59 (m, 2 H), 8.40 (s, 1 H), 7.94 (d, J = 7.2 Hz, 1 H), 7.73 (d, J = 4.8 Hz, 1 H), 7.05-7.00 (m, 2 H), 6.85 (s, 1 H), 5.96 (s, 2 H), 4.75 (s, 2 H), 4.65 (d, J = 4.4 Hz, 2 H), 3.97 (d, J = 6.0 Hz, 2 H), 1.22-1.20 (m, 1 H), 0.56-0.54 (m, 2 H), 0.32-0.30 (m, 2 H); m/z (ESI+) (M + H)$^+$ = 467.60; HPLC tR = 6.42 min | + |
| AC47 | 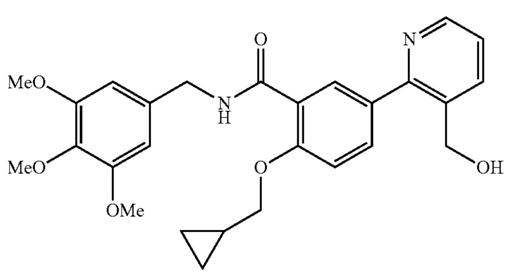 [SMILES: COc1cc(CNC(=O)c2cc(-c3ncccc3CO)ccc2OCC2CC2)cc(OC)c1OC] | 478.54 | $^1$H NMR (400 MHz, CDCl$_3$): δ 8.59-8.54 (m, 2 H), 8.42 (s, 1 H), 7.94 (d, J = 7.6 Hz, 1 H), 7.70 (d, J = 8.8 Hz, 1 H), 7.30-7.26 (m, 1 H), 6.99 (d, J = 8.0 Hz, 1 H), 6.61 (s, 2 H), 4.75 (s, 2 H), 4.60 (d, J = 4.0 Hz, 2 H), 3.94 (d, J = 7.2 Hz, 2 H), 3.85-3.82 (m, 9 H), 1.22-1.20 (m, 1 H), 0.56-0.54 (m, 2 H), 0.32-0.30 (m, 2 H); m/z (ESI+) (M + H)$^+$ = 479.75; HPLC tR = 6.11 min | |

TABLE 3-continued

Analytical Data of Compounds

| ID | Structure | MW | Analytical Data | ALDH2 Activity with 20 μM of the compound* |
|---|---|---|---|---|
| AC48 | 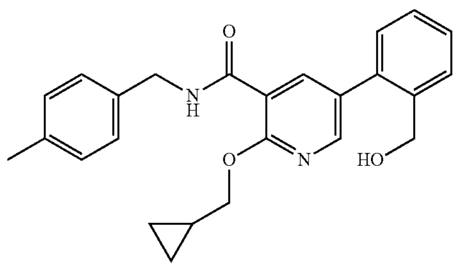 [SMILES: Cc1ccc(CNC(=O)c2cc(-c3ccccc3CO)cnc2OCC2CC2)cc1] | 402.5 | $^1$H NMR (400 MHz, CDCl$_3$): δ 8.59 (br s, 1 H), 8.58 (d, J = 2.0 Hz, 1 H), 8.25 (d, J = 2.4 hz, 1 H), 7.56 (d, J = 8.0 Hz, 1 H), 7.42-7.34 (m, 4 H), 7.24-7.18 (m, 2 H), 4.98 (d, J = 5.6 Hz, 2 H), 4.59 (s, 2 H), 4.27 (d, J = 7.2 Hz, 2 H), 2.34 (s, 3 H), 1.25-1.21 (m, 1 H), 0.50-0.46 (m, 2 H), 0.28-0.26 (m, 2 H); m/z (ESI+) (M + H)$^+$ = 457.25; HPLC tR = 8.57 min | + |
| AC49 | 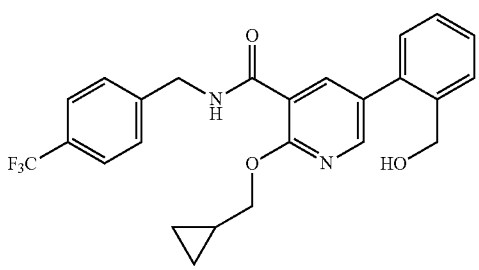 [SMILES: O=C(NCc1ccc(C(F)(F)F)cc1)c1cc(-c2ccccc2CO)cnc1OCC1CC1] | 456.5 | $^1$H NMR (400 MHz, CDCl$_3$): δ 8.64-8.62 (m, 1 H), 8.59 (s, 1 H), 8.29 (s, 1 H), 7.62-7.50 (m, 4 H), 7.44-7.36 (m, 2 H), 7.26 (d, J = 8.4 Hz, 1 H), 4.75 (d, J = 5.6 Hz, 2 H), 4.60 (s, 2 H), 4.32 (d, J = 7.2 Hz, 2 H), 1.25-1.21 (m, 1 H), 0.55-0.53 (m, 2 H), 0.32-0.31 (m, 2 H); m/z (ESI+) (M + H)$^+$ = 457.30; HPLC tR = 8.28 min | + |
| AC50 | 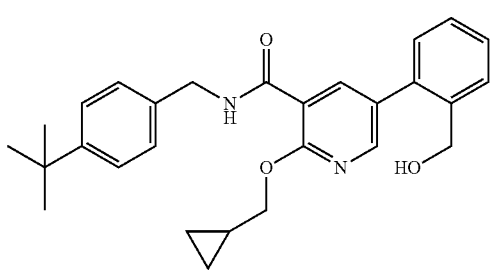 [SMILES: CC(C)(C)c1ccc(CNC(=O)c2cc(-c3ccccc3CO)cnc2OCC2CC2)cc1] | 444.6 | $^1$H NMR (400 MHz, CDCl$_3$): δ 8.59 (d, J = 2.4 Hz, 1 H), 8.50-8.53 (m, 1 H), 8.26 (d, J = 2.4 Hz, 1 H), 7.57 (d, J = 6.8 Hz, 1 H), 7.42-7.32 (m, 4 H), 7.28-7.25 (m, 2 H), 4.65 (d, J = 5.2 Hz, 2 H), 4.60 (s, 2 H), 4.28 (d, J = 7.2 Hz, 2 H), 1.36 (s, 9 H), 1.25-1.21 (m, 1 H), 0.48-0.46 (m, 2 H), 0.27-0.25 (m, 2 H); m/z (ESI+) (M + H)$^+$ = 445.60; HPLC tR = 8.80 min | + |
| AC51 | 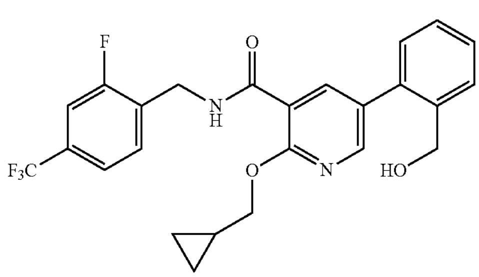 [SMILES: O=C(NCc1ccc(C(F)(F)F)cc1F)c1cc(-c2ccccc2CO)cnc1OCC1CC1] | 474.5 | $^1$H NMR (400 MHz, CDCl$_3$): δ 8.72-8.70 (m, 1 H), 8.56 (d, J = 2.0 Hz, 1 H), 8.29 (d, J = 2.0 Hz, 1 H), 7.61-7.55 (m, 2 H), 7.42-7.33 (m, 4 H), 7.25 (s, 1 H), 4.77 (d, J = 5.6 Hz, 2 H), 4.59 (s, 2 H), 4.35 (d, J = 7.2 Hz, 2 H), 1.29-1.25 (m, 1 H), 0.63-0.61 (m, 2 H), 0.39-0.37 (m, 2 H); m/z (ESI+) (M + H)$^+$ = 475.40; HPLC tR = 8.07 min | + |

TABLE 3-continued

Analytical Data of Compounds

| ID | Structure | MW | Analytical Data | ALDH2 Activity with 20 μM of the compound* |
|---|---|---|---|---|
| AC52 | 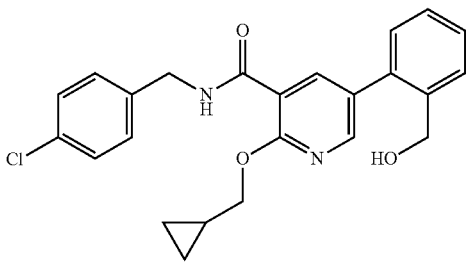 [SMILES: O=C(NCc1ccc(Cl)cc1)c1cc(-c2ccccc2CO)cnc1OCC1CC1] | 422.9 | $^1$H NMR (400 MHz, CDCl$_3$): δ 8.58 (d, J = 2.4 Hz, 1 H), 8.56-8.54 (m, 1 H), 8.28 (d, J = 2.8 Hz, 1 H), 7.58 (d, J = 7.2 Hz, 1 H), 7.43-7.36 (m, 2 H), 7.33 (s, 4 H), 7.26 (d, J = 10.0 Hz, 1 H), 4.66 (d, J = 5.6 Hz, 2 H), 4.60 (s, 2 H), 4.31 (d, J = 7.6 Hz, 2 H), 1.25-1.21 (m, 1 H), 0.55-0.53 (m, 2 H), 0.32-0.31 (m, 2 H); m/z (ESI+) (M + H)$^+$ = 423.30; HPLC tR = 8.27 min | + |
| AC53 | 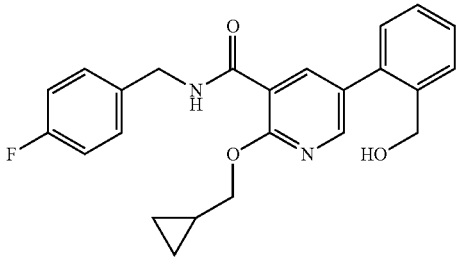 [SMILES: O=C(NCc1ccc(F)cc1)c1cc(-c2ccccc2CO)cnc1OCC1CC1] | 406.5 | $^1$H NMR (400 MHz, CDCl$_3$): δ 8.59 (d, J = 2.8 Hz, 1 H), 8.54-8.52 (m, 1 H), 8.28 (d, J = 2.4 Hz, 1 H), 7.57 (d, J = 7.2 Hz, 1 H), 7.43-7.36 (m, 4 H), 7.26 (d, J = 10.4 Hz, 1 H), 7.04 (t, J = 8.8 Hz, 1 H), 4.65 (d, J = 5.2 Hz, 2 H), 4.60 (s, 2 H), 4.30 (d, J = 7.2 Hz, 2 H), 1.25-1.21 (m, 1 H), 0.53-0.49 (m, 2 H), 0.31-0.29 (m, 2 H); m/z (ESI+) (M + H)$^+$ = 407.30; HPLC tR = 7.91 min | + |
| AC54 | 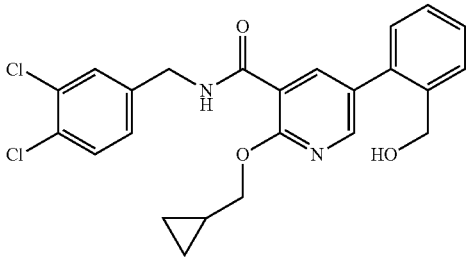 | 457.4 | $^1$H NMR (400 MHz, CDCl$_3$): δ 8.58 (br s, 1 H), 8.58 (d, J = 2.8 Hz, 1 H), 8.29 (d, J = 2.8 hz, 1 H), 7.57 (d, J = 6.8 Hz, 1 H), 7.49 (d, J = 2.0 Hz, 1 H), 7.43-7.38 (m, 3 H), 7.28-7.24 (m, 2 H), 4.65 (d, J = 6.0 Hz, 2 H), 4.61 (s, 2 H), 4.34 (d, J = 7.2 Hz, 2 H), 1.31-1.25 (m, 1 H), 0.59-0.57 (m, 2 H), 0.35-0.33 (m, 2 H); m/z (ESI+) (M + H)$^+$ = 457.30; HPLC tR = 8.59 min | ++ |
| AC55 | 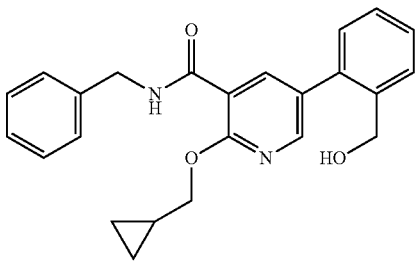 [SMILES: O=C(NCc1ccccc1)c1cc(-c2ccccc2CO)cnc1OCC1CC1] | 388.5 | $^1$H NMR (400 MHz, CDCl$_3$): δ 8.63 (d, J = 2.8 Hz, 1 H), 8.59-8.57 (m, 1 H), 8.30 (d, J = 2.8 hz, 1 H), 7.61 (d, J = 7.2 Hz, 1 H), 7.47-7.38 (m, 6 H), 7.35-7.29 (m, 2 H), 4.72 (d, J = 5.2 Hz, 2 H), 4.63 (s, 2 H), 4.32 (d, J = 7.2 Hz, 2 H), 1.31-1.25 (m, 1 H), 0.55-0.50 (m, 2 H), 0.33-0.30 (m, 2 H); m/z (ESI+) (M + H)$^+$ = 389.30; HPLC tR = 7.93 min | + |

TABLE 3-continued

Analytical Data of Compounds

| ID | Structure | MW | Analytical Data | ALDH2 Activity with 20 μM of the compound* |
|---|---|---|---|---|
| AC56 | 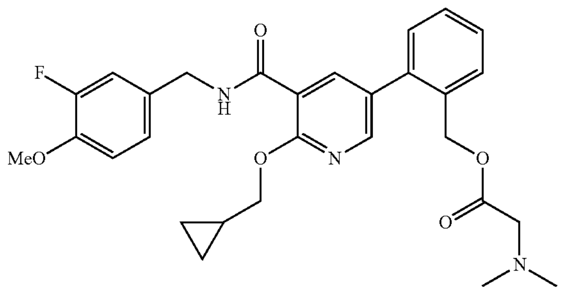 | 521.6 | ¹H NMR (400 MHz, CDCl₃): δ 8.53 (d, J = 2.0 Hz, 1 H), 8.51 (t, J = 4.8 Hz, 1 H), 7.50 (t, J = 4.4 Hz, 1 H), 7.40 (t, J = 4.0 Hz, 2 H), 7.27 (t, J = 4.4 Hz, 1 H), 7.10 (dd, J = 13.8, 10.6 Hz, 2 H), 6.92 (t, J = 8.4 Hz, 1 H), 5.00 (s, 2 H), 4.58 (d, J = 5.2 Hz, 2 H), 4.29 (d, J = 8.0 Hz, 2 H), 3.87 (s, 3 H), 3.28 (s, 2 H), 2.36 (s, 6 H), 1.20 (dd, J = 13.0, 5.4 Hz, 3 H), 0.54 (dd, J = 14.0, 5.0 Hz, 2 H), 0.30 (dd, J = 10.2, 5.0 Hz, 2 H); m/z (ESI+) (M + H)⁺ = 522.5; HPLC tR = 5.32 min. | |
| AC57 | 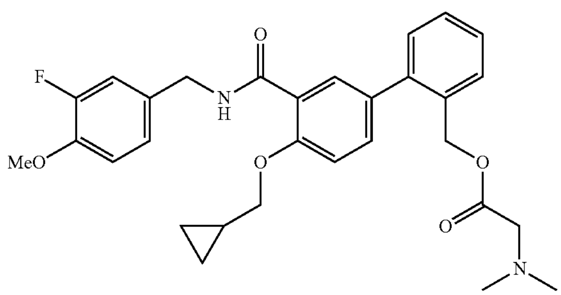 | 520.6 | ¹H NMR (400 MHz, CDCl₃): δ 8.55 (s, 1 H), 8.23 (d, J = 2.4 Hz, 1 H), 7.46 (d, J = 6.4 Hz, 1 H), 7.37 (dd, J = 6.0, 2.4 Hz, 1 H), 7.34 (s, 2 H), 7.30-7.26 (m, 1 H), 7.14 (d, J = 12.0 Hz, 1 H), 7.09 (d, J = 9.2 Hz, 1 H), 6.09 (dd, J = 8.4, 6.6 Hz, 2 H), 5.03 (s, 2 H), 4.58 (d, J = 5.2 Hz, 2 H), 3.92 (d, J = 7.6 Hz, 2 H), 3.87 (s, 3 H), 3.29 (s, 2 H), 2.38 (s, 6 H), 1.24-1.17 (m, 1 H), 0.53 (dd, J = 13.2, 5.2 Hz, 2 H), 0.29 (d, J = 4.8 Hz, 2 H); m/z (ESI+) (M + H)⁺ = 521.5; HPLC tR = 7.23 min. | |
| AC58 | 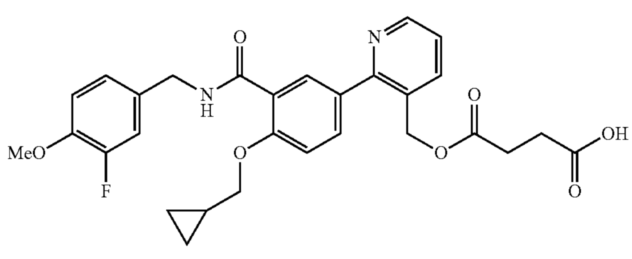 [SMILES: COc1ccc(CNC(=O)c2cc(-c3ncccc3COC(=O)CCC(=O)O)ccc2OCC2CC2)cc1F] | 536.6 | ¹H NMR (400 MHz, DMSO-d⁶): δ 8.71 (m, 2 H), 8.31 (s, 1 H), 7.86 (d, J = 7.2 Hz, 1 H), 7.71 (d, J = 8.4 Hz, 1 H), 7.28 (m, 2 H), 7.22 (m, 2 H), 7.12 (d, J = 7.2 Hz, 1 H), 6.91 (t, J = 6.8 Hz, 1 H), 5.01 (s, 2 H), 4.61 (d, J = 4.8 Hz, 2 H), 3.96 (d, J = 7.6 Hz, 2 H), 3.89 (s, 3 H), 2.70 (m, 4 H), 1.25 (m, 1 H), 0.53 (d, J = 6.8 Hz, 2 H), 0.30 (d, J = 4.4 Hz, 2 H); m/z (ESI+) (M + H)⁺ = 537.35; HPLC tR = 7.76 min | |

TABLE 3-continued

Analytical Data of Compounds

| ID | Structure | MW | Analytical Data | ALDH2 Activity with 20 μM of the compound* |
|---|---|---|---|---|
| AC59 | 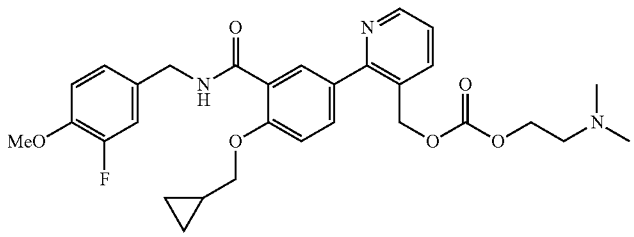 [SMILES: COc1ccc(CNC(=O)c2cc(-c3ncccc3COC(=O)OCCN(C)C)ccc2OCC2CC2)cc1F] | 551.6 | $^1$H NMR (400 MHz, DMSO-d$^6$): δ 8.66 (s, 1 H), 8.51 (s, 1 H), 8.37 (s, 1 H), 7.88 (d, J = 7.2 Hz, 1 H), 7.71 (d, J = 6.8 Hz, 1 H), 7.31 (m, 1 H), 7.13 (m, 2 H), 7.01 (d, J = 6.8 Hz, 1 H), 6.95 (t, J = 8.0 Hz, 1 H), 5.16 (s, 2 H), 4.59 (s, 2 H), 4.37 (s, 2 H), 3.96 (d, J = 4.8 Hz, 2 H), 3.88 (s, 3 H), 2.44 (s, 6 H), 2.35 (s, 2 H), 1.25 (m, 1 H), 0.54 (d, J = 6.4 Hz, 2 H), 0.31 (d, J = 4.8 Hz, 2 H); m/z (ESI+) (M + H)$^+$ = 552.70; HPLC tR = 5.49 min | |
| AC60 | 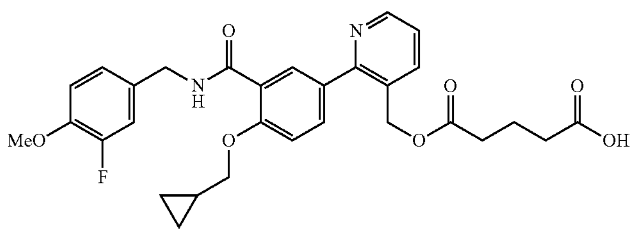 [SMILES: COc1ccc(CNC(=O)c2cc(-c3ncccc3COC(=O)CCCC(=O)O)ccc2OCC2CC2)cc1F] | 550.6 | $^1$H NMR (400 MHz, DMSO-d$^6$): δ 8.70 (t, J = 3.6 Hz, 1 H), 8.39 (d, J = 8.4 Hz, 1 H), 8.18 (s, 1 H), 7.74 (m, 2 H), 7.32 (d, J = 8.4 Hz, 1 H), 7.16 (m, 1 H), 7.06 (m, 1 H), 5.15 (s, 2 H), 4.73 (s, 2 H), 4.08 (d, J = 7.2 Hz, 2 H), 3.86 (s, 3 H), 2.42 (m, 2 H), 2.29 (m, 2 H), 1.84 (t, J = 7.2 Hz, 2 H), 1.29 (m, 1 H), 0.55 (d, J = 6.4 Hz, 2 H), 0.35 (d, J = 4.4 Hz, 2 H); m/z (ESI+) (M + H)$^+$ = 551.35; HPLC tR = 5.98 min | |
| AC61 | 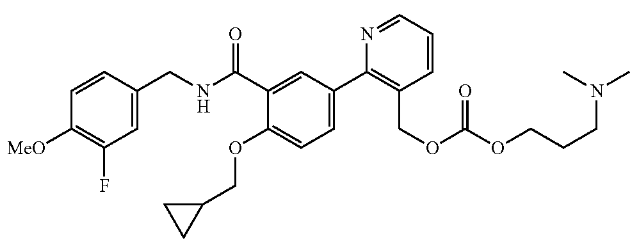 [SMILES: COc1ccc(CNC(=O)c2cc(-c3ncccc3COC(=O)OCCCN(C)C)ccc2OCC2CC2)cc1F] | 565.6 | $^1$H NMR (400 MHz, MeOD-d$^4$): δ 8.85-8.78 (m, 2 H), 8.24 (s, 1 H), 8.09 (m, 1 H), 7.81 (d, J = 8.8 Hz, 1 H), 7.41 (m, 1 H), 7.21-7.08 (m, 3 H), 5.32 (s, 2 H), 4.58 (s, 2 H), 4.24 (t, J = 5.2 Hz, 2 H), 4.13 (d, J = 7.2 Hz, 2 H), 3.86 (s, 3 H), 3.24 (m, 2 H), 2.86 (s, 6 H), 2.11 (m, 2 H), 1.29 (m, 1 H), 0.59 (d, J = 6.8 Hz, 2 H), 0.37 (d, J = 4.8 Hz, 2 H); m/z (ESI+) (M + H)$^+$ = 566.45; HPLC tR = 5.75 min | |
| AC62 | 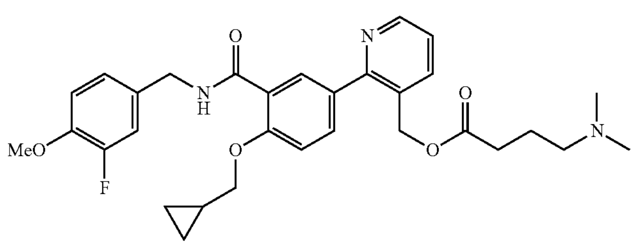 [SMILES: COc1ccc(CNC(=O)c2cc(-c3ncccc3COC(=O)CCCN(C)C)ccc2OCC2CC2)cc1F] | 549.6 | $^1$H NMR (400 MHz, MeOD-d$^4$): δ 8.65 (d, J = 5.2 Hz, 2 H), 8.19 (m, 2 H), 7.71 (m, 1 H), 7.62 (m, 1 H), 7.28 (d, J = 8.4 Hz, 2 H), 7.17-7.06 (m, 3 H), 5.12 (s, 2 H), 4.57 (s, 2 H), 4.07 (d, J = 6.4 Hz, 2 H), 3.86 (s, 3 H), 3.16 (m, 2 H), 2.87 (s, 6 H), 2.56 (t, J = 6.8 Hz, 2 H), 1.99 (s, 2 H), 1.27 (m, 1 H), 0.55 (d, J = 7.2 Hz, 2 H), 0.35 (d, J = 4.4 Hz, 2 H); m/z (ESI+) (M + H)$^+$ = 550.40; HPLC tR = 5.79 min | |

TABLE 3-continued

Analytical Data of Compounds

| ID | Structure | MW | Analytical Data | ALDH2 Activity with 20 μM of the compound* |
|---|---|---|---|---|
| AC63 | 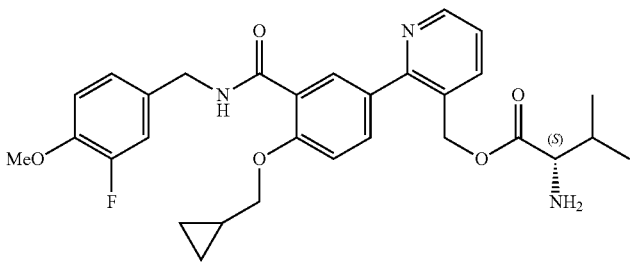 | 535.6 | $^1$H NMR (400 MHz, DMSO-d$^6$): δ 8.74 (d, J = 4.4 Hz, 2 H), 8.64 (s, 3 H), 8.31 (d, J = 6.0 Hz, 1 H), 8.01 (s, 1 H), 7.71 (m, 1 H), 7.30-7.12 (m, 4 H), 5.27 (s, 2 H), 4.55 (s, 2 H), 4.05 (d, J = 7.2 Hz, 2 H), 3.81 (s, 3 H), 1.27 (m, 1 H), 0.52 (d, J = 7.2 Hz, 2 H), 0.35 (d, J = 3.6 Hz, 2 H); m/z (ESI+) (M + H)$^+$ = 536.45; HPLC tR = 5.83 min | |
| AC64 | 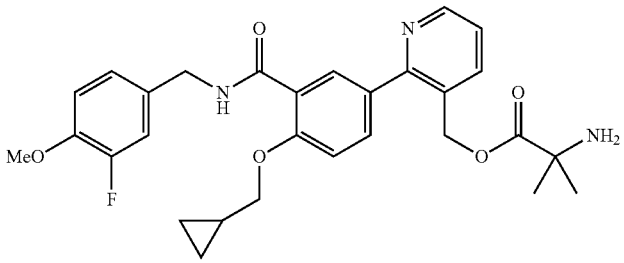 [SMILES: COc1ccc(CNC(=O)c2cc(-c3ncccc3COC(=O)C(C)(C)N)ccc2OCC2CC2)cc1F] | 521.6 | $^1$H NMR (400 MHz, DMSO-d$^6$): δ 8.76 (s, 5 H), 8.45 (s, 1 H), 8.16 (d, J = 6.8 Hz, 1 H), 7.98 (s, 1 H), 7.69 (d, J = 8.4 Hz, 1 H), 7.59 (d, J = 3.6 Hz, 1 H), 7.28-7.22 (m, 2 H), 7.15 (t, J = 8.4 Hz, 1 H), 5.24 (s, 2 H), 4.47 (d, J = 4.8 Hz, 2 H), 4.27 (d, J = 4.0 Hz, 2 H), 3.95 (s, 3 H), 1.45 (s, 6 H), 1.23 (m, 1 H), 0.52 (d, J = 7.2 Hz, 2 H), 0.35 (d, J = 3.6 Hz, 2 H); m/z (ESI+) (M + H)+ = 522.50; HPLC tR = 5.72 min | |
| AC65 | 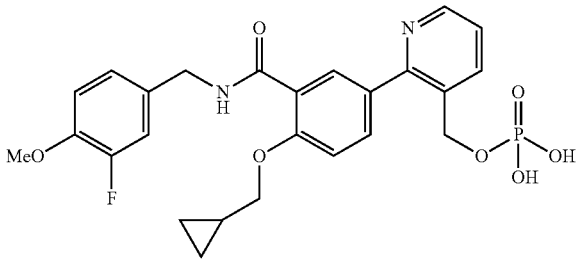 [SMILES: COc1ccc(CNC(=O)c2cc(-c3ncccc3COP(=O)(O)O)ccc2OCC2CC2)cc1F] | 516.5 | $^1$H NMR (400 MHz, CD$_3$OD): δ 8.69 (br.s, 1 H), 8.54 (d, J = 6.8 Hz, 1 H), 8.14 (s, 1 H), 7.84 (t, J = 7.1 Hz, 1 H), 7.76 (d, J = 8.4 Hz, 1 H), 7.31 (d, 8.4 Hz, 1 H), 7.20-7.08 (m, 2 H), 7.08 (t, J = 8.4 Hz, 1 H), 5.01 (d, J = 6.8 Hz, 2 H), 4.76 (d, J = 8.4 Hz, 2 H), 4.08 (d, J = 8.4 Hz, 2 H), 3.86 (s, 3 H), 1.29-1.25 (m, 2 H), 0.57-0.55 (m, 2 H), 0.36-0.34 (m, 2 H); m/z (ESI+) (M + H)$^+$ = 517.30; HPLC tR = 5.56 min | |
| AC66 | 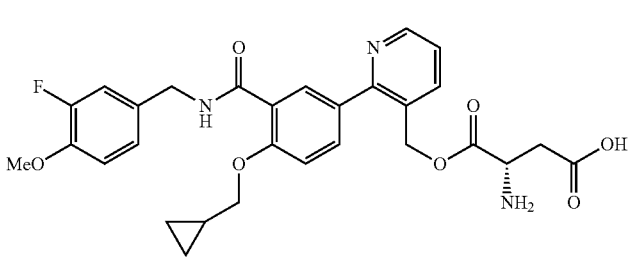 [SMILES: COc1ccc(CNC(=O)c2cc(-c3ncccc3COC(=O)[C@@H](N)CC(=O)O)ccc2OCC2CC2)cc1F] | 551.6 | $^1$H NMR (400 MHz, DMSO-d$^6$): δ 8.71-8.66 (m, 2 H), 8.40 (br, s, 2 H), 8.00-7.96 (m, 2 H), 7.66-7.62 (m, 1 H), 7.47-7.44(m, 2 H), 7.26-7.24 (m, 2 H), 7.16-7.12 (m, 2 H), 5.21 (s, 2 H), 4.48 (d, J = 5.2 Hz, 2 H), 4.13-4.11 (m, 1 H), 4.17-4.11 (m, 2 H), 3.81 (s, 3 H), 2.94-2.80 (m, 2 H), 1.28-1.24 (m, 1 H), 0.53-0.51 (m, 2 H), 0.35-0.33 (m, 2 H); m/z (ESI+) (M + H)$^+$ = 552.35; HPLC tR = 5.54 min | |

TABLE 3-continued

Analytical Data of Compounds

| ID | Structure | MW | Analytical Data | ALDH2 Activity with 20 μM of the compound* |
|---|---|---|---|---|
| AC67 | 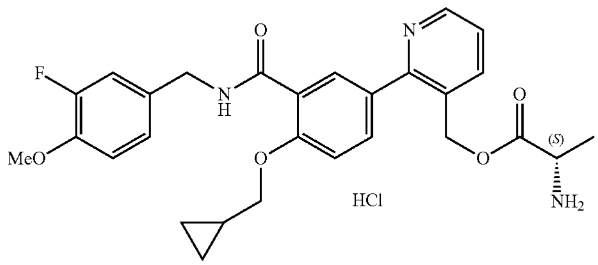 | | $^1$H NMR (400 MHz, DMSO-d$^6$): δ 8.71 (br.s, 2 H), 8.58-8.49 (m, 2 H), 8.26-8.23 (m, 1 H), 7.99-7.98 (m, 1 H), 7.68-7.62 (m, 2 H), 7.28-7.22 (m, 2 H), 7.16-7.09 (m, 2 H), 5.21 (s, 2 H), 4.46 (d, J = 5.2 Hz, 2 H), 4.13-4.03 (m, 3 H), 3.80 (s, 3 H), 1.38 (d, J = 7.2 Hz, 3 H), 1.28-1.24 (m, 1 H), 0.52-0.50 (m, 2 H), 0.34-0.30 (m, 2 H); m/z (ESI+) (M + H)$^+$ = 508.35; HPLC tR = 5.62 min | |
| AC68 | 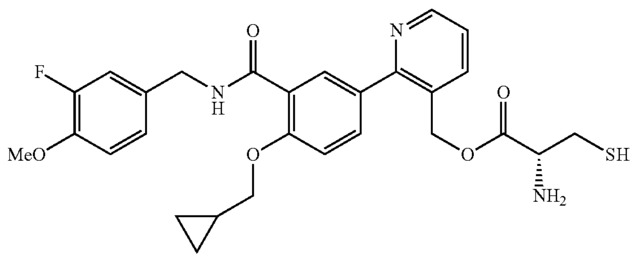 [SMILES: COc1ccc(CNC(=O)c2cc(-c3ncccc3COC(=O)[C@@H](N)CS)ccc2OCC2CC2)cc1F] | 539.6 | $^1$H NMR (400 MHz, CD$_3$OD): δ 8.70-8.68 (m, 1 H), 8.27 (d, J = 7.6 Hz, 1 H), 8.20 (d, J = 2.4 Hz, 1 H), 7.73 (dd, J1 = 8.4 Hz, J2 = 2.0 Hz, 1 H), 7.65 (dd, J1 = 8.0 hz, J2 = 2.0 Hz, 1 H, 7.30 (d, J = 8.8 Hz, 1 H), 7.19-7.15 (m, 2 H), 7.08 (d, J = 8.4 Hz, 1 H), 5.29 (s, 2 H), 4.58 (s, 2 H), 4.44-4.43 (m, 1 H), 4.08 (d, J = 6.8 Hz, 2 H), 3.85 (s, 3 H), 3.08 (d, J = 4.8 Hz, 2 H), 1.28-1.24 (m, 1 H), 0.52-0.50 (m, 2 H), 0.34-0.30 (m, 2 H); m/z (ESI+) (M + H)$^+$ = 540.30; HPLC tR = 5.78 min | |
| AC69 | 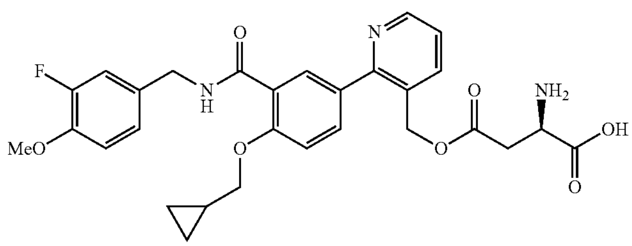 [SMILES: COc1ccc(CNC(=O)c2cc(-c3ncccc3COC(=O)C[C@@H](N)C(=O)O)ccc2OCC2CC2)cc1F] | 551.6 | $^1$H NMR (400 MHz, CD$_3$OD): δ 8.66 (br, s, 1 H), 8.20 (br, s, 2 H), 7.72 (dd, J1 = 8.4 Hz, J2 = 2.4 Hz, 1 H), 7.62 (d, J = 4.4 Hz, 1 H), 7.28 (d, J = 8.8 Hz, 1 H), 7.19-7.15 (m, 2 H), 7.08 (d, J = 8.4 Hz, 1 H), 5.17 (s, 2 H), 4.57 (s, 2 H), 4.44-4.43 (m, 1 H), 4.07 (d, J = 7.2 Hz, 2 H), 3.85 (s, 3 H), 3.22-3.14 (m, 2 H), 1.28-1.24 (m, 1 H), 0.52-0.50 (m, 2 H), 0.34-0.30 (m, 2 H); m/z (ESI+) (M + H)$^+$ = 552.40; HPLC tR = 5.57 min | |
| AC70 | 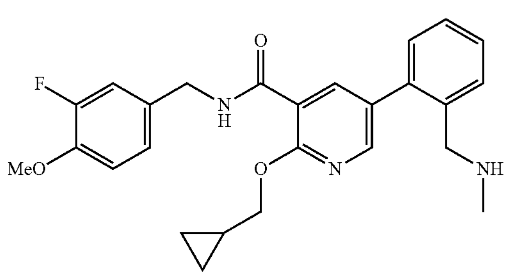 [SMILES: CNCc1ccccc1-c1cnc(OCC2CC2)c(C(=O)NCc2ccc(OC)c(F)c2)c1] | 449.5 | $^1$H NMR (400 MHz, CDCl$_3$): δ 8.53 (t, J = 5.2 Hz, 1 H), 8.41 (d, J = 2.4 Hz, 1 H), 8.18 (d, J = 2.4 Hz, 1 H), 7.95 (d, J = 7.2 Hz, 1 H), 7.49-7.41 (m, 2 H), 7.28 (d, J = 10.4 Hz, 1 H), 7.15 (t, J = 12.0 Hz, 2 H), 6.94 (t, J = 8.0 Hz, 1 H), 4.58 (d, J = 5.2 Hz, 2 H), 4.31 (d, J = 7.6 Hz, 2 H), 4.05 (s, 2 H), 3.88 (s, 3 H), 2.38 (s, 3 H), 1.27-1.22 (m, 1 H), 0.56-0.53 (m, 2 H), 0.33-0.31 (m, 2 H); m/z (ESI+) (M + H)$^+$ = 450.30; HPLC tR = 6.67 min. | + |

TABLE 3-continued

Analytical Data of Compounds

| ID | Structure | MW | Analytical Data | ALDH2 Activity with 20 μM of the compound* |
|---|---|---|---|---|
| AC71 | 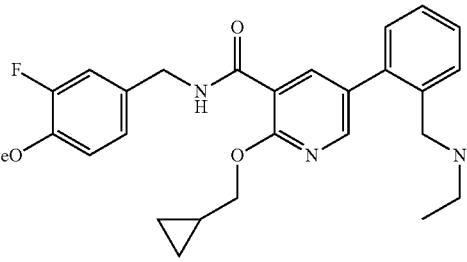 | 463.5 | $^1$H NMR (400 MHz, CDCl$_3$): δ 8.52 (t, J = 5.2 Hz, 1 H), 8.41 (d, J = 2.4 Hz, 1 H), 8.19 (d, J = 2.4 Hz, 1 H), 8.08 (d, J = 8.0 Hz, 1 H), 7.49 (t, J = 7.2 Hz, 1 H), 7.41 (t, J = 7.2 Hz, 1 H), 7.26 (d, J = 6.8 Hz, 1 H), 7.16-7.09 (m, 2 H), 6.94 (t, J = 8.4 Hz, 1 H), 4.59 (d, J = 5.6 Hz, 2 H), 4.31 (d, J = 7.2 Hz, 2 H), 4.05 (s, 2 H), 3.88 (s, 3 H), 2.69 (q, J = 7.2 Hz, 2 H), 1.23 (t, J = 7.2 Hz, 3 H), 1.27-1.22 (m, 1 H), 0.57-0.53 (m, 2 H), 0.34-0.31 (m, 2 H); m/z (ESI+) (M + H)$^+$ = 464.45; HPLC tR = 6.81 min. | |
| AC72 | 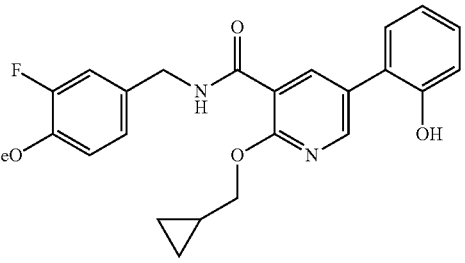 | 422.5 | $^1$H NMR (400 MHz, CDCl$_3$): δ 8.87 (d, J = 2.4 Hz, 1 H), 8.66-8.63 (m, 1 H), 8.37 (d, J = 2.4 Hz, 1 H), 7.26 (dd, J1 = 8.8 Hz, J2 = 2.0 Hz, 1 H), 7.20 (td, J1 = 8.0 Hz, J2 = 1.6 Hz, 1 H), 7.14 (dd, J1 = 12 Hz, J2 = 2.0 Hz, 1 H), 7.10 (d, J = 8.8 Hz, 1 H), 7.04-7.02 (m, 2 H), 6.97-6.92 (m, 2 H), 4.63 (d, J = 5.2 Hz, 2 H), 4.30 (d, J = 7.6 Hz, 2 H), 3.88 (s, 3 H), 1.25-1.20 (m, 1 H), 0.56-0.52 (m, 2 H), 0.32-0.28 (m, 2 H); m/z (ESI+) (M + H)$^+$ = 423.25; HPLC tR = 7.86 min | |
| AC73 | 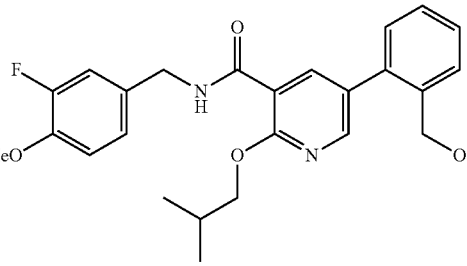 | 438.5 | $^1$H NMR (400 MHz, CDCl$_3$): δ 8.58 (d, J = 2.8 Hz, 1 H), 8.34-8.33 (m, 1 H), 8.29 (d, J = 2.4 Hz, 1 H), 7.58 (d, J = 6.0 Hz, 1 H), 7.41 (td, J1 = 8.8 Hz, J2 = 1.6 Hz, 1 H), 7.37 (td, J1 = 7.2 Hz, J2 = 1.6 Hz, 1 H), 7.28 (d, J = 7.2 Hz, 1 H), 7.12-7.07 (m, 2 H), 6.93 (t, J = 8.4 Hz, 1 H), 4.60 (s, 2 H), 4.59 (d, J = 5.6 Hz, 2 H), 4.27 (d, J = 5.6 Hz, 2 H), 3.88 (s, 3 H), 2.06-2.03 (m, 1 H), 0.93 (d, J = 7.2 Hz, 6 H); m/z (ESI+) (M + H)$^+$ = 439.30; HPLC tR = 6.72 min | |

TABLE 3-continued

Analytical Data of Compounds

| ID | Structure | MW | Analytical Data | ALDH2 Activity with 20 μM of the compound* |
|---|---|---|---|---|
| AC74 | 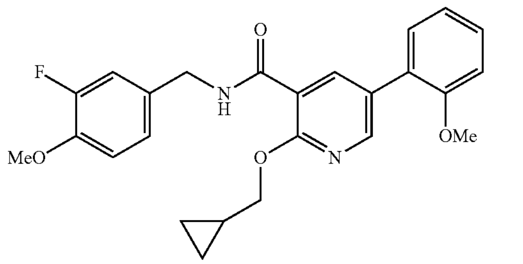 [SMILES: COc1ccc(CNC(=O)c2cc(-c3ccccc3OC)cnc2OCC2CC2)cc1F] | 436.5 | $^1$H NMR (400 MHz, CDCl$_3$): δ 8.71 (d, J = 2.0 Hz, 1 H), 8.52-8.50 (m, 1 H), 8.40 (d, J = 2.4 Hz, 1 H), 7.36-7.31 (m, 2 H), 7.16-7.09 (m, 2 H), 7.05-6.91 (m, 3 H), 4.61 (d, J = 5.6 Hz, 2 H), 4.29 (d, J = 7.6 Hz, 2 H), 3.88 (s, 3 H), 3.81 (s, 3 H), 1.25-1.20 (m, 1 H), 0.56-0.51 9 m, 2 H), 0.32-0.28 (m, 2 H); m/z (ESI+) (M + H)$^+$ = 423.25; HPLC tR = 7.86 min | + |
| AC75 | 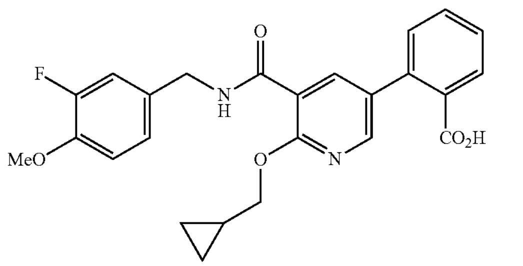 | 450.5 | $^1$H NMR (400 MHz, CDCl$_3$): δ 8.54-8.52 (m, 2 H), 8.20 (s, 1 H), 8.03 (d, J = 7.6 Hz, 1 H), 7.58 (t, J = 7.2 Hz, 1 H), 7.47 (d, J = 8.0 hz, 1 H), 7.34 (d, J = 8.0 Hz, 1 H), 7.13 (dd, J1 = 13.6 Hz, J2 = 2.0 Hz, 1 H), 7.09 (d, J = 8.0 Hz, 1 H), 6.93 (t, J = 8.4 hz, 1 H), 4.59 (d, J = 5.2 Hz, 2 H), 4.28 (d, J = 7.2 Hz, 2 H), 3.88 (s, 3 H), 1.25-1.20 (m, 1 H), 0.56-0.51 9 m, 2 H), 0.32-0.28 (m, 2 H); m/z (ESI+) (M + H)$^+$ = 451.25; HPLC tR = 6.61 min | + |
| AC76 | 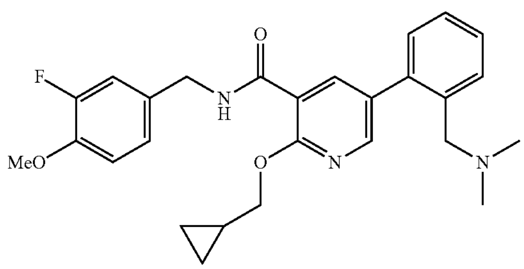 [SMILES: COc1ccc(CNC(=O)c2cc(-c3ccccc3CN(C)C)cnc2OCC2CC2)cc1F] | 463.5 | $^1$H NMR (400 MHz, CDCl$_3$): δ 8.54-8.52 (m, 1 H), 8.51 (d, J = 2.4 Hz, 1 H), 8.19 (d, J = 2.8 hz, 1 H), 7.77 (d, J = 6.8 Hz, 1 H), 7.47-7.37 (m, 2 H), 7.25-7.24 (m, 1 H), 7.14 (dd, J1 = 13.6 Hz, J2 = 2.0 Hz, 1 H), 7.11 (d, J = 9.2 Hz, 1 H), 6.94 (t, J = 8.4 Hz, 1 H), 4.61 (d, J = 5.6 Hz, 2 H), 4.32 (J = 7.6 Hz, 2 H), 3.88 (s, 3 H), 3.72 (s, 2 H), 2.32 (s, 6 H), 1.25-1.20 (m, 1 H), 0.59-0.54 (m, 2 H), 0.34-0.31 (m, 2 H); m/z (ESI+) (M + H)$^+$ = 464.35; HPLC tR = 6.77 min | + |
| AC77 | 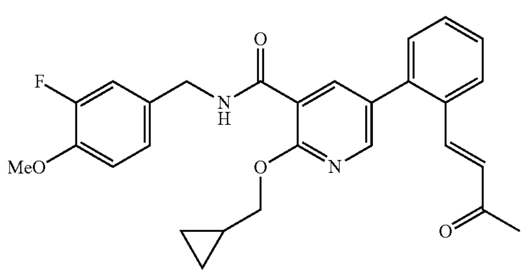 [SMILES: COc1ccc(CNC(=O)c2cc(-c3ccccc3/C=C/C(C)=O)cnc2OCC2CC2)cc1F] | 474.5 | $^1$H NMR (400 MHz, CDCl$_3$): δ 8.56 (d, J = 2.8 Hz, 1 H), 8.50-8.48 (m, 1 H), 8.16 (d, J = 2.8 hz, 1 H), 7.71 (d, J = 7.2 Hz, 1 H), 7.50-7.41 (m, 3 H), 7.37-7.35 (m, 1 H), 7.14 (dd, J1 = 13.6 Hz, J2 = 2.0 Hz, 1 H), 7.11 (d, J = 9.2 Hz, 1 H), 6.94 (t, J = 8.4 Hz, 1 H), 6.68 (d, J = 16.4 Hz, 1 H), 4.61 (d, J = 5.6 Hz, 2 H), 4.32 (J = 7.2 Hz, 2 H), 3.88 (s, 3 H), 2.26 (s, 3 H), 1.25-1.20 (m, 1 H), 0.59-0.54 (m, 2 H), 0.34-0.31 (m, 2 H); m/z (ESI+) (M + H)$^+$ = 475.35; HPLC tR = 5.44 min | + |

TABLE 3-continued

Analytical Data of Compounds

| ID | Structure | MW | Analytical Data | ALDH2 Activity with 20 μM of the compound* |
|---|---|---|---|---|
| AC78 | 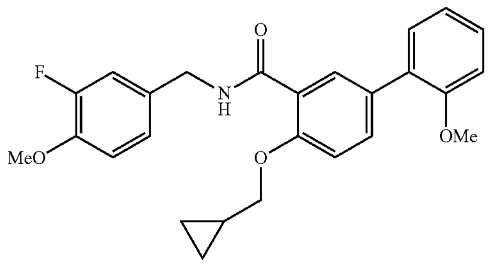 | 435.5 | ¹H NMR (400 MHz, CDCl₃): δ 8.57-8.55 (m, 1 H), 8.41 (s, 1 H), 7.61 (d, J = 8.0 Hz, 1 H), 7.34-7.26 (m, 2 H), 7.16-6.89 (m, 6 H), 4.60 (d, J = 5.6 Hz, 2 H), 3.93 (d, J = 7.2 Hz, 2 H), 3.87 (s, 3 H), 3.80 (s, 3 H), 1.25-1.20 (m, 1 H), 0.53-0.51 (m, 2 H), 0.29-0.27 (m, 2 H); m/z (ESI+) (M + H)⁺ = 436.30; HPLC tR = 6.51 min | + |
| AC79 | 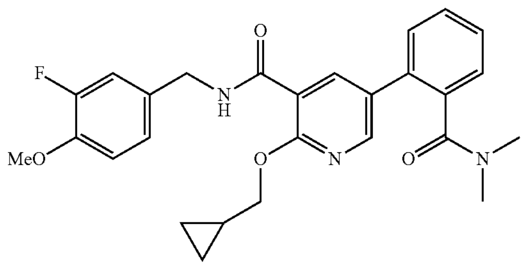 [SMILES: COc1ccc(CNC(=O)c2cc(-c3ccccc3C(=O)N(C)C)cnc2OCC2CC2)cc1F] | 477.5 | ¹H NMR (400 MHz, CDCl₃): δ 8.57 (d, J = 2.4 Hz, 1 H), 8.52-8.50 (m, 1 H), 8.32 (d, J = 2.4 Hz, 1 H), 7.47-7.36 (m, 4 H), 7.13 (dd, J1 = 12.0 Hz, J2 = 2.0 Hz, 1 H), 7.11 (d, J = 8.8 Hz, 1 H), 6.93 (t, J = 8.4 hz, 1 H), 4.60 (d, J = 5.6 Hz, 2 H), 4.29 (d, J = 7.2 Hz, 2 H), 3.88 (s, 3 H), 2.95 (s, 3 H), 2.67 (s, 3 H), 1.25-1.20 (m, 1 H), 0.56-0.51 (m, 2 H), 0.32-0.29 (m, 2 H); m/z (ESI+) (M + H)⁺ = 478.35; HPLC tR = 6.63 min | + |
| AC80 | 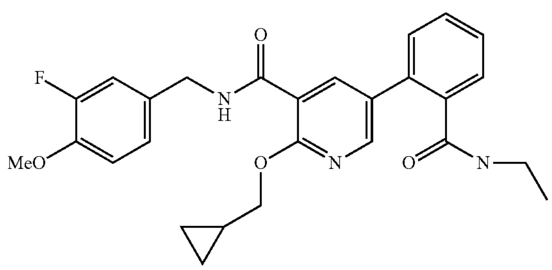 [SMILES: CCNC(=O)c1ccccc1-c1cnc(OCC2CC2)c(C(=O)NCc2ccc(OC)c(F)c2)c1] | 476.5 | ¹H NMR (400 MHz, CDCl₃): δ 8.59 (d, J = 2.4 Hz, 1 H), 8.49-8.47 (m, 1 H), 8.28 (d, J = 2.4 Hz, 1 H), 7.58 (dd, J1 = 8.0 Hz, J2 = 2.4 Hz, 1 H), 7.49 (td, J1 = 8.0 Hz, J2 = 2.4 Hz, 1 H), 7.41 (td, J1 = 8.0 Hz, J2 = 2.4 hz, 1 H), 7.37 (d, J = 8.0 Hz, 1 H), 7.13 (dd, J1 = 12.0 Hz, J2 = 2.0 Hz, 1 H), 7.10 (d, J = 8.8 Hz, 1 H), 6.93 (t, J = 8.4 hz, 1 H), 5.53-5.50 (m, 1 H), 4.60 (d, J = 5.6 Hz, 2 H), 4.29 (d, J = 7.2 Hz, 2 H), 3.89 (s, 3 H), 3.35-3.28 (m, 2 H), 1.25-1.20 (m, 1 H), 1.01 (t, J = 7.2 Hz, 3 H), 0.56-0.52 (m, 2 H), 0.32-0.29 (m, 2 H); m/z (ESI+) (M + H)⁺ = 478.40; HPLC tR = 6.41 min | + |
| AC81 | 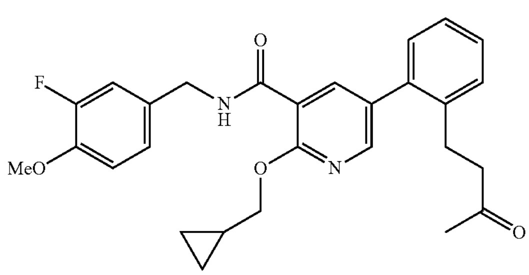 [SMILES: COc1ccc(CNC(=O)c2cc(-c3ccccc3CCC(C)=O)cnc2OCC2CC2)cc1F] | 476.5 | ¹H NMR (400 MHz, CDCl₃): δ 8.54-8.52 (m, 1 H), 8.50 (d, J = 2.4 Hz, 1 H), 8.17 (d, J = 2.4 Hz, 1 H), 7.34-7.24 (m, 3 H), 7.18-7.09 (m, 3 H), 6.94 (t, J = 8.4 Hz, 1 H), 4.61 (d, J = 5.2 Hz, 2 H), 4.31 (J = 7.2 Hz, 2 H), 3.88 (s, 3 H), 2.05 (s, 3 H), 1.25-1.20 (m, 1 H), 0.59-0.54 (m, 2 H), 0.34-0.30 (m, 2 H); m/z (ESI+) (M + H)⁺ = 477.40; HPLC tR = 8.36 min | + |

TABLE 3-continued

Analytical Data of Compounds

| ID | Structure | MW | Analytical Data | ALDH2 Activity with 20 μM of the compound* |
|---|---|---|---|---|
| AC82 | 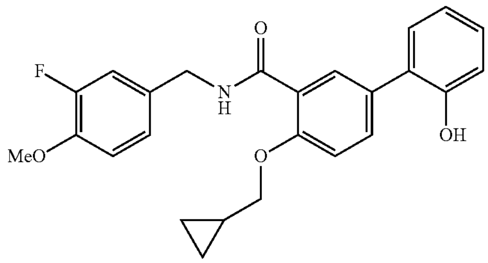 [SMILES: COc1ccc(CNC(=O)c2cc(-c3ccccc3O)ccc2OCC2CC2)cc1F] | 421.5 | $^1$H NMR (400 MHz, CDCl$_3$): δ 8.54-8.52 (m, 1 H), 8.40 (s, 1 H), 7.54 (d, J = 8.8 Hz, 1 H), 7.24-7.21 (m, 1 H), 7.15-7.11(m, 2 H), 6.98-6.90 (m, 4 H), 4.61 (d, J = 5.2 Hz, 2 H), 3.94 (d, J = 7.2 Hz, 2 H), 3.88 (s, 3 H), 1.25-1.20 (m, 1 H), 0.55-0.52 (m, 2 H), 0.30-0.28 (m, 2 H); m/z (ESI+) (M + H)$^+$ = 422.30; HPLC tR = 5.19 min | + |
| AC83 | 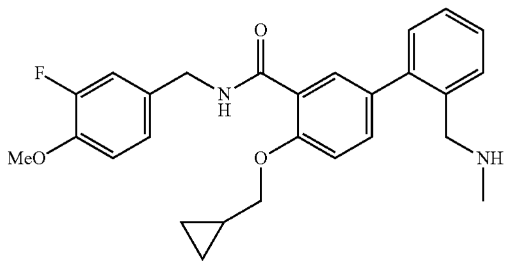 [SMILES: CNCc1ccccc1-c1ccc(OCC2CC2)c(C(=O)NCc2ccc(OC)c(F)c2)c1] | 448.5 | $^1$H NMR (400 MHz, CDCl$_3$): δ 8.58-8.55 (m, 1 H), 8.08 (d, J = 2.8 Hz, 1 H), 7.92 (d, J = 6.8 Hz, 1 H), 7.41-7.35 (m, 3 H), 7.13 (dd, J1 = 12.0 Hz, J2 = 2.0 Hz, 1 H), 7.10 (d, J = 9.2 Hz, 1 H), 6.97 (d, J = 8.8 Hz, 1 H), 6.92 (t, J = 8.4 Hz, 1 H), 4.58 (d, J = 5.2 Hz, 1 H), 4.06 (s, 2 H), 3.94 (d, J = 7.2 Hz, 2 H), 3.86 (s, 3 H), 2.33 (s, 3 H), 1.25-1.20 (m, 1 H), 0.55-0.51 (m, 2 H), 0.32-0.29 (m, 2 H); m/z (ESI+) (M + H)$^+$ = 449.40; HPLC tR = 6.69 min | ++ |
| AC84 | 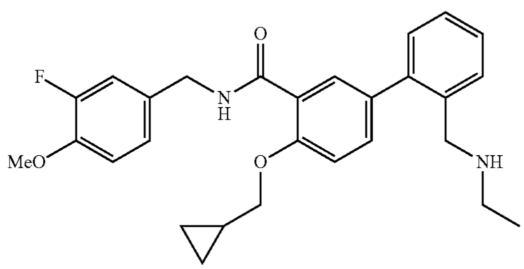 [SMILES: CCNCc1ccccc1-c1ccc(OCC2CC2)c(C(=O)NCc2ccc(OC)c(F)c2)c1] | 462.6 | $^1$H NMR (400 MHz, CDCl$_3$): δ 8.58-8.55 (m, 1 H), 8.09 (d, J = 2.4 Hz, 1 H), 8.01 (d, J = 7.2 Hz, 1 H), 7.42-7.35 (m, 3 H), 7.25 (d, J = 7.6 Hz, 1 H), 7.13 (dd, J1 = 12.4 Hz, J2 = 2.4 Hz, 1 H), 7.09 (d, J = 8.8 Hz, 1 H), 6.96 (d, J = 8.8 Hz, 1 H), 6.92 (t, J = 8.4 Hz, 1 H), 4.58 (d, J = 4.8 Hz, 1 H), 4.06 (s, 2 H), 3.94 (d, J = 7.2 Hz, 2 H), 3.86 (s, 3 H), 2.67 (q, J = 7.2 Hz, 2 H), 1.25-1.20 (m, 1 H), 1.17 (t, J = 6.8 Hz, 3 H), 0.55-0.51 (m, 2 H), 0.32-0.29 (m, 2 H); m/z (ESI+) (M + H)$^+$ = 463.35; HPLC tR = 6.70 min | ++ |
| AC85 | 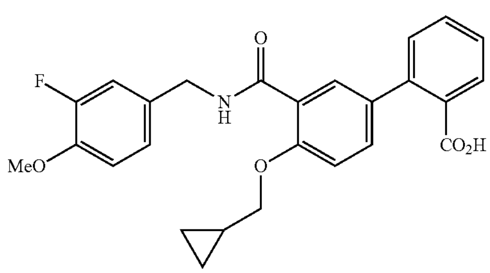 [SMILES: COc1ccc(CNC(=O)c2cc(-c3ccccc3C(=O)O)ccc2OCC2CC2)cc1F] | 449.5 | $^1$H NMR (400 MHz, CDCl$_3$): δ 8.56-8.54 (m, 1 H), 8.25 (d, J = 1.2 Hz, 1 H), 7.92 (d, J = 7.2 Hz, 1 H), 7.54-7.51 (m, 1 H), 7.41-7.36 (m, 3 H), 7.14-7.07 (m, 2 H), 6.93-6.89 (m, 2 H), 4.58 (d, J = 5.6 Hz, 2 H), 3.92 (d, J = 7.2 Hz, 2 H), 3.87 (s, 3 H), 1.25-1.20 (m, 1 H), 0.55-0.51 (m, 2 H), 0.32-0.29 (m, 2 H); m/z (ESI+) (M + H)$^+$ = 450.30; HPLC tR = 7.53 min | + |

TABLE 3-continued

Analytical Data of Compounds

| ID | Structure | MW | Analytical Data | ALDH2 Activity with 20 μM of the compound* |
|---|---|---|---|---|
| AC86 | 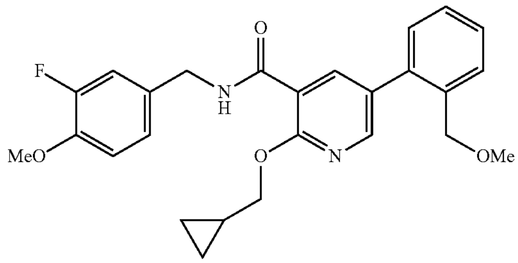 [SMILES: COCc1ccccc1-c1cnc(OCC2CC2)c(C(=O)NCc2ccc(OC)c(F)c2)c1] | 450.5 | $^1$H NMR (400 MHz, CDCl$_3$): δ 8.59 (d, J = 2.8 Hz, 1 H), 8.54-8.52 (m, 1 H), 8.27 (d, J = 2.8 Hz, 1 H), 7.53 (d, J = 7.2 Hz, 1 H), 7.41-7.35 (m, 2 H), 7.29-7.26 (m, 1 H), 7.14 (dd, J1 = 13.6 Hz, J2 = 2.0 Hz, 1 H), 7.11 (d, J = 8.4 Hz, 1 H), 6.94 (t, J = 8.4 Hz, 1 H), 4.61 (d, J = 5.2 Hz, 2 H), 4.32 (d, J = 6.0 Hz, 2 H), 4.31 (s, 2 H), 3.88 (s, 3 H), 3.35 (s, 2 H), 1.25-1.20 (m, 1 H), 0.59-0.54 (m, 2 H), 0.34-0.31 (m, 2 H); m/z (ESI+) (M + H)$^+$ = 451.30; HPLC tR = 5.72 min | |
| AC87 | 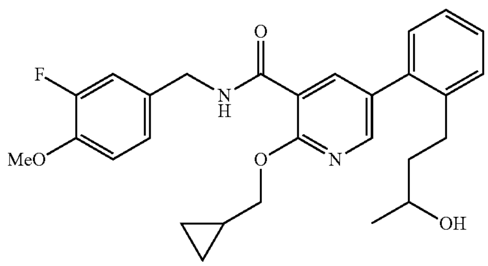 [SMILES: COc1ccc(CNC(=O)c2cc(-c3ccccc3CCC(C)O)cnc2OCC2CC2)cc1F] | 478.6 | $^1$H NMR (400 MHz, CDCl$_3$): δ 8.54 (d, J = 2.4 Hz, 1 H), 8.54 (br.s, 1 H), 8.19 (d, J = 2.4 Hz, 1 H), 7.33-7.32 (m, 2 H), 7.27-7.23 (m, 2 H), 7.14 (dd, J1 = 13.6 Hz, J2 = 2.0 Hz, 1 H), 7.11 (d, J = 8.4 Hz, 1 H), 6.94 (t, J = 8.4 Hz, 1 H), 4.61 (d, J = 5.2 Hz, 2 H), 4.30 (d, J = 7.6 Hz, 2 H), 3.88 (s, 3 H), 3.75 (q, J = 6.0 Hz, 1 H), 2.76-2.57 (m, 2 H), 1.76-1.69 (m, 2 H), 1.25-1.20 (m, 1 H), 1.15 (d, J = 6.0 Hz, 3 H), 0.59-0.54 (m, 2 H), 0.34-0.31 (m, 2 H); m/z (ESI+) (M + H)$^+$ = 479.40; HPLC tR = 6.94 min | |
| AC88 | 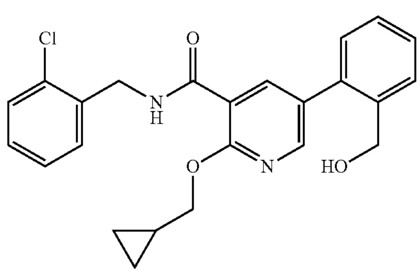 [SMILES: O=C(NCc1ccccc1Cl)c1cc(-c2ccccc2CO)cnc1OCC1CC1] | 422.9 | $^1$H NMR (400 MHz, CDCl$_3$): δ 8.75-8.72 (m, 1 H), 8.53 (d, J = 2.4 Hz, 1 H), 8.22 (d, J = 2.8 hz, 1 H), 7.54-7.49 (m, 2 H), 7.39-7.30 (m, 3 H), 7.25-7.19 (m, 2 H), 4.73 (d, J = 5.6 Hz, 2 H), 4.53 9 s, 2 H), 4.30 (d, J = 7.6 Hz, 2 H), 1.27-1.24 (m, 1 H), 0.57-0.52 (m, 2 H), 0.33-0.30 (m, 2 H); m/z (ESI+) (M + H)$^+$ = 423.20; HPLC tR = 8.27 min | |

TABLE 3-continued

Analytical Data of Compounds

| ID | Structure | MW | Analytical Data | ALDH2 Activity with 20 μM of the compound* |
|---|---|---|---|---|
| AC89 | 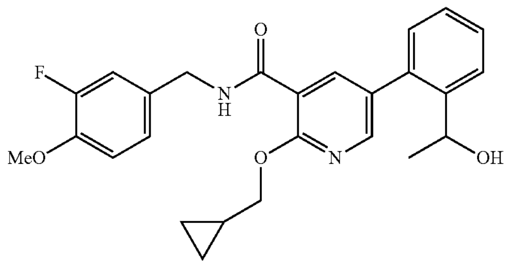 | 450.5 | $^1$H NMR (400 MHz, CDCl$_3$): δ 8.52 (br s, 1 H), 8.51 (d, J = 2.4 Hz, 1 H), 8.18 (d, J = 2.8 hz, 1 H), 7.70 (d, J = 8.0 Hz, 1 H), 7.44 (t, J = 7.6 Hz, 1 H), 7.33 (t, J = 7.6 Hz, 1 H), 6.94 (t, J = 8.4 Hz, 1 H), 4.90 (q, = 5.6 Hz, 1 H), 4.60 (d, J = 5.6 Hz, 2 H), 4.31 (d, J = 7.6 Hz, 2 H), 3.88 (s, 3 H), 1.41 (d, J = 5.6 Hz, 3 H), 1.27-1.24 (m, 1 H), 0.58-0.53 (m, 2 H), 0.33-0.30 (m, 2 H); m/z (ESI+) (M + H)$^+$ = 473.30; HPLC tR = 6.42 min | + |
| AC90 | 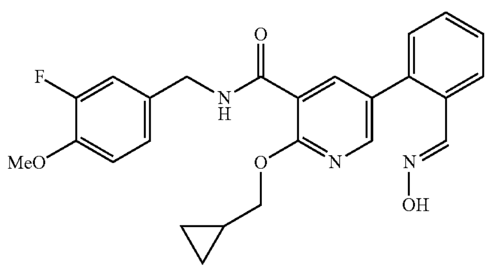 [SMILES: COc1ccc(CNC(=O)c2cc(-c3ccccc3/C=N/O)cnc2OCC2CC2)cc1F] | 449.5 | $^1$H NMR (400 MHz, CDCl$_3$): δ 8.56 (d, J = 2.4 Hz, 1 H), 8.52-8.50 (m, 1 H), 8.16 (d, J = 2.8 Hz, 1 H), 8.04 (s, 1 H), 7.89 (d, J = 8.0 Hz, 1 H), 7.49 (s, 1 H), 7.46-7.37 (m, 2 H), 7.30 (d, J = 7.2 Hz, 1 H), 7.15 (dd, J1 = 13.2 Hz, J2 = 1.2 Hz, 1 H), 7.11 (d, J = 8.4 Hz, 1 H), 6.94 (t, J = 8.0 Hz, 1 H), 4.62 (d, J = 5.2 Hz, 2 H), 4.32 (d, J = 7.2 Hz, 2 H), 3.89 (s, 3 H), 1.25-1.22 (m, 1 H), 0.59-0.54 (m, 2 H), 0.34-0.31 (m, 2 H); m/z (ESI+) (M + H)$^+$ = 450.45; HPLC tR = 6.36 min | + |
| AC91 | 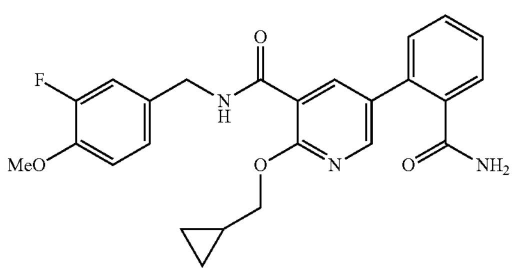 [SMILES: COc1ccc(CNC(=O)c2cc(-c3ccccc3C(N)=O)cnc2OCC2CC2)cc1F] | 449.5 | $^1$H NMR (400 MHz, CDCl$_3$): δ 8.58 (d, J = 2.0 Hz, 1 H), 8.50-8.48 (m, 1 H), 8.29 (d, J = 2.0 Hz, 1 H), 7.63 (d, J = 8.0 Hz, 1 H), 7.49 (t, J = 7.6 Hz, 1 H), 7.41 (t, J = 7.6 Hz, 1 H), 7.35 (d, J = 7.6 Hz, 1 H), 7.14-7.07 (m, 2 H), 6.93 (t, J = 8.4 Hz, 1 H), 5.84 (br s, 1 H), 5.78 (br s, 1 H), 4.58 (d, J = 5.6 Hz, 2 H), 4.28 (d, J = 8.0 Hz, 2 H), 3.88 (s, 3 H), 1.27-1.22 (m, 1 H), 0.56-0.52 (m, 2 H), 0.31-0.28 (m, 2 H); m/z (ESI+) (M + H)$^+$ = 450.30; HPLC tR = 5.13 min | + |

TABLE 3-continued

Analytical Data of Compounds

| ID | Structure | MW | Analytical Data | ALDH2 Activity with 20 μM of the compound* |
|---|---|---|---|---|
| AC92 | 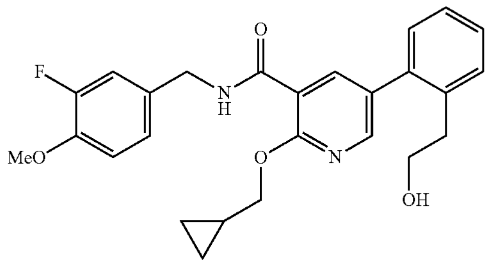 [SMILES: COc1ccc(CNC(=O)c2cc(-c3ccccc3CCO)cnc2OCC2CC2)cc1F] | 450.5 | ¹H NMR (400 MHz, CDCl₃): δ 8.53 (d, J = 2.0 Hz, 1 H), 8.53 (br.s, 1 H), 8.19 (d, J = 2.4 Hz, 1 H), 7.34 (d, J = 3.6 Hz, 2 H), 7.31-7.27 (m, 1 H), 7.22-7.20 (m, 1 H), 7.16-7.09 (m, 2 H), 6.94 (t, J = 8.4 Hz, 1 H), 4.61 (d, J = 4.8 Hz, 2 H), 4.30 (d, J = 7.2 Hz, 2 H), 3.89 (s, 3 H), 3.72 (t, J = 6.8 Hz, 2 H), 2.85 (t, J = 6.8 Hz, 2 H), 1.25-1.20 (m, 1 H), 0.56-0.53 (m, 2 H), 0.34-0.31 (m, 2 H); m/z (ESI+) (M + H)⁺ = 451.35; HPLC tR = 6.29 min | + |
| AC93 | 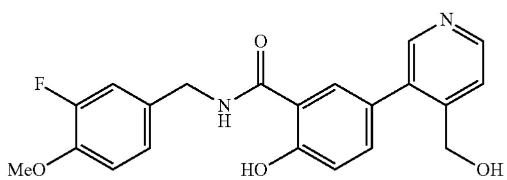 [SMILES: COc1ccc(CNC(=O)c2cc(-c3cnccc3CO)ccc2O)cc1F] | 382.4 | ¹H NMR (400 MHz, CDCl₃): δ 8.51 (d, J = 4.8 Hz, 1 H), 8.37 (s, 1 H), 7.48 (d, J = 4.8 Hz, 1 H), 7.41 9 s, 1 H), 7.36-7.34 (m, 1 H), 7.16-7.06 (m, 3 H), 6.92 (t, J = 8.0 Hz, 1 H), 4.60 (s, 2 H), 4.56 (d, J = 5.2 Hz, 2 H), 3.86 (s, 3 H); m/z (ESI+) (M + H)⁺ = 383.05; HPLC tR = 5.60 min | + |
| AC94 | 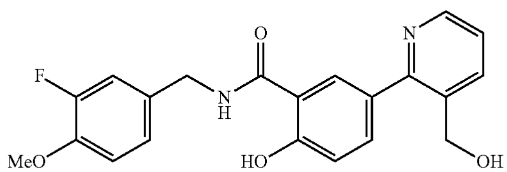 [SMILES: COc1ccc(CNC(=O)c2cc(-c3ncccc3CO)ccc2O)cc1F] | 382.4 | ¹H NMR (400 MHz, CDCl₃): δ 8.44 (d, J = 4.0 Hz, 1 H), 7.87 (s, 1 H), 7.82 (d, J = 7.6 Hz, 1 H), 7.58-7.56 (m, 1 H), 7.44-7.42 (m, 1 H), 7.25-7.23 (m, 1 H), 7.01-6.95 (m, 3 H), 6.84 (t, J = 8.0 Hz, 1 H), 4.60 (s, 2 H), 4.44 (d, J = 5.6 Hz, 2 H), 3.86 (s, 3 H); m/z (ESI+) (M + H)⁺ = 383.05; HPLC tR = 5.60 min | + |
| AC95 | 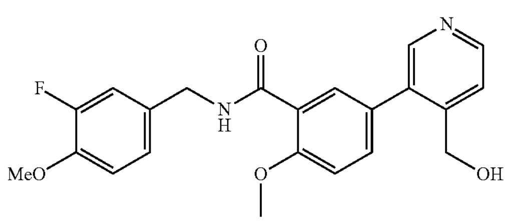 | 396.4 | ¹H NMR (400 MHz, CDCl₃): δ 8.59 (s, 1 H), 8.41 (s, 1 H), 8.20-8.18 (m, 1 H), 7.57-7.56 (m, 1 H), 7.44-7.42 (m, 1 H), 7.12-7.07 (m, 3 H), 6.93 (t, J = 8.4 Hz, 1 H), 4.70 (d, 2 H), 4.60 (d, J = 6.0 Hz, 2 H), 3.99 (s, 3 H), 3.88 (s, 3 H); m/z (ESI+) (M + H)⁺ = 397.05; HPLC tR = 5.63 min | ++ |
| AC96 | 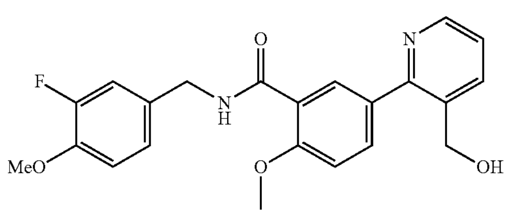 [SMILES: COc1ccc(CNC(=O)c2cc(-c3ncccc3CO)ccc2OC)cc1F] | 396.4 | ¹H NMR (400 MHz, CDCl₃): δ 8.59 (d, J = 4.4 Hz, 1 H), 8.32 (d, J = 2.0 Hz, 1 H), 8.20 (s, 1 H), 8.08 (d, J = 7.6 Hz, 1 H), 7.77 (d, J = 6.8 Hz, 1 H), 7.38-7.35 (m, 1 H), 7.11-7.06 (m, 3 H), 6.92 (t, J = 8.0 Hz, 1 H), 4.73 (s, 2 H), 4.59 (d, J = 5.2 Hz, 2 H), 3.98 (s, 3 H), 3.87 (s, 3 H); m/z (ESI+) (M + H)⁺ = 397.05; HPLC tR = 5.59 min | ++ |

TABLE 3-continued

Analytical Data of Compounds

| ID | Structure | MW | Analytical Data | ALDH2 Activity with 20 μM of the compound* |
|---|---|---|---|---|
| AC97 | 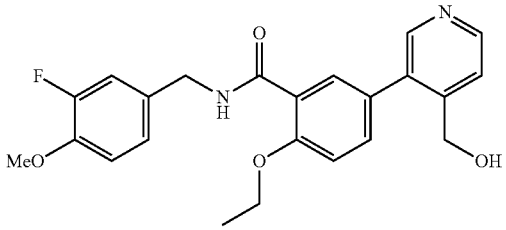 | 410.5 | $^1$H NMR (400 MHz, CDCl$_3$): δ 8.71 (d, J = 4.8 Hz, 1 H), 8.62 (s, 1 H), 8.37 (t, J = 4.8 Hz, 1 H), 8.21 (d, J = 4.8 Hz, 1 H), 8.13 (s, 1 H), 7.41 (d, J = 8.0 Hz, 1 H), 7.12-7.06 (m, 3 H), 6.94 (t, J = 8.4 Hz, 1 H), 4.83 (s, 2 H), 4.56 (d, J = 5.6 Hz, 2 H), 4.26-4.21 (m, 2 H), 3.88 (s, 3 H), 1.42 (t, J = 6.8 Hz, 3 H); m/z (ESI+) (M + H)$^+$ = 411.00; HPLC tR = 5.70 min | ++ |
| AC98 | 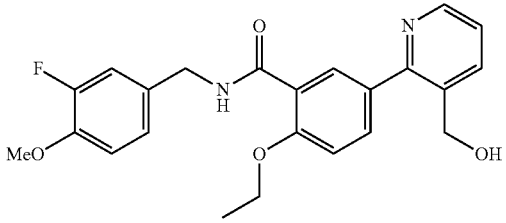 [SMILES: CCOc1ccc(-c2ncccc2CO)cc1C(=O)NCc1ccc(OC)c(F)c1] | 410.5 | $^1$H NMR (400 MHz, CDCl$_3$): δ 8.59 (d, J = 4.4 Hz, 1 H), 8.39 (d, J = 2.4 Hz, 1 H), 8.31 (s, 1 H), 7.94 (d, J = 7.6 Hz, 1 H), 7.73 (dd, J1 = 8.4 Hz, J2 = 2.0 hz, 1 H), 7.31-7.26 (m, 1 H), 7.13-7.05 (m, 3 H), 6.93 (t, J = 8.0 Hz, 1 H), 4.75 (s, 2 H), 4.59 (d, J = 5.2 Hz, 2 H), 4.21 (q, J = 6.8 Hz, 2 H), 3.88 (s, 3 H), 1.40 (t, J = 6.8 Hz, 3 H); m/z (ESI+) (M + H)$^+$ = 411.00; HPLC tR = 6.06 min | ++ |
| AC99 | 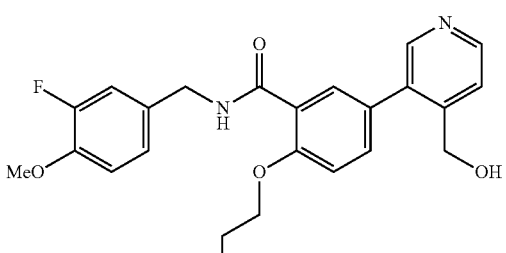 | 424.5 | $^1$H NMR (400 MHz, CDCl$_3$): δ 8.57 (d, J = 4.8 Hz, 1 H), 8.41 (s, 1 H), 8.35-8.33 (m, 1 H), 8.15 (s, 1 H), 7.58 (d, J = 5.2 Hz, 1 H), 7.39-7.36 (m, 1 H), 7.12-7.03 (m, 3 H), 6.92 (t, J = 8.4 Hz, 1 H), 4.66 (s, 2 H), 4.57 (d, J = 5.6 Hz, 2 H), 4.09 (t, J = 6.8 Hz, 2 H), 3.88 (s, 3 H), 1.82-1.72 (m, 3 H), 0.92 (t, J = 7.2 Hz, 3 H); m/z (ESI+) (M + H)$^+$ = 425.15; HPLC tR = 6.01 min | ++ |
| AC100 | 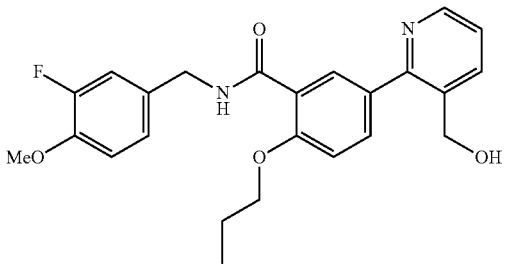 [SMILES: CCCOc1ccc(-c2ncccc2CO)cc1C(=O)NCc1ccc(OC)c(F)c1] | 424.5 | $^1$H NMR (400 MHz, CDCl$_3$): δ 8.58-8.56 (m, 1 H), 8.37 (s, 1 H), 8.33-8.30 (m, 1 H), 7.93 (d, J = 6.8 Hz, 1 H), 7.73-7.70 (m, 1 H), 7.29-7.27 (m, 1 H), 7.12-7.03 (m, 3 H), 6.92 (t, J = 8.4 Hz, 1 H), 4.73 (s, 2 H), 4.57 (d, J = 5.6 Hz, 2 H), 4.08 (t, J = 6.8 Hz, 2 H), 3.88 (s, 3 H), 1.82-1.72 (m, 3 H), 0.92 (t, J = 7.2 Hz, 3 H); m/z (ESI+) (M + H)$^+$ = 425.10; HPLC tR = 6.91 min | ++ |

TABLE 3-continued

Analytical Data of Compounds

| ID | Structure | MW | Analytical Data | ALDH2 Activity with 20 μM of the compound* |
|---|---|---|---|---|
| AC101 | 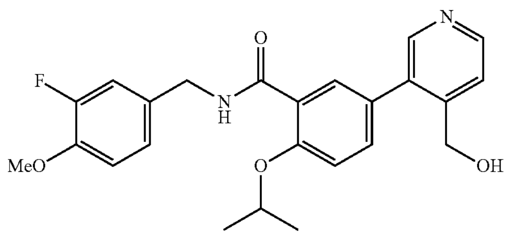 | 424.5 | $^1$H NMR (400 MHz, CDCl$_3$): δ 8.53 (d, J = 4.8 Hz, 1 H), 8.44-8.38 (m, 2 H), 8.10 (s, 1 H), 7.58 (d, J = 5.2 Hz, 1 H), 7.34 (dd, J1 = 8.8 Hz, J2 = 2.4 Hz, 1 H), 7.12-7.02 (m 3 H), 6.93 (t, J = 8.0 Hz, 1 H), 4.76 (q, J = 5.2 Hz, 1 H), 4.65 (s, 2 H), 4.55 (d, J = 6.0 Hz, 2 H), 3.88 (s, 3 H), 1.34 (d, J = 5.6 Hz, 6 H); m/z (ESI+) (M + H)$^+$ = 425.60; HPLC tR = 5.86 min | +++ |
| AC102 | 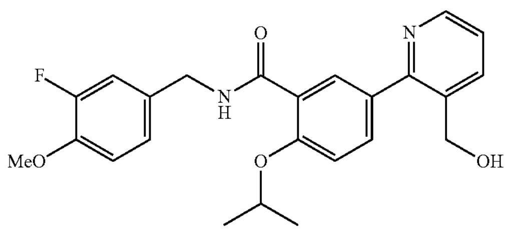 [SMILES: COc1ccc(CNC(=O)c2cc(-c3ncccc3CO)ccc2OC(C)C)cc1F] | 424.5 | $^1$H NMR (400 MHz, CDCl$_3$): δ 8.57-8.55 (m, 1 H), 8.41-8.36 (m, 2 H), 7.94 (d, J = 8.0 Hz, 1 H), 7.29-7.25 (m, 1 H), 7.12-7.04 (m, 3 H), 6.93 (t, J = 8.4 Hz, 1 H), 4.78-4.74 (m, 3 H), 4.56 (d, J = 5.2 Hz, 2 H), 3.88 (s, 3 H), 1.32 (t, J = 5.2 Hz, 6 H); m/z (ESI+) (M + H)$^+$ = 425.60; HPLC tR = 5.81 min | +++ |
| AC103 | 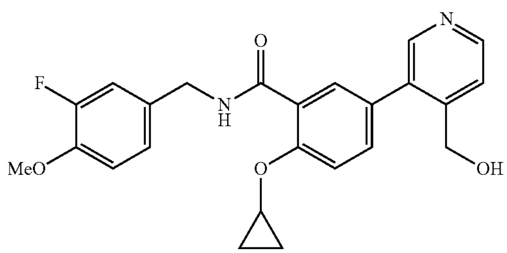 [SMILES: COc1ccc(CNC(=O)c2cc(-c3cnccc3CO)ccc2OC2CC2)cc1F] | 422.5 | $^1$H NMR (400 MHz, CDCl$_3$): δ 8.60 (d, J = 5.2 Hz, 1 H), 8.45 (s, 1 H), 8.14 (d, J = 2.0 Hz, 1 H), 8.07-8.05 (m, 1 H), 7.57 (d, J = 4.8 Hz, 1 H), 7.47-7.41 (m, 2 H), 7.11-7.06 (m, 2 H), 6.94 (t, J = 8.0 Hz, 1 H), 4.68 (s, 2 H), 4.57 (d, J = 5.6 Hz, 2 H), 3.88 (s, 3 H), 2.08-2.01 (m, 1 H), 0.94-0.88 (m, 2 H), 0.84-0.79 (m, 2 H); m/z (ESI+) (M + H)$^+$ = 423.50; HPLC tR = 6.90 min | ++ |
| AC104 | 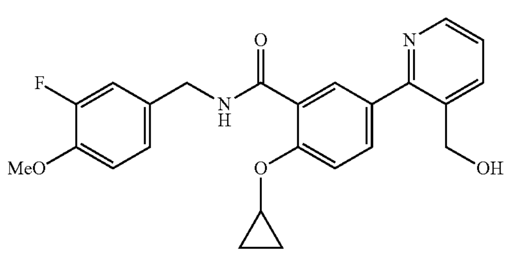 [SMILES: COc1ccc(CNC(=O)c2cc(-c3ncccc3CO)ccc2OC2CC2)cc1F] | 422.5 | $^1$H NMR (400 MHz, CDCl$_3$): δ 8.61-8.59 (m, 1 H), 8.37 (br. s, 1 H), 8.03-8.00 (m, 1 H), 7.95 (d, J = 7.6 Hz, 1 H), 7.76 (dd, J1 = 8.4 Hz, J2 = 2.4 Hz, 1 H), 7.52-7.46 (m, 1 H), 7.36-7.30 (m, 1 H), 7.12-7.06 (m, 2 H), 6.94 (t, J = 8.4 Hz, 1 H), 4.76 (s, 2 H), 4.58 (d, J = 5.2 Hz, 2 H), 3.88 (s, 3 H), 2.07-2.04 (m, 1 H), 0.92-0.88 (m, 2 H), 0.85-0.79 (m, 2 H); m/z (ESI+) (M + H)$^+$ = 423.50; HPLC tR = 6.83 min | ++ |

TABLE 3-continued

Analytical Data of Compounds

| ID | Structure | MW | Analytical Data | ALDH2 Activity with 20 μM of the compound* |
|---|---|---|---|---|
| AC105 | 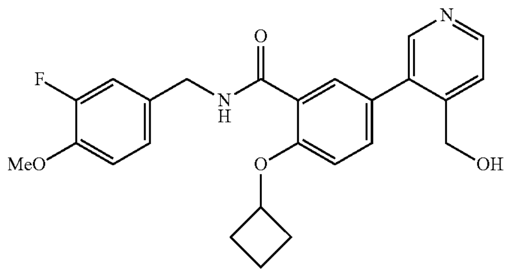 [SMILES: COc1ccc(CNC(=O)c2cc(-c3cnccc3CO)ccc2OC2CCC2)cc1F] | 436.5 | ¹H NMR (400 MHz, CDCl₃): δ 8.55 (d, J = 5.2 Hz, 1 H), 8.40 (s, 1 H), 8.37-8.33 (m, 1 H), 8.11 (d, J = 2.4 Hz, 1 H), 7.56 (d, J = 5.2 Hz, 1 H), 7.33 (dd, J1 = 8.8 Hz, J2 = 2.4 Hz, 1 H), 7.14-7.08 (m, 2 H), 6.93 (t, J = 8.0 Hz, 1 H), 6.87 (d, J = 8.4 Hz, 1 H), 4.83-4.80 (m, 1 H), 4.66 (s, 2 H), 4.58 (d, J = 5.6 Hz, 2 H), 3.88 (s, 3 H), 2.52-2.45 (m, 2 H), 2.16-2.04 (m, 2 H), 1.96-1.60 (m, 2 H); m/z (ESI+) (M + H)⁺ = 437.55; HPLC tR = 6.11 min | ++ |
| AC106 | 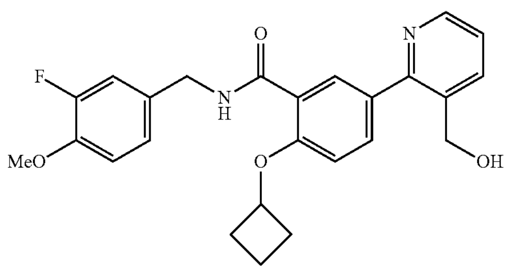 [SMILES: COc1ccc(CNC(=O)c2cc(-c3ncccc3CO)ccc2OC2CCC2)cc1F] | 436.5 | ¹H NMR (400 MHz, CDCl₃): δ 8.60-8.58 (m, 1 H), 8.38 (br. s, 1 H), 8.28 (s, 1 H), 7.94 (d, J = 8.0 Hz, 1 H), 7.71 (dd, J1 = 8.4 Hz, J2 = 2.4 Hz, 1 H), 7.30-7.27 (m, 1 H), 7.15-7.09 (m, 2 H), 7.09-6.89 (m, 2 H), 4.83-4.80 (m, 1 H), 4.76 (s, 2 H), 4.60 (d, J = 5.2 Hz, 2 H), 3.88 (s, 3 H), 2.52-2.45 (m, 2 H), 2.16-2.04 (m, 2 H), 1.96-1.60 (m, 2 H); m/z (ESI+) (M + H)+ = 437.55; HPLC tR = 6.03 min | ++ |
| AC107 | 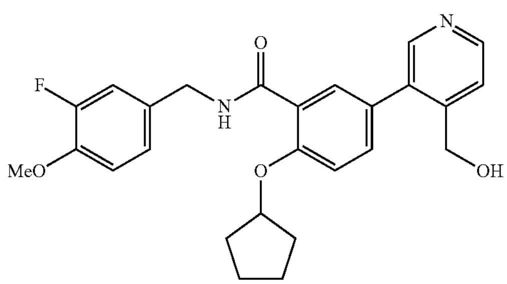 [SMILES: COc1ccc(CNC(=O)c2cc(-c3cnccc3CO)ccc2OC2CCCC2)cc1F] | 450.5 | ¹H NMR (400 MHz, CDCl₃): δ 8.59 (d, J = 4.8 Hz, 1 H), 8.42 (s, 1 H), 8.34-8.32 (m, 1 H), 8.14 (d, J = 2.4 Hz, 1 H), 7.57 (d, J = 5.2 Hz, 1 H), 7.37 (dd, J1 = 8.4 Hz, J2 = 2.4 Hz, 1 H), 7.12-7.02 (m, 3 H), 6.93 (t, J = 8.0 Hz, 1 H), 4.98-4.95 (m, 1 H), 4.67 (s, 2 H), 4.55 (d, J = 5.2 Hz, 2 H), 3.88 (s, 3 H), 1.95-1.74 (m, 4 H), 1.65-1.60 (m, 4 H); m/z (ESI+) (M + H)⁺ = 451.10; HPLC tR = 6.22 min | +++ |
| AC108 | 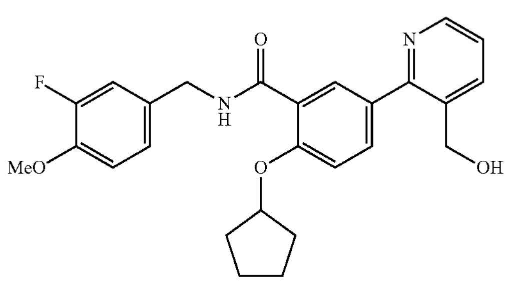 [SMILES: COc1ccc(CNC(=O)c2cc(-c3ncccc3CO)ccc2OC2CCCC2)cc1F] | 450.5 | ¹H NMR (400 MHz, CDCl₃): δ 8.57-8.55 (m, 1 H), 8.37 (s, 1 H), 8.30 (br. s, 1 H), 7.93 (d, J = 7.2 Hz, 1 H), 7.70 (dd, J1 = 8.4 Hz, J2 = 1.6 Hz, 1 H), 7.29-7.27 (m, 1 H), 7.12-7.03 (m, 3 H), 6.93 (t, J = 8.4 Hz, 1 H), 4.96 (br.s, 1 H), 4.74 (s, 2 H), 4.54 (d, J = 5.2 Hz, 2 H), 3.88 (s, 3 H), 1.92-1.52 (m, 4 H), 1.27-1.22 (m, 4 H); m/z (ESI+) (M + H)⁺ = 451.60; HPLC tR = 6.30 min | +++ |

TABLE 3-continued

Analytical Data of Compounds

| ID | Structure | MW | Analytical Data | ALDH2 Activity with 20 μM of the compound* |
|---|---|---|---|---|
| AC109 | 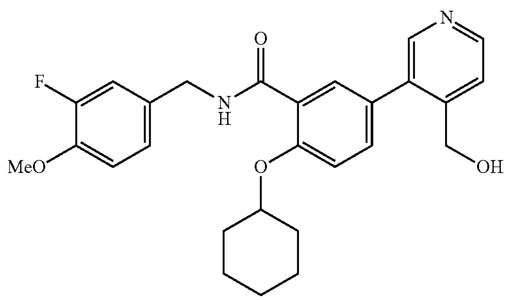 [SMILES: COc1ccc(CNC(=O)c2cc(-c3cnccc3CO)ccc2OC2CCCCC2)cc1F] | 464.5 | ¹H NMR (400 MHz, CDCl₃): δ 8.59 (d, J = 4.4 Hz, 1 H), 8.48-8.44 (m, 2 H), 8.18 (s, 1 H), 7.57 (d, J = 5.2 Hz, 1 H), 7.37 (dd, J1 = 8.8 Hz, J2 = 2.4 Hz, 1 H), 7.14-7.05 (m, 3 H), 6.93 (t, J = 8.0 Hz, 1 H), 4.68 (d, J = 4.4 Hz, 2 H), 4.59 (d, J = 5.6 Hz, 2 H), 4.55-4.50 (m, 1 H), 3.89 (s, 3 H), 1.99-1.95 (m, 2 H), 1.60-1.20 (m, 8 H); m/z (ESI+) (M + H)⁺ = 465.65; HPLC tR = 6.41 min | +++ |
| AC110 | 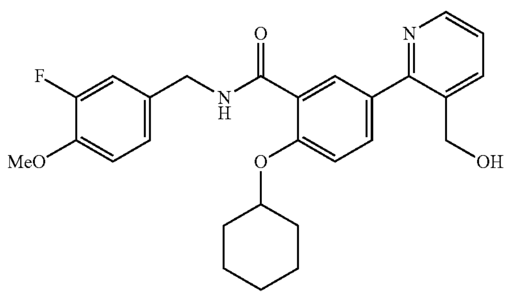 [SMILES: COc1ccc(CNC(=O)c2cc(-c3ncccc3CO)ccc2OC2CCCCC2)cc1F] | 464.5 | ¹H NMR (400 MHz, CDCl₃): δ 8.59-8.57 (m, 1 H), 8.45-8.39 (m, 2 H), 7.94 (d, J = 8.0 Hz, 1 H), 7.71 (dd, J1 = 8.4 Hz, J2 = 2.4 Hz, 1 H), 7.30-7.27 (m, 1 H), 7.14-7.06 (m, 3 H), 6.93 (t, J = 8.4 Hz, 1 H), 4.76 (s, 2 H), 4.58 (d, J = 5.2 Hz, 2 H), 4.51-4.49 (m, 1 H), 3.88 (s, 3 H), 1.98-1.92 (m, 2 H), 1.62-1.24 (m, 8 H); m/z (ESI+) (M + H)⁺ = 465.45; HPLC tR = 6.62 min | +++ |
| AC111 | 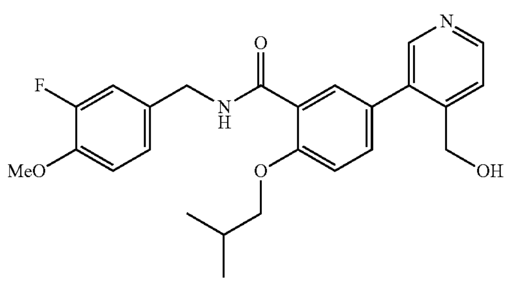 | 438.5 | ¹H NMR (400 MHz, CDCl₃): δ 8.60 (d, J = 5.2 Hz, 1 H), 8.44 (s, 1 H), 8.35-8.33 (m, 1 H), 8.16 (d, J = 2.4 Hz, 1 H), 7.58 (d, J = 5.2 Hz, 1 H), 7.39 (dd, J1 = 8.4 Hz, J2 = 2.4 Hz, 1 H), 7.13-7.02 (m, 3 H), 6.93 (t, J = 8.0 Hz, 1 H), 4.69 (s, 2 H), 4.60 (d, J = 8.4 Hz, 2 H), 3.91 (s, 2 H), 3.88 (s, 3 H), 2.07-2.00 (m, 1 H), 0.93 (d, J = 5.6 Hz, 6 H); m/z (ESI+) (M + H)⁺ = 439.75; HPLC tR = 5.88 min | +++ |
| AC112 | 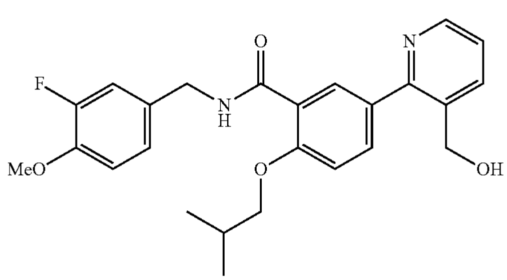 [SMILES: COc1ccc(CNC(=O)c2cc(-c3ncccc3CO)ccc2OCC(C)C)cc1F] | 438.5 | ¹H NMR (400 MHz, CDCl₃): δ 8.60-8.58 (m, 1 H), 8.41-8.39 (m, 1 H), 8.29 (br. s, 1 H), 7.94 (d, J = 8.0 Hz, 1 H), 7.73 (dd, J1 = 8.4 Hz, J2 = 2.0 Hz, 1 H), 7.30-7.26 (m, 1 H), 7.12-7.03 (m, 3 H), 6.92 (t, J = 8.4 Hz, 1 H), 4.75 (s, 2 H), 4.58 (d, J = 5.6 hz, 2 H), 3.90 (s, 2 H), 3.88 (s, 3 H), 2.05-2.00 (m, 1 H), 0.93 (d, J = 5.6 Hz, 6 H); m/z (ESI+) (M + H)⁺ = 439.65; HPLC tR = 6.07 min | +++ |

TABLE 3-continued

Analytical Data of Compounds

| ID | Structure | MW | Analytical Data | ALDH2 Activity with 20 μM of the compound* |
|---|---|---|---|---|
| AC145 | 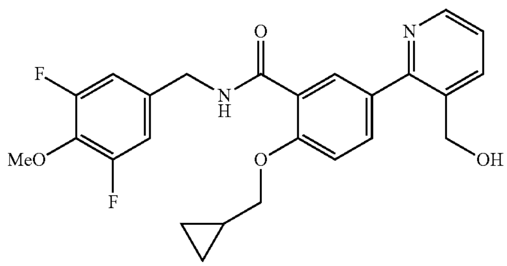 | 454.5 | $^1$H NMR (400 MHz, CDCl$_3$): δ 8.60-8.58 (m, 2 H), 8.40 (s, 1 H), 7.94 (d, J = 7.6 Hz, 1 H), 7.73 (dd, J1 = 8.4 Hz, J2 = 2.8 Hz, 1 H), 7.31-7.25 (m, 1 H), 7.02 (d, J = 8.4 Hz, 1 H), 6.95 (d, J = 8.4 Hz, 2 H), 4.75 (d, J = 4.8 Hz, 2 H), 4.59 (d, J = 5.6 Hz, 2 H), 3.99 (d, J = 7.2 Hz, 3 H), 3.97 (s, 3 H), 1.29-1.24 (m, 1 H), 0.62-0.57 (m, 2 H), 0.36-0.32 (m, 2 H); m/z (ESI+) (M + H)$^+$ = 455.65; HPLC tR = 6.16 min | ++ |
| AC146 | 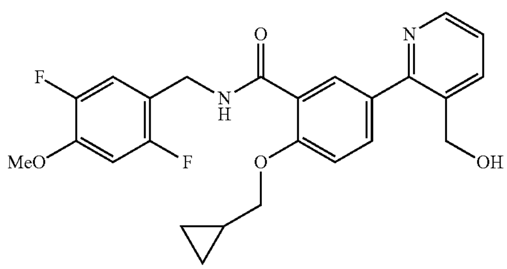 [SMILES: COc1cc(F)c(CNC(=O)c2cc(-c3ncccc3CO)ccc2OCC2CC2)cc1F] | 454.5 | $^1$H NMR (400 MHz, CDCl$_3$): δ 8.62-8.58 (m, 2 H), 8.39 (s, 1 H), 7.94 (d, J = 7.6 Hz, 1 H), 7.72 (dd, J1 = 8.4 Hz, J2 = 2.8 Hz, 1 H), 7.31-7.25 (m, 1 H), 7.22-7.17 (m, 1 H), 7.00 (d, J = 8.8 Hz, 1 H), 6.70 (dd, J1 = 11.2 Hz, J2 = 6.8 Hz, 1 H), 4.74 (s, 2 H), 4.63 (d, J = 6.0 Hz, 2 H), 3.97 (d, J = 7.2 Hz, 2 H), 3.78 (s, 3 H), 1.29-1.24 (m, 1 H), 0.62-0.57 (m, 2 H), 0.36-0.32 (m, 2 H); m/z (ESI+) (M + H)$^+$ = 455.65; HPLC tR = 5.75 min | +++ |
| AC147 | 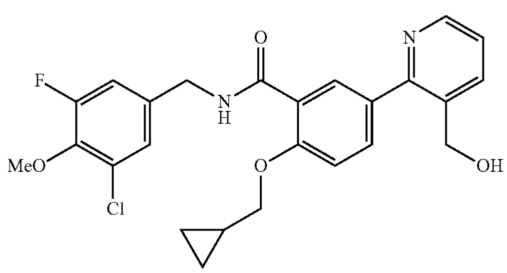 | 470.9 | $^1$H NMR (400 MHz, CDCl$_3$): δ 8.59 (d, J = 4.4 Hz, 1 H), 8.40 (d, J = 2.4 Hz, 1 H), 7.94 (d, J = 6.8 Hz, 1 H), 7.74 (dd, J1 = 8.4 Hz, J2 = 2.4 Hz, 1 H), 7.31-7.26 (m, 1 H), 7.20 (s, 1 H), 7.09-7.01 (m, 2 H), 4.75 (s, 2 H), 4.59 (d, J = 5.2 Hz, 2 H), 3.99 (d, J = 6.8 Hz, 3 H), 3.95 (s, 3 H), 1.29-1.24 (m, 1 H), 0.62-0.57 (m, 2 H), 0.36-0.32 (m, 2 H); m/z (ESI+) (M + H)$^+$ = 471.05; HPLC tR = 6.31 min | ++ |
| AC148 | 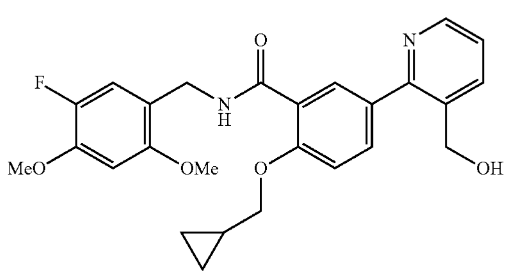 [SMILES: COc1cc(OC)c(CNC(=O)c2cc(-c3ncccc3CO)ccc2OCC2CC2)cc1F] | 466.5 | $^1$H NMR (400 MHz, CDCl$_3$): δ 8.83 (d, J = 5.2 Hz, 1 H), 8.58 (d, J = 7.2 Hz, 1 H), 8.48 (s, 1 H), 8.35 (d, J = 1.6 Hz, 1 H), 7.78-7.73 (m, 2 H), 7.15-7.09 (m, 2 H), 6.54 (d, J = 7.2 Hz, 1 H), 4.81 (s, 2 H), 4.56 (d, J = 6.0 Hz, 2 H), 4.00 (d, J = 7.2 Hz, 3 H), 3.90 (s, 3 H), 3.86 (s, 3 H), 1.29-1.24 (m, 1 H), 0.62-0.57 (m, 2 H), 0.36-0.32 (m, 2 H); m/z (ESI+) (M + H)$^+$ = 467.70; HPLC tR = 6.04 min | ++ |

TABLE 3-continued

Analytical Data of Compounds

| ID | Structure | MW | Analytical Data | ALDH2 Activity with 20 μM of the compound* |
|---|---|---|---|---|
| AC150 | 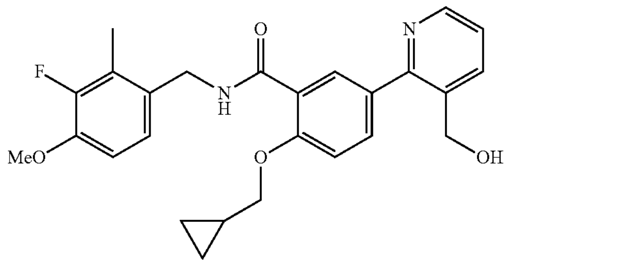 | 450.5 | ¹H NMR (400 MHz, CDCl₃): δ 8.60 (d, J = 4.0 Hz, 1 H), 8.42-8.40 (m, 1 H), 8.37 (d, J = 1.2 Hz, 1 H), 7.95 (d, J = 8.0 Hz, 1 H), 7.71 (dd, J1 = 8.0 Hz, J2 = 2.0 Hz, 1 H), 7.35-7.27 (m, 1 H), 7.09 (d, J = 8.4 Hz, 1 H), 6.98 (d, J = 8.8 Hz, 1 H), 6.77 (t, J = 8.4 Hz, 1 H), 4.76 (s, 2 H), 4.59 (d, J = 4.8 Hz, 2 H), 3.91 (d, J = 7.2 Hz, 2 H), 3.85 (s, 3 H), 2.31 (s, 3 H), 1.22-1.20 (m, 1 H), 0.45-0.40 (m, 2 H), 0.25-0.22 (m, 2 H); m/z (ESI+) (M + H)⁺ = 451.60; HPLC tR = 6.10 | ++ |
| AC151 | 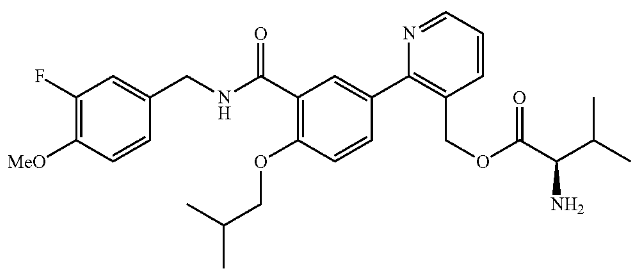 [SMILES: COc1ccc(CNC(=O)c2cc(-c3ncccc3COC(=O)[C@H](N)C(C)C)ccc2OCC(C)C)cc1F] | 537.6 | ¹H NMR (400 MHz, CD₃OD): δ 8.76 (d, J = 4.0 Hz, 1 H), 8.68 (d, J = 4.0 Hz, 2 H), 8.61 (t, J = 2.4 Hz, 1 H), 8.40 (d, J = 8.0 Hz, 1 H), 7.94 (d, J = 2.4 Hz, 1 H), 7.95-7.93 (m, 2 H), 7.30 (d, J = 8.8 Hz, 1 H), 7.19 (d, J = 12.0 Hz, 1 H), 7.12-7.09 (m, 2 H), 5.27 (s, 2 H), 4.32 (d, J = 5.6 Hz, 2 H), 3.94-3.88 (m, 3 H), 3.80 (s, 3 H), 2.15-2.13 (m, 1 H), 2.05-2.02 (m, 1 H), 0.98-0.87 (m, 12 H); m/z (ESI+) (M + H)⁺ = 538.7; HPLC tR = 5.92 min | |
| AC152 | 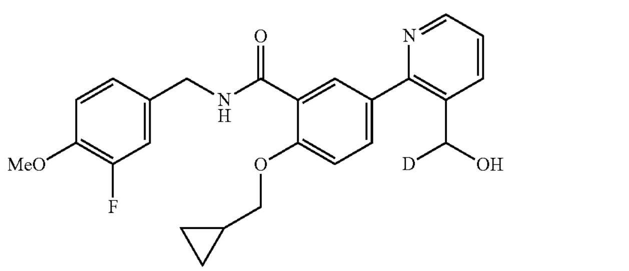 [SMILES: [2H]C(O)c1cccnc1-c1ccc(OCC2CC2)c(C(=O)NCc2ccc(OC)c(F)c2)c1] | 437.5 | ¹H NMR (400 MHz, CDCl₃): δ 8.76 (br.s, 1 H), 8.57-8.53 (m, 2 H), 8.33 (s, 1 H), 7.73 (d, J = 7.2 Hz, 1 H), 7.13-7.07 (m, 3 H), 6.92 (t, J = 8.8 Hz, 2 H), 4.73 (s, 1 H), 4.55 (d, J = 4.2 Hz, 2 H), 3.98 (d, J = 7.2 Hz, 2 H), 3.85 (s, 3 H), 1.24-1.17 (m, 1 H), 0.58-0.52 (m, 2 H), 0.33-0.30 (m, 2 H); m/z (ESI+) (M + H)⁺ = 438.15; HPLC tR = 6.12 min | +++ |
| AC153 | 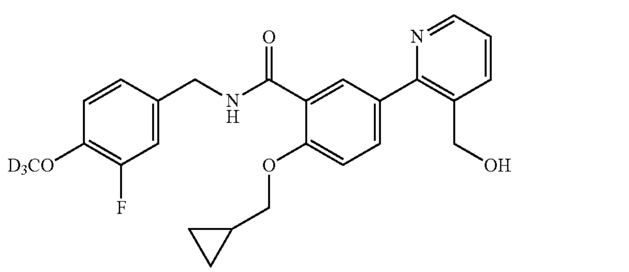 | 439.5 | ¹H NMR (400 MHz, CDCl₃): δ 8.77 (d, J = 4.8 Hz, 1 H), 8.52 (d, J = 8.8 Hz, 1 H), 8.47 (d, J = 4.8 Hz, 1 H), 8.33 (s, 1 H), 7.74 (d, J = 8.8 Hz, 1 H), 7.66 (t, J = 5.6 Hz, 1 H), 7.15-7.06 (m, 3 H), 6.92 (t, J = 8.8 Hz, 2 H), 4.76 (s, 2 H), 4.57 (d, J = 4.2 Hz, 2 H), 3.98 (d, J = 7.2 Hz, 2 H), 1.25-1.18 (m, 1 H), 0.58-0.52 (m, 2 H), 0.33-0.30 (m, 2 H); m/z (ESI+) (M + H)⁺ = 440.20; HPLC tR = 6.14 min | +++ |

TABLE 3-continued

Analytical Data of Compounds

| ID | Structure | MW | Analytical Data | ALDH2 Activity with 20 μM of the compound* |
|---|---|---|---|---|
| AC154 | 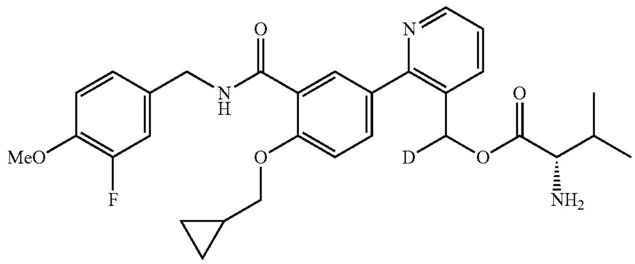 [SMILES: [2H]C(OC(=O)[C@@H](N)C(C)C)c1cccnc1-c1ccc(OCC2CC2)c(C(=O)NCc2ccc(OC)c(F)c2)c1] | 536.6 | $^1$H NMR (400 MHz, CDCl$_3$): δ 8.84 (br.s, 1 H), 8.70-8.67 (m, 1 H), 8.46-8.25 (m, 2 H), 7.77-7.72 (m, 2 H), (s, 1 H), 7.13-7.03 (m, 3 H), 6.92 (t, J = 8.8 Hz, 2 H), 5.17-5.08 (m, 1 H), 4.50-4.47 (m, 2 H), 4.00 (d, J = 6.8 Hz, 2 H), 3.86 (s, 3 H), 2.35-2.31 (m, 1 H), 1.24-1.17 (m, 1 H), 1.06-1.03 (m, 6 H), 0.58-0.52 (m, 2 H), 0.33-0.30 (m, 2 H); m/z (ESI+) (M + H)$^+$ = 537.45; HPLC tR = 5.63 min | |
| AC155 | 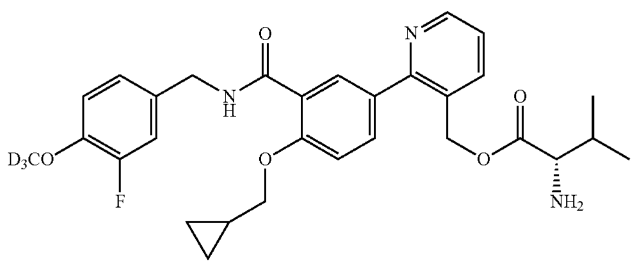 | 538.6 | $^1$H NMR (400 MHz, CDCl$_3$): δ 8.84 (br.s, 1 H), 8.70-8.67 (m, 1 H), 8.46-8.25 (m, 2 H), 7.79-7.72 (m, 2 H), (s, 1 H), 7.13-7.03 (m, 3 H), 6.92 (t, J = 8.8 Hz, 2 H), 5.20 (d, J = 11.6 Hz, 1 H), 5.05 (d, J = 12.0 Hz, 1 H), 4.55-4.47 (m, 2 H), 4.01 (d, J = 6.8 Hz, 2 H), 2.37-2.33 (m, 1 H), 1.24-1.17 (m, 1 H), 1.06-1.03 (m, 6 H), 0.58-0.52 (m, 2 H), 0.33-0.30 (m, 2 H); m/z (ESI+) (M + H)$^+$ = 539.20; HPLC tR = 5.64 min | |
| AC156 | 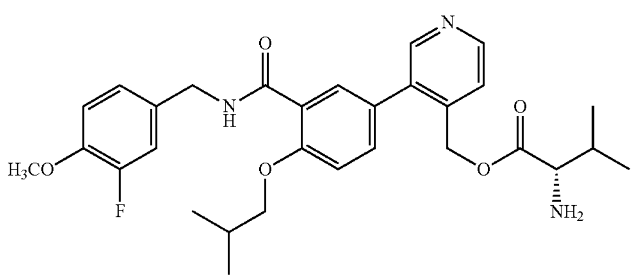 [SMILES: COc1ccc(CNC(=O)c2cc(-c3cnccc3COC(=O)[C@@H](N)C(C)C)ccc2OCC(C)C)cc1F] | 537.6 | $^1$H NMR (400 MHz, d$^6$-DMSO): δ 8.81 (d, J = 5.6 Hz, 1 H), 8.73 9 s, 1 H), 8.65 (d, J = 4.4 Hz, 1 H), 8.62-8.60 (m, 1 H), 8.01 (d, J = 5.2 Hz, 1 H), 7.76 (d, J = 2.4 Hz, 1 H), 7.59 (dd, J1 = 8.4 hz, J2 = 2.4 Hz, 1 H), 7.28 (d, J = 8.4 Hz, 1 H), 7.20-7.08 (m, 3 H), 5.34-5.32 (m, 2 H), 4.42 (d, J = 6.0 Hz, 2 H), 4.00-3.90 (m, 3 H), 3.81 (s, 3 H), 2.05-2.03 (m, 1 H), 2.01-1.98 (m, 1 H), 0.93-0.88 (m, 12 H); m/z (ESI+) (M + H)$^+$ = 538.55; HPLC tR = 5.84 min | |
| AC157 | 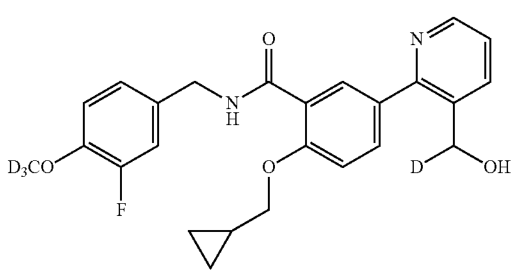 | 440.5 | $^1$H NMR (400 MHz, CDCl$_3$): δ 8.59-8.52 (m, 2 H), 8.37 (s, 1 H), 8.04 (d, J = 7.6 Hz, 1 H), 7.74 (d, J = 8.8 Hz, 1 H), 7.35 9dd, J1 = 7.6 Hz, J2 = 5.2 Hz, 1 H), 7.16-7.08 (m, 2 H), 7.01 (d, J = 8.8 Hz, 1 H), 6.92 (t, J = 8.8 Hz, 2 H), 4.72 (s, 1 H), 4.58 (d, J = 4.2 Hz, 2 H), 3.95 (d, J = 7.2 Hz, 2 H), 1.25-1.18 (m, 1 H), 0.58-0.52 (m, 2 H), 0.33-0.30 (m, 2 H); m/z (ESI+) (M + H)$^+$ = 441.15; HPLC tR = 5.85 min | +++ |

TABLE 3-continued

Analytical Data of Compounds

| ID | Structure | MW | Analytical Data | ALDH2 Activity with 20 μM of the compound* |
|---|---|---|---|---|
| AC158 | 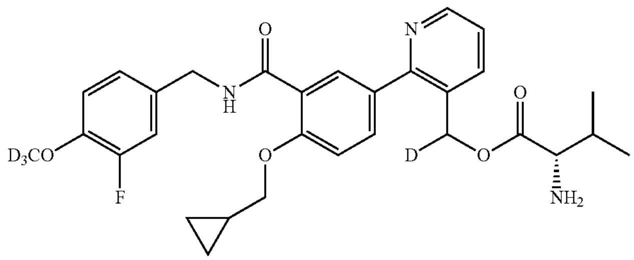 | 539.6 | $^1$H NMR (400 MHz, CDCl$_3$): δ 8.73-8.55 (m, 4 H), 8.46-8.25 (m, 1 H), 7.99 (s, 1 H), 7.72-7.68 (m, 2 H), 7.28-7.07 (m, 4 H), 5.20 (d, J = 4.8 Hz, 1 H), 4.45 (d, J = 5.6 Hz, 2 H), 4.02 (d, J = 6.8 Hz, 2 H), 2.15-2.12 (m, 1 H), 1.28-1.24 (m, 1 H), 0.89-0.86 (m, 6 H), 0.54-0.48 (m, 2 H), 0.35-0.32 (m, 2 H); m/z (ESI+) (M + H)$^+$ = 540.50; HPLC tR = 5.70 min | |
| AC159 | 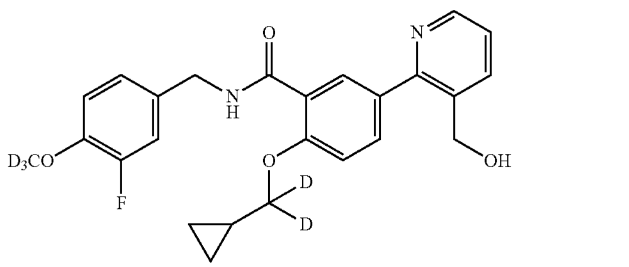 | 441.5 | $^1$H NMR (400 MHz, CDCl$_3$): δ 8.58 (dd, J1 = 4.8 hz, J2 = 2.0 hz, 1 H, 8.54-8.52 (m, 1 H), 8.40 9d, J = 2.8 Hz, 1 H), 7.93 (dd, J1 = 8.0 Hz, J2 = 2.0 Hz, 1 H), 7.71 9dd, J1 = 8.4 hz, J2 = 2.8 Hz, 1 H), 7.31-7.25 (m, 1 H), 7.16-7.11 (m, 1 H), 6.99 (d, J = 8.8 Hz, 1 H), 6.92 (t, J = 8.8 Hz, 2 H), 4.74 (s, 1 H), 4.60 (d, J = 4.2 Hz, 2 H), 1.25-1.18 (m, 1 H), 0.56-0.52 (m, 2 H), 0.32-0.30 (m, 2 H); m/z (ESI+) (M + H)$^+$ = 442.15; HPLC tR = 6.04 min | +++ |
| AC160 | 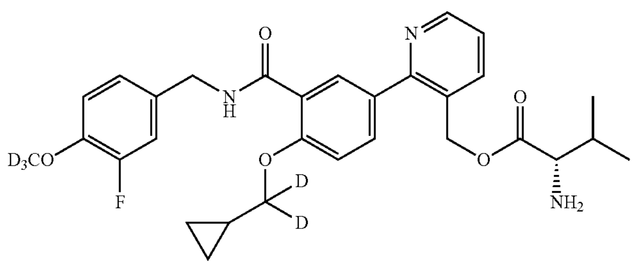 | 540.6 | $^1$H NMR (400 MHz, d$^6$-DMSO): δ 8.73-8.71 (m, 2 H), 8.58-8.56 (m, 2 H), 8.27 (d, J = 8.0 Hz, 1 H), 7.98 (d, J = 2.4 Hz, 1 H), 7.71-7.63 (m, 2 H), 7.27-7.20 (m, 2 H), 7.13-7.07 (m, 2 H), 5.25 (s, 2 H), 4.45 (d, J = 5.6 Hz, 2 H), 2.15-2.10 (m, 1 H), 1.26-1.21 (m, 1 H), 0.88-0.84 (m, 6 H), 0.53-0.48 (m, 2 H), 0.35-0.32 (m, 2 H); m/z (ESI+) (M + H)$^+$ = 541.50; HPLC tR = 5.62 min | |
| AC161 | 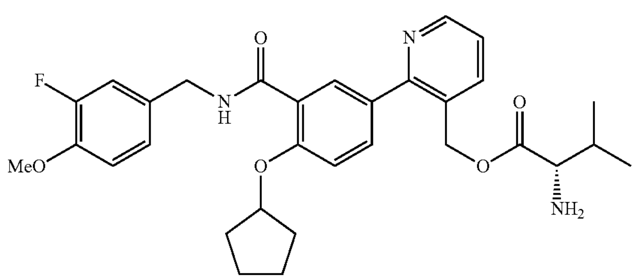 [SMILES: COc1ccc(CNC(=O)c2cc(-c3ncccc3COC(=O)[C@@H](N)C(C)C)ccc2OC2CCCC2)cc1F] | 549.6 | $^1$H NMR (400 MHz, CDCl$_3$): δ 8.86 (d, J = 5.2 Hz, 1 H), 8.80 (d, J = 7.2 Hz, 1 H), 8.21 (s, 1 H), 8.10 (t, J = 6.0 Hz, 1 H), 7.83 (d, J = 8.8 Hz, 1 H), 7.44 (d, J = 8.8 Hz, 1 H), 7.17-7.08 (m, 3 H), 5.44-5.34 (m, 2 H), 5.16-5.14 (m, 1 H), 4.55-4.53 (m, 2 H), 4.10-4.08 (m, 1 H), 3.87 (s, 3 H), 2.32-2.88 (m, 1 H), 2.02-1.98 (m, 3 H), 1.84-1.80 (m, 2 H), 1.62-1.58 (m, 4 H), 1.05-1.00 (m, 6 H); m/z (ESI+) (M + H)$^+$ = 550.30; HPLC tR = 5.89 min | |

TABLE 3-continued

Analytical Data of Compounds

| ID | Structure | MW | Analytical Data | ALDH2 Activity with 20 μM of the compound* |
|---|---|---|---|---|
| AC162 | 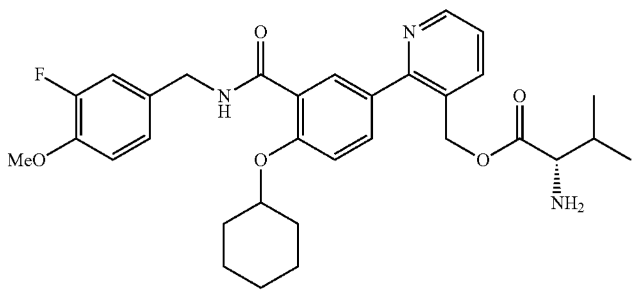 [SMILES: COc1ccc(CNC(=O)c2cc(-c3ncccc3COC(=O)[C@@H](N)C(C)C)ccc2OC2CCCCC2)cc1F] | 563.7 | ¹H NMR (400 MHz, d⁶-DMSO): δ 8.73 (d, J = 5.2 Hz, 1 H), 8.63-8.57 (m, 3 H), 8.34 (d, J = 6.8 Hz, 1 H), 7.96 (d, J = 2.4 Hz, 1 H), 7.70 (dd, J1 = 8.0 Hz, J2 = 2.4 Hz, 2 H), 7.35 (d, J = 8.8 Hz, 1 H), 7.18 (d, J = 13.2 Hz, 1 H), 7.12-7.10 (m, 2 H), 5.27 (s, 2 H), 4.64-4.60 (m, 1 H), 4.43 (d, J = 5.6 Hz, 2 H), 4.04-3.95 (m, 1 H), 2.15-2.10 (m, 1 H), 1.97-1.88 (m, 2 H), 1.59-1.46 (m, 4 H), 1.37-1.30 (m, 4 H), 1.20-1.12 (m, 4 H), 0.88-0.86 (m, 6 H); m/z (ESI+) (M + H)⁺ = 564.35; HPLC tR = 6.14 min | |
| AC163 | 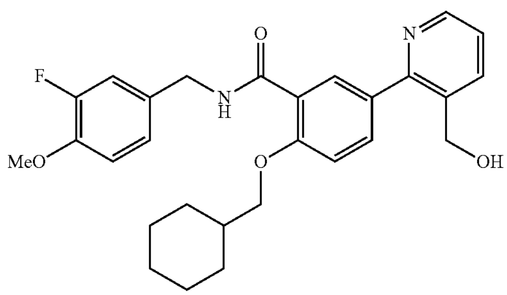 [SMILES: COc1ccc(CNC(=O)c2cc(-c3ncccc3CO)ccc2OCC2CCCCC2)cc1F] | 478.6 | ¹H NMR (400 MHz, CDCl₃): δ 8.61-8.58 (m, 1 H), 8.42-8.40 (m, 2 H), 8.28 (br. s, 1 H), 7.94 (d, J = 8.0 Hz, 1 H), 7.71 (dd, J1 = 8.4 Hz, J2 = 2.4 Hz, 1 H), 7.35-7.26 (m, 1 H), 7.13-7.03 (m, 3 H), 6.93 (t, J = 8.4 Hz, 1 H), 4.70 (s, 2 H), 4.58 (d, J = 5.2 Hz, 2 H), 3.91 (d, J = 6.0 Hz, 1 H), 3.88 (s, 3 H), 2.35-2.28 (m, 1 H), 1.65-1.55 (m, 4 H), 1.25-0.80 (m, 6 H); m/z (ESI+) (M + H)⁺ = 479.25; HPLC tR = 6.57 min | ++ |
| AC164 | 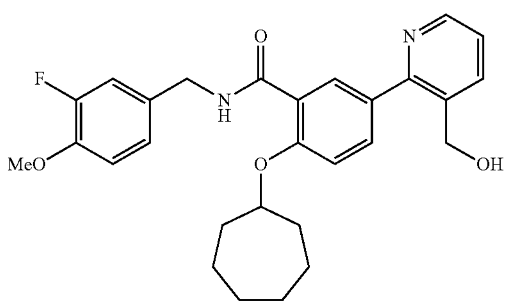 [SMILES: COc1ccc(CNC(=O)c2cc(-c3ncccc3CO)ccc2OC2CCCCCC2)cc1F] | 478.6 | ¹H NMR (400 MHz, CDCl₃): δ 8.58 (d, J = 4.8 Hz, 1 H), 8.43-8.39 (m, 2 H), 7.94 (d, J = 8.4 Hz, 1 H), 7.71 (dd, J1 = 8.4 Hz, J2 = 2.4 Hz, 1 H), 7.31-7.27 (m, 1 H), 7.14-7.06 (m, 3 H), 6.93 (t, J = 8.4 Hz, 1 H), 4.76 (s, 2 H), 4.68-4.65 (m, 1 H), 4.58 (d, J = 5.2 Hz, 2 H), 3.88 (s, 3 H), 2.39-2.35 (m, 1 H), 2.05-2.00 (m, 2 H), 1.73-1.24 (m, 10 H); m/z (ESI+) (M + H)⁺ = 479.25; HPLC tR = 6.45 min | +++ |
| AC165 | 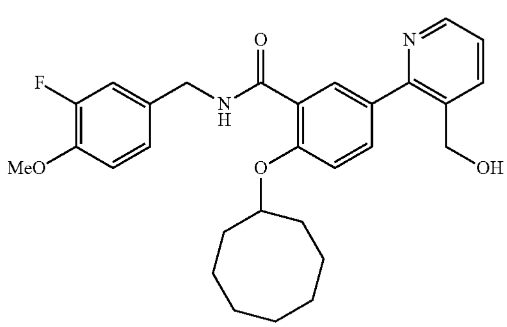 [SMILES: COc1ccc(CNC(=O)c2cc(-c3ncccc3CO)ccc2OC2CCCCCCC2)cc1F] | 492.6 | ¹H NMR (400 MHz, CDCl₃): δ 8.57 (d, J = 4.4 Hz, 1 H), 8.43 (d, J = 4.4 Hz, 1 H), 8.38 (s, 1 H), 7.93 (d, J = 8.0 Hz, 1 H), 7.70 (d, J = 8.0 Hz, 1 H), 7.29-7.26 (m, 1 H), 7.13-7.07 (m, 2 H), 7.01 (d, J = 8.0 Hz, 1 H), 6.93 (t, J = 8.0 Hz, 1 H), 4.74 (s, 2 H), 4.67-4.62 (m, 1 H), 4.56 (d, J = 5.6 Hz, 2 H), 3.87 (s, 3 H), 1.95-1.24 (m, 14 H); m/z (ESI+) (M + H)⁺ = 493.20; HPLC tR = 6.71 min | ++ |

TABLE 3-continued

Analytical Data of Compounds

| ID | Structure | MW | Analytical Data | ALDH2 Activity with 20 μM of the compound* |
|---|---|---|---|---|
| AC166 | (structure: F, MeO-phenyl-CH2-NH-C(O)-phenyl(O-CH2-cyclopentyl)-pyridine with CH2OH) | 464.5 | $^1$H NMR (400 MHz, CDCl$_3$): δ 8.61-8.58 (m, 1 H), 8.42-8.40 (m, 2 H), 8.28 (br. s, 1 H), 7.94 (d, J = 8.0 Hz, 1 H), 7.71 (dd, J1 = 8.4 Hz, J2 = 2.4 Hz, 1 H), 7.35-7.26 (m, 1 H), 7.13-7.03 (m, 3 H), 6.93 (t, J = 8.4 Hz, 1 H), 4.75 (s, 2 H), 4.58 (d, J = 5.2 Hz, 2 H), 3.99 (d, J = 6.0 Hz, 1 H), 3.88 (s, 3 H), 2.27-2.22 (m, 1 H), 1.65-1.55 (m, 4 H), 1.25-0.80 (m, 6 H); m/z (ESI+) (M + H)$^+$ = 465.25; HPLC tR = 6.39 min | +++ |

*A range of about 100-150% is designated as +, about 150-250% is designated as ++ and greater than about 250% is designated with +++.

Example 7

Proliferation of FANCA Deficient Lymphocytes

FANCA deficiency lymphocyte cell line (Fanconi Anemia, Complementation Group A, FANCA B-lymphocyte, GM13022) was purchased from Coriell Cell Repositories (403 Haddon Ave, Camden, N.J. 08103).

Culture of FANCA Lymphocytes

Standard cell culture conditions were used in this experiment. The culture medium (CM) consisted of culture medium RPMI1640, 15% heat-inactivated FBS, 2 mM L-glutamine, 1% Pen/Strep. Cells were suspended in 10-20 ml CM in T25 tissue culture flask in an upright position and incubated in a 37° C., 5% CO2 incubator. Cells were counted daily and diluted with fresh CM to $3 \times 10^5$ cells/ml. Cells thawed and maintained in culture for 3-12 days were used in these studies.

General Protocol for Plating Cells onto Poly-D-Lysine Coated 96-Well Black/Clear Plate Cell densities of FANCA lymphocytes were determined and cells were diluted in RPMI1640 medium containing 15% FBS, 2 mM L-glutamine, 1% Pen/Strep to desired cell density. 4000 cells in 50-75 μl were plated onto each well in total 48 wells in columns 3-10 and rows B-G. This plating arrangement provided 6-replicates per column for each experimental condition. Plate was then centrifuged at 500 rpm for 2 min to ensure better distribution of cells across the well. For background medium controls, equal volume (50-75 μl) of dilution medium were added to wells B2, C2, D2.

For minimizing cells/medium drying in sample wells, 150 μl of 1xDPBS was added to each well of the 45 wells surrounding the sample and control wells. Plate was then incubated in a 37° C. 5% CO2 incubator for at least 4 hours before addition of new reagent.

Compounds were diluted from 20 mM stocks in DMSO with RPMI1640 medium containing 15% FBS. RPMI1640 medium containing 15% FBS and corresponding volume of DMSO was used as controls.

4 HNE (64 mM in 100% ethanol) was diluted to desired concentrations with RPMI1640 base medium.

AlamarBlue was added to each well to final 9.1 or 10% of the total volume in each well. Plate was further incubated in the 37° C. 5% CO$_2$ incubator. The alamarBlue assay is designed to measure quantitatively the proliferation of human and animal cell lines in culture versus incubation time period.

Plate was removed from the CO$_2$ incubator at a pre-designated time and placed in the microplate reader. The fluorescence level in each well was monitored at Ex 554 nm and Em 590 nm. Afterwards the numeric numbers/units were used for data analyses.

Data Analyses

A) Time Course of Cell Proliferation Rate

Fluorescence units in all wells were acquired by the microplate reader at each time point. Data were then exported to scientist's computer equipped with SoftMax ProS software. The average of Background units (Blk, 3x) and the average of each sample set (6 replicates) were determined. For data collected at each time point (cell culture incubation period), the average of Blk units were subtracted from the average of each set of the Sample units. These "net fluorescence unit" data were then presented in a plot consisted of different culture incubation time periods (the x-axis) versus the corresponding net fluorescence units (y-axis).

B) Time Course of Cell Proliferation as Percentages Relative to the Control Sample without any Treatment The "net fluorescence units" of each sample set were also compared to those of the "control" at each time point. "Control fluorescence units" were considered to be 100% at all the time points. Each set of "net fluorescence units" were divided by the "Control fluorescent units" and multiplied by 100 to obtain corresponding percentages. These "relative percentage" data were then presented in a plot consisted of time points (the x-axis) versus the corresponding relative percentages to control of 100 (y-axis).

Inhibition of FANCA-Deficiency Cell Growth in Culture by 4 HNE Treatment is 4 HNE Concentration-Dependent The inhibitory effect of 4 HNE on the proliferation of FANCA lymphocytes was examined. 4000 cells in 75 μl of RPMI1640 medium containing 15% FBS were plated onto each sample well in a 96-well poly D-lysine coated black/ clear cell culture plate and the plate was incubated in a 37° C. 5% $CO_2$ incubator for 7 hours.

Stock of 4 HNE at 64 mM was diluted with RPMI1640 medium to 10 µM, 20 µM, 30 µM, 40 µM, 60 µM, 80 µM, and 120 µM. 25 µl of diluted 4 HNE at each concentration was added to designated wells in 6-replicates for final 4 HNE concentrations of 2.5 µM, 5 µM, 7.5 µM, 10 µM, 15 µM, 20 µM, or 30 µM. In control wells, 25 µl of RPMI1640 culture medium was added. Cells were further incubated in the 37° C. 5% $CO_2$ incubator for 16 hours. 10 µl of alamarBlue was added to each well as an indicator for quantitative cell growth. At selected time points, the fluorescence units in all wells were determined by the microplate reader. The data were analyzed as described in the "Data Analyses" section above.

Figure 1B:
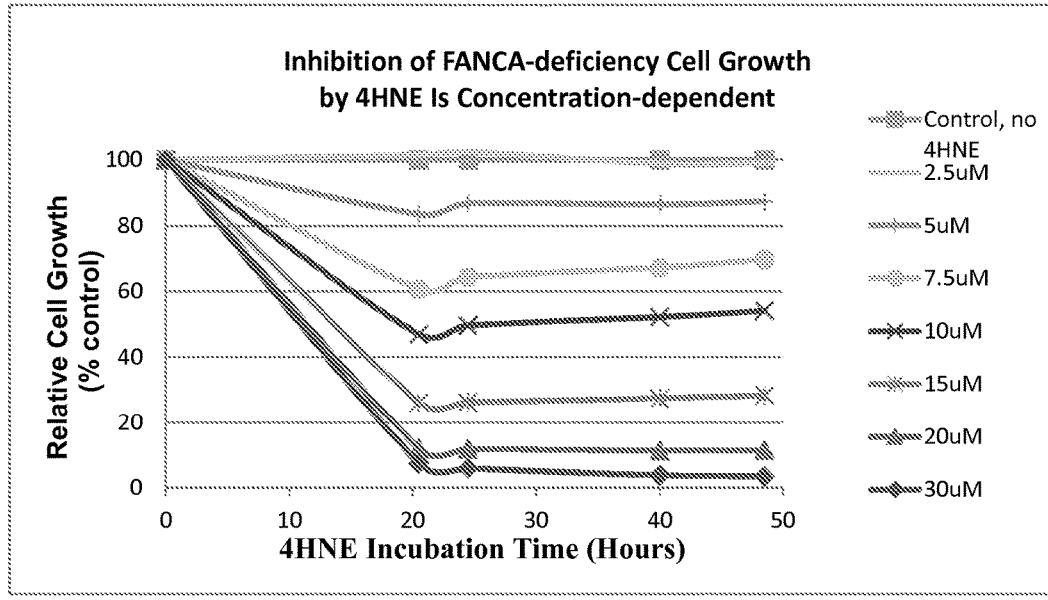

As shown in FIGS. 1A and 1B, treatment of FANCA cells with 4 HNE resulted in reduction of the level of cell proliferation in a concentration-dependent manner.

Example 8

ALDH2 Activators Rescued FANCA-Deficiency Cell Growth in the Presence of 3.5 uM 4 HNE or 6 uM 4 HNE Compounds AC32 and AC6 were examined for their capabilities to rescue FANCA-deficiency lymphocytes growth in the presence of 4 HNE treatment. 4000 cells in 50 µl of RPMI1640 culture medium containing 15% FBS were plated onto each sample well and then incubated in the incubator for 4 hours.

AC32 and AC6 were diluted from 20 mM stock in DMSO with RPMI1640 culture medium containing 15% FBS to 8 µM or 40 µM. Diluted AC32 or AC6 of about 25 µl was then added to designated wells in 6-replicates to obtain final compound concentrations of 2 or 10 µM. For control samples, 25 µl of equivalent volume of DMSO diluted with RPMI1640 culture medium containing 15% FBS was added to each well. 2 hours later 25 µl of 14 µM or 24 µM 4 HNE diluted in RPMI1640 base medium was added to designated wells in 6-replicates for final 3.5 µM or 6 µM 4 HNE. After overnight incubation, 10 µl of alamarBlue was added to each well. At selected time points, the fluorescence units in all wells were determined by the micro-plate reader. The data were analyzed as described in the "Data Analyses" section above.

Figure 2A:
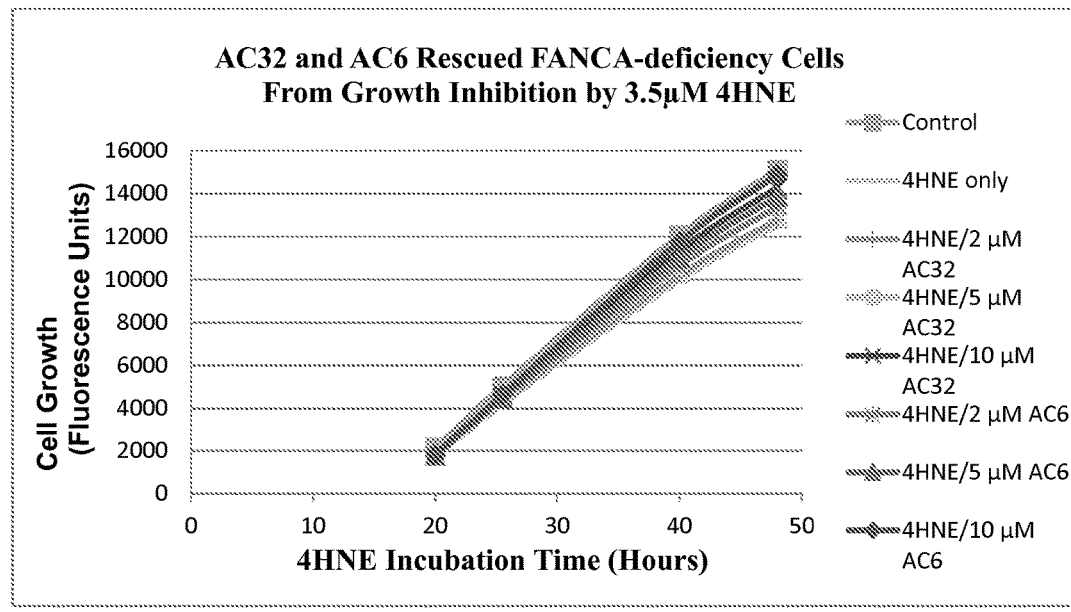
FIGS. 2(A)-(B) depict line graphs showing the inhibition of FANCA-deficient cell growth over time by 3.5 µM 4 HNE in the presence of the ALDH2 activators AC32 and AC6 concentrations ranging from 2 to 10 µM. Cells treated with 10 µM AC6 and AC32 showed more efficient growth than control up to 48 hours, 2(A) cell growth measured by fluorescence, 2(B) relative cell growth.
Figure 2B:
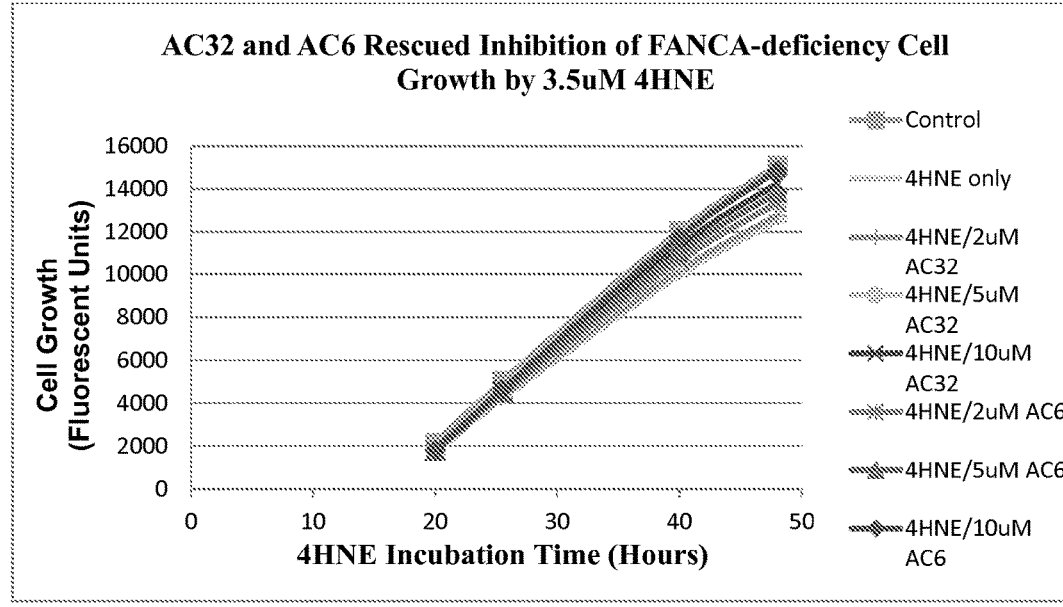

AC6 and AC32 Rescued FANCA-Deficiency Cells from Growth Inhibition by 3.5 µM 4 HNE As shown in FIG. 2, pretreatment of FANCA-deficiency lymphocytes with AC32 or AC6 for 2 hours before 3.5 µM 4 HNE challenge resulted in higher levels of cell growth than those of cells without any ALDH2 activator (4 HNE only). This protection of cell growth by ALDH2 activators is concentration-dependent. Furthermore, AC6 showed higher efficacy than AC32 did at similar concentrations. As shown in FIG. 2B, the inhibitory effect of exogenous 3.5 µM 4 HNE in FANCA cells was no longer detected in sample "4 HNE only" at 20 hours after 4 HNE treatment. The relative cell proliferation rates for "4 HNE only" cells and "control" cells were not changed from 25 hours to 48 hours (83% vs 100%) after 4 HNE treatment.

The relative cell proliferation rates in cells treated with 5 µM and 10 µM AC6 as well as in cells treated with 10 µM AC32 showed higher levels of cell growth than "control" without AC compounds from 25 hours to 48 hours after 4 HNE treatment. These results agreed with our earlier in house findings that treatment of FANCA lymphocytes with ALDH2 activators promoted cell growth for at least 48 hours.

Example 9

Figure 3A:
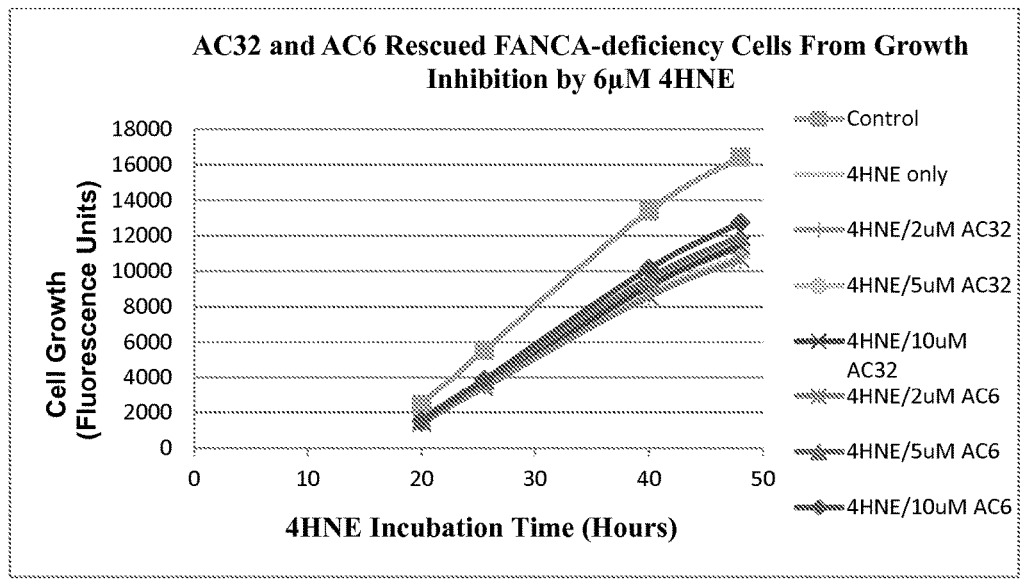
FIGS. 3(A)-(B) depict line graphs showing the inhibition of FANCA-deficient cell growth over time by 6 µM 4 HNE in the presence of the ALDH2 activators AC32 at a concentration of 10 µM and AC6 at concentrations of 5 µM and 10 µM.

Higher Concentrations of AC6 and AC32 are Required to Rescue FANCA-Deficiency Cells from Growth Inhibition by 6 µM 4 HNE The capabilities of AC6 and AC32 to rescue FANCA lymphocytes from growth inhibition by 4 HNE challenge were also examined at higher concentration of 4 HNE. As shown in FIG. 3, pretreatment of FANCA-deficiency lymphocytes with 10 µM AC32 or AC6 for 2 hours before 6 µM 4 HNE challenge resulted in higher levels of cell growth than those of cells without any ALDH2 activator (4 HNE only) or with 2 µM ALDH2 activators. These results strongly supported the notion that ALDH2 activity was directly involved in reduction of 4 HNE toxicity in FANCA lymphocytes at higher concentration of 4 HNE. Only higher ALDH2 activities in FANCA cells resulting from treatment with either 10 µm AC6 or 10 µM AC32 were able to rescue the inhibition of FANCA cell growth by 6 µM 4 HNE.

Figure 3B:
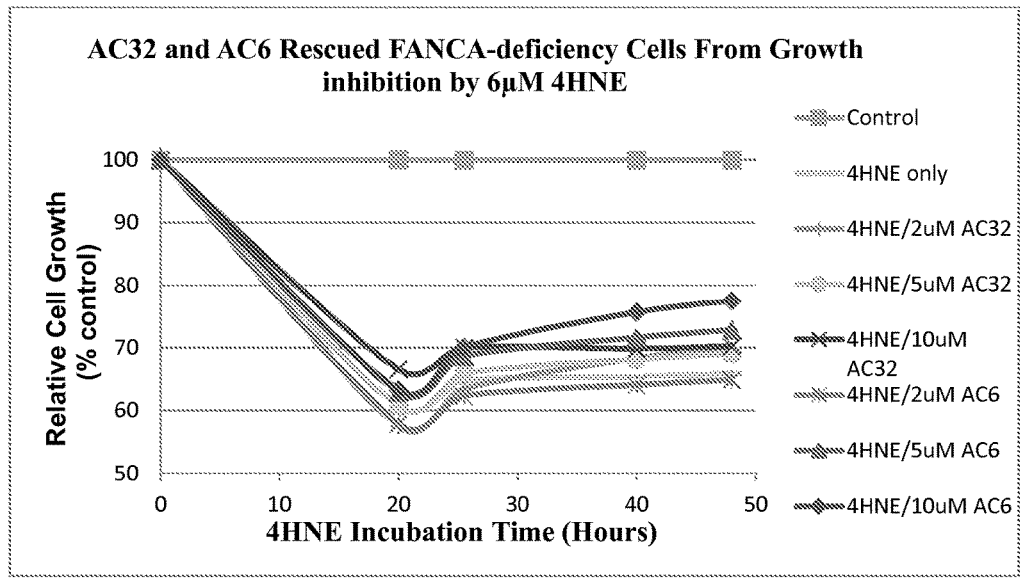

The capability of AC6 to promote FANCA cell growth detected in FIG. 2B was also shown in FIG. 3B. FANCA cells treated with 10 µM AC6 exhibited an increase in the cell proliferation rate between 25 and 48 hours after 4 HNE treatment. These results suggested that the cell-protective effect of AC6 is active for at least 48 hours in FANCA cells.

Example 10

Analgesic Effects of the Compounds of Formula (I) in a Carrageenan Inflammatory Pain Model The analgesic effects of AC151 and Alda-1 were evaluated using the carrageenan inflammatory pain model in male C57BL/6 mice. The mice were administered AC151, Alda-1 and vehicle (saline) as a control.

Male C57BL/6J mice from Jackson Laboratories (Bar Harbor, Me.) were used in this study. Mice were received at 6-7 weeks of age. Upon receipt, mice were assigned unique identification numbers (tail marked) and were group housed in OPTImice cages. All animals were acclimated to the colony room for at least 1 week prior to testing. During the period of acclimation, animals were examined on a regular basis, handled, and weighed to assure adequate health and suitability. Animals were maintained on a 12 hour/12 hour light/dark cycle. The room temperature was maintained between 20° C. and 23° C. with a relative humidity maintained between 30% and 70%. Chow and water were provided ad libitum for the duration of the study. All testing was performed during the animal's light cycle phase.

To induce plantar sensitivity to tactile stimuli, a single injection of carrageenan was administered to the plantar hindpaw of the mice and three hours later withdrawal from a mechanical stimulus is measured by applying Von Frey filaments of ascending bending force (0.02 to 6 grams) to the plantar surface of the hind paws (ipsilateral and contralateral to injection). A positive response was defined as withdrawal from the Von Frey filament. Confirmation of threshold is tested by examining the filament above and below the withdrawal response. A significant decrease in withdrawal threshold is interpreted as mechanical hyperalgesia. Prior to drug or carrageenan treatment, baseline Von Frey measures were taken and used to balance animals across treatment groups.

Alda-1 (1, 2, and 5 mg/kg) was dissolved in 50% DMSO/50% PEG and administered subcutaneous (sc), 15 min prior to carrageenan administration and twice again 30 and 150 minutes after carrageenan injections at a dose volume of 5 ml/kg. AC151 (40 and 80 mg/kg) was dissolved in saline and administered orally (po), 30 min after carrageenan administration. For one group, AC151 (80 mg/kg) was administered 15 min prior to carrageenan injections. The dose volume for this compound was 10 ml/kg.

The initial injections of AC151 (80 mg/kg) and Alda-1 were made 15 min prior to carrageenan injections. Then, a single 3.5 µl injection of 3% carrageenan was administered to the right plantar hindpaw. Alda-1 was then administered twice, once 30 minutes after carrageenan and again 150 minutes post-carrageenan. In separate treatment groups AC151 (40 mg/kg and 80 mg/kg) as well as saline vehicle were administered 30 minutes after carrageenan injection. Von Frey measures were taken 180 minutes after carrageenan injection.

Data were analyzed by analysis of variance (ANOVA) followed by post-hoc comparisons with Fisher Tests when appropriate. An effect was considered significant if $p<0.05$. An effect was considered significant if $p<0.05$.

Average body weights of animals prior to testing were measured. ANOVA found no significant differences between the various treatment groups prior to testing.

Figure 4A:
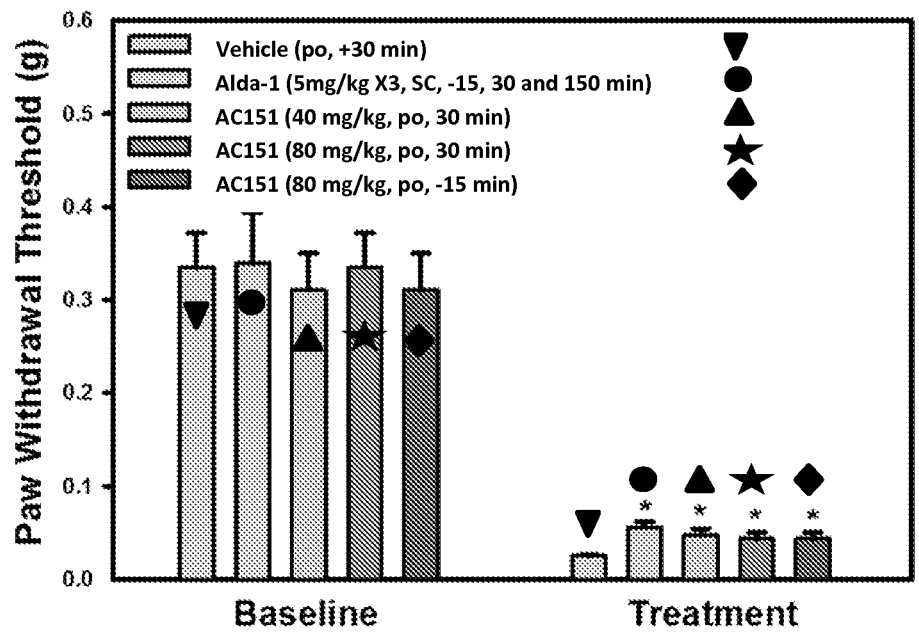
FIG. 4(A) depicts a bar graph showing ipsilateral paw withdrawal thresholds for baseline and following treatment with Alda-1 or AC151 compound.
Figure 4B:
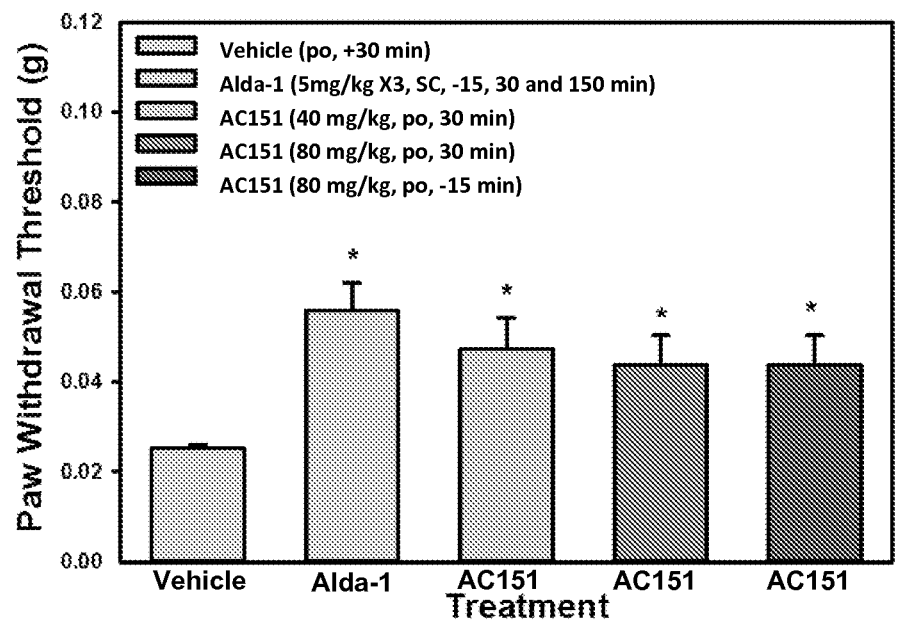
FIG. 4(B) depicts a bar graph showing ipsilateral paw withdrawal thresholds following treatment with Alda-1 or AC151 compound. Data are presented as mean±SEM. Asterisks (*p<0.05) indicate a significant difference compared to vehicle.
Figure 5:
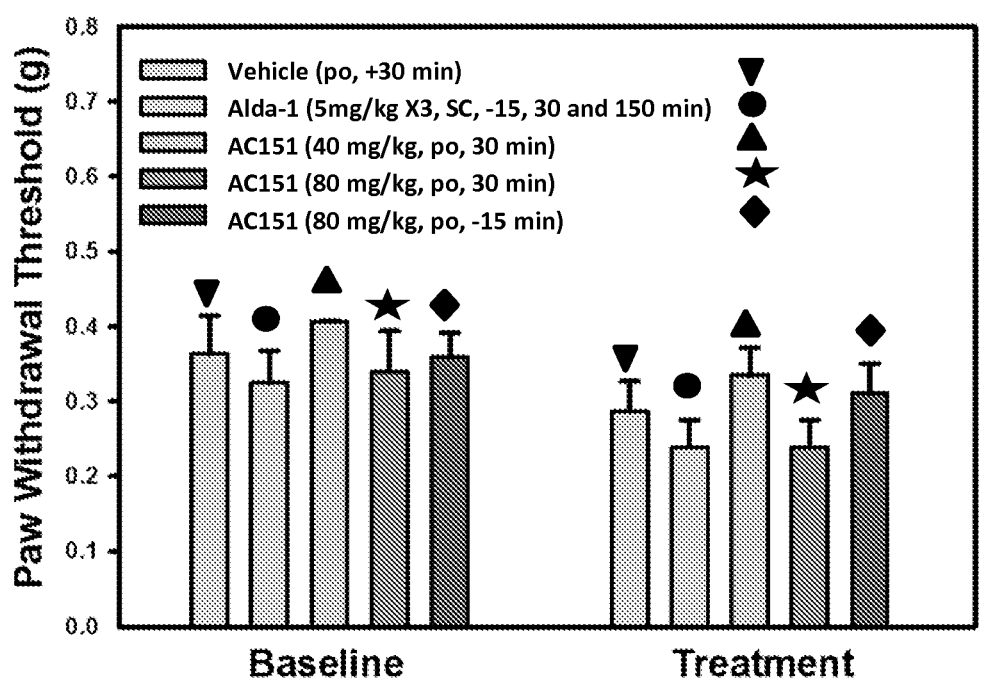
FIG. 5 depicts a bar graphs showing contralateral paw withdrawal thresholds for baseline and following treatment with Alda-1 or AC151 compound. Data are presented as mean±SEM.
Figure 6:
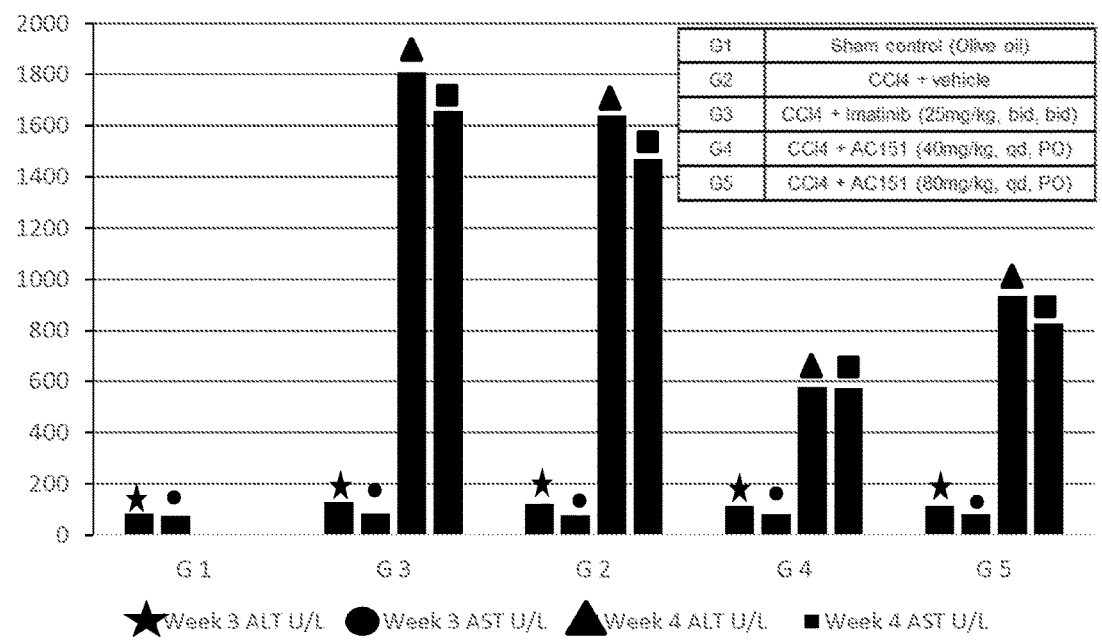
FIG. 6 depicts a bar graph showing alanine aminotransferase (ALT) and aspartate aminotransferase (AST) levels in mice when treated with AC151, Imatinib, vehicle (saline) and a sham control (olive oil).
Figure 7:
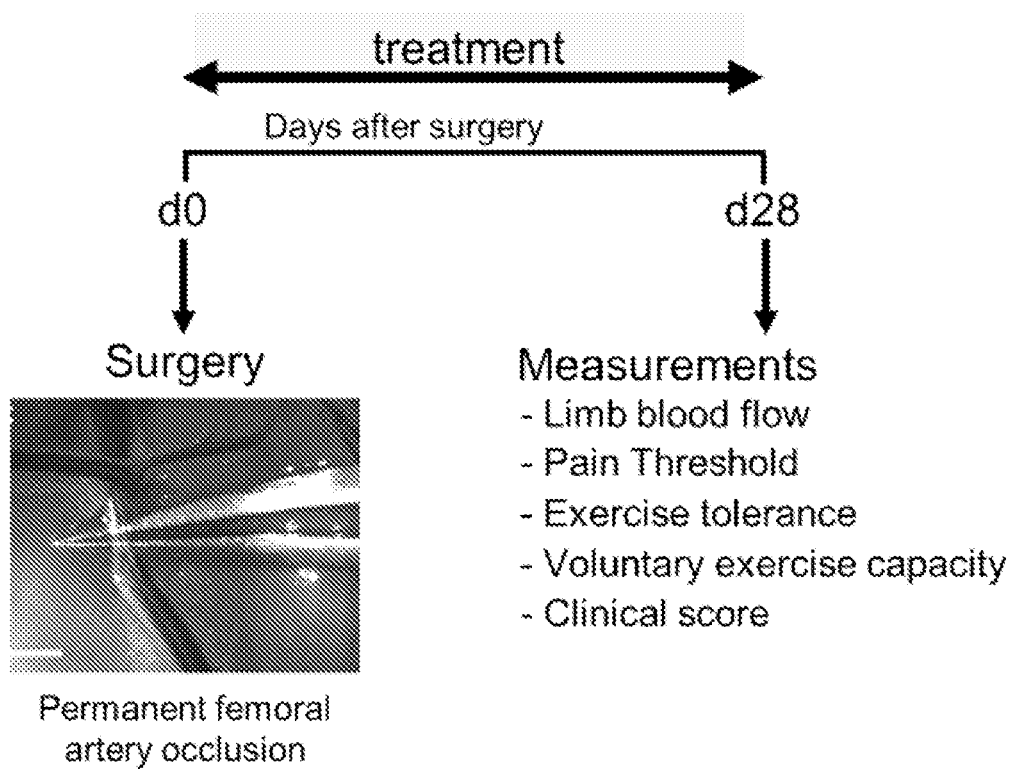
FIG. 7 is a schematic representation of the limb ischemia—murine animal study design utilized as a surrogated model for Peripheral Arterial Disease.

The effects of AC151 or Alda-1 compound on carrageenan-induced paw inflammation are shown in FIG. 4A and FIG. 4B. One way ANOVA showed a significant treatment effect. (FIG. 4A and FIG. 4B) Post hoc analysis demonstrated that AC151 (all groups) as well as Alda-1 (5 mg/kg) significantly increased paw withdrawal threshold compared to vehicle, indicating diminished hypersensitivity to tactile stimuli. For comparison purposes, the effects of AC151 and Alda-1 compound on carrageenan-induced contralateral paw inflammation are shown in FIG. 5. No treatment effects were noted with this measure. (FIG. 5)

AC151 and Alda-1 attenuated carrageenan-induced mechanical hyperalgesia as measured by the significant increase in ipsilateral paw withdrawal threshold. No significant differences were found between AC151 and Alda-1 suggesting similar efficacy of both compounds. (FIG. 4A and FIG. 4B) The response observed was specific as both compounds only affected the ipsilateral, but not contralateral paw withdrawal thresholds.

Example 11

Effects of the Compounds of Formula (I) on Liver Fibrosis and Cirrhosis in a Carbon Tetrachloride Induced Fibrosis Model The efficacy of AC151 was evaluated on liver fibrosis induced by carbon tetrachloride ($CCl_4$) administration in BALB/c mice. The mice were administered AC151, Imatinib mesylate, and vehicle (saline) as a control. $CCl_4$ induced hepatic fibrosis and cirrhosis in rodents is a widely accepted experimental model for the study of liver fibrosis and cirrhosis. In many aspects this model mirrors the pattern of human disease progression associated with toxic damages such as viral hepatitis, alcohol abuse, metabolic diseases due to overload of iron or copper, etc. The current proposal is to establish the chronic $CCl_4$ induced liver fibrosis in BALB/c mice and to evaluate the efficacy of test compound on this animal model.

Reagents: Olive oil (Sinopharm Chemical), Carbon tetrachloride (China-reagent Co., Ltd), and Isoflurane (Hebei Jiupai Pharmaceutical Co., Ltd). 25% $CCl_4$ in olive oil solution was prepared by mixing 1 ml of $CCl_4$ with 3 ml olive oil.

45 male BALB/c mice from Shanghai SLAC Laboratory Animal Co. Ltd. were used in this study. Mice were received at 6-7 weeks of age with a body weight between 18 g to 25 g. Upon receipt, mice were assigned unique identification numbers and were group housed in clear polycarbonate plastic cages. All animals were acclimated to the colony room for at least 1 week prior to testing. During the period of acclimation, animals were examined on a regular basis, handled, and weighed to assure adequate health and suitability. Animals were maintained on a 12 hour/12 hour light/dark cycle. The room temperature was maintained between 20° C. and 26° C. with a relative humidity maintained between 40% and 70%. Chow and water were provided ad libitum for the duration of the study. All testing was performed during the animal's light cycle phase.

After the acclimation period, mice were administered $CCl_4$ for a total period of 8 weeks to establish liver fibrosis. From day 0, all animals except group 1 (sham control group) were injected intraperitoneally with $CCl_4$ (i.p.) 2 mL/kg 25% $CCl_4$ in olive oil (50 µL for a regular mouse with body weight of 25 g), twice per week for a total period of 8 weeks. At the end of week 3, forty $CCl_4$ treated mice were randomly grouped into 4 groups (n=10/group prior to treatment start) according to ALT and AST value first and body weight second. Starting from week 4, animals from groups 2-5 were treated with vehicle or testing compounds correspondingly ($CCl_4$ treatment continues as the model requires). Each dosing was administered from 30 to 60 minutes prior to $CCl_4$ administration. The treatment groups are shown below in Table 4.

TABLE 4

Treatment Groups

| | | Test Article | N | Route | Conc. mg/mL | Dosage mL/kg | Dosage mg/kg | Regimen |
|---|---|---|---|---|---|---|---|---|
| | Groups | | | | | | | |
| 1 | Sham control (Olive oil) | N/A | 5 | N/A | N/A | 10 | N/A | q.d. from weeks 4-8 |
| 2 | CCl4 only | Vehicle (Saline) | 10 | p.o. | N/A | 10 | N/A | q.d. from weeks 4-8 |
| 3 | CCl4 + positive control | Imatinib | 10 | p.o. | 2.5 | 10 | 25 | bid for 8 weeks |
| 4 | CCl4 + test compound low dose treatment | AC-151 | 10 | p.o. | 4 | 10 | 40 | q.d. from weeks 4-8 |

TABLE 4-continued

| | Treatment Groups | | | | | | |
|---|---|---|---|---|---|---|---|
| | | Test | | | Conc. | Dosage | |
| | Groups | Article | N | Route | mg/mL | mL/kg | mg/kg | Regimen |
| 5 | CCl4 + test compound high dose treatment | AC151 | 10 | p.o. | 8 | 10 | 80 | q.d. from weeks 4-8 |

Animals in group 1 were administered with vehicle treatment for 5 weeks, p.o. q.d., (3 weeks olive oil followed by 5 weeks olive oil plus vehicle). Animals in group 2 were administered $CCl_4$ 1 mL/kg (2 mL/kg of 25% $CCl_4$ olive solution, twice a week, i.p.) for 3 weeks followed by 5 weeks of $CCl_4$ plus vehicle treatment. Animals in group 3 were administered $CCl_4$ 1 mL/kg (2 mL/kg of 25% $CCl_4$ olive solution, twice a week, i.p.) for 8 weeks. Imatinib treatment coincided with the beginning of $CCl_4$ administration and throughout the entire study (25 mg/kg, bid, p.o.).

Animals in group 4 were administered $CCl_4$ 1 mL/kg (2 mL/kg of 25% $CCl_4$ olive solution, twice a week, i.p.) for 3 weeks followed by 5 weeks of $CCl_4$ plus test compound low dosage treatment (40 mg/kg, q.d, p.o.). Animals in group 5 were administered $CCl_4$ 1 mL/kg (2 mL/kg of 25% $CCl_4$ olive solution, twice a week, i.p.) for 3 weeks followed by 5 weeks of $CCl_4$ plus test compound high dosage treatment (80 mg/kg, q.d, p.o.).

300 µL of blood samples (non-fasting) were collected at the end of week 3 and of week 8 to prepare serum samples for blood chemistry analysis (ALT and AST). Blood samples were obtained through retro-orbital puncture under anesthesia with isoflurane (3-5% Isoflurane for 3-5 min) in fume hood 24 hrs after $CCl_4$ administration. After collection, the blood was allowed to clot at ambient temperature for a minimum of 30 minute and then refrigerated at 4° C. for 30 minutes to allow the clot to contract. Serum samples were prepared by centrifugation at 4° C., 3500×g for 10 minutes. Serum alanine aminotransferase (ALT) and aspartate aminotransferase (AST) levels were measured at the end of week 3 and week 8 using automatic biochemistry analyzer (HITACHI 7020). Serum samples were placed in −70° C. to −80° C. for storage. For the final serum samples, TGF-beta is detected by ELISA Kit according to the manufacture's instruction. 48 hours after the last $CCl_4$ administration, following blood sampling, the animals were sacrificed.

Whole liver tissue is quickly flushed with ice-cold PBS, blotted briefly on paper towel, and weighed. Liver tissue is dissected into pieces for later use. The right lobe is fixed in 10% neutral formalin for histopathology and immunohistochemistry (IHC) analysis. The left lobe and middle lobe is separately shock frozen in liquid nitrogen and stored at −80° C. for further analysis.

Serum levels of TGF-beta are measured at the end of week 8 and body weight (twice per week) and liver weight are also measured. HE staining of liver sections with inflammation scoring, quantification of fibrotic tissue in liver (Sirius red staining with quantitation), alpha-SMA (IHC) in liver sections with quantitation and hepatic macrophage infiltration (F4/80 antibody staining for IHC with quantitation) are also performed for all treated animals in the study.

Data will be presented as mean±SEM. and be analyzed using corresponding tests. $p<0.05$ is considered statistically significant. Statistics will be done on raw data after outlier removal. Outliers will be defined as greater than 2 SD from the mean.

Example 12

Effects on Modulation of Mitochondrial Aldehyde Dehydrogenase in Limb Ischemia Model for Peripheral Arterial Disease (PAD)

The effects of ALDH2 modulation were assessed in ALDH2*2 knock-in mice. ALDH2*2 knock-in mice were treated with AC151 and vehicle as a control. ALDH2*2 knock-in mice have only 10% of the ALDH2 activity in comparison to wild-type mice.

The limb ischemia-murine animal model was utilized as a surrogated model for peripheral arterial disease as described in Nature Protocols, 4, 1737-1748 (2009). (Limbourg, A., et. als., Evaluation of postnatal arteriogenesis and angiogenesis in a mouse model of hind-limb ischemia, Nature Protocols, 4, 1737-1748 (2009)). The study design is summarized in FIG. 1. All experiments were run according to national and institutional regulations concerning the use of animals for research purposes and permissions to carry out experiments have to be obtained.

The animals, WT mice age 18-22 weeks, were anesthetized with an intraperitoneal (IP) injection of esketamine (100 mg/ml) dose 80-100 mg/kg and xylazine (20 mg/ml) dose 4-6 mg/kg. Hair was entirely removed from the surgical area and a longitudinal incision was made beginning at the inguinal crease along the femoral vessels. The connective tissue sheet between the femoral artery and vein was then carefully dissected and an opening between the femoral artery and vein was made. Artery ligation thread was then used to occlude the femoral artery using triple surgical knots. The incision was then closed and the animals were administered a single dose of buprenorphine (0.1 mg/kg) subcutaneously to control ischemic pain.

The animals under permanent femoral artery occlusion at day zero, were treated with ALDH2 activators, Alda-1 and AC112, via osmotic pump for 28 days. The effects of the compounds of the present invention on functional capacity were assessed in mice using treadmill exercise in a metabolic chamber.

$V_{O2}$ max and respiratory exchange ratios are measured by dynamic $O_2$ and $CO_2$ measurements as well as anaerobic threshold by serum lactate assays. Cristae regularity, intraorganelle condensation, mitochondrial membrane irregularity, and associated vacuolization/lysosomes) is also accessed. Biomarkers of mitochondrial damage including mitochondrial protein adducts with reactive aldehydes (i.e., 4-HNE) and mitochondrial structure is measured by transmission electron microscopy (TEM) (i.e., mitochondrial volume and location (subsarcolemma/sarcomeric).

Mitochondrial function is also accessed by measuring mitochondrial membrane potential and activities of the respiratory chain complexes, as well as employing a Clark electrode to measure skeletal muscle $O_2$ consumption. In addition, the effect of pharmacologic or genetic modulation of ALDH2 activity on muscle structure by LM and TEM is accessed, the fragmentation of actin filaments within the myofibril with fluorescent phalloidin and apoptosis with TUNEL/Caspase-3 staining; and contractile function of gastrocnemius muscle in vitro using electrical stimulation and a force microtransducer is quantified.

Figure 8:
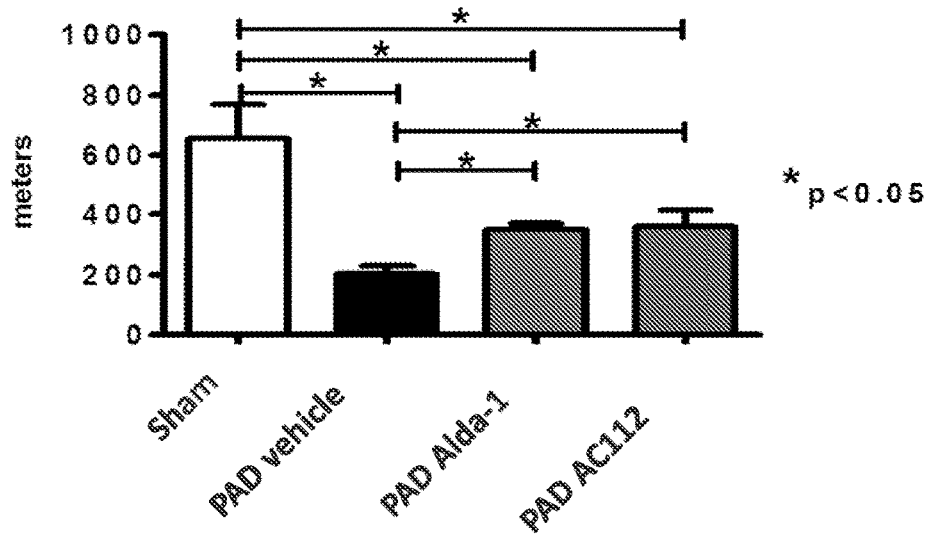
FIGS. 8(A) and 8(B) are bar graphs showing the effects on running distance and time observed in animals treated with AC112 or Alda-1.
Figure 8:
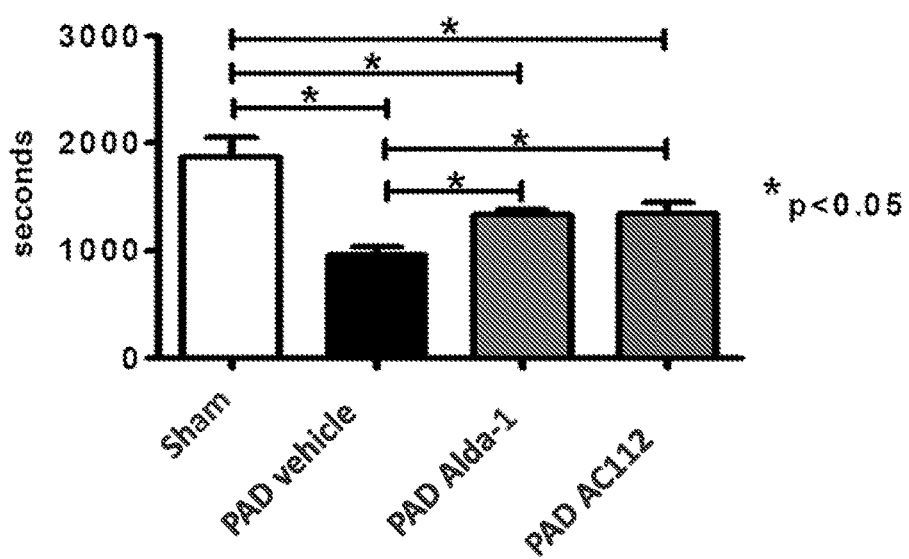
Figure 9:
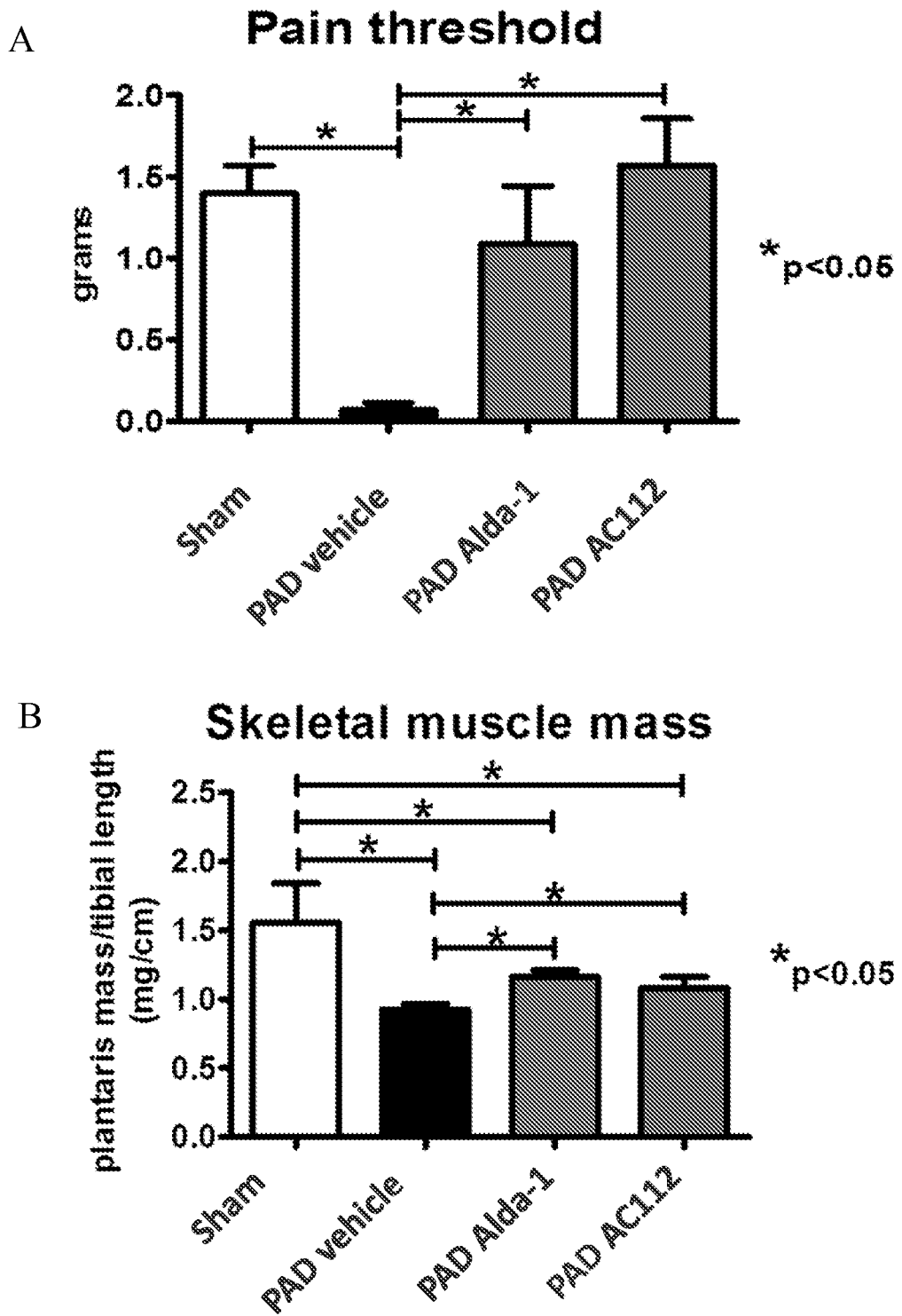
FIGS. 9(A) and 9(B) are bar graphs showing the effects on pain threshold and skeletal muscle observed in animals treated with AC112 or Alda-1.
Figure 10:
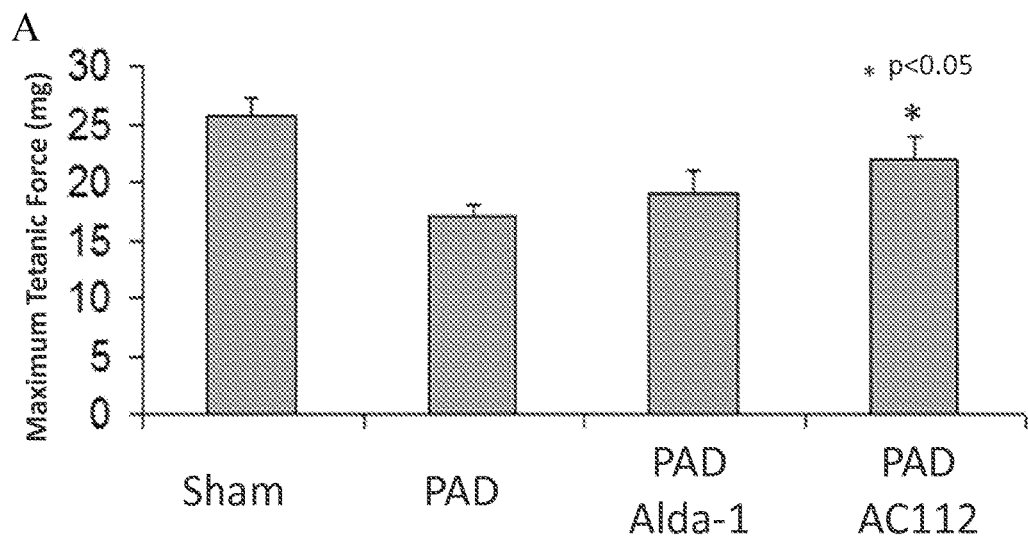
FIGS. 10(A) and 10(B) are bar graphs showing the effects on skeletal muscle measurements (e.g., skeletal muscle contractility and skeletal muscle resistance) and ALDH2 activity of muscle tissue observed in animals treated with AC112 or Alda-1.
Figure 10:
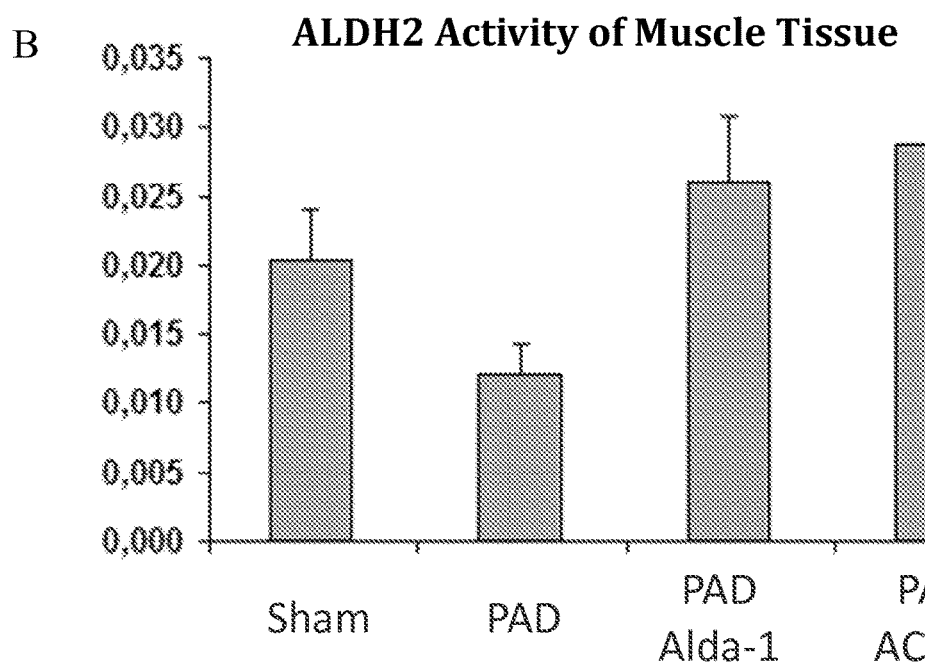

ALDH2 Agonists AC112 has demonstrated to improve both running distance and running time in PAD wild type mice (FIGS. 8A and 8B). AC112 also improve pain threshold in PAD mice (FIG. 9A) and minimizes PAD-induced skeletal muscle atrophy in WT Mice (FIG. 9B). The skeletal muscle contractility has been measured ex vivo, the result has demonstrated that the treatment of AC112 can improve the skeletal muscle resistance to fatigue in PAD mice (FIG. 10A). In this study we have also determined the ALDH2 activity in muscle tissue. AC112 treatment increased the ALDH2 activity of muscle tissue in PAD mice (FIG. 10B).

INCORPORATION BY REFERENCE

The entire disclosure of each of the patent documents and scientific articles referred to herein is incorporated by reference for all purposes. In the present disclosure the host document is identified with sufficient particularity and materials that are relevant to the disclosure is construed based on the context of the reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and the foregoing description and examples are for purposes of illustration and not limitation of the claims that follow.

EQUIVALENTS

The invention can be embodies in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of formula I:

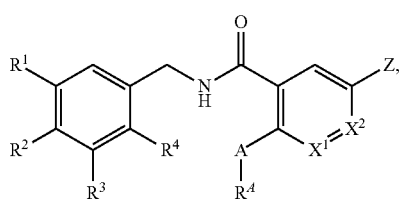

(I)

or a pharmaceutically acceptable salt, or ester thereof, wherein:
A is O, S, NH, or N—$R^C$;
$R^A$ is H, $C_1$-$C_6$ alkyl optionally substituted with one or more $R^B$, or $C_3$-$C_8$ cycloalkyl;
$R^B$ is $R^C$ or a 3-14 membered carbocycle optionally substituted with $R^C$;
$R^C$ is D or $C_1$-$C_6$ alkyl;
$X^1$ and $X^2$ are independently N or CH;
$R^1$, $R^3$, and $R^4$ are independently chosen from —H, —F, —Cl, —$CH_3$, —$CF_3$, —$C(CH_3)_3$, —$OCH_3$, and —$OCD_3$;

$R^2$ is independently chosen from —F, —Cl, —$CH_3$, —$CF_3$, —$C(CH_3)_3$, —$OCH_3$, and —$OCD_3$;
wherein $R^2$ is not —F when $R^1$, or $R^3$, or $R^4$ is —F; alternatively, $R^1$ and $R^2$ together form a 5-membered, partially saturated heterocycle containing two oxygen atoms;
Z is a substituted ring structure chosen from

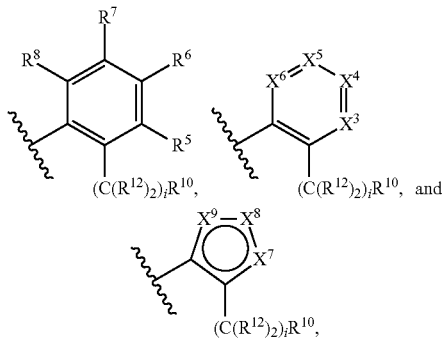

wherein i is 0, 1, 2, or 3;
$R^5$, $R^6$, $R^7$, and $R^8$ are independently chosen from H, F, and $N(CH_3)_2$;
$X^3$, $X^4$, $X^5$, and $X^6$ are independently chosen from N, NO, and CH;
$X^7$, $X^8$, and $X^9$ are independently chosen from S, O, N, $NR^9$, and $CR^9$;
$R^9$ is H or $CH_3$;
$R^{10}$ is $R^{11}$, —CH=$CHR^{11}$,

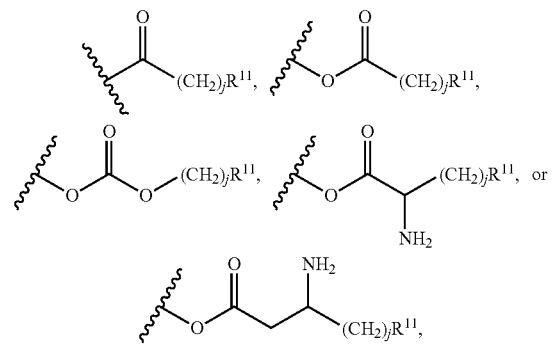

wherein j is 0, 1, 2, or 3;
$R^{11}$ is —$C(CH_3)_2NH_2$, —$CH(CH_3)_2$, —$CH(CH_3)OH$, —$NH_2$, —$NHR^C$, —$NR^C_2$, —$OCH_3$, —$C(O)CH_3$, —$OPO_3H_2$, —COOH, —CH=NOH, —$CH_3$, —SH, —OH, or —H; and
each $R^{12}$ is independently H or D.

2. The compound of claim 1, having formula (Ia):

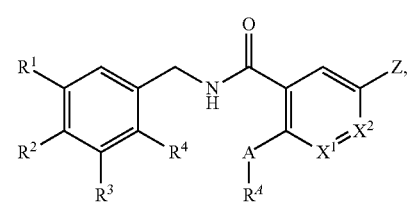

(Ia)

or a pharmaceutically acceptable salt, or ester, or thereof,
$R^A$ is H, $C_1$ -$C_6$ alkyl optionally substituted with $R^B$, or $C_3$-$C_6$ cycloalkyl;

$R^C$ is $C_1$-$C_6$ alkyl;
$R^1$, $R^3$, and $R^4$ are independently chosen from —H, —F, —Cl, —CH$_3$, —CF$_3$, —C(CH$_3$)$_3$, and —OCH$_3$;
$R^2$ is independently chosen from —F, —Cl, —CH$_3$, —CF$_3$, —C(CH$_3$)$_3$, —OCH$_3$, and —OCD$_3$;
wherein $R^2$ is not —F when $R^1$, or $R^3$, or $R^4$ is —F;
alternatively, $R^1$ and $R^2$ together form a 5-membered, partially saturated heterocycle containing two oxygen atoms; and
$R^{12}$ is H.

3. The compound of claim 1, having formula (Ib):

(Ib)

or a pharmaceutically acceptable salt, or ester thereof, wherein:
$R^A$ is H, $C_1$-$C_6$ alkyl optionally substituted with $R^B$, or $C_3$-$C_6$ cycloalkyl;
$R^C$ is $C_1$-$C_6$ alkyl; and
$R^{12}$ is H.

4. The compound of claim 1, having formula (Ic):

(Ic)

or a pharmaceutically acceptable salt, or ester thereof, wherein:
$R^A$ is H, $C_1$-$C_6$ alkyl optionally substituted with $R^B$, or $C_3$-$C_6$ cycloalkyl;
$R^C$ is $C_1$-$C_6$ alkyl; and
$R^{12}$ is H.

5. The compound of claim 1, having formula (Id):

(Id)

or a pharmaceutically acceptable salt, or ester thereof, wherein:
$R^A$ is H, $C_1$-$C_6$ alkyl optionally substituted with $R^B$, or $C_3$-$C_6$ cycloalkyl;
$R^C$ is $C_1$-$C_6$ alkyl; and
$R^{12}$ is H.

6. The compound of claim 1, having formula (Ie):

(Ie)

or a pharmaceutically acceptable salt, or ester thereof, wherein:
$R^A$ is H, $C_1$-$C_6$ alkyl optionally substituted with $R^B$, or $C_3$-$C_6$ cycloalkyl; and
$R^C$ is $C_1$-$C_6$ alkyl.

7. The compound of claim 1, having formula (If):

(If)

or a pharmaceutically acceptable salt, or ester thereof, wherein:
$R^A$ is H, $C_1$-$C_6$ alkyl optionally substituted with $R^B$, or $C_3$-$C_6$ cycloalkyl; and
$R^C$ is $C_1$-$C_6$ alkyl.

8. The compound of claim 1, having formula (If):

(If)

or a pharmaceutically acceptable salt, or ester thereof, wherein:
$R^A$ is H, $C_1$-$C_6$ alkyl optionally substituted with $R^B$, or $C_3$-$C_6$ cycloalkyl; and
$R^C$ is $C_1$-$C_6$ alkyl.

9. The compound according to claim 1, wherein the compound is selected from Table 1.

10. The compound of claim 1 selected from the group consisting of:

AC1
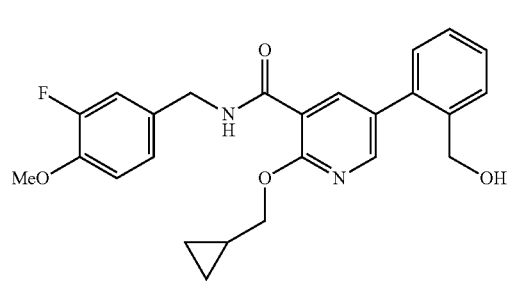
AC2
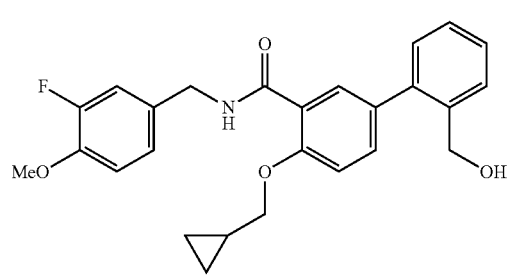
AC3
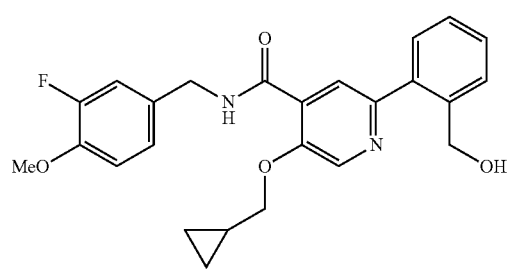
AC5
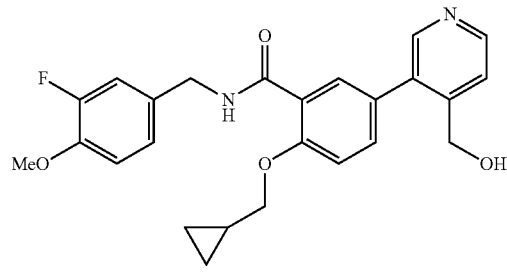
AC6
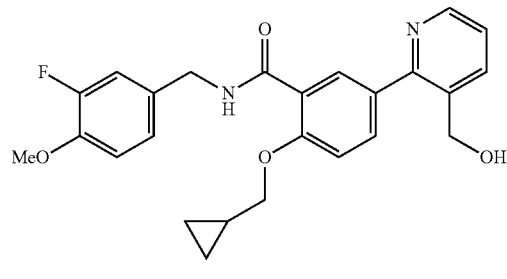
AC8
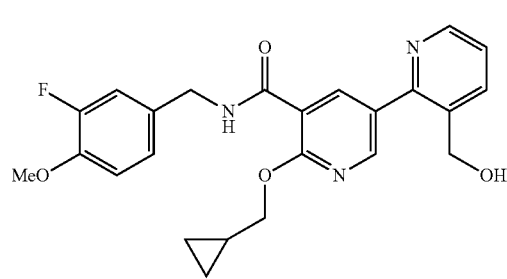
-continued
AC10
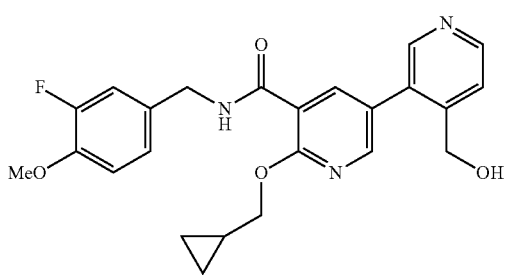
AC13
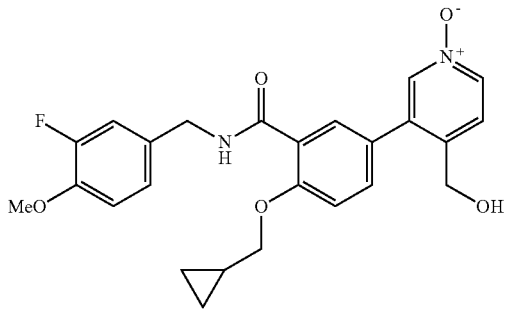
AC14
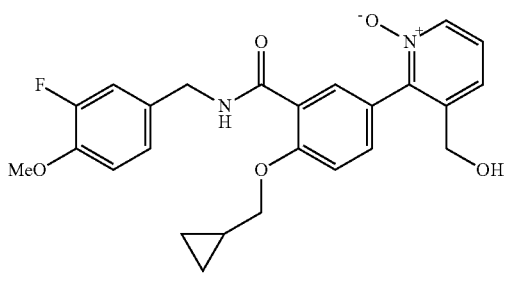
AC63
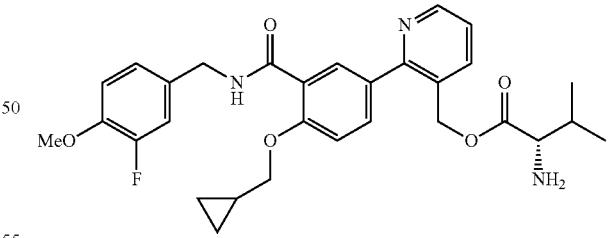
AC67
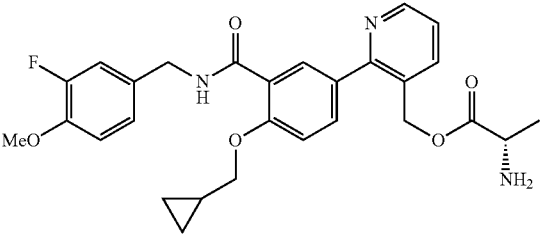

AC68
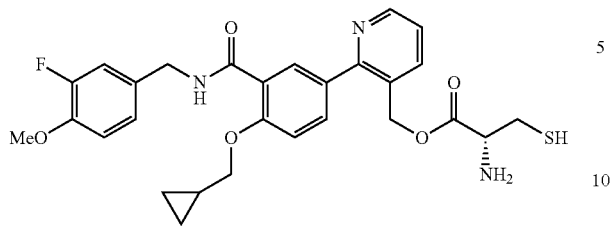
AC73
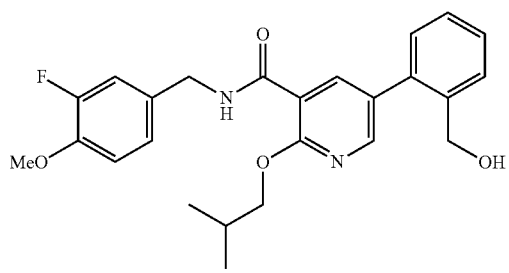
AC101
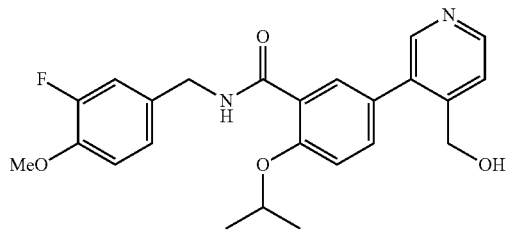
AC102
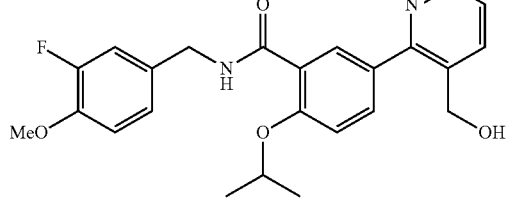
AC107
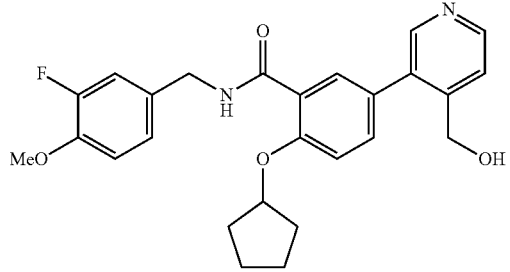
AC108
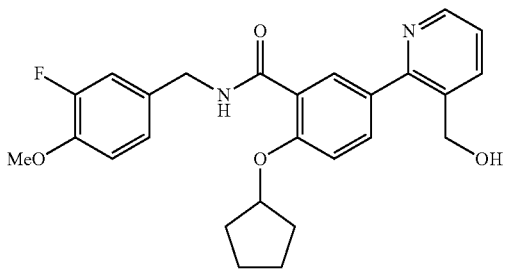
AC109
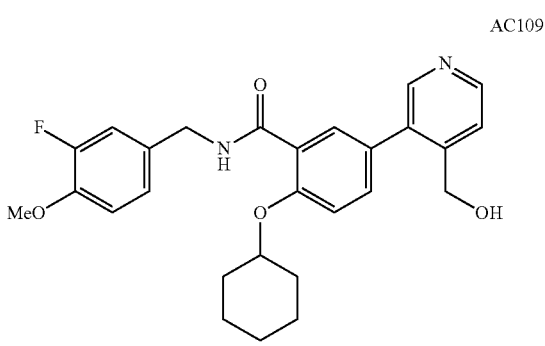
AC110
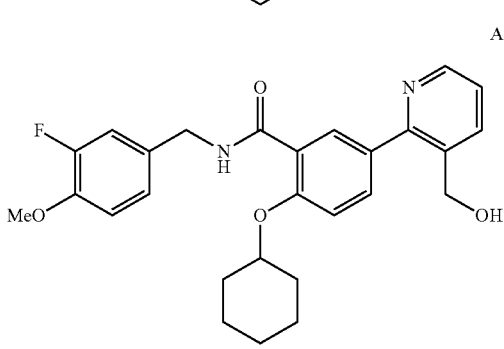
AC111
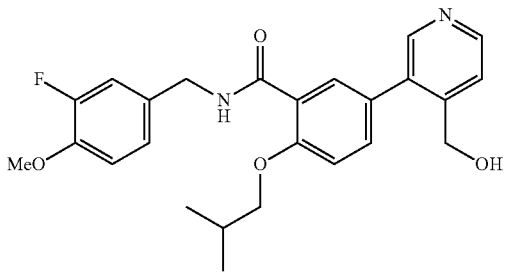
AC112
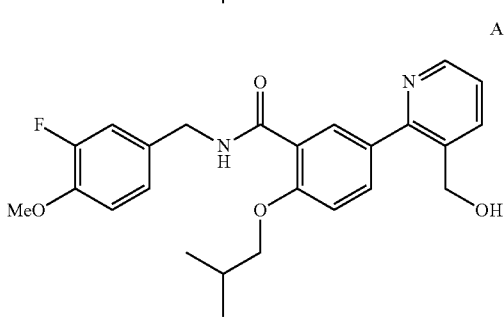

AC113
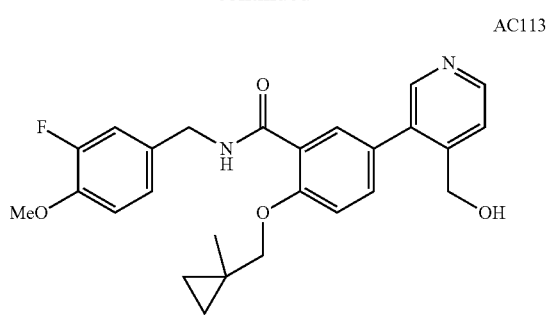
AC114
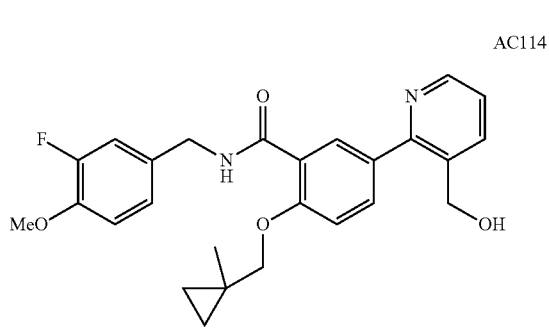
AC115
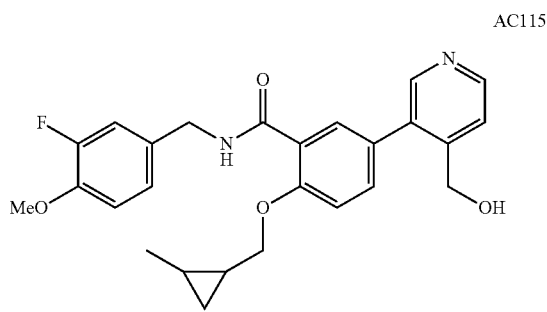
AC116
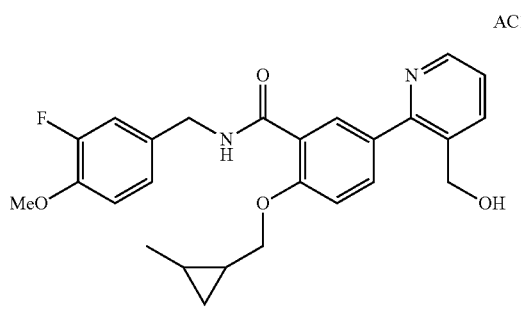
AC151
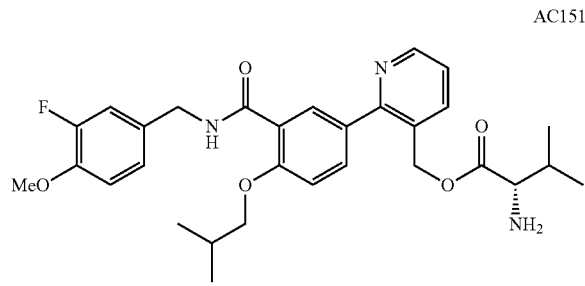
AC156
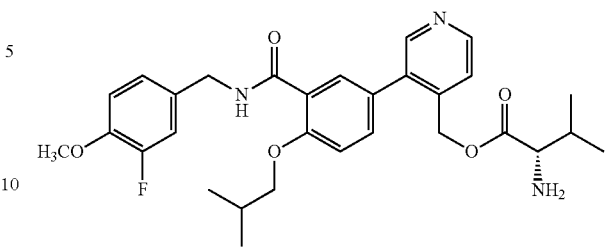
AC161
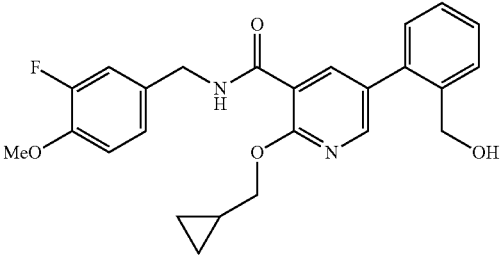
and
AC162
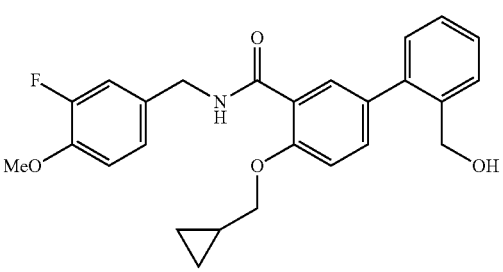
11. The compound of claim 1 selected from the group consisting of:
AC1
AC2

-continued
AC3
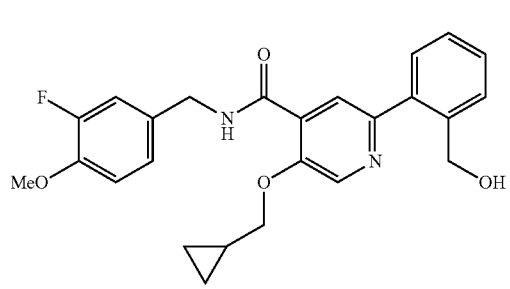
AC5
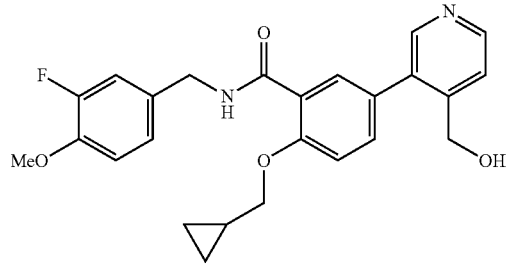
AC6
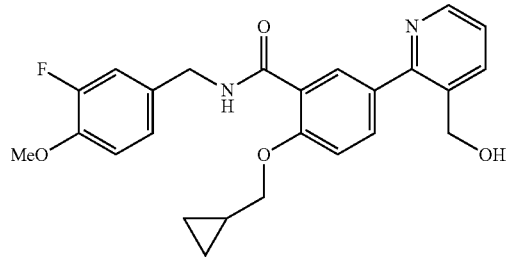
AC8
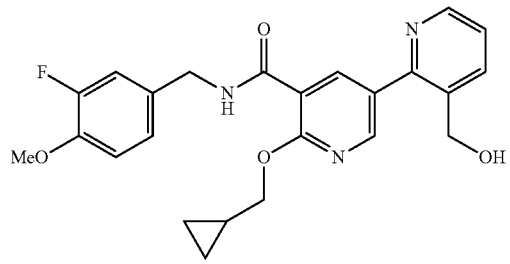
AC10
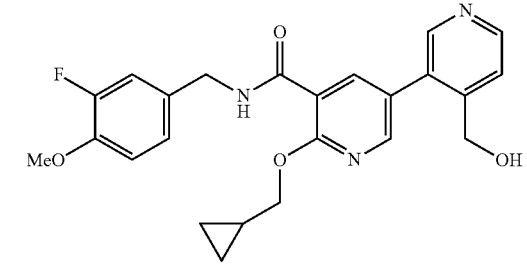
-continued
AC13
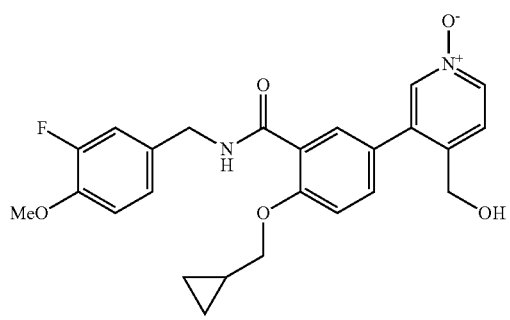
AC14
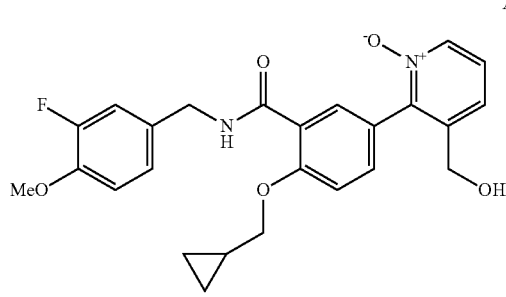
AC63
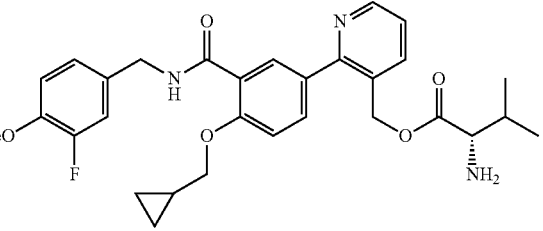
AC67
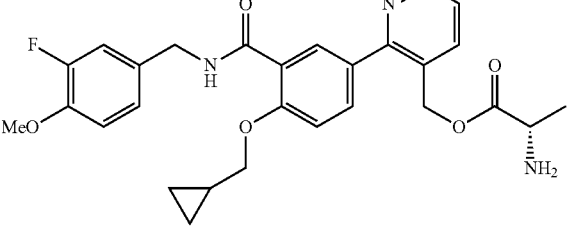
AC68
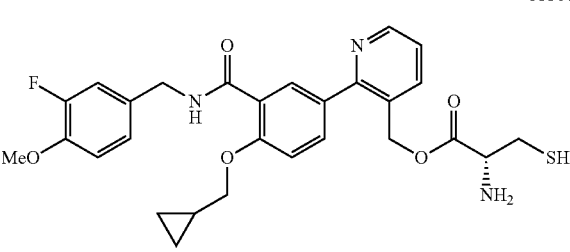

-continued
AC101
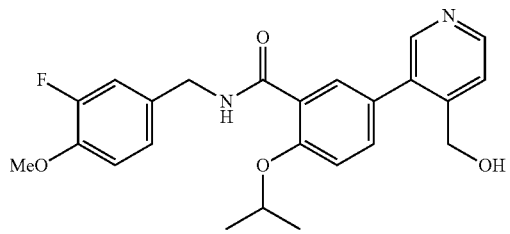
AC102
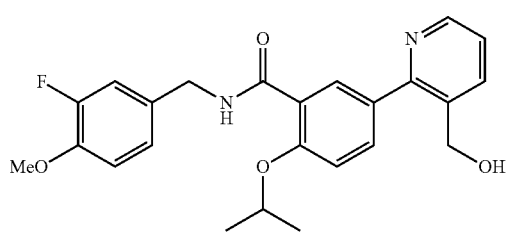
AC107
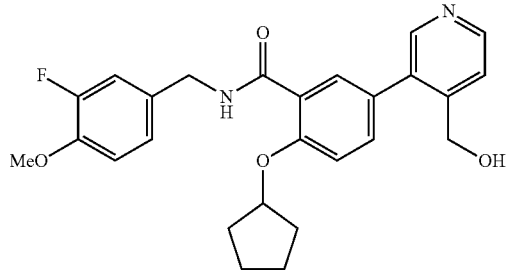
AC108
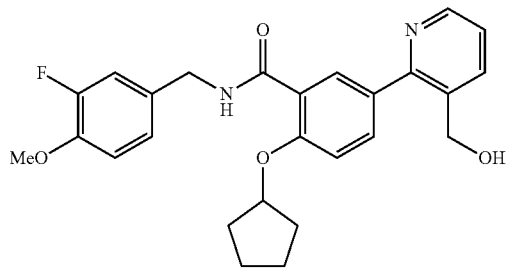
AC109
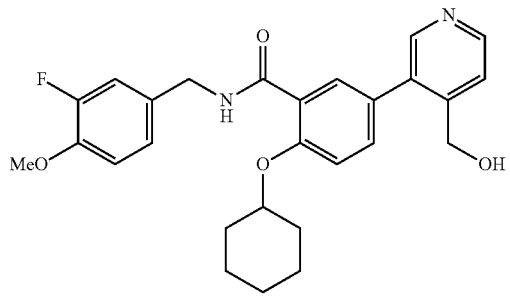
-continued
AC110
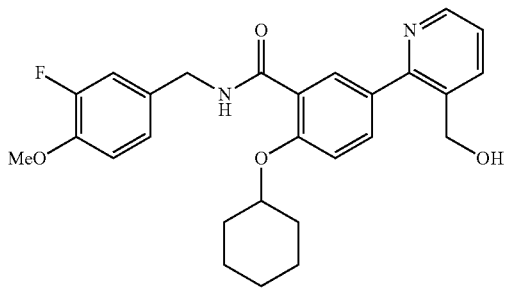
AC111
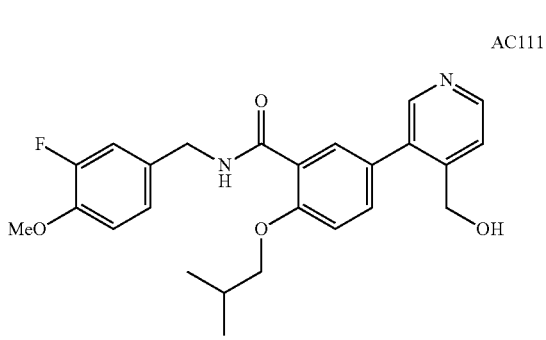 [SMILES: COc1ccc(CNC(=O)c2cc(-c3cnccc3CO)ccc2OCC(C)C)cc1F]
AC112
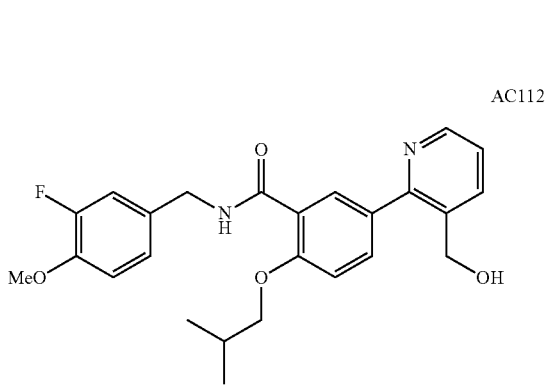
AC151
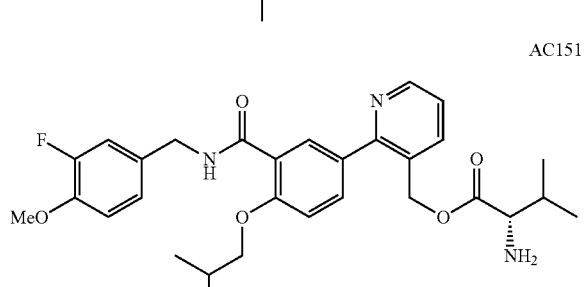
AC156
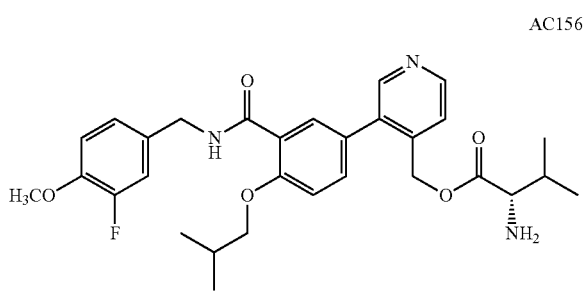

-continued

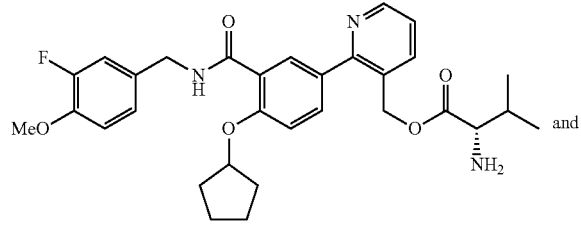
AC161

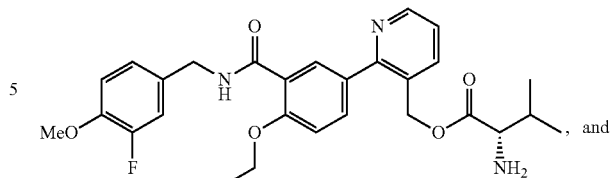
and

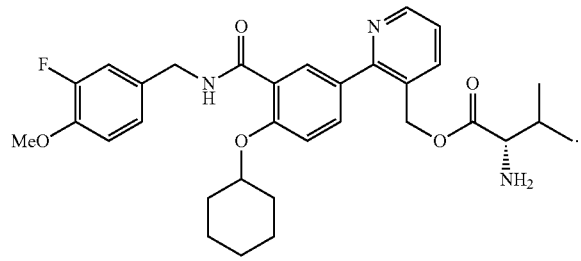
AC162

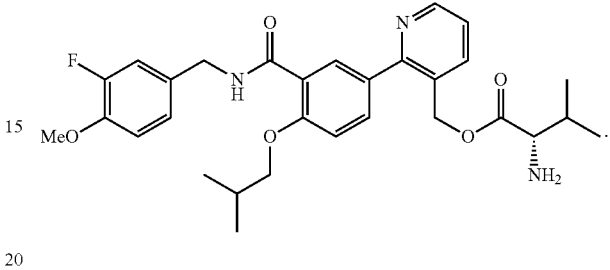

12. The compound of claim 1 selected from the group consisting of:

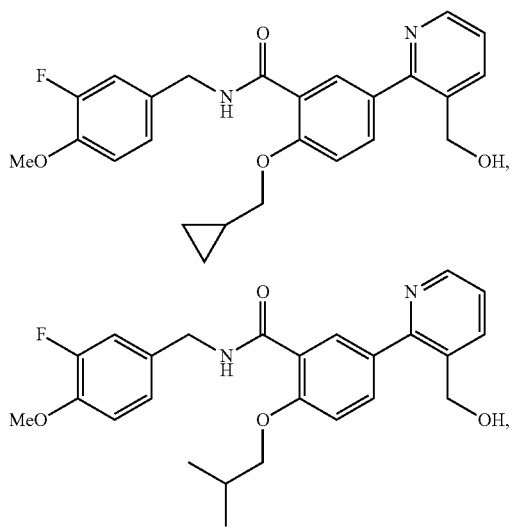

13. A method for treating Fanconi Anemia in a subject in need thereof, comprising administering to the subject the compound of claim 1 or a pharmaceutically acceptable salt, or ester thereof.

14. A method for treating peripheral artery disease in a subject in need thereof, comprising administering to the subject the compound of claim 1, or a pharmaceutically acceptable salt, or ester thereof.

15. A method for treating liver injury and/or damage in a subject in need thereof, comprising administering to the subject the compound of claim 1, or a pharmaceutically acceptable salt, or ester thereof.

16. The method of claim 15, wherein the liver injury and/or damage is liver fibrosis.

17. A method for treating Acute Inflammatory Pain in a subject in need thereof, comprising administering to the subject the compound of claim 1, or a pharmaceutically acceptable salt, or ester thereof.

18. A method for treating alcohol addiction, comprising administering to the subject the compound of claim 1, or a pharmaceutically acceptable salt, or ester thereof.

* * * * *